(12) United States Patent
Rezania

(10) Patent No.: US 10,344,264 B2
(45) Date of Patent: *Jul. 9, 2019

(54) CULTURING OF HUMAN EMBRYONIC STEM CELLS AT THE AIR-LIQUID INTERFACE FOR DIFFERENTIATION INTO PANCREATIC ENDOCRINE CELLS

(71) Applicant: Janssen Biotech, Inc., Horsham, PA (US)

(72) Inventor: Alireza Rezania, Skillman, NJ (US)

(73) Assignee: JANSSEN BIOTECH, INC., Horsham, PA (US)

( * ) Notice: Subject to any disclaimer, the term of this patent is extended or adjusted under 35 U.S.C. 154(b) by 350 days.

This patent is subject to a terminal disclaimer.

(21) Appl. No.: 13/998,884

(22) Filed: Dec. 18, 2013

(65) Prior Publication Data

US 2014/0186305 A1 Jul. 3, 2014

Related U.S. Application Data

(60) Provisional application No. 61/747,662, filed on Dec. 31, 2012.

(51) Int. Cl.
*C12N 5/00* (2006.01)
*C12N 5/071* (2010.01)
*G01N 33/50* (2006.01)
*C12N 5/0735* (2010.01)

(52) U.S. Cl.
CPC ......... *C12N 5/0676* (2013.01); *C12N 5/0606* (2013.01); *G01N 33/507* (2013.01); *C12N 2500/25* (2013.01); *C12N 2501/105* (2013.01); *C12N 2501/115* (2013.01); *C12N 2501/117* (2013.01); *C12N 2501/15* (2013.01); *C12N 2501/385* (2013.01); *C12N 2501/395* (2013.01); *C12N 2501/415* (2013.01); *C12N 2501/727* (2013.01); *C12N 2501/999* (2013.01); *C12N 2506/02* (2013.01); *C12N 2533/30* (2013.01); *C12N 2533/90* (2013.01)

(58) Field of Classification Search
CPC combination set(s) only.
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A * | 8/1999 | Wheeler ................. 435/325 |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

Brevini et al., 2010, Theriogenology, vol. 74, pp. 544-550.*

(Continued)

*Primary Examiner* — Thaian N Ton
*Assistant Examiner* — David A. Montanari
(74) *Attorney, Agent, or Firm* — Klarquist Sparkman, LLP

(57) ABSTRACT

The present invention provides methods, cell cultures and differentiation media to promote differentiation of pluripotent stem cells to pancreatic endocrine cells expressing PDX1, NKX6.1, and HB9 by culturing in a culture vessel at the air-liquid interface. The invention also provides for in vivo maturation of cells cultured at the air-liquid interface.

35 Claims, 69 Drawing Sheets

(56) References Cited

U.S. PATENT DOCUMENTS

| | | |
|---|---|---|
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 8,987,471 B2 | 3/2015 | Takeuchi et al. |
| 10,066,210 B2 | 9/2018 | Rezania |
| 2002/0072117 A1 | 7/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0148070 A1 | 7/2005 | Thomson et al. |
| 2005/0158852 A1 | 7/2005 | D'Amour et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003313 A1 | 1/2006 | D'Amour et al. |
| 2006/0003446 A1* | 1/2006 | Keller et al. ............ 435/366 |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0139662 A1 | 6/2008 | Brinkmann et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1* | 1/2009 | Martinson ............ A61K 38/28 424/93.7 |
| 2009/0029462 A1 | 1/2009 | Beardsley et al. |
| 2009/0029947 A1 | 1/2009 | Wallace et al. |
| 2009/0053182 A1 | 2/2009 | Ichim et al. |
| 2009/0093055 A1 | 4/2009 | Fisk et al. |
| 2009/0170198 A1* | 7/2009 | Rezania ........................ 435/377 |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1* | 10/2010 | Rezania ............... C12N 5/0606 435/377 |
| 2011/0014702 A1 | 1/2011 | Xu et al. |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0109092 A1 | 5/2013 | Matsuyama et al. |
| 2013/0189777 A1 | 7/2013 | Rezania |
| 2013/0224156 A1 | 8/2013 | Takahashi et al. |
| 2014/0186953 A1 | 7/2014 | Rezania |
| 2014/0228324 A1 | 8/2014 | Takeuchi et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2559756 A1 | 2/2013 |
| EP | 2674485 A1 | 12/2013 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| JP | A-2011-172586 | 9/2011 |
| KR | 10-2008-0020098 A | 3/2008 |
| KZ | 18625 | 7/2007 |
| RU | 2215029 C2 | 2/2000 |

(56) References Cited

FOREIGN PATENT DOCUMENTS

| | | |
|---|---|---|
| RU | 2359030 C1 | 6/2009 |
| RU | 2359671 C2 | 6/2009 |
| WO | 199219759 A2 | 2/1992 |
| WO | 1996040172 A1 | 12/1996 |
| WO | 199847892 A1 | 10/1998 |
| WO | 199920741 A1 | 4/1999 |
| WO | 200029549 A1 | 5/2000 |
| WO | WO 2000/47717 | 8/2000 |
| WO | 200123528 A1 | 4/2001 |
| WO | 200151616 A2 | 7/2001 |
| WO | 200181549 A3 | 11/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A2 | 4/2003 |
| WO | 2003042405 A2 | 5/2003 |
| WO | 200305049 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | 2003102134 A2 | 12/2003 |
| WO | 2004011621 A2 | 2/2004 |
| WO | 2004016747 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |
| WO | 2004090110 A2 | 10/2004 |
| WO | 2004067001 A1 | 12/2004 |
| WO | 2005001077 A2 | 1/2005 |
| WO | 2005080598 A1 | 1/2005 |
| WO | 2005014799 A1 | 2/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | 2005116073 A3 | 12/2005 |
| WO | 2006016999 A1 | 2/2006 |
| WO | 2006020919 A2 | 2/2006 |
| WO | 2006088867 A2 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A1 | 8/2006 |
| WO | 2006094286 A2 | 9/2006 |
| WO | 2006100490 A1 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007027157 A1 | 3/2007 |
| WO | 2007030870 A1 | 3/2007 |
| WO | 2007047509 A2 | 4/2007 |
| WO | 2007051038 A2 | 5/2007 |
| WO | 2007069666 A1 | 6/2007 |
| WO | 2007082963 A1 | 7/2007 |
| WO | 2007101130 A2 | 9/2007 |
| WO | 2007103282 A1 | 9/2007 |
| WO | 2007127927 A2 | 11/2007 |
| WO | 2007139929 A2 | 12/2007 |
| WO | 2007143193 A1 | 12/2007 |
| WO | 2007149182 A2 | 12/2007 |
| WO | 2008004990 A2 | 1/2008 |
| WO | 2008013664 A1 | 1/2008 |
| WO | 2008015682 A2 | 2/2008 |
| WO | 2008035110 A1 | 3/2008 |
| WO | 2008036447 A2 | 3/2008 |
| WO | 2008048647 A1 | 4/2008 |
| WO | 2008048671 A1 | 4/2008 |
| WO | 2009096049 A1 | 5/2008 |
| WO | 2008086005 A1 | 7/2008 |
| WO | 2008094597 A2 | 8/2008 |
| WO | 2008102118 A1 | 8/2008 |
| WO | 2009012428 A1 | 1/2009 |
| WO | WO 2009/006399 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | 2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | WO 2011/019092 A1 | 2/2011 |
| WO | WO 2011/058558 A2 | 5/2011 |
| WO | 2011067465 A1 | 6/2011 |
| WO | WO 2011/079017 A2 | 6/2011 |
| WO | WO 2011/081222 A1 | 7/2011 |
| WO | 2011096223 A1 | 8/2011 |
| WO | 2011108993 A1 | 9/2011 |
| WO | 2011123572 A1 | 10/2011 |
| WO | 2011139628 A1 | 11/2011 |
| WO | WO 2011/158960 A1 | 12/2011 |
| WO | WO 2011/160066 A1 | 12/2011 |
| WO | 2012019122 A2 | 2/2012 |
| WO | WO 2012/030540 A2 | 3/2012 |
| WO | 2012117333 A1 | 9/2012 |
| WO | 2013055397 A1 | 4/2013 |
| WO | 2013055834 A2 | 4/2013 |
| WO | WO 2013/056072 A1 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Paris et al., 2010, Theriogenology, vol. 74, pp. 516-524.*
Munoz et al., 2008, Theriogenology, vol. 69, pp. 1159-1164.*
D'Amour et al., 2006, Nat. Biotechnology, vol. 24(11), pp. 1392-1401.*
Inman et al., 2002, Molecular Pharmacology, vol. 62(1), pp. 65-74.*
Ostrom et al. (2008, PLoS One, vol. 3(7), pp. 1-7).*
Kelly et al. (2011, Nature Biotech., vol. 29(8), pp. 750-758).+ Supplemental Figures.*
Rezania et al. (ePUB Oct. 22, 2010, Diabetes, vol. 60(1), pp. 239-247).*
Guillemain et al., 2007, JBC, vol. 282(20), pp. 15228-15237.*
Abe, et al., Evidence That P13K, Rac, Rho, and Rho Kinase Are Involved in Basic Fibroblast Growth Factor Stimulated Fibroblast-Collagen Matrix Contraction, Journal of Cellular Biochemistry, 2007, pp. 1290-1299, vol. 102.

(56) References Cited

OTHER PUBLICATIONS

Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.

Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

Ackermann, et al., Molecular Regulation of Pancreatic B-Cell Mass Development, Maintenance, and Expansion, Journal of Molecular Endocrinology, 2007, pp. 193-206, vol. 38.

Adams, J., Proteasome Inhibition in Cancer: Development of PS-341, Seminars in Oncology, 2001, pp. 613-619, vol. 28, No. 6.

Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Allegrucci, et al., Differences between Human Embryonic Stem Cell Lines, Human Reproduction Update, Aug. 26, 2006, pp. 1-18, Advance Access.

Almond, et al., The Proteasome: A Novel Target for Cancer Chemotherapy, Leukemia, 2002, pp. 433-443, vol. 16.

Amit et al., Human Feeder Layers for Human Embryonic Stem Cells, Biology of Reproduction, Jan. 22, 2003, 2150-2156, 68, No. 6, Society for the Study of Reproduction, Inc.

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

Amit, et al., Feeder Layer-and Serum-Free Culture of Human Embryonic Stem Cells, Biology of Reproduction, 2004, pp. 837-845, vol. 70.

Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.

Assady, et al., Insulin Production by Human Embryonic Stem Cells, Diabetes, 2001, pp. 1691-1697, vol. 50.

Baetge, Production of B-Cells from Human Embryonic Stem Cells, Diabetes, Obesity, Metabolism, 2008, pp. 186-194, vol. 10, Supplement 4.

Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.

Balsam, et al., Haematopoeitic Stem Cells Adopt Mature Haeatopoietic Fates in Ischaemic Myocardium, Nature, Apr. 8, 2004, pp. 668-673, Nature Publishing Group.

Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.

Barclay, et al., The Leucocyte Antigen Facts Book, The Leucocyte Antigen Facts Book, 1997, Textbook, 2[sup] edition, Academic Press.

Beltrami, et al., Adult Cardiac Stem Cells are Multipotent and Support Myocardial Regeneration, Cell, Sep. 19, 2003, pp. 763-776, vol. 114, Cell Press.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.

Bocian-Sobkowska, et al., Polyhormonal Aspect of the Endocrine Cells of the Human Fetal Pancreas, Histochem Cell Biol, 1999, pp. 147-153, vol. 112, Issue 2.

Bonner-Weir et al., In vitro cultivation of human islets from expanded ductal tissue, Proceedings of the National Academy of Sciences, Jul. 5, 2000, 7999-8004, 97-14, National Academy of Sciences.

Borowiak, et al., How to Make AB Cells, Current Opinion Cell Biology, 2009, pp. 727-732, vol. 21, Issue 6.

Borowitz, et al., Prognostic Significance of Fluorescence Intensity of Surface Marker . . . , Blood, Jun. 1, 1997, 3960-3966, 89-11, American Society of Hematology, Washington, D.C., US.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, 86-93, 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, 381-382, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.

Chen, et al., Differentiation of Rat Marrow Mesencymal Stem Cells in Pancreatic Islet Beta-Cells, World Journal of Gastroenterology, Oct. 15, 2004, pp. 3016-3020.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

(56) References Cited

OTHER PUBLICATIONS

Cheon, et al., Defined Feeder-Free Culture System of Human Embryonic Stem Cells, Biol Reprod, 2005, 105.046870, DOI10/1095.
Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al., Efficient differentiation of human embryonic stem cells to definitive endoderm, Nature Biotechnology, Oct. 28, 2005, 1-8, :W.1038/nbt1163, Nature Publishing Group.
D'Amour et al., Production of pancreatic hormone-expressing endocrine cells from human embryonic stem cells, Nature Biotechnology, Oct. 19, 2006, 1392-1401, 24-11, Nature Publishing Group, US.
Damy, et al., Increased Neuronal Nitric Oxide Synthase-Derived NO Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Coppi, et al., Isolation of Amniotic Stem Cell Lines with Potential for Therapy, Nature Biotechnology, 2007, pp. 100-106, vol. 25, No. 1.
De Rosa, 11-color, 13-parameter flow cytometry: Identification of . . . , Nature, Feb. 1, 2001, 245-248, 7-2, Nature Publishing Group, US.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331 XP002699177, vol. 11, No. 9/10.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, 524-532, 3, Nature Publishing Group, US.

Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 2006, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Fok, et al., Shear-Controlled Single-Step Mouse Embryonic Stem Cell Expansion and Embryoid Body-Based Differentiation, Stem Cells, 2005, pp. 1333-1342, vol. 23.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, 2261-2264, 306, US.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gittest, Developmental Biology of the Pancreas: A comprehensive Review, Developmental Biology, 2009, pp. 4-35 XP025995041, vol. 326, No. 1.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.

(56) References Cited

OTHER PUBLICATIONS

Guo, et al., Stem Cells to Pancreatic B-Cells: New Sources for Diabetes Cell Therapy, Endocrine Reviews, May 2009, pp. 214-227, vol. 30, No. 3, The Endocrine Society.

Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.

Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.

Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.

Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.

Hasegawa, et al., A Method for the Selection of Human Embryonic Stem Cell Sublines with High Replating Efficiency After Single-Cell Dissociation, Stem Cells, 2006, pp. 2649-2660, vol. 24.

Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.

Heinis, et al., HIF1a and Pancreatic Beta-Cell Development, The FASEB Journal, 2012, pp. 2734-2742, vol. 26.

Heinis, et al., Oxygen Tension Regulates Pancreatic Beta-Cell Differentiation Through Hypoxia-Inducible Factor 1x, Diabetes, 2010, pp. 662-669, vol. 59.

Heit, et al., Embryonic Stem Cells and Islet Replacement in Diabetes Mellitus, Pediatric Diabetes, 2004, pp. 5-15, vol. 5.

Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

Henderson, et al., Preimplantation Human Embryos and Embryonic Stem Cells Show Comparable Expression of Stage-Specific Embryonic Antigens, Stem Cells, 2002, pp. 329-337, vol. 20.

Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.

Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.

Herrera, Adult-Insulin-and Glucagon-Producing Cells Differentiate from Two Independent Cell Lineages, Development, 2000, pp. 2317-2322 XP001004766, vol. 127, No. 11.

Herzenberg, et al., Fluorescence-activated Cell Sorting, Scientific American, 1976, 108-117, 234, Scientific American, US.

Hess, et al., Bone Marrow-Derived Stem Cells Initiate Pancreatic Regeneration, Nature Biotechnology, Jul. 2003, pp. 763-770, vol. 21, No. 7.

Ho, et al., Animal Cell Bioreactors, Animal Cell Bioreactors, 1991, 1-512, Hardcover, Butterworth-Heinemann.

Hoehn, et al., Morphological and Biochemical Heterogeneity of Amniotic Fluid Cells in Culture, Methods in Cell Biology, 1982, pp. 11-34, vol. 26, Academic Press, Inc.

Hoffman, et al., Characterization and Culture of Human Embryonic Stem Cells, Nature Biotechnology, 2005, pp. 699-708, vol. 23, No. 6.

Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.

Hosoya, et al., Induction of Differentiation of Undifferentiated Cells into Pancreatic Beta-Cells in Vertebrates, Int. J. Dev. Biol., 2012, pp. 313-323, vol. 56.

Hussain, et al., Stem-Cell Therapy for Diabetes Mellitus, Lancet, 2004, pp. 203-205, vol. 364.

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.

Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.

Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al., Differentiation of Marrow Stromal Cells into Photoreceptors in the Rat Eye, The Journal of Neuroscience, Aug. 27, 2003, pp. 7742-7749, vol. 23, Issue 21.

Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.

Kinkel, et al., Cyp26 Enzymes Function in Endoderm to Regulate Pancreatic Field Size, PNAS, May 12, 2009, pp. 7864-7869, vol. 106, No. 19.

Kleinman et al., Basement Membrane Complexes with Biological Activity, Biochemistry, 1986, 312-318, 25, American Chemical Society.

Klimanskaya, et al., Human Embryonic Stem Cells Derived without Feeder Cells, Lancet, May 2005, pp. 1636-1641, vol. 365, No. 9471.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Biointerphases, Dec. 2009, pp. 6979.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Konstantinova et al., EphA-Ephrin-A-Mediated Beta Cell Communication Regulates Insulin Secretion from Pancreatic Islets, Cell, Apr. 20, 2007, pp. 359-370, vol. 129.

Koyangi et al., Inhibitio nof the Rho/ROCK Pathway Reduces Apoptosis During Transplantatation of Embryonic Stem Cell-

(56) References Cited

OTHER PUBLICATIONS

Derived Neural Precursors, Journal of Neurosciene Research, Sep. 7, 2007, 270-280, 86, Wiley-Liss, Inc.

Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.

Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.

Ku et al., Committing Embryonic Stem Cells to Early Endocrine Pancreas In Vitro, Stem Cells, 2004, 1205-1217, 22, AlphaMed Press.

Kubo et al., Development of definitive endoderm from embryonic stem cells in culture, Development, 2004, 1651-1662, 131, The Company of Biologists.

Lanza, et al., Characteristics and Characterization of Human Pluripotent Stem Cells, Stem Cell Anthology, 2010, pp. 141, 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Lee, et al., Protein Kinase A- and C-Induced Insulin Release from Ca2+-Insensitive Pools, Cellular Signalling, 2003, pp. 529-537, vol. 15.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Leon-Quinto, et al., In Vitro Directed Differentiation of Mouse Embryonic Stem Cells into Insulin-Producing Cells, Diabetologia, 2004, pp. 1442-1451 XP002699175, vol. 47, No. 8.

Levenstein et al., Basic Fibroblast Growth Factor Support of Human Embryonic Stem Cell Self-Renewal, Stem Cells, Nov. 10, 2005, 568-574, 24, AlphaMed Press.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Li, et al., Pluripotency Can be Rapidly and Efficiently Induced in Human Amniotic Fluid-Derived Cells, Human Molecular Genetics, 2009, pp. 4340-4349, vol. 18, No. 22.

Lilja et al., Cyclin-dependent Kinase 5 Promotes Insulin Exocytosis, Journal of Biological Chemistry, Jul. 6, 2001, 34199-34205, 36-7, JBC Papers in Press.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Derivation of Human Embryonic Stem Cells in Defined Conditions, Nature Biotechnology, Feb. 2006, pp. 185-187, vol. 24 No. 2.

Lumelsky, et al., Differentiation of Embryonic Stem Cells to Insulin-Secreting Structures Similar to Pancreatic Islets, Science, 2001, 1389-1394, 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

(56) References Cited

OTHER PUBLICATIONS

Micallef et al., Retinoic Acid Induces Pdx1-Positive Endoderm in Differentiating Mouse Embryonic Stem Cells, Diabetes, Feb. 2005, 301-305, 54, American Diabetes Association.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Mitalipova, et al., Preserving the Genetic Integrity of Human Embyonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moore, et al., The Corneal Epithelial Stem Cell, DNA and Cell Biology, 2002, pp. 443-451, vol. 21, No. 5/6.
Moran, et al., Bidirectional-Barbed Sutured Knotless Running Anastomosis v Classic van Velthoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2010, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nishimura, et al., Expression of MafA in Pancreatic Progenitors is Detrimental for Pancreatic Development, Developmental Biology, 2009, pp. 108-120, vol. 333.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Pancreatic Endoderm, http://www.mdsystems.com/molecule_group.aspx?g=801&,r, 1 page web printout.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Corning CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, The EMBO Journal, 2007, pp. 4744-4755, vol. 26.
Phillips, et al., Attachment and Growth of Human Embryonic Stem Cells on Microcarriers, Journal of Biotechnology, 2008, pp. 24-32, vol. 138.
Phillips, et al., Directed Differentiation of Human Embryonic Stem Cells into the Pancreatic Endocrine Lineage, Stem Cells and Development, 2007, pp. 561-578 XP009090586, vol. 16, No. 4.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct. 4—Expressing Cells in Human Amniotic Fluid: a New Source for Stem Cell Research?, Human Reproduction, 2003, pp. 1489-1493, vol. 18, No. 7.
Ptasznik, et al., Phosphatidylinositol 3-Kinase Is a Negative Regulator of Cellular Differentiation, The Journal of Cell Biology, 1997, pp. 1127-1136, vol. 137, No. 5.
R&D Systems, Embryonic & Induced Pluripotent Stem Cell Transcription Factors, http://www.mdsystems.com/molecule_group.aspx?r=1&g-3041, 2 page web printout dated May 31, 2013.
Rajagopal, et al., Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.

(56) References Cited

OTHER PUBLICATIONS

Reubinoff et al., Embryonic stem cell lines from human blastocysts: somatic differentiation in vitro, Nature Biotech, Apr. 18, 2000, 399-404, 18, Nature America Inc.
Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adult mesenchymal Stem Cells in the CNS, Society for Neuroscience Abstract Viewer and Itineray Planner, 2002, XP002519394, Program 237.18.
Sander, et al., Homeobox Gene Nkk6.1 Lies Downstream of Nkx2.2 in the Major Pathway of Betta-Cell Formation in the Pancreats, Development, 2000, pp. 5533-5540, vol. 127.
Sato et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, XP002699176, vol. 102, No. 20.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Scullica, et al., Diagnosis and Classification of Macular Degenerations: an Approach Based on Retinal Function Testing, Documenta Ophthalmologica, 2001, pp. 237-250, vol. 102.
Seaberg et al., Clonal identification of multipotent precursors from adult~mouse pancreas that generate neural and pancreatic lineages, Nature Biotechnology, Sep. 2004, 1115-1124, 22, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.

Shackleton, et al., Generation of a Functional Mammary Gland from a Single Stem Cell, Nature, Jan. 5, 2006, pp. 84-88, XP002567665, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Shim, et al., Directed Differentiation of Human Embryonic Stem Cells Towards a Pancreatic Cell Fate, Diabetologia, 2007, pp. 1228-1238, vol. 50.
Schindler et al., A synthetic nanofibrillar matrix promotes in vivo-like organization and morphogenesis for cells in culture, Biomaterials, Apr. 18, 2005, 5624-5631, 26, Elsevier.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, 61-69, 15, Mary Ann Liebert, Inc.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.

(56) References Cited

OTHER PUBLICATIONS

Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Current Topics in Developmental Biology, 1998, 133-154, 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 8770886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.

Vacanti, et al., Selective Cell Transplantation Using Bioabsorbable Artificial Polymers as Matrices, Journal of Pediactric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Choice of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Vacuum Cell Seeding: a New Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structures of Anthraquinones with their Effects on the Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.

(56) References Cited

OTHER PUBLICATIONS

Xu et al., Immortalized Fibroblast-Like Cells Derived from Human Embryonic Stem Cells Support Undifferentiated Cell Growth, Stem Cells, 2004, 972-980, 22, AlphaMed Press.

Xu, et al., Basic FGF and Suppression of BMP Signalling Sustain Undifferentiated Proliferation of Human ES Cells, Nature Methods, 2005, pp. 185-189, vol. 2, Issue 3.

Xu, et al., Feeder-free Growth of Undifferentiated Human Embryonic Stem Cells, Nature Biotechnology, 2001, pp. 971-974, vol. 19.

Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.

Yang, et al., Survival of Pancreatic Islet Xenografts in NOD Mice with the Theracyte Device, Transplantation Proceedings, 2002, pp. 3349-3350, vol. 34.

Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.

Yoneda, et al., The Rho Kinases I and II Regulate Different Aspects of Myosin II Acitivity, The Journal of Cell Biology, 2005, pp. 443-445, vol. 170, No. 3.

Young, et al., Three-Dimensional Culture of Human Uterine Smooth Muscle Nyocytes on a Resorbably Scaffolding, Tissue Engineering, 2003, pp. 451-459, vol. 9, No. 3.

Yu, et al., Induced Pluripotent Stem Cell Lines Derived from Human Somatic Cells, Science, Dec. 21, 2007, pp. 1917-1920, vol. 318.

Yu, et al., Isolation of a Novel Population of Multipotent Adult Stem Cells from Human Hair Follicles, American Journal of Pathology, Jun. 6, 2006, pp. 1879-1888, vol. 168, No. 6.

Zembower, et al., Peptide Boronic Acids Versatile Synthetic Ligands for Affinity Chromatography of Serine Proteinases, International Journal Peptide Protein, 1996, pp. 405-413, vol. 47.

Zhang et al., MafA Is a Key Regulator of Glucose-Stimulated Insulin Secretion, Molecular and Cellular Biology, Jun. 2005, 4969-4976, 25-12, American Society for Microbiology.

Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.

Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127 (with English Abstract).

Zhang et al, Highly Efficient Differentiation of Human ES Cells and iPS Cells into Mature Pancreatic Insulin-Producing Cells, Cell Research, 2009, pp. 429-438, vol. 19, Issue 14.

Zhao et al, The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.

Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.

Zorn, et al., Vertebrate Endoderm Development and Organ Formation, Annual Review Cell Development Biology, 2009, pp. 221-251, vol. 25.

Zubaty, et al., Transplantation of Mesenchymal Stem Cells into RCS Rats for Retinal Repair, Investigative Ophthalmology and Visual Science, 2005, pp. 4160-B518, vol. 46, Supplement S.

Sneddon, et al., Self-Renewal of Embryonic-Stem-Cell-Derived Progenitors by Organ-Matched Mesenchyme, Nature, Nov. 29, 2012, pp. 765-770, vol. 491.

International Search Report and Written Opinion for PCT/US2013/075939.

Ali, et al., Exploitation of Protein Kinase C: A Useful Target for Cancer Therapy, Cancer Treatment Reviews, 2009, pp. 1-8, vol. 35.

Amit, et al., Dynamic Suspension Culture for Scalable Expansion of Undifferentiated Human Pluripotent Stem Cells, Nature Protocols, Apr. 7, 2011, pp. 572-579, vol. 6, No. 5.

Baertschiger, et al., Mesenchymal Stem Cells Derived From Human Exocrine Pancrea Express Transcription Factors Implicated in Beta-Cell Development, Pancreas, 2008, pp. 75-84, vol. 37, No. 1.

Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.

Best, et al., Embryonic Stem Cells to Beta-Cells by Understanding Pancreas Development, Molecular and Cellular Endorinology, 2008, pp. 86-94, vol. 288.

Bo, et al., Research Progress of Pancreatic Islet Development and Pancreatic Stem Cells, Journal of Clinical Surgery, 2009, pp. 208-210, vol. 17, No. 3.

Brevini et al., Embryonic Stem Cells in Domestic Animals, Theriogenology, 2010, pp. 544-550, vol. 74.

Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.

Chetty, et al., A Simple Tool to Improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.

Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.

Eguizabal, et al., Embryonic Stem Cells/Induced Pluriptent Stem Complete Meiosis from Human Induced Pluripotent Stem Cells, Stem Cells, 2011, pp. 1186-1195, vol. 29.

Florio, et al., Activin A Stimulates Insulin Secretion in Cultured Human Pancreatic Islets, J. Endocrinol. Invest., 2000, pp. 231-234, vol. 23.

Foster, et al., Differentiation of Transplanted Microencapsulated Fetal Pancreatic Cells, Experimental Transplantation, Jun. 15, 2007, pp. 1440-1448, vol. 83, No. 11.

Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.

Gibco, Solutions for Life Science Research and Drug Discovery, Catalogue Cell Culture Products, 2004-2005, pp. 1-4E, 281406 26 5 27.

Gordon Weir, Do stem cells hold the key to creation of a cure for diabetes?, Diabetes Voice, 2008, pp. 29-31, Edition 53, No. 2.

Gregg Duester, Retionoic Acid Synthesis and Signaling During Early Organogenesis, Cell, 2008, pp. 921-931, vol. 134.

Hainsworth, et al., Retinal Capillar Basement Membrane Thickening in a Porcine Model of Diabetes Mellitus, Comp Med, 2002, pp. 523-529, vol. 52.

Harmon, et al., GDF11 Modulates NGN3+ Islet Progenitor Cell Number and Promotes B-Cell Differentiation in Pancreas Development, Development, 2004, pp. 6163-6174, vol. 131.

Hay, et al., Highly Ethicent Differentiation of hESCs to Functional Hepatic Endoderm Requires ActivinA and Wnt3a Signaling, PNAS, 2008, pp. 12301-12306, vol. 105, No. 34.

Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.

Jiang, et al., In Vitro Derivation of Functional Insulin-Producing Cells from Human Embryonic Stem Cells, Cell Research, 2007, pp. 333-344, vol. 17.

Karvonen, et al., Incidene of Childhood Type 1 Diabetes Worldwide, Diabetes Care, 2000, pp. 1516-1526, vol. 23, No. 10.

(56) References Cited

OTHER PUBLICATIONS

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.
Larsen, et al., Use of the Gootingen Minipig as a Model of Diabetes, with Special Focus on Type 1 Diabetes Research, ILAR Journal, 2004, pp. 303-313, vol. 45, No. 3.
Lee, et al., PKC-Inhibitors Sustain Self-Renewal of Mouse Embryonic Stem Cells Under Hypoxia in Vitro, Experimental and Molecular Medicine, Apr. 2010, pp. 294-301, vol. 43, No. 4.
Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.
Ludwig, et al., Defined Culture Media for Human Embryonic Stem Cells, Embryonic Stem Cells, 2007, pp. 1-16, Springer.
Mathis, et al., B-Cell Death During Progression to Diabetes, Nature, 2001, pp. 792-798, vol. 414.
Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Munoz et al, Conventional Pluripotency Markers are Unspecific for Bovine Embryonic-Derived Cell-Lines, Theriogenology, 2008, pp. 1159-1164, vol. 69.
Nie, et al., Scalable Passaging of Adherent Human Pluripotent Stem Cells, PLOS One, 2014, pp. 1-9, vol. 9, Issue 1.
Nostro, et al., Generation of Beta Cells from Human Pluripotent Stem Cells: Potential for Regenerative Medicine, Seminars in Cell & Developmental Biology, 2012, pp. 701-710, vol. 23.
Ouziel-Yahalom, et al., Expansion and Redifferentiation of Adult Human Pancreatic islet Cells, Biochemical and Biophysical Research Communications, 2006, pp. 291-298, vol. 341.
Paris, et al, Equine Embryos and Embryonic Stem Cells: Defining Reliable Markers of Pluripotency, Theriogenology, 2010, pp. 516-524, vol. 74.
Park, et al., Effects of Activin a on Pancreatic Ductal Cells in Streptozotocin-Inducted Diabetic Rats, Experimental Transplantation, 2007, pp. 925-930, vol. 83.
Perrier, et al., Derivation of Midbrain Dopamine Neurons from Human Embryonic Stem Cells, PNAS, Aug. 24, 2004, pp. 12543-12548, vol. 101, No. 34.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Ramiya, et al., Reversal of Insulin-Dependent Diabetes Using Islets Generated in vitro from Pancreatic Stem Cells, Nature Medicine, 2000, pp. 278-281, vol. 6.
Rezania, e al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Rezania, et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.
Rezania, et al., Reversal of Diabetes with Insulin-Producing Cells Derived in vitro from Human Pluripotent Stem Cells, Nature Biotechnology, 2014, pp. 1121-1133, vol. 32, No. 11.
Richards, et al., Development of Defined Media for the Serum-Free Expansion of Primary Keratinocytes and Human Embryonic Stem Cells, Tissue Engineering, 2008, pp. 221-232, vol. 14, No. 3.
Ross, et al., Cytochrome P450s in the Regulation of Cellular Retinoic Acid Metabolism, Annu. Rev. Nutr., 2011, pp. 65-87, vol. 31.
Rowley, et al., Meeting Lot-Size Challenges of Manufacturing Adherent Cells for Therapy, Cell Therapies Manufacturing, 2012, pp. 16-22, vol. 10, No. 3.
Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Schulz, et al., A Scalable System for Production of Functional Pancreatic Progenitors from Human Embryonic Stem Cells, PLOS One, 2012, pp. 1-17, vol. 7, Issue 5.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Soria, et al., From Stem Cells to Beta Cells: New Strategies in Cell Therapy of Diabetes Mellitus, Diabetologia, 2001, pp. 407-415, vol. 44.
Stacpoole, et al., Efficient Derivation of Neural Precursor Cells, Spinal Motor Neurons and Midbrain Dopaminergic Neurons from human ES Cells at 3% Oxygen, Nat Protoc., 2012, pp. 1-26, vol. 6, Issue 8.
Stafford, et al., Retinoids Signal Directly to Zebrafish Endoderm to Specify Insuilin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Tsuchida, et al., Activin Isoforms Signal Through Type I Receptor Serine/Threonin Kinase ALK7, Molecular and Cellular Endocrinology, 2004, pp. 59-65, vol. 22.
Vieira, et al., Modulation of Neuronal Stem Cell Differentiation by Hypoxia and Reactive Oxygen Species, Progress in Neurobiology, 2011, pp. 444-455, vol. 93.
Wachs, et al., High Efficacy of Clonal Growth and Expansion of Adult Neural Stem Cells, Laboratory Investigation, 2003, pp. 949-962, vol. 83, No. 7.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Yang, et al., Evaluation of Humam MSCs Cell Cycle, Viability and Differentiation in Micromass Culture, Biorheology, 2006, p. 489-496, vol. 43 (English Abstract Only).
Zalzman, et al., Differentiation of Human Liver-Derived, Insulin-Producing Cells Toward the B-Cell Phenotype, Diabetes, 2005, pp. 2568-2575, vol. 54.
Zuscik, et al., Regulation of Chondrogenesis and Chondrocyte Differentiation by Stress, J Clin Invest, 2008, pp. 129-438, vol. 118, Issue 2.
Cohick, et al., The Insulin-Like Growth Factors, Annual Reviews Physiol, 1993, pp. 131-153, vol. 55, Annual Reviews Inc.

(56) References Cited

OTHER PUBLICATIONS

Hebrok, et al., Notochord repression of endodermal Sonic hedgehog permits pancreas development, Genes & Development, Jun. 1, 1998, pp. 1705-1713, vol. 12, Issue 11, Cold Spring Harbor Laboratory Press.

Jaenisch, et al., Stem Cells, the Molecular Circuitry of Pluripotency and Nuclear Reprogramming, cell, Feb. 22, 2008, pp. 567-582, vol. 132, Elsevier Inc.

Klajnert, et al., Fluorescence studies on PAMAM dendrimers interactions with bovine serum albumin, Bioelectrochemistry, 2002, pp. 33-35, vol. 55.

Kubota,et al., Growth factors essential for self-renewal and expansion of mouse spermatogonial stem cells, cell Biology, Nov. 23, 2004, pp. 16489-16494, vol. 101, Issue 47.

Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34, Issue 4.

Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182, Issue 2.

Balajthy, et al., Molecular therapies, 2011, pp. 1-6.

Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.

Brimble, S., et al., The Cell Surface Glycosphingolipis SSEA-3 and SSEA-4 Are Not Essential for Human ESC Pluripotency, Stem Cells, Jan. 2007, pp. 54-62, vol. 25.

Buta, et al., Reconsidering pluripotency tests: Do we still need teratoma assays?, Stem Cell Research, Mar. 26, 2013, pp. 552-562, vol. 11.

Chen, et al., Retinoic acid signaling is essential for pancreas development and promotes endocrine at the expense of exocrine cell differentiation in Xenopus, Developmental Biology, May 4, 2004, pp. 144-160, vol. 271.

Chen, et al., Scalable GMP Compliant Suspension Culture System for Human ES Cells, Stem Cell Research, 2012, pp. 388-402, vol. 8.

Cirulli, et al., Netrins: beyond the brain, Molecular Cell Biology, Apr. 2007, pp. 296-306, vol. 8.

Condic, et al., Alternative Sources of Pluripotent Stem Cells: Ethical and Scientific Issues Revisited, Stem Cells and Development, 2010, pp. 1121-1129, vol. 19, Issue 8, Mary Ann Liebert, Inc.

Daheron, et al., LIF/STAT3 Signaling Fails to Maintain Self-Renewal of Human Embryonic Stem Cells, Stem Cells, 2004, pp. 770-778, vol. 22.

Findikli, et al., Establishment and characterization of new human embryonic stem cell lines, Reproductive BioMedicine Online, Mar. 3, 2005, pp. 617-627, vol. 10, Issue 5.

Furue, et al., Heparin promotes the growth of human embryonic stem cells in a defined serum-free medium, PNAS, Sep. 9, 2008, pp. 13409-13414, vol. 105, Issue 36.

Gibco, Insulin-Transferin-Selenium-X 100X, Invitrogen Cell Culture, Apr. 2005, pp. 1, Form No. 3032.

Gomez, et al., Derivation of cat embryonic stem-like cells from in vitro-produced blastocysts on homologous and heterologous feeder cells, Theriogenology, May 11, 2010, pp. 498-515, vol. 74.

Gordon Weir., Do stem cells hold the key to a future cure for diabetes?, DiabetesVoice, Jun. 2008, pp. 29-31, vol. 53, Issue 2.

Guillemain, et al., Glucose is Necessary for Embryonic Pancreatic Endocrine Cell Differentiation*, The Journal of Biological Chemistry, May 18, 2007, pp. 15228-15237, vol. 282, Issue 20.

Guo, et al., Efficient differentiation of insulin-producing cells from skin-derived stem cells, Cell Proliferation, 2009, pp. 49-62, vol. 42.

Hiemisch, H., et al., Transcriptional Regulation in Endoderm Development: Characterization of an Enhancer controlling Hnf3g Expression by Transgenesis and Targeted Mutagenesis, The EMBO Journal, 1997, pp. 3995-4006, vol. 16.

Jean, et al., Pluripotent genes in avian stem cells, Development Growth & Differentiation, 2013, pp. 41-51, vol. 55.

Kang, et al., Plasma treatment of textiles—Synthetic Polymer-Based Textiles, AATCC Review, 2004, pp. 29-33.

Kehoe, et al., Scalable Stirred-Suspension Bioreactor Culture of Human Pluripotent Stem Cells, Tissue Eng Part A, 2010, pp. 405-421, vol. 16, Issue 2.

Kim, et al., Reprogrammed Pluripotent Stem Cells from Somatic Cells, International Journal of Stem Cells, 2011, pp. 1-8, vol. 4, Issue 1.

King, et al., Bioreactor development for stem cell expansion and controlled differentiation, Current Opinion in Chemical Biology, Jul. 25, 2007, pp. 394-398, vol. 11, Elsevier Ltd.

Kunisada, et al., Small molecules induce efficient differentiation into insulin-producing cells from human induced pluripotent stem cells, Stem Cell Research, Oct. 11, 2011, pp. 274-284, vol. 8.

Lavial, etal., Chicken Embryonic Stem Cells as a Non-Mammalian Embryonic Stem Cell Model, Development Growh Differentiation, Jan. 2010, pp. 101-114, vol. 52(1).

Lee, et al., Available human feeder cells for the maintenance of human embryonic stem cells, Reproduction, 2004, pp. 727-735, vol. 128.

Lin, C., et al., Coagulation Dysregulatin as a Barrier to Xenotransplantation in the Primate, Transplant Immunology, 2009, pp. 75-80, vol. 21.

Ludwig, et al., Defined, Feeder-Independent Medium for human Embryonic Stem Cell Culture, Current Protocols in Stem Cell Biology, 2007, pp. 1C.2.1-1C.2.16, vol. 1, John Wiley & Sons, Inc.

Maimets, et al., Activation of p53 by nutlin leads to rapid differentiation of human embryonic stem cells, Oncogene, Jun. 2, 2008, pp. 5277-5287, vol. 27.

Maria-Jesus Obregon, Thyroid hormone and adipocyte differentiation, Thyroid, 2008, pp. 185-195, vol. 18, Issue 2.

McMahon, et al., Noggin-mediated antagonsim of BMP signaling is required for growth and patterning of the neural tube and somite, Genes & Development, Mar. 16, 1998, pp. 1438-1452, vol. 12.

Misiti, et al., 3,5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204.

Nakase, et al., Myeliod Antigen, CD13, CD14, and/ or CD33 Expression Is Restricted to Certain Lymphiod Neoplasms, Hematopathology, Jun. 1996, pp. 761-768, vol. 105 Issue 6.

Narang, A., et al., Biological and Biomaterial Approaches for Improved Islet Transplantation, Pharmacological Review, Jun. 2006, pp. 194-243, vol. 58(2).

Nekrasov, et al., Induced pluripotent stem cells as a model for studying human diseases, Cellular Transplantology and Tissue Engineering, 2011, pp. 32-37, vol. 6, Issue 2 (English Abstract).

Olmer, et al., Long Term Expansion of Undifferentiated Human iPS and ES Cells in Suspension Culture Using Defined Medium, Stem Cell Research, 2010, pp. 51-64, vol. 5.

Osafune, et al., Marked differences in differentiation propensity among human embryonic stem cell lines, Nature Biotechnology, Feb. 17, 2008, pp. 313-315, vol. 26, Issue 3.

Ouziel-Yahalom, et al., Expansion and redifferentiation of adult human pancreatic islet cells, Biochemical and Biophysical Research Communications, Jan. 19, 2006, pp. 291-298, vol. 341.

Petitte, J., et al., Avian Pluripotent Stem Cells, Mechanisms of Development, 2004, pp. 1159-1168, vol. 121.

Ramiya, et al., Reversal of insulin-dependent diabetes using islets generated in vitro from pancreatic stem cells, Nature Medicine, Mar. 2000, pp. 278-282, vol. 6, Issue 3.

Rother, et al., Challenges facing islet transplantation for the treatment of type 1 diabetes mellitus, The Journal of Clinical Investigation, 2004, pp. 877-883, vol. 114, Issue 7.

Rowley, et al., Meeting Lot-size Challenges of Manufacturing Adherent Cells for Therapy, Bio Process International, Mar. 2012, pp. 16-22, vol. 10, Issue 3.

(56) References Cited

OTHER PUBLICATIONS

Sjoegren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118, Issue 20.
Suzuken., Differentiation of Multifunctional Stem Cells Using Human Feeder Cells, Research Papers of the Suzuken Memorial Foundation, 2007, pp. 193-197, vol. 2.
Thomson, Bioprocessing of Embryonic Stem Cells for Drug Disvoery, Trends in Biotechnology, 2007, pp. 224-230, vol. 25, No. 5.
Wang, et al., Scalable expansion of human induced pluripotent stem cells in the defined xeno-free E8 medium under adherent and suspension culture conditions, Stem Cell Research, Nov. 2013, pp. 1103-1116, vol. 11, Issue 3.
Yadlin, et al., Small-molecule inducers of insulin expression in pancreatic α-cells, PNAS, Aug. 24, 2010, pp. 15099-15104, vol. 107, Issue 34.
Yang JW, et al., Evaluation of human MSCs cell cycle, viability and differentiation in micromass culture, Biorheology, 2006, pp. 1-2, vol. 43, Issue (3-4).
Yim,et al., Proliferation and differentiation of human embryonic germ cell derivatives in bioactive polymeric fibrous scaffold, J.Biomater. Sci.Polymer Edn, Jan. 19, 2005, pp. 1193-1217, vol. 16, Issue 10.
Zhu, et al., A Small Molecule Primes Embryonic Stem Cells for Differentiation, Cell Stem Cell, May 8, 2009, pp. 416-426, vol. 4.
Zulewski, et al., Multipotentital Nestin-Positive Stem Cells Isolated From Adult Pancreatic Islets Differentiate Ex Vivo Into Pancreatic Endocrine, Exocrine, and Hepatic Phenotypes, Diabetes, 2001, pp. 521-533, vol. 50.
Blazhevich Kul'tivirovanie kletok. Kurs lektsij.—Mn.: BGU, (78 pages); pp. 56, 57, 59, with English translation (9 pages) (2004).
Cameron et al., "Improved development of human embryonic stem cell-derived embryoid bodies by stirred vessel cultivation," *Biotechnol Bioeng.* 94: 938-948 (2006).
Cimbaljuk et al. "Spinnoj mozg. Jelegija nadezhdy: monografija", *Novaja kniga*. 944 pages (p. 245) (2010). Relevance is based on English translation of Russian OA, No. 2018108851, dated Oct. 17, 2018.
Gerecht-Nir et al., "Bioreactor cultivation enhances the efficiency of human embryoid body (hEB) formation and differentiation," *Biotechnol Bioeng.* 86: 493-502 (2004).
Gilbert, "Developmental Biology," 3 volumes, the first volume: translation from English—M.: Mir, (228 pages): p. 187, with English translation (5 pages) (1993).
Kozhukharova I.V., "Novye linii ehmbrional'nykh stvolovykh kletok cheloveka S612 I S90," *Tsitologiya* 51: 551-558 (2009). (Relevance is based on the English translations of two Office Actions from Russian Application No. 2018108850 and Russian Application No. 2018108847, both attached).
Lian et al., "Directed cardiomyocyte differentiation from human pluripotent stem cells by modulating Wnt/β-catenin signaling under fully defined conditions," *Nat. Protoc.* 8: 162-175 (2013).
Menzorov "Embryonic Stem Cells of the Mouse and Human," *Vavilov J Genet Breed*. 17: 234-245(p. 237) with English translation (5 pages) (2013).
Rezania et al., "Reversal of diabetes with insulin-producing cells derived in vitro from human pluripotent stem cells," *Nature Biotechnology* 32(11): 1121-1133 (e-PUB Sep. 11, 2014).
Serafimidis et al., "Novel effectors of directed and Ngn3-mediated differentiation of mouse embryonic stem cells into endocrine pancreas progenitors," *Stem Cells* 26(1): 3-16 (e-PUB Oct. 11, 2007).
Stacpoole et al., "Efficient derivation of neural precursor cells, spinal motor neurons and midbrain dopaminergic neurons from human ES cells at 3% oxygen," *Nat Protoc.* 6: 1229-1240 (2012).
Stanford et al., "Sphingosine 1-phosphate S1P regulates glucose-stimulated insulin secretion in pancreatic beta cells," *J Biol. Chem.* 287: 13457-13464 (2012).
Nelson et al., "Therapeutic Potential of the Inhibition of the Retinoic Acid Hydroxylases CYP26A1 and CYP26B1 by Xenobiotics," *Curr Top Med Chem*. 13:1402-1428 (2013).
Serafimidis et al., "G Protein-Coupled Receptor Signaling and Sphingosine-1-Phosphate Play a Phylogenetically Conserved Role in Endocrine Pancreas Morphogenesis," *Mol Cell Biol.* 31:4442-4453 (2011).

\* cited by examiner

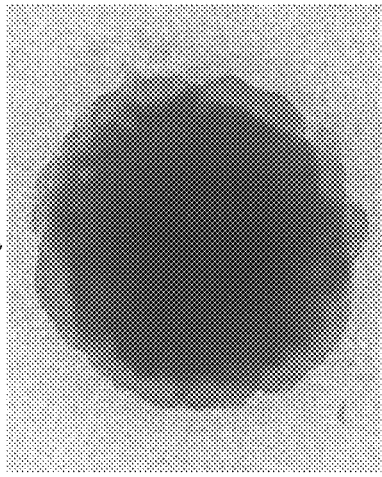
FIG. 1A Day 1
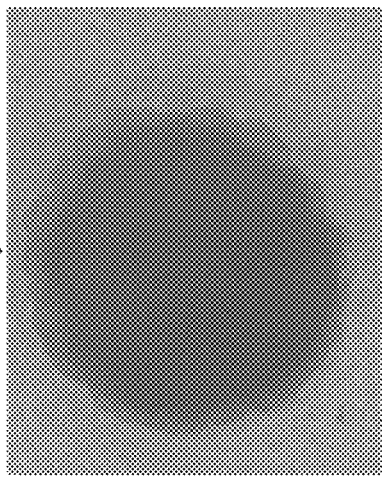
FIG. 1B Day 5
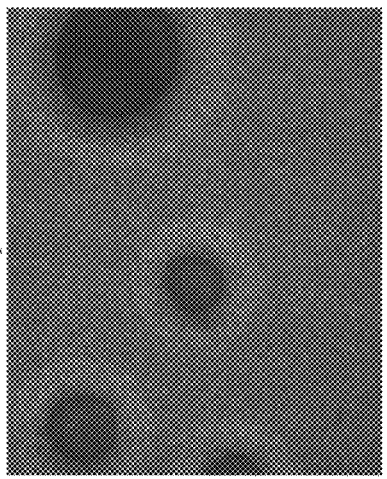
FIG. 1C Day 6
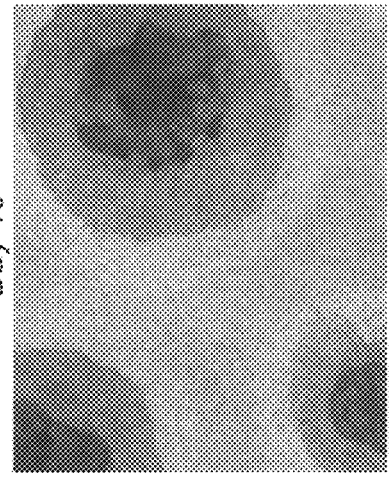
FIG. 1D Day 7
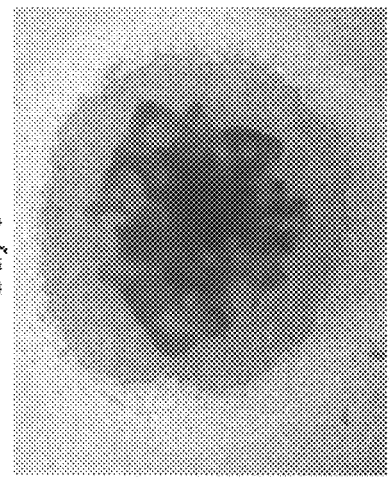
FIG. 1E Day 9
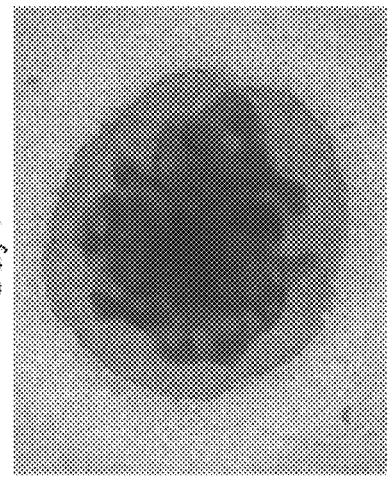
FIG. 1F Day 13

Day 16

Day 21

Hb9

Insulin

Insulin

Glucagon

DAPI

DAPI

Somatostatin

Insulin

Insulin

DAPI

NKX6.1

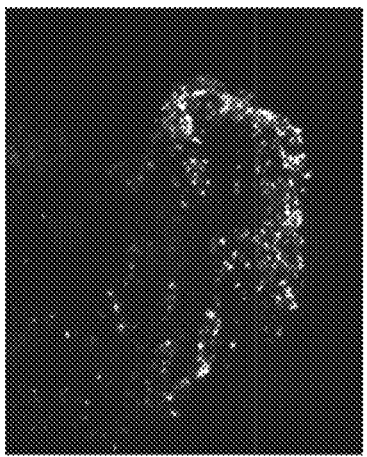
FIG. 3A Insulin
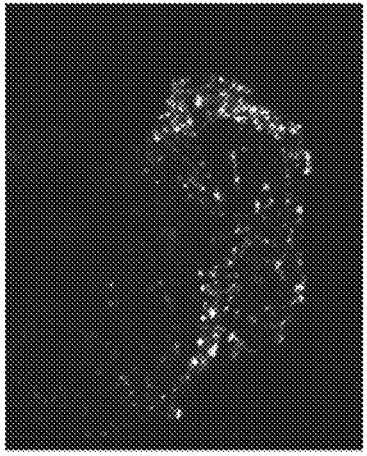
FIG. 3B Glucagon
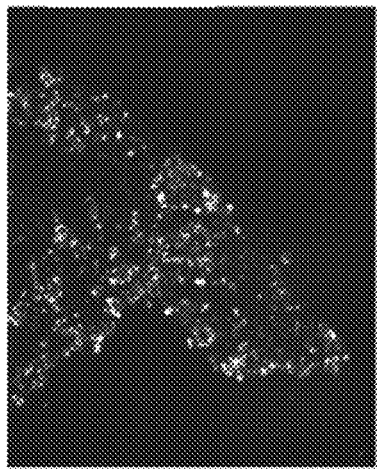
FIG. 3C Insulin
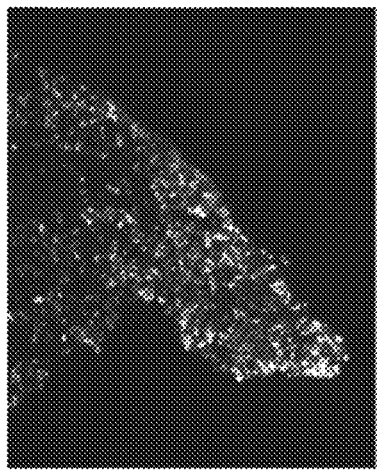
FIG. 3D Somatostatin Insulin

NKX6.1

Hb9

NKX6.1

Insulin

Glucagon

Insulin

Somatostatin

ABCC8

Chromogranin-A

PCSK1

PDX-1

NKX6.1

Pax4

ABCC8

Chromogranin-A

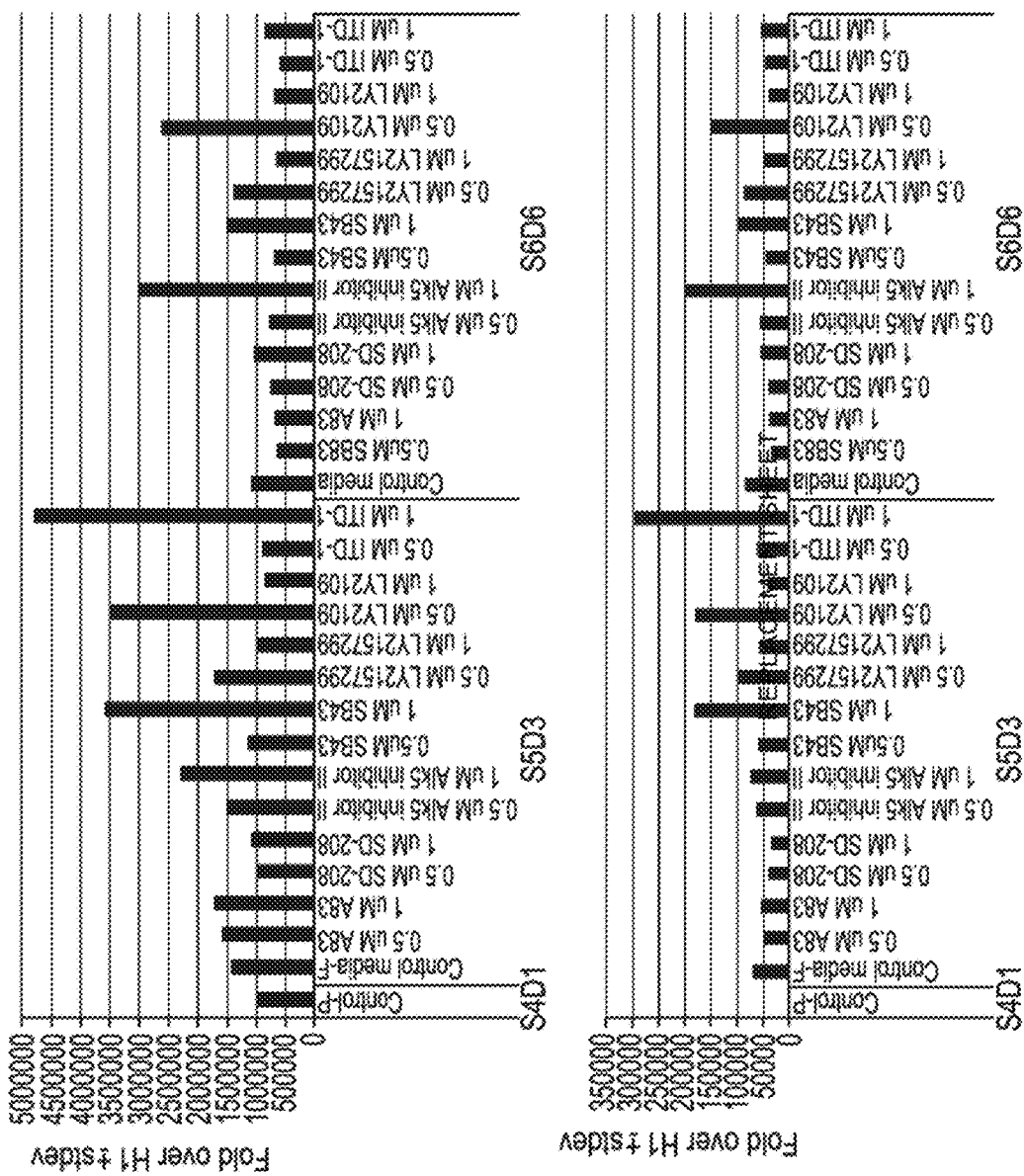
FIG. 8A PDX1
FIG. 8B NKX6.1

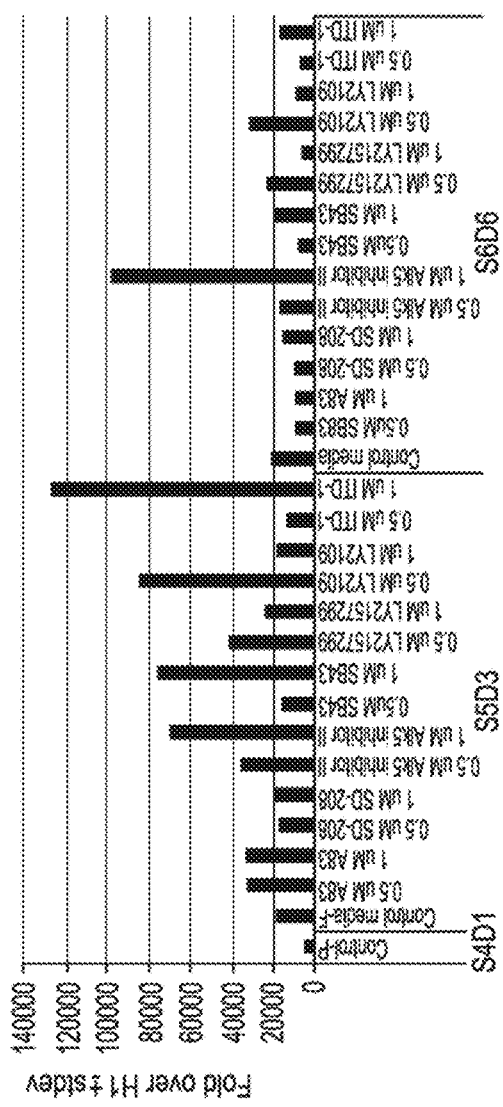
FIG. 8C
NGN3
FIG. 8D
ABCC8

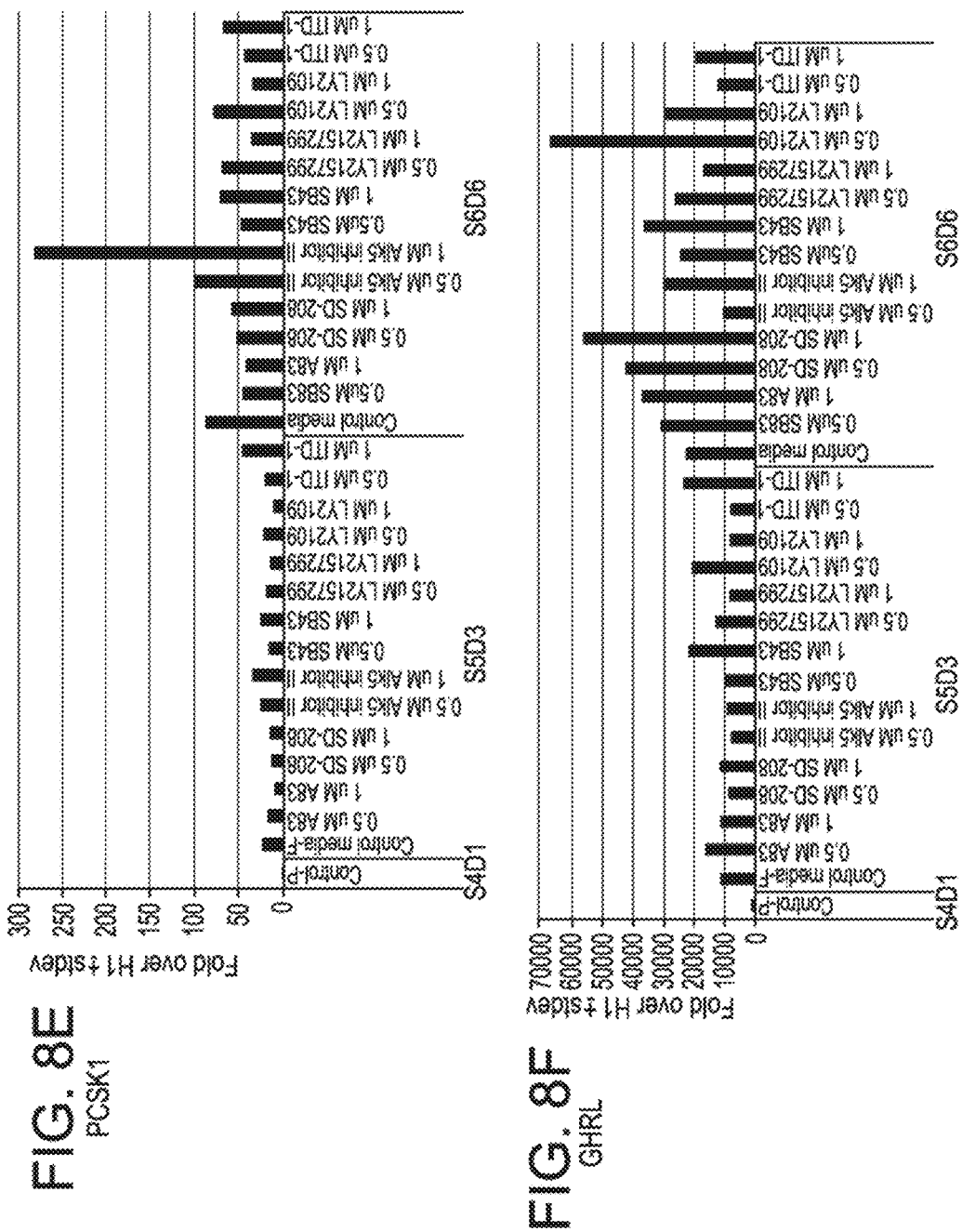

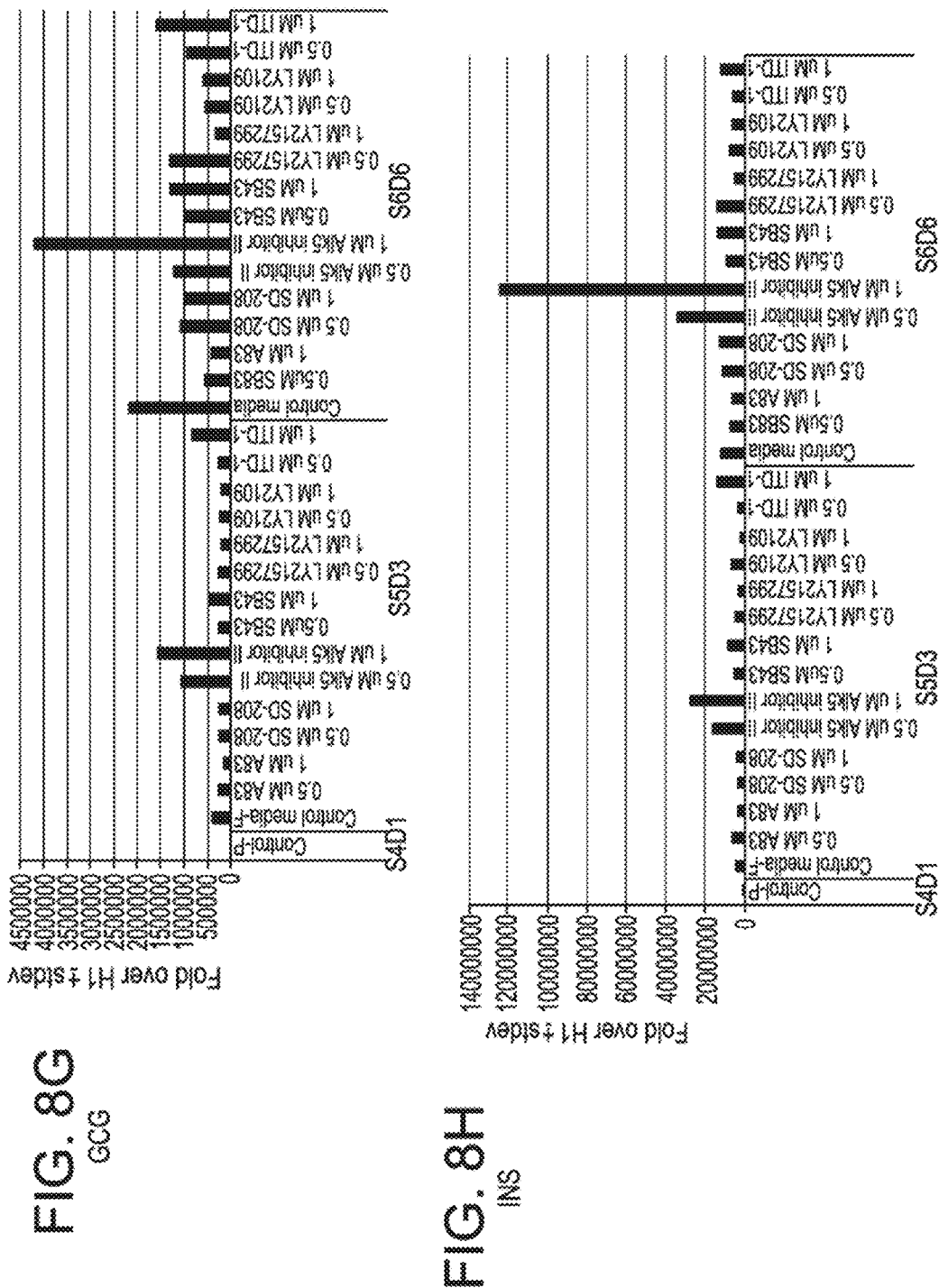
FIG. 8G GCG
FIG. 8H INS

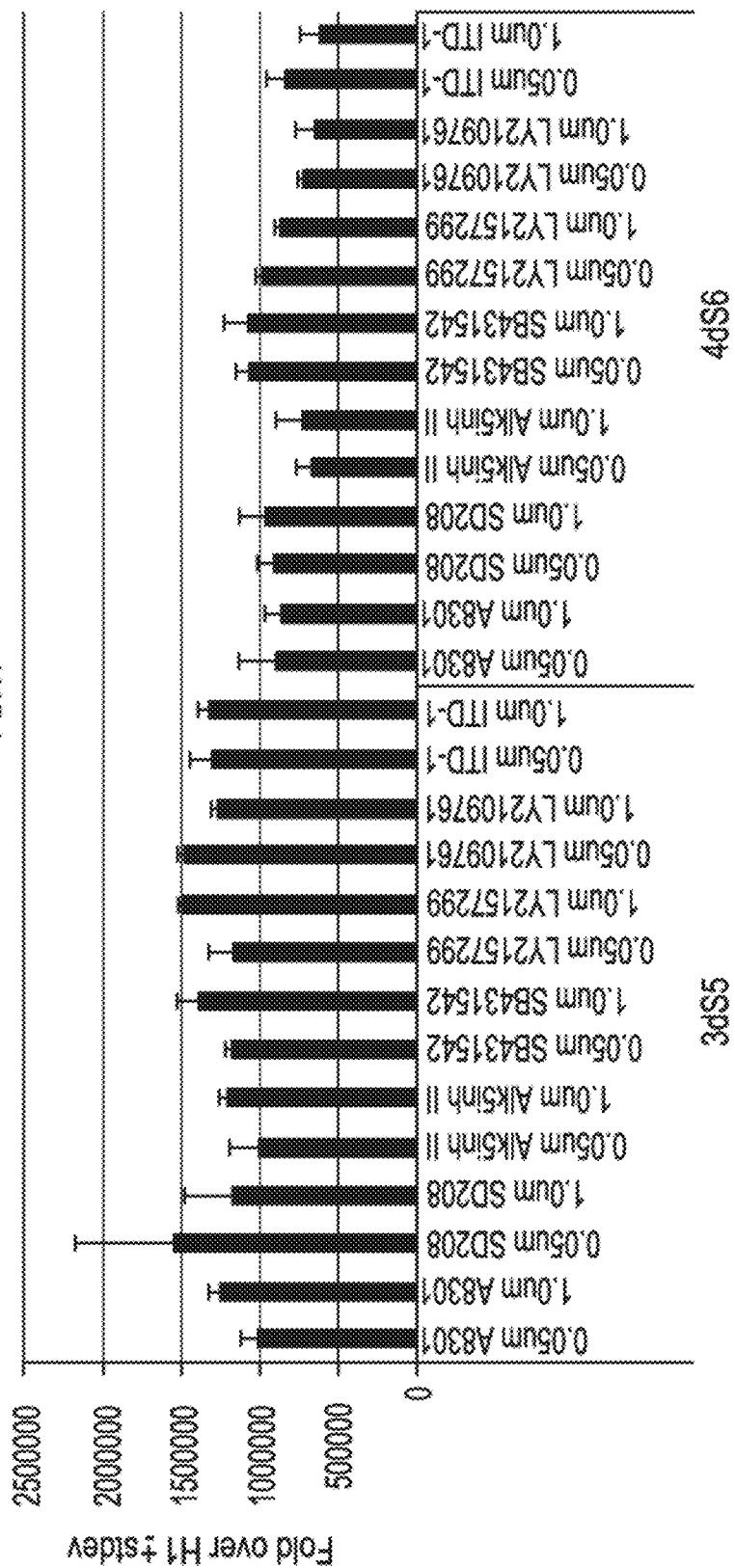

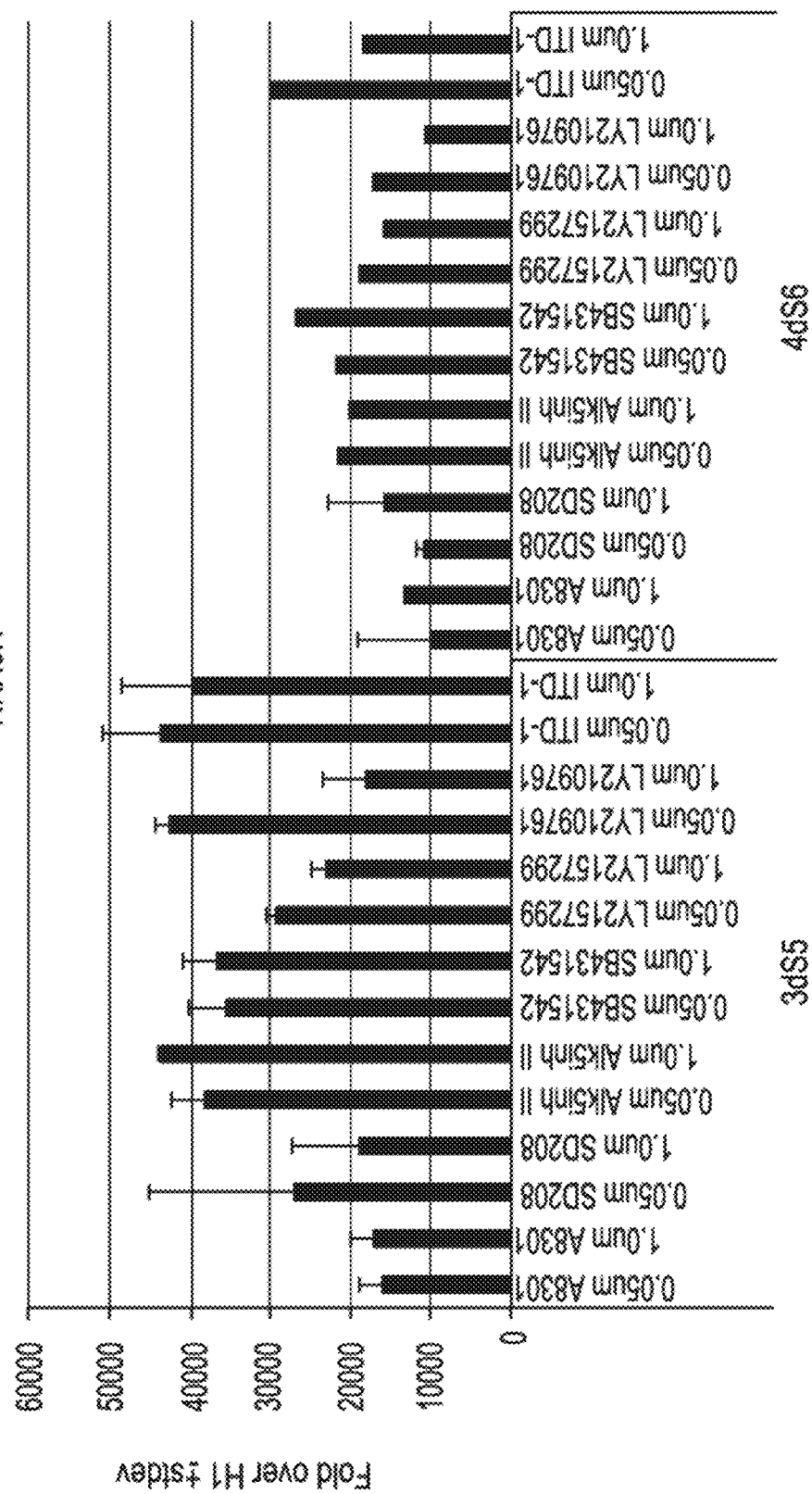

NGN3

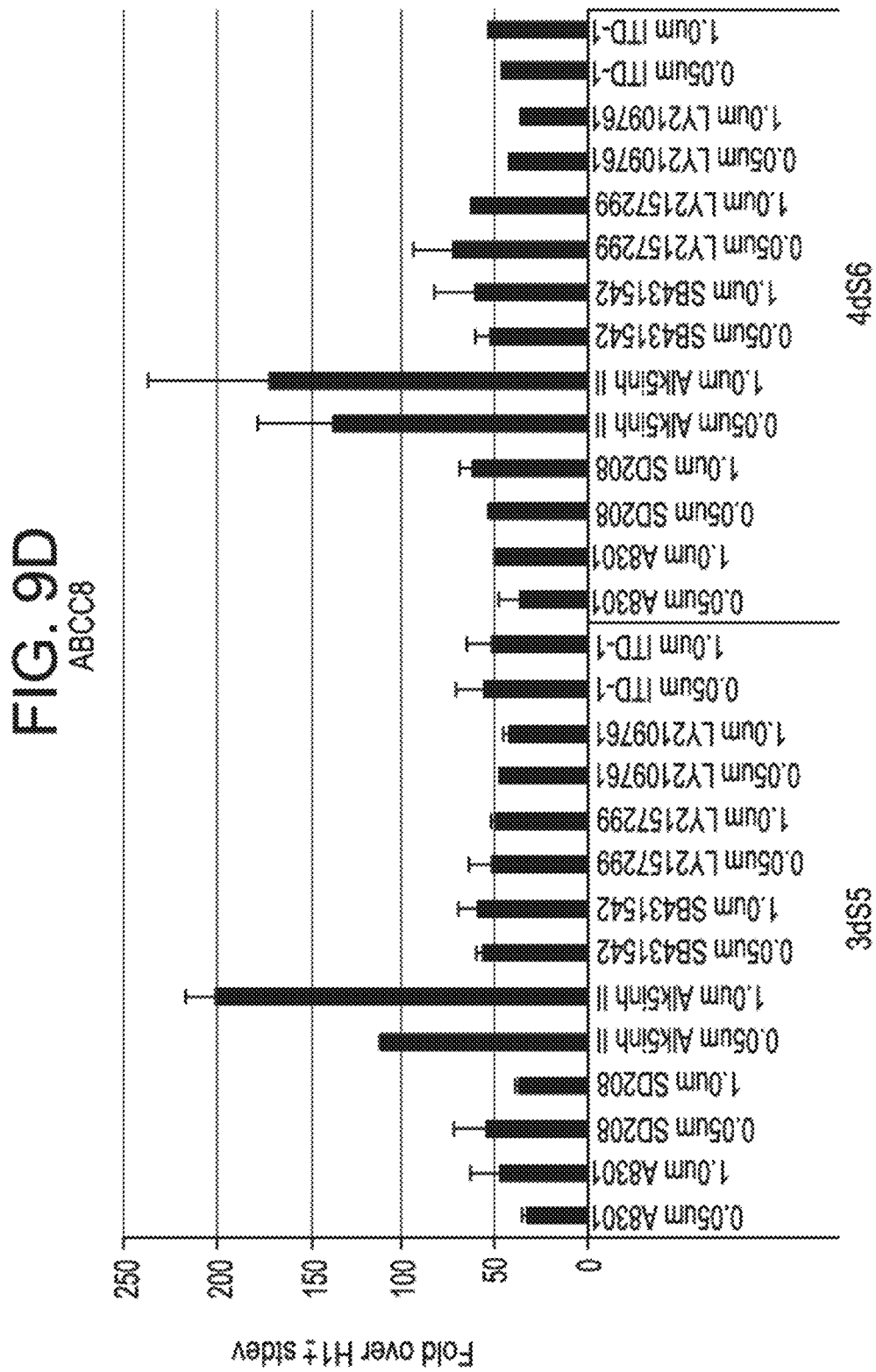

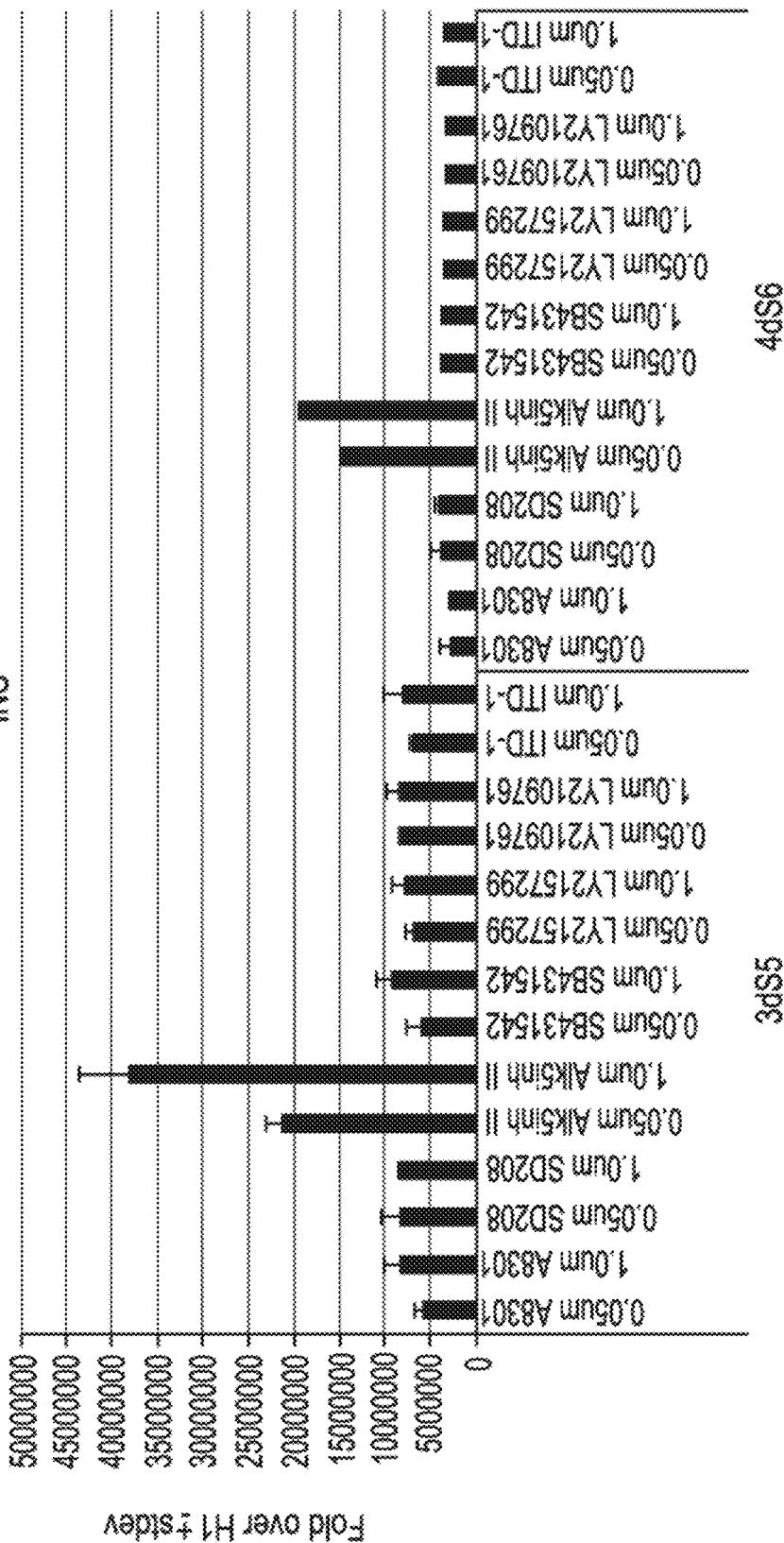

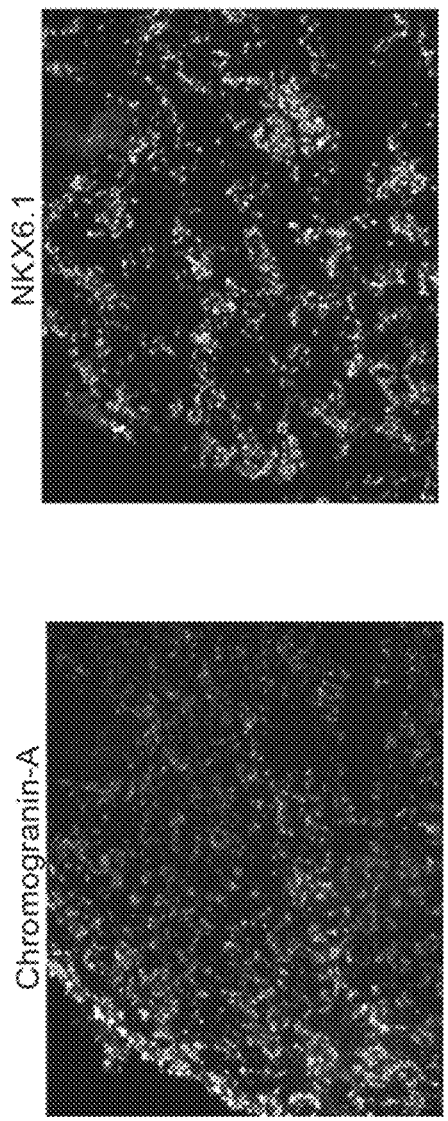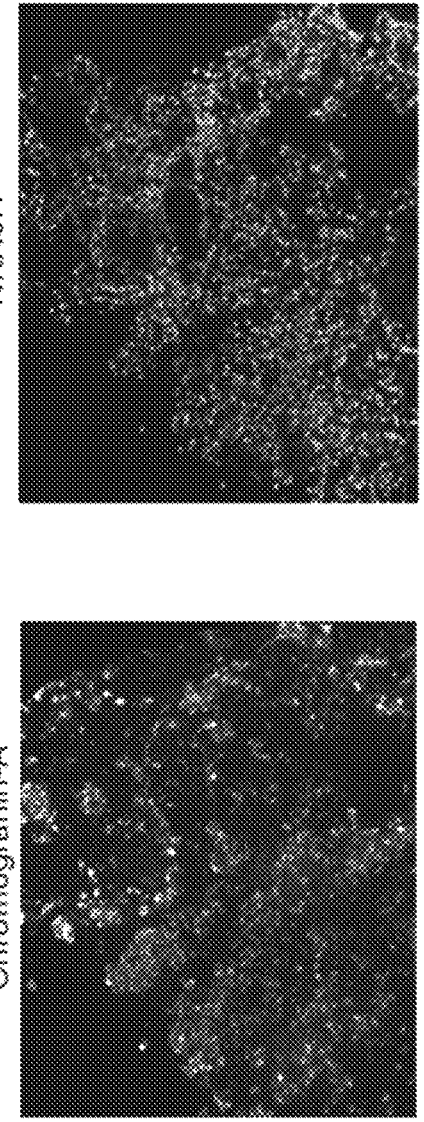

NGN3

NKX2.2

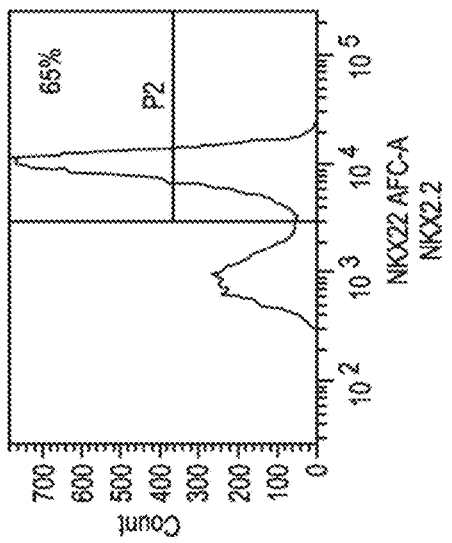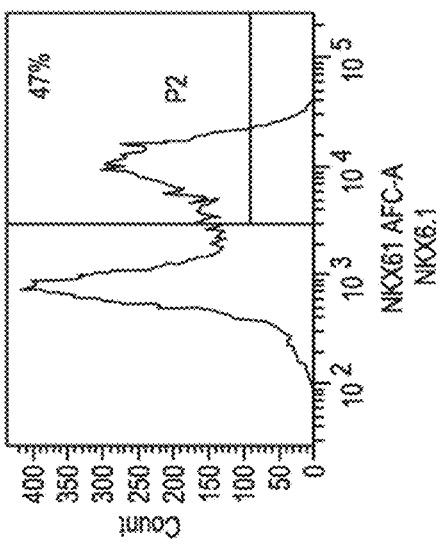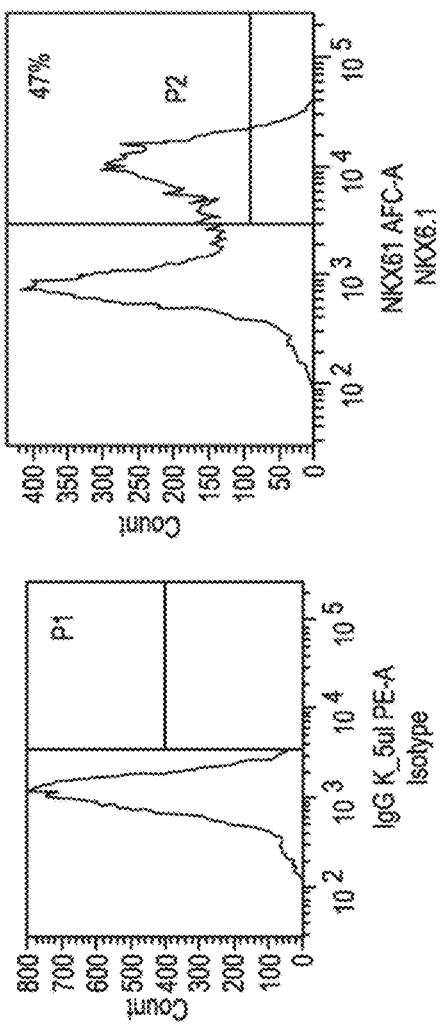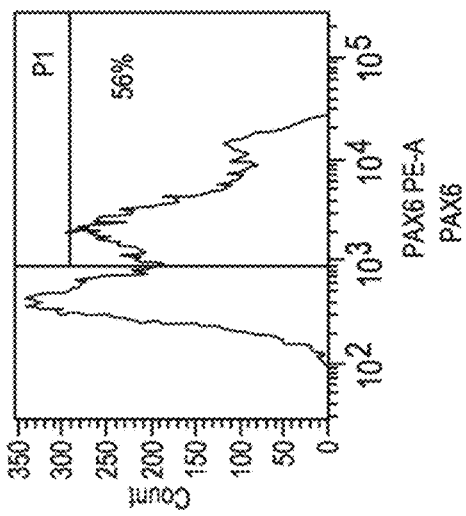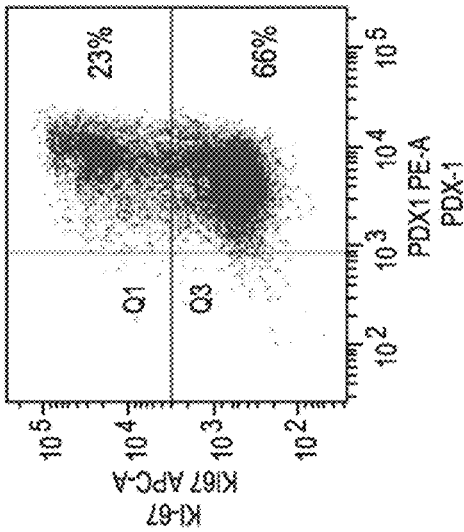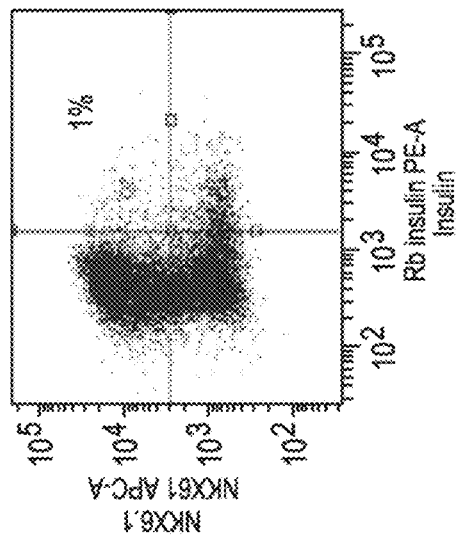

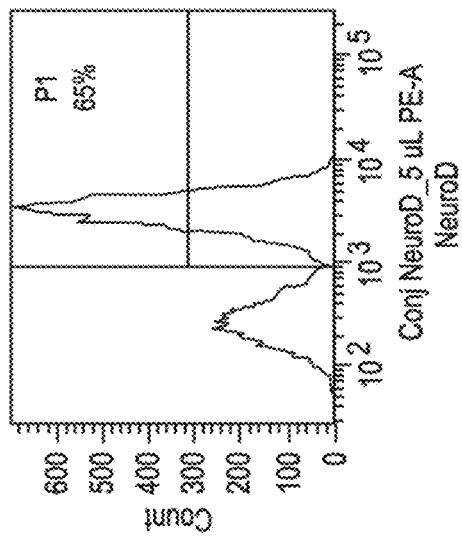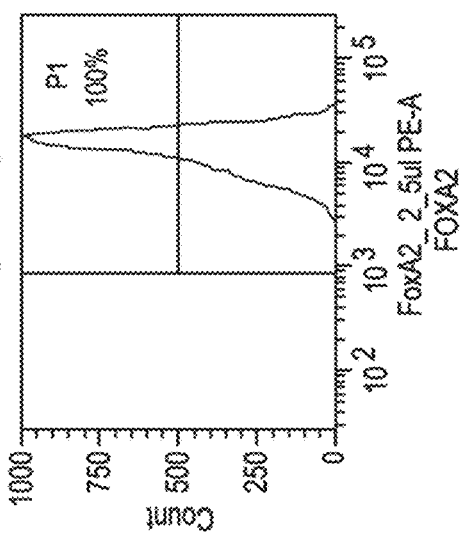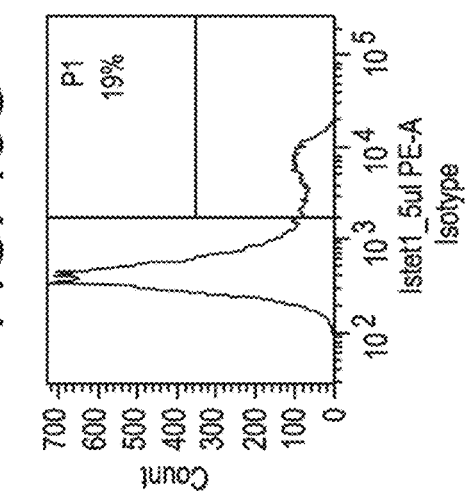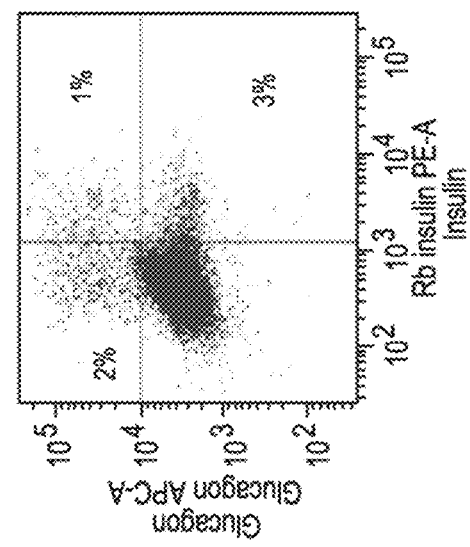

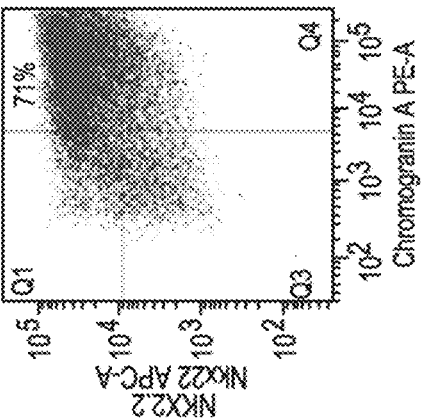
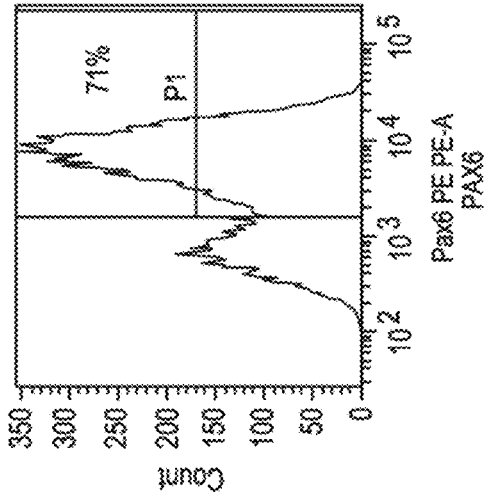
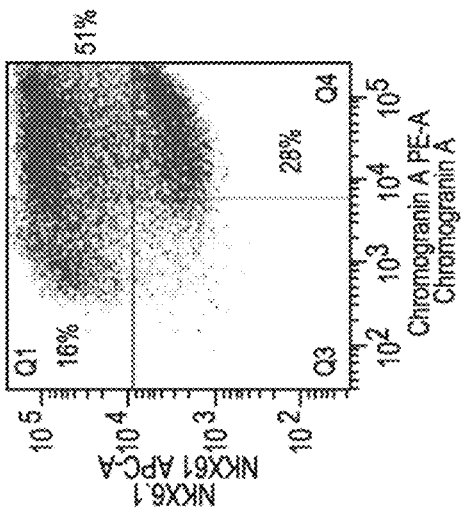
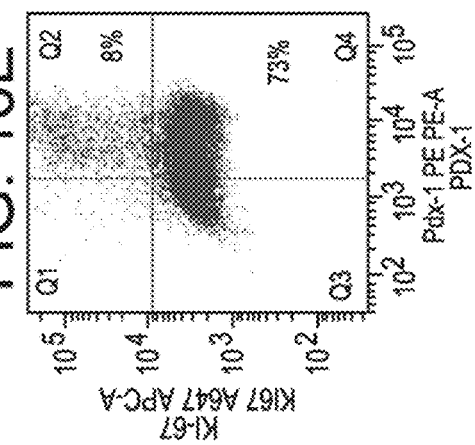
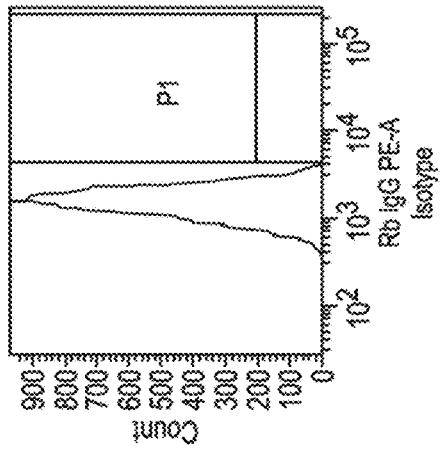
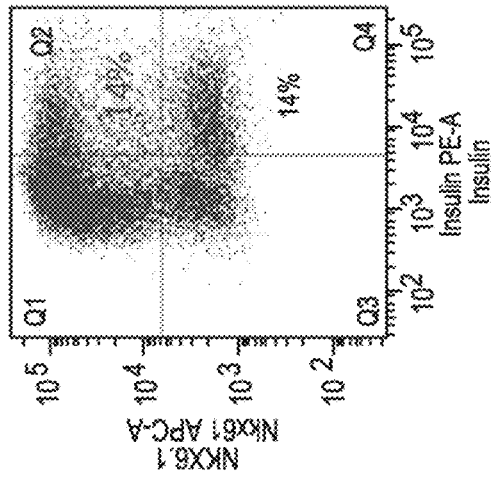

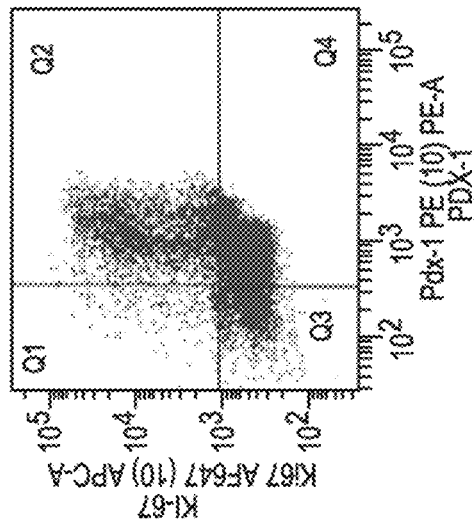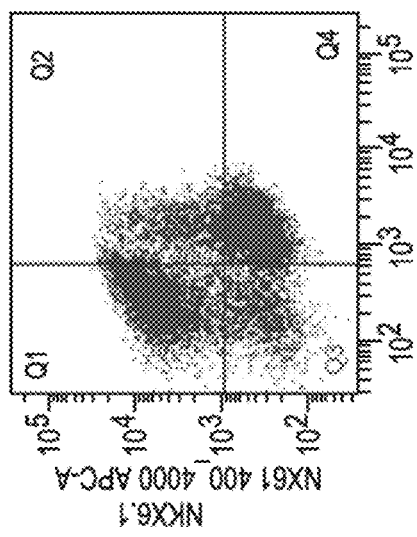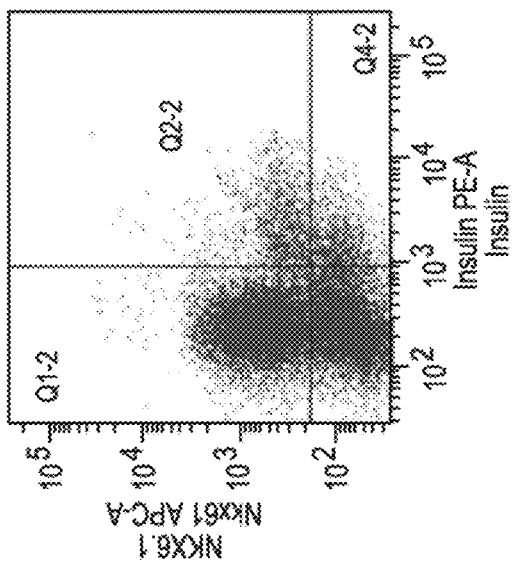

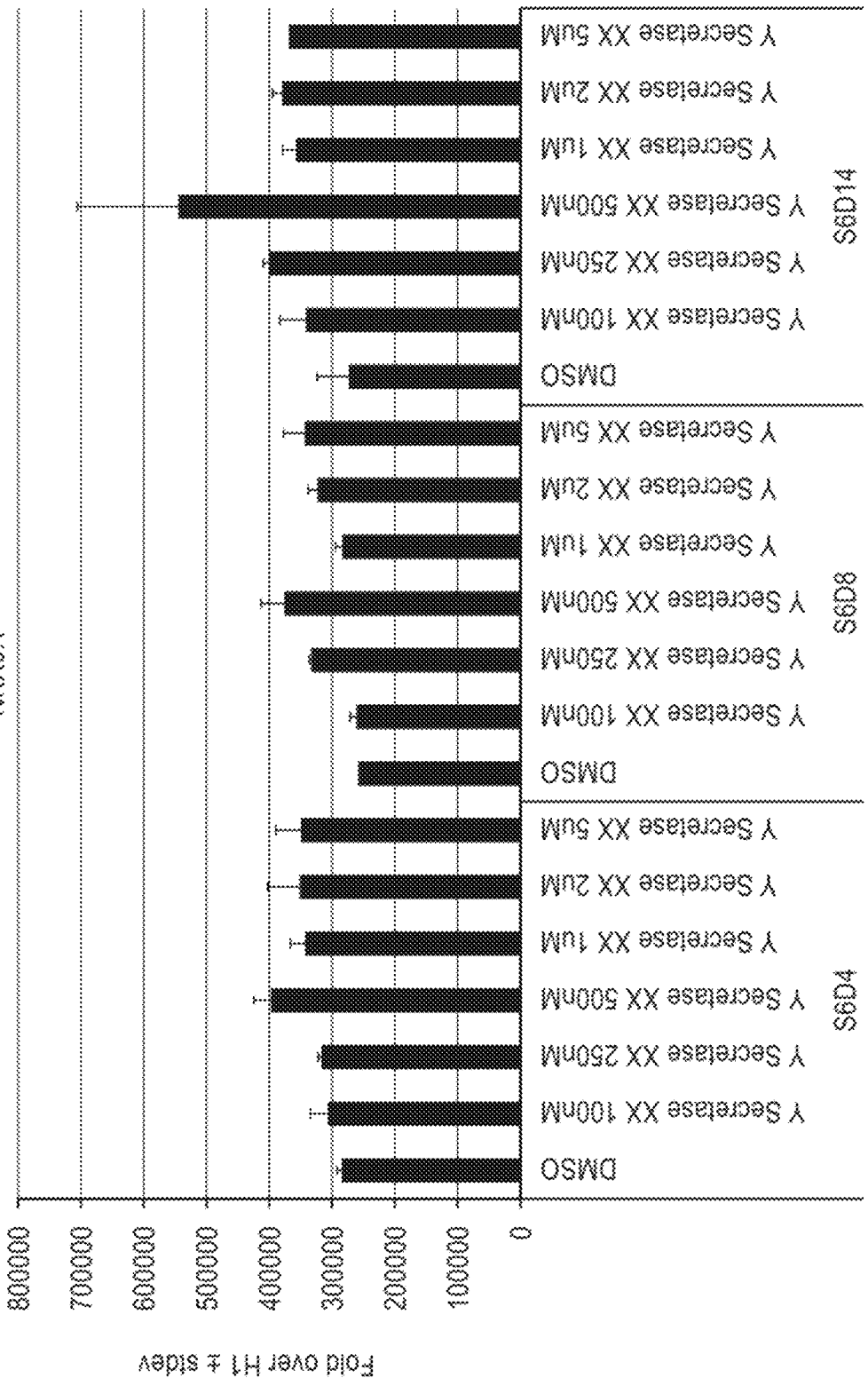

PDX1

NKX6.1

NGN3

ABCC8

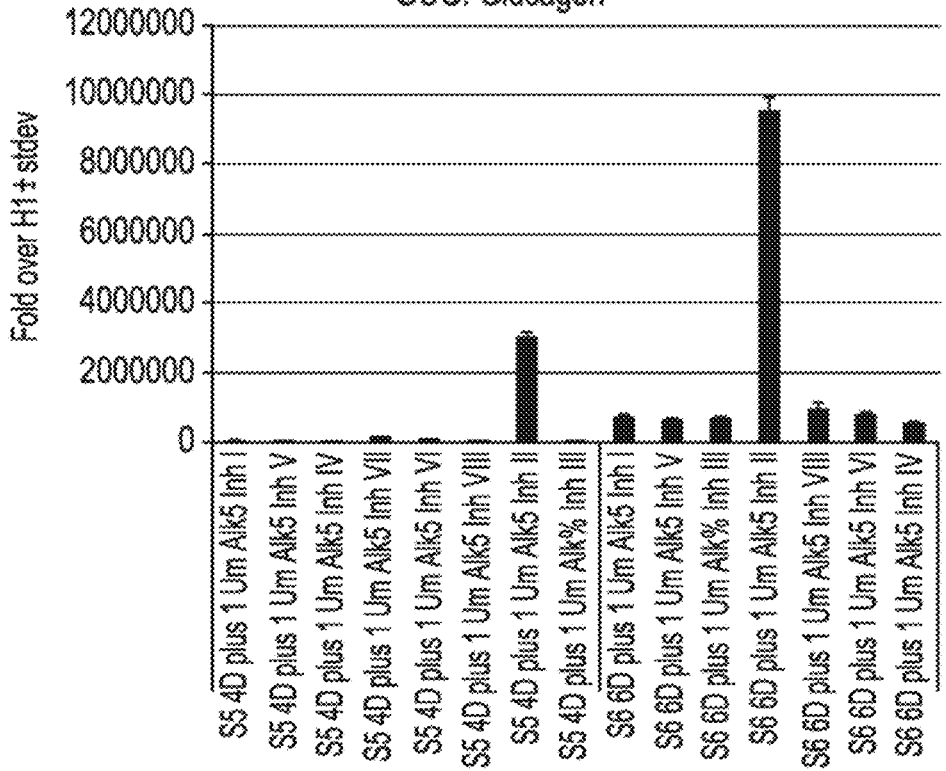
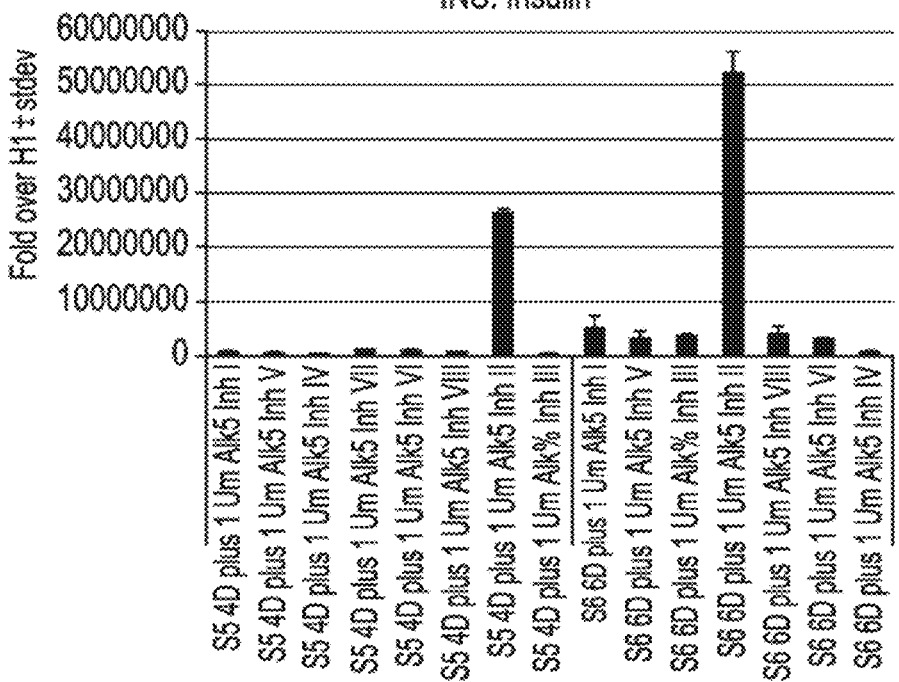

CULTURING OF HUMAN EMBRYONIC STEM CELLS AT THE AIR-LIQUID INTERFACE FOR DIFFERENTIATION INTO PANCREATIC ENDOCRINE CELLS

CROSS-REFERENCE TO RELATED APPLICATIONS

This application claims priority to U.S. Provisional Application 61/747,662 (filed on Dec. 31, 2012) which is incorporated by reference in its entirety.

FIELD OF THE INVENTION

The present invention is in the field of cell differentiation. More specifically, the present invention provides methods, cell cultures and media for generating pancreatic endoderm, pancreatic endocrine precursor cells, and single-hormone pancreatic endocrine cells from human pluripotent stem cells by culturing cells at the air-liquid interface.

BACKGROUND

Advances in cell-replacement therapy for Type I diabetes mellitus and a shortage of transplantable islets of Langerhans have focused interest on developing sources of insulin-producing cells, or beta (β) cells, appropriate for engraftment. One approach is the generation of functional β cells from pluripotent stem cells, such as, embryonic stem cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver, will develop from the endoderm, via an intermediate stage. The intermediate stage in this process is the formation of definitive endoderm.

By the end of gastrulation, the endoderm is partitioned into anterior-posterior domains that can be recognized by the expression of a panel of factors that uniquely mark anterior, mid, and posterior regions of the endoderm. For example, HHEX, and SOX2 identify the anterior region while CDX1, 2, and 4 identify the posterior region of the endoderm.

Migration of endoderm tissue brings the endoderm into close proximity with different mesodermal tissues that help in regionalization of the gut tube. This is accomplished by a plethora of secreted factors, such as FGFs, WNTS, TGF-βs, retinoic acid (RA), and BMP ligands and their antagonists. For example, FGF4 and BMP promote CDX2 expression in the presumptive hindgut endoderm and repress expression of the anterior genes Hhex and SOX2 (2000 *Development,* 127:1563-1567). WNT signaling has also been shown to work in parallel to FGF signaling to promote hindgut development and inhibit foregut fate (2007 *Development,* 134:2207-2217). Lastly, secreted retinoic acid by mesenchyme regulates the foregut-hindgut boundary (2002 *Curr Biol,* 12:1215-1220).

The level of expression of specific transcription factors may be used to designate the identity of a tissue. During transformation of the definitive endoderm into a primitive gut tube, the gut tube becomes regionalized into broad domains that can be observed at the molecular level by restricted gene expression patterns. The regionalized pancreas domain in the gut tube shows a very high expression of PDX1 and very low expression of CDX2 and SOX2. PDX1, NKX6.1, PTF1A, and NKX2.2 are highly expressed in pancreatic tissue; and expression of CDX2 is high in intestinal tissue.

Formation of the pancreas arises from the differentiation of definitive endoderm into pancreatic endoderm. Dorsal and ventral pancreatic domains arise from the foregut epithelium. Foregut also gives rise to the esophagus, trachea, lungs, thyroid, stomach, liver, and bile duct system.

Cells of the pancreatic endoderm express the pancreatic-duodenal homeobox gene PDX1. In the absence of PDX1, the pancreas fails to develop beyond the formation of ventral and dorsal buds. Thus, PDX1 expression marks a critical step in pancreatic organogenesis. The mature pancreas contains, both exocrine and endocrine tissues arising from the differentiation of pancreatic endoderm.

D'Amour et al. describe the production of enriched cultures of human embryonic stem cell-derived definitive endoderm in the presence of a high concentration of activin and low serum (*Nature Biotechnology* 2005, 23:1534-1541; U.S. Pat. No. 7,704,738). Transplanting these cells under the kidney capsule of mice reportedly resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF10 and retinoic acid (U.S. Patent App. Pub. No. 2005/0266554). Subsequent transplantation of these pancreatic precursor cells in the fat pad of immune deficient mice resulted in the formation of functional pancreatic endocrine cells following a 3-4 months maturation phase (U.S. Pat. No. 7,993,920 and U.S. Pat. No. 7,534,608).

Fisk et al. report a system for producing pancreatic islet cells from human embryonic stem cells (U.S. Pat. No. 7,033,831). In this case, the differentiation pathway was divided into three stages. Human embryonic stem cells were first differentiated to endoderm using a combination of sodium butyrate and activin A (U.S. Pat. No. 7,326,572). The cells were then cultured with BMP antagonists, such as Noggin, in combination with EGF or betacellulin to generate PDX1 positive cells. The terminal differentiation was induced by nicotinamide.

Small molecule inhibitors have also been used for induction of pancreatic endocrine precursor cells. For example, small molecule inhibitors of TGF-β receptor and BMP receptors (*Development* 2011, 138:861-871; *Diabetes* 2011, 60:239-247) have been used to significantly enhance the number of pancreatic endocrine cells. In addition, small molecule activators have also been used to generate definitive endoderm cells or pancreatic precursor cells (*Curr Opin Cell Biol* 2009, 21:727-732; *Nature Chem Biol* 2009, 5:258-265).

HB9 (also known as H1XB9 and MNX1) is a BHLH transcriptional activator protein expressed early in pancreas development starting at approximately embryonic day 8. HB9 is also expressed in notochord and spinal cord. Expression of HB9 is transient and peaks at about day 10.5 in pancreatic epithelium being expressed in PDX1 and NKX6.1 expressing cells. At about day 12.5, HB9 expression declines and at later stages it becomes restricted only to β cells. In mice homozygous for a null mutation of HB9, the dorsal lobe of the pancreas fails to develop (*Nat Genet.* 23:67-70, 1999; *Nat Genet.* 23:71-75, 1999). HB9−/− β-cells express low levels of the glucose transporter, GLUT2, and NKX6.1. Furthermore, HB9−/− pancreas shows a significant reduction in the number of insulin positive cells while not significantly affecting expression of other pancreatic hormones. Thus, temporal control of HB9 is essential to normal β cell development and function. While not much is known about factors regulating HB9 expression in β cells, a recent study in zebrafish suggests that retinoic acid can positively regulate expression of HB9 (*Development*, 138, 4597-4608, 2011).

The thyroid hormones, thyroxine ("T4") and triiodothyronine ("T3"), are tyrosine-based hormones produced by the thyroid gland and are primarily responsible for regulation of metabolism. The major form of thyroid hormone in the blood is T4, which has a longer half-life than T3. The ratio of T4 to T3 released into the blood is roughly 20 to 1. T4 is converted to the more active T3 (three to four times more potent than T4) within cells by deiodinase.

T3 binds to thyroid hormone receptors, TRα1 and TRβ1 (TR). TR is a nuclear hormone receptor, which heterodimerizes with retinoid X receptor. The dimers bind to the thyroid response elements (TREs) in the absence of ligand and act as transcriptional repressors. Binding of T3 to TR reduces the repression of TRE dependent genes and induces the expression of various target genes. While numerous studies have suggested a role for T3 in increasing β cell proliferation, reducing apoptosis, and improving insulin secretion, its role in cell differentiation is undefined.

Transforming growth factor β ("TGF-β") is a member of a large family of pleiotropic cytokines that are involved in many biological processes, including growth control, differentiation, migration, cell survival, fibrosis and specification of developmental fate. TGF-β superfamily members signal through a receptor complex comprising a type II and type I receptor. TGF-B ligands (such as activins, and growth differentiation factors ("GDF"s)) bring together a type II receptor with a type I receptor. The type II receptor phosphorylates and activates the type I receptor in the complex. There are five mammalian type II receptors: TβR-II, ActR-II, ActR-IIB, BMPR-II, and AMHR-II and seven type I receptors (ALKs 1-7). Activin and related ligands signal via combinations of ActR-II or ActR-IIB and ALK4 or ALK5, and BMPs signal through combinations of ALK2, ALK3, and ALK6 with ActR-II, ActR-IIB, or BMPR-II. AMH signals through a complex of AMHR-II with ALK6, and nodal has been shown to signal through a complex of ActR-IIB and ALK7 (*Cell*. 2003,113(6):685-700). Following binding of the TGF-B ligand to the appropriate receptor, the ensuing signals are transduced to the nucleus primarily through activation of complexes of Smads. Upon activation, the type I receptors phosphorylate members of the receptor-regulated subfamily of Smads. This activates them and enables them to form complexes with a common mediator Smad, Smad4. Smads 1, 5, and 8 are substrates for ALKs 1, 2, 3, and 6, whereas Smads 2 and 3 are substrates for ALKs 4, 5, and 7 (*FASEB J* 13:2105-2124). The activated Smad complexes accumulate in the nucleus, where they are directly involved in the transcription of target genes, usually in association with other specific DNA-binding transcription factors. Compounds that selectively inhibit the receptors for TGF-β, have been developed for therapeutic applications and for modulating cell fate in the context of reprogramming and differentiation from various stem cell populations. In particular, ALK5 inhibitors have been previously used to direct differentiation of embryonic stem cells to an endocrine fate (*Diabetes*, 2011, 60(1):239-47).

In general, the process of differentiating progenitor cells to functional β cells goes through various stages; and great strides have been made in improving protocols to generate pancreatic cells from progenitor cells such as human pluripotent stem cells. Despite these advances in research, each step in the process of differentiating progenitor cells presents a unique challenge. As such, there is still a need for a protocol resulting in functional endocrine cells and, in particular, functional β cells.

BRIEF DESCRIPTION OF THE DRAWINGS

FIGS. 1A to 1H show phase contrast images of cells cultured at the air-liquid interface using the methods described in Example 1 at the following time points: Day 1 (FIG. 1A); Day 5 (FIG. 1B); Day 6 (FIG. 1C); Day 7 (FIG. 1D); Day 9 (FIG. 1E); Day 13 (FIG. 1F); Day 16 (FIG. 1G); and Day 21 (FIG. 1H).

FIGS. 3A to 3H show images of cells differentiated for two weeks at the air-liquid interface using the methods described in Example 1 and immunostained for the following: insulin (FIG. 3A); glucagon (FIG. 3B); insulin (FIG. 3C); somatostatin (FIG. 3D); insulin (FIG. 3E); NKX6.1 (FIG. 3F); HB9 (FIG. 3G); and NKX6.1 (FIG. 2H). Panels A-B, C-D, E-F, and G-H were taken from the same field.

FIGS. 8A to 8H depict data from real-time PCR analyses of the expression of the following genes in cells of the human embryonic stem cell line H1 differentiated as outlined in Example 4: PDX1 (FIG. 8A); NKX6.1 (FIG. 8B); NGN3 (FIG. 8C); ABCC8 (FIG. 8D); PCSK1 (FIG. 8E); Ghrelin (FIG. 8F); glucagon (FIG. 8G); and insulin (FIG. 8H).

FIGS. 9A to 9F depict data from real-time PCR analyses of the expression of the following genes in cells of the human embryonic stem cell line H1 differentiated as outlined in Example 4: PDX1 (FIG. 9A); NKX6.1 (FIG. 9B); NGN3 (FIG. 9C); ABCC8 (FIG. 9D); glucagon (FIG. 9E); and insulin (FIG. 9F).

FIGS. 10A to 10B depict the results of immunostaining Stage 6 cells cultured at the air-liquid interface according to Example 4 and treated either with 1 micro molar SD208 inhibitor (FIG. 10A) or 1 micro molar ALK5 inhibitor II (FIG. 10B) and stained for chromogranin-A (pan-endocrine marker) and NKX6.1 (Pancreatic precursor marker and β cell specific marker).

FIGS. 15A to 15J show FACS profile of Stage 5 day 3 cells, differentiated according to Example 10, and stained for: Isotype control (FIG. 15A); NKX6.1 (FIG. 15B); NKX2.2 (FIG. 15C); NKX6.1 (Y-axis) co-stained with insulin (X-axis) (FIG. 15D); PDX1 (X-axis) co-stained with KI-67 (Y-axis) (FIG. 15E); PAX6 (FIG. 15F); ISL-1 (FIG. 15G); FOXA2 (FIG. 15H); NeuroD (FIG. 15I); and glucagon (Y-axis) co-stained with insulin (X-axis) (FIG. 15J).

FIGS. 16A to 16I show FACS profile of Stage 6 day 5 cells, differentiated according to Example 10, and stained for: Isotype control (FIG. 16A); NKX6.1 (Y-axis) co-stained with chromogranin-A (X-axis) (FIG. 16B); NKX2.2 (Y-axis) co-stained with chromogranin-A α-axis) (FIG. 16C); NKX6.1 (Y-axis) co-stained with insulin (X-axis) (FIG. 16D); PDX1 (X-axis) co-stained with KI-67 (Y-axis) (FIG. 16E); PAX6 (FIG. 16F); ISL-1 (FIG. 16G); FOXA2 (FIG. 16H); and NeuroD (FIG. 16I).

FIG. 19A to 19C show the FACS (Fluorescence-activated cell sorting) profile of Stage 6 day 6 cells, differentiated according to Example 11, and stained for: NKX6.1 (Y-axis) co-stained with chromogranin-A (X-axis) (FIG. 19A); PDX1 (X-axis) co-stained with KI-67 (Y-axis) (FIG. 19B); and NKX6.1 (Y-axis) co-stained with insulin (X-axis) (FIG. 19C).

FIGS. 21A to 21F depict data from real-time PCR analyses of the expression of the following genes in cells of the human embryonic stem cell line H1 differentiated as outlined in Example 12: Amylin (FIG. 21A); insulin (FIG. 21B); MAFA (FIG. 21C); NKX6.1 (FIG. 21D); PTF1a (FIG. 21E); and SOX9 (FIG. 21F).

FIGS. 23A to 23F depict data from real-time PCR analyses of the expression of the following genes in cells of the human embryonic stem cell line H1 differentiated as outlined in Example 5: PDX1 (FIG. 23A); NKX6.1 (FIG. 23B); NGN3 (FIG. 23C); ABCC8 (FIG. 23D); glucagon (FIG. 23E); and insulin (FIG. 23F).

DETAILED DESCRIPTION

Figure 1G:
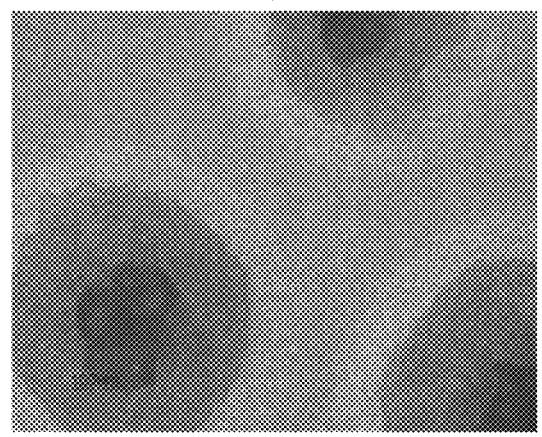

The following detailed description of the invention will be better understood when read in conjunction with the appended figures. Figures are provided for the purpose of illustrating certain embodiments of the present invention. However, the invention is not limited to the precise arrangements, examples, and instrumentalities shown. For clarity of disclosure, and not by way of limitation, the detailed description of the invention is divided into subsections that describe or illustrate certain features, embodiments, or applications of the present invention.

The present invention is directed to differentiating endoderm progenitor cells, such as pluripotent stem cells, into cells exhibiting characteristics of pancreatic endocrine cells by culturing said progenitor cells, at least in part, at the air-liquid interface that exists in an open culture vessel or a culture vessel partially filled with medium. Although referred to herein as "air" for convenience, the invention is not limited to the mixture of gasses and compositions found in the ambient environment. The invention specifically contemplates and includes gaseous mixtures having compositions different from the ambient environment including, for example, mixtures enriched for a particular component or in which a particular component has been depleted or eliminated.

Additionally, the present invention provides cell cultures for differentiating pluripotent stem cells into cells exhibiting characteristics of pancreatic endocrine cells, as well as differentiation media that initiates and facilitates such differentiation. Advantageously, these cell cultures and differentiation media may be used in conjunction with differentiation at the air-liquid interface to provide previously unattained yields of cells expressing markers characteristic of pancreatic endocrine cells.

The culturing may occur at the air-liquid interface for all stages involved in the differentiation pathway from pluripotent stem cell to pancreatic endocrine cell, or it may involve culturing on a planar culture submersed in medium for the early stages of differentiation, and culturing at the air-liquid interface during the later stages of differentiation. Preferably, the process of the invention involves the combination of culturing pluripotent stem cells on a support surface submerged in medium through the early stages, and then culturing at the air-liquid interface for the later stages of differentiation. In such embodiments, the cells may initially be seeded on a solid surface for submerged culturing and then removed from the solid support and re-seeded on a porous support for culturing at the air-liquid interface. Alternatively, the cells may be seeded initially on a porous support that is then submerged in media for the early stages of differentiation and subsequently positioned at the air-liquid interface for the later stages of differentiation. Culturing at the air-liquid interface for the later stages of differentiation significantly enhances the expression of endocrine markers in comparison to culturing the cells in a submerged state for the entire process, indicating that a greater percentage of the cells have differentiated into pancreatic endocrine cells.

In one embodiment, the present invention is directed to differentiating endoderm progenitor cells at the air-liquid interface of a culture vessel partially filled with media into pancreatic endoderm progenitor cells that are positive for NKX6.1, PDX1, and HB9. This invention is based, in part, on the discovery that culturing at the air-liquid interface significantly enhances expression of endocrine markers. Furthermore, it was discovered that pancreatic endocrine precursor cells can be readily generated at the air-liquid interface resulting in generation of predominantly single hormone insulin positive cells. Single-cell seeding at the air-liquid interface was found to improve consistency of insulin production.

DEFINITIONS

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm, and ectoderm). Stem cells also give rise to tissues of multiple germ layers following transplantation and contribute substantially to most, if not all, tissues following injection into blastocysts.

Stem cells are classified by their developmental potential. Pluripotent stem cells are able to give rise to all embryonic cell types.

Differentiation is the process by which an unspecialized ("uncommitted") or less specialized cell acquires the features of a specialized cell such as, for example, a nerve cell or a muscle cell. A differentiated cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and to what cells it can give rise. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is sufficiently detected in the cell. Similarly, the cell is "negative for" a specific marker, or "negative" when the specific marker is not sufficiently detected in the cell. In particular, positive by FACS is usually greater than 2%, whereas the negative threshold by FACS is usually less than 1%. Positive by PCR is usually less than 34 cycles (Cts); whereas negative by PCR is usually more than 34.5 cycles.

In attempts to replicate the differentiation of pluripotent stem cells into functional pancreatic endocrine cells in static in vitro cell cultures, the differentiation process is often viewed as progressing through a number of consecutive stages. In particular, the differentiation process is commonly viewed as progressing through six stages. In this step-wise progression, "Stage 1" refers to the first step in the differentiation process, the differentiation of pluripotent stem cells into cells expressing markers characteristic of definitive endoderm cells (hereinafter referred to alternatively as "Stage 1 cells"). "Stage 2" refers to the second step, the differentiation of cells expressing markers characteristic of definitive endoderm cells into cells expressing markers characteristic of gut tube cells (hereinafter referred to alternatively as "Stage 2 cells"). "Stage 3" refers to the third step, the differentiation of cells expressing markers characteristic of gut tube cells into cells expressing markers characteristic of foregut endoderm cells (hereinafter referred to alternatively as "Stage 3 cells"). "Stage 4" refers to the fourth step, the differentiation of cells expressing markers characteristic of foregut endoderm cells into cells expressing markers characteristic of pancreatic foregut precursor cells (hereinafter referred to alternatively as "Stage 4 cells"). "Stage 5" refers to the fifth step, the differentiation of cells expressing markers characteristic of pancreatic foregut precursor cells into cells expressing markers characteristic of pancreatic endoderm cells and/or pancreatic endocrine precursor cells (hereinafter referred to collectively as "pancreatic endoderm/endocrine precursor cells" or alternatively as "Stage 5 cells"). "Stage 6" refers to the differentiation of cells expressing markers characteristic of pancreatic endoderm/endocrine precursor cells into cells expressing markers characteristic of pancreatic endocrine cells (hereinafter referred to alternatively as "Stage 6 cells").

However, it should be noted that not all cells in a particular population progress through these stages at the same rate. Consequently, it is not uncommon in in vitro cell cultures to detect the presence of cells that have progressed less, or more, down the differentiation pathway than the majority of cells present in the population, particularly at the later differentiation stages. For example, it is not uncommon to see the appearance of markers characteristic of pancreatic endocrine cells during the culture of cells at Stage 5. For purposes of illustrating the present invention, characteristics of the various cell types associated with the above-identified stages are described herein.

"Definitive endoderm cells," as used herein, refers to cells which bear the characteristics of cells arising from the epiblast during gastrulation and which form the gastrointestinal tract and its derivatives. Definitive endoderm cells express at least one of the following markers: FOXA2 (also known as hepatocyte nuclear factor 3β ("HNF3β")), GATA4, SOX17, CXCR4, Brachyury, Cerberus, OTX2, goosecoid, C-Kit, CD99, and MIXL1. Markers characteristic of the definitive endoderm cells include CXCR4, FOXA2 and SOX17. Thus, definitive endoderm cells may be characterized by their expression of CXCR4, FOXA2 and SOX17. In addition, depending on the length of time cells are allowed to remain in Stage 1, an increase in HNF4α may be observed.

"Gut tube cells," as used herein, refers to cells derived from definitive endoderm that can give rise to all endodermal organs, such as lungs, liver, pancreas, stomach, and intestine. Gut tube cells may be characterized by their substantially increased expression of HNF4α over that expressed by definitive endoderm cells. For example, ten to forty fold increase in mRNA expression of HNF4α may be observed during Stage 2.

"Foregut endoderm cells," as used herein, refers to endoderm cells that give rise to the esophagus, lungs, stomach, liver, pancreas, gall bladder, and a portion of the duodenum. Foregut endoderm cells express at least one of the following markers: PDX1, FOXA2, CDX2, SOX2, and HNF4α. Foregut endoderm cells may be characterized by an increase in expression of PDX1, compared to gut tube cells. For example, greater than fifty percent of the cells in Stage 3 cultures typically express PDX1.

"Pancreatic foregut precursor cells," as used herein, refers to cells that express at least one of the following markers: PDX1, NKX6.1, HNF6, NGN3, SOX9, PAX4, PAX6, ISL1, gastrin, FOXA2, PTF1a, PROX1 and HNF4α. Pancreatic foregut precursor cells may be characterized by being positive for the expression of PDX1, NKX6.1, and SOX9.

"Pancreatic endoderm cells," as used herein, refers to cells that express at least one of the following markers: PDX1, NKX6.1, HNF1 β, PTF1 α, HNF6, HNF4 α, SOX9, NGN3; gastrin; HB9, or PROX1. Pancreatic endoderm cells may be characterized by their lack of substantial expression of CDX2 or SOX2.

"Pancreatic endocrine precursor cells," as used herein, refers to pancreatic endoderm cells capable of becoming a pancreatic hormone expressing cell. Pancreatic endocrine precursor cells express at least one of the following markers: NGN3; NKX2.2; NeuroD1; ISL1; PAX4; PAX6; or ARX. Pancreatic endocrine precursor cells may be characterized by their expression of NKX2.2 and NeuroD1.

"Pancreatic endocrine cells," as used herein, refer to cells capable of expressing at least one of the following hormones: insulin, glucagon, somatostatin, ghrelin, and pancreatic polypeptide. In addition to these hormones, markers characteristic of pancreatic endocrine cells include one or more of NGN3, NeuroD1, ISL1, PDX1, NKX6.1, PAX4, ARX, NKX2.2, and PAX6. Pancreatic endocrine cells expressing markers characteristic of B cells can be characterized by their expression of insulin and at least one of the following transcription factors: PDX1, NKX2.2, NKX6.1, NeuroD1, ISL1, HNF3O, MAFA and PAX6.

Used interchangeably herein are "d1", "1d", and "day 1"; "d2", "2d", and "day 2", and so on. These number letter combinations refer to a specific day of incubation in the different stages during the stepwise differentiation protocol of the instant application.

"Glucose" is used herein to refer to dextrose, a sugar commonly found in nature.

"NeuroD1" is used herein to identify a protein expressed in pancreatic endocrine progenitor cells and the gene encoding it.

"LDN-193189" refers to ((6-(4-(2-(piperidin-1-yl) ethoxy)phenyl)-3-(pyridin-4-yl)pyrazolo[1,5-a]pyrimidine, hydrochloride; DM-3189)) a BMP receptor inhibitor available under the trademark STEMOLECULE™ from Stemgent, Inc., Cambridge, Mass., USA.

Characterization, Source, Expansion and Culture of Pluripotent Stem Cells

A. Characterization of Pluripotent Stem Cells

Pluripotent stem cells may express one or more of the designated TRA-1-60 and TRA-1-81 antibodies (Thomson et al. 1998, *Science* 282:1145-1147). Differentiation of pluripotent stem cells in vitro results in the loss of TRA-1-60 and TRA-1-81 expression. Undifferentiated pluripotent stem cells typically have alkaline phosphatase activity, which can be detected by fixing the cells with 4% paraformaldehyde, and then developing with an alkaline phosphatase substrate kit sold under the trademark VECTOR® Red as a substrate, as described by the manufacturer (Vector Laboratories, CA, USA). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm. Pluripotency of stem cells may be confirmed, for example, by injecting cells into severe combined immunodeficiency (SCID) mice, fixing the teratomas that form using 4% paraformaldehyde, and then examining histologically for evidence of cell types from these three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

B. Sources of Pluripotent Stem Cells

Exemplary types of pluripotent stem cells that may be used include established lines of pluripotent cells, including pre-embryonic tissue (such as, a blastocyst), embryonic tissue, or fetal tissue taken any time during gestation, typically but not necessarily, before approximately 10 to 12 weeks gestation. Non-limiting examples are established lines of human embryonic stem cells or human embryonic germ cells, such as, the human embryonic stem cell lines H1, H7, and H9 (WiCell Research Institute, Madison, Wis., USA). Cells taken from a pluripotent stem cell population already cultured in the absence of feeder cells are also suitable. Induced pluripotent cells (IPS), or reprogrammed pluripotent cells, derived from adult somatic cells using forced expression of a number of pluripotent related transcription factors, such as OCT4, NANOG, SOX2, KLF4, and ZFP42 (*Annu Rev Genomics Hum Genet.* 2011, 12:165-185; see also IPS, *Cell,* 126(4): 663-676) may also be used. The human embryonic stem cells used in the methods of the invention may also be prepared as described by Thomson et al. (U.S. Pat. No. 5,843,780; *Science,* 1998, 282:1145-1147; *Curr Top Dev Biol* 1998, 38:133-165; *Proc Natl Acad Sci U.S.A.* 1995, 92:7844-7848). Mutant human embryonic stem cell lines, such as, BG01v (BresaGen, Athens, Ga.), or cells derived from adult human somatic cells, such as, cells disclosed in Takahashi et al., *Cell* 131: 1-12 (2007) may also be used. In certain embodiments, pluripotent stem cells suitable for use in the present invention may be derived according to the methods described in: Li et al. (*Cell Stem Cell* 4: 16-19, 2009); Maherali et al. (*Cell Stem Cell* 1: 55-70, 2007); Stadtfeld et al. (*Cell Stem Cell* 2: 230-240); Nakagawa et al. (*Nature Biotechnol* 26: 101-106, 2008); Takahashi et al. (*Cell* 131: 861-872, 2007); and U.S. Patent App. Pub. No. 2011/0104805. In certain embodiments, the pluripotent stem cells may be of non-embryonic origins. All of these references, patents, and patent applications are herein incorporated by reference in their entirety, in particular, as they pertain to the isolation, culture, expansion and differentiation of pluripotent cells.

C. Expansion and Culture of Pluripotent Stem Cells

Pluripotent stem cells are typically cultured on a layer of feeder cells that support the pluripotent stem cells in various ways. Alternatively, pluripotent stem cells may be cultured in a culture system that is essentially free of feeder cells, but nonetheless supports proliferation of pluripotent stem cells without undergoing substantial differentiation. The growth of pluripotent stem cells in feeder-free culture without differentiation is often supported using a medium conditioned by culturing previously with another cell type. Alternatively, the growth of pluripotent stem cells in feeder-free culture without differentiation can be supported using a chemically defined medium.

Pluripotent cells may be readily expanded in culture using various feeder layers or by using matrix protein coated vessels. Alternatively, chemically defined surfaces in combination with defined media such as media sold under the trademark mTESR®1 (StemCell Technologies, Vancouver, Canada) may be used for routine expansion of the cells. Pluripotent cells may be readily removed from culture plates using enzymatic digestion, mechanical separation, or various calcium chelators such as ethylenediaminetetraacetic acid (EDTA). Alternatively, pluripotent cells may be expanded in suspension in the absence of any matrix proteins or feeder layer.

Many different methods of expanding and culturing pluripotent stem cells may be used in the claimed invention. For example, the methods of the invention may use the methods of Reubinoff et al., Thompson et al., Richard et al. and U.S. Patent App. Pub. No. 2002/0072117. Reubinoff et al. (*Nature Biotechnology* 18: 399-404 (2000)) and Thompson et al. (*Science* 282: 1145-1147 (1998)) disclose the culture of pluripotent stem cell lines from human blastocysts using a mouse embryonic fibroblast feeder cell layer. Richards et al. (*Stem Cells* 21: 546-556, 2003) evaluated a panel of eleven different human adult, fetal, and neonatal feeder cell layers for their ability to support human pluripotent stem cell culture, noting that human embryonic stem cell lines cultured on adult skin fibroblast feeders retain human embryonic stem cell morphology and remain pluripotent. U.S. Patent App. Pub. No. 2002/0072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. U.S. Patent App. Pub. No. 2002/072117 also discloses the use of the cell lines as a primary feeder cell layer.

Other suitable methods of expanding and culturing pluripotent stem cells are disclosed, for example, in Wang et al., Stojkovic et al., Miyamoo et al. and Amit et al. Wang et al. (*Stem Cells* 23: 1221-1227, 2005) disclose methods for the long-term growth of human pluripotent stem cells on feeder cell layers derived from human embryonic stem cells. Stojkovic et al. (*Stem Cells* 2005 23: 306-314, 2005) disclose a feeder cell system derived from the spontaneous differentiation of human embryonic stem cells. Miyamoto et al. (*Stem Cells* 22: 433-440, 2004) disclose a source of feeder cells obtained from human placenta. Amit et al. (*Biol. Reprod* 68: 2150-2156, 2003) disclose a feeder cell layer derived from human foreskin.

Other suitable methods of expanding and culturing pluripotent stem cells are disclosed, for example, in Inzunza et al., U.S. Pat. No. 6,642,048, WO 2005/014799, Xu et al. and U.S. Patent App. Pub. No. 2007/0010011. Inzunza et al. (*Stem Cells* 23: 544-549, 2005) disclose a feeder cell layer from human postnatal foreskin fibroblasts. U.S. Pat. No. 6,642,048 discloses media that support the growth of primate pluripotent stem cells in feeder-free culture, and cell lines useful for production of such media. U.S. Pat. No. 6,642,048 reports mesenchymal and fibroblast-like cell lines obtained from embryonic tissue or differentiated from embryonic stem cells; as well as methods for deriving such cell lines, processing media, and growing stem cells using such media. WO 2005/014799 discloses a conditioned medium for the maintenance, proliferation, and differentiation of mammalian cells. WO 2005/014799 reports that the culture medium produced via the disclosure is conditioned by the cell secretion activity of murine cells; in particular, those differentiated and immortalized transgenic hepatocytes, named MMH (Met Murine Hepatocyte). Xu et al. (*Stem Cells* 22: 972-980, 2004) discloses a conditioned medium obtained from human embryonic stem cell derivatives that have been genetically modified to over express human telomerase reverse transcriptase. U.S. Patent App. Pub. No. 2007/0010011 discloses a chemically defined culture medium for the maintenance of pluripotent stem cells.

An alternative culture system employs serum-free medium supplemented with growth factors capable of promoting the proliferation of embryonic stem cells. Examples of such culture systems include, but are not limited, to Cheon et al., Levenstein et al. and U.S. Patent App. Pub. No. 2005/0148070. Cheon et al. (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal. Levenstein et al. (*Stem Cells* 24: 568-574, 2006) disclose methods for the long-term culture of human embryonic stem cells in the absence of fibroblasts or conditioned medium, using media supplemented with bFGF. U.S. Patent App. Pub. No. 2005/0148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

Other suitable methods of culturing and expanding pluripotent stem cells are disclosed in U.S. Patent App. Pub. No. 2005/0233446, U.S. Pat. No. 6,800,480, U.S. Patent App. Pub. No. 2005/0244962 and WO 2005/065354. U.S. Patent App. Pub. No. 2005/0233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells. U.S. Pat. No. 6,800,480 reports that a cell culture medium for growing primate-derived primordial stem cells in a substantially undifferentiated state is provided which includes a low osmotic pressure, low endotoxin basic medium that is effective to support the growth of primate-derived primordial stem cells. The disclosure of the 6,800,480 patent further reports that the basic medium is combined with a nutrient serum effective to support the growth of primate-derived primordial stem cells and a substrate selected from the group consisting of feeder cells and an extracellular matrix component derived from feeder cells. This medium is further noted to include non-essential amino acids, an anti-oxidant, and a first growth factor selected from the group consisting of nucleosides and a pyruvate salt. U.S. Patent App. Pub. No. 2005/0244962 reports that one aspect of the disclosure provides a method of culturing primate embryonic stem cells and that the stem cells in culture are essentially free of mammalian fetal serum (preferably also essentially free of any animal serum) and in the presence of fibroblast growth factor that is supplied from a source other than just a fibroblast feeder layer.

WO 2005/065354 discloses a defined, isotonic culture medium that is essentially feeder-free and serum-free, comprising: a basal medium, bFGF, insulin and ascorbic acid in amounts sufficient to support growth of substantially undifferentiated mammalian stem cells. Furthermore, WO 2005/086845 discloses a method for maintenance of an undifferentiated stem cell, said method comprising exposing a stem cell to a member of the transforming growth factor-β (TGF-β) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as those derived from basement membrane or that may form part of adhesion molecule receptor-ligand couplings. A suitable culture substrate is a reconstituted basement membrane sold under the trademark MATRIGEL™ (BD Biosciences, Franklin Lakes, N.J.). MATRIGEL™ is a soluble preparation from Engelbreth-Holm Swarm tumor cells that gels at room temperature to form a reconstituted basement membrane.

Other extracellular matrix components and component mixtures known in the art are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium, which promotes cell survival, propagation, and retention of the desirable characteristics. All these characteristics benefit from careful attention to the seeding distribution and can readily be determined by one of skill in the art. Suitable culture media may be made from the following components, Dulbecco's modified Eagle's medium (DMEM) sold under the trademark GIBCO™ (Part #11965-092) by Life Technologies Corporation, Grand Island, N.Y.; Knockout Dulbecco's modified Eagle's medium (KO DMEM) sold under the trademark GIBCO™ (Part #10829-018) by Life Technologies Corporation, Grand Island, N.Y.; Ham's F12/50% DMEM basal medium; 200 mM L-glutamine sold under the trademark GIBCO™ (Part #15039-027) by Life Technologies Corporation, Grand Island, N.Y.; non-essential amino acid solution sold under the trademark GIBCO™ (Part #11140-050) by Life Technologies Corporation, Grand Island, N.Y.; β-mercaptoethanol, Sigma-Aldrich Company, LLC Saint Louis, Mo., (Part #M7522); human recombinant basic fibroblast growth factor (bFGF) sold under the trademark GIBCO™ (Part #13256-029) by Life Technologies Corporation, Grand Island, N.Y.

Differentiation of Pluripotent Stem Cells

As pluripotent cells differentiate towards β cells, they differentiate through various stages each of which may be characterized by the presence or absence of particular markers. Differentiation of the cells into these stages is achieved by the specific culturing conditions including the presence and lack of certain factors added to the culture media. In general, this differentiation may involve differentiation of pluripotent stem cells into definitive endoderm cells. These definitive endoderm cells may then be further differentiated into gut tube cells, which may, in turn, be differentiated into foregut endoderm cells. Foregut endoderm cells may be differentiated into pancreatic foregut precursor cells which can, in turn, be further differentiated into pancreatic endoderm cells, pancreatic endocrine precursor cells or both. These cells may then be differentiated into pancreatic hormone producing cells (such as β cells). This invention provides for staged differentiation of pluripotent stem cells toward pancreatic endocrine cells by culturing the cells at the air-liquid interface that exists within a culture vessel partially filled with medium, specifically by culturing Stage 4 to Stage 6 cells at the air-liquid interface.

Differentiation of Pluripotent Stem Cells into Cells Expressing Markers Characteristic of Pancreatic Endocrine Cells Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, TRA-1-60, TRA-1-81.

Exemplary pluripotent stem cells include the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden).

Also suitable are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, TRA-1-60, and TRA-1-81.

Also, suitable for use in the present invention is a cell that expresses at least one of the markers characteristic of the definitive endoderm lineage. In one embodiment of the present invention, a cell expressing markers characteristic of the definitive endoderm lineage is a primitive streak precursor cell. In an alternate embodiment, a cell expressing markers characteristic of the definitive endoderm lineage is a mesendoderm cell. In an alternate embodiment, a cell expressing markers characteristic of the definitive endoderm lineage is a definitive endoderm cell.

Also suitable for use in the present invention is a cell that expresses at least one of the markers characteristic of the pancreatic endoderm lineage. In one embodiment of the present invention, a cell expressing markers characteristic of the pancreatic endoderm lineage is a pancreatic endoderm cell wherein the expression of PDX1 and NKX6.1 are substantially higher than the expression of CDX2 and SOX2. In certain embodiments, more than thirty percent of the cells express PDX1 and NKX6.1 and less than thirty percent of the cells express CDX2 or SOX2 as measured by FACS. Particularly useful are cells in which the expression of PDX1 and NKX6.1 is at least two-fold higher than the expression of CDX2 or SOX2.

Also suitable for use in the present invention is a cell that expresses at least one of the markers characteristic of the pancreatic endocrine lineage. In one embodiment of the invention, a cell expressing markers characteristic of the pancreatic endocrine lineage is a pancreatic endocrine cell. In one embodiment, the pancreatic endocrine cell is capable of expressing at least one of the following hormones: insulin, glucagon, somatostatin, or pancreatic polypeptide. In a preferred embodiment, the pancreatic endocrine cell is an insulin-producing β cell.

In certain embodiments of the invention, to arrive at cells expressing markers characteristic of pancreatic endocrine cells, a protocol starting with pluripotent stem cells or inducible pluripotent cells, preferably pluripotent stem cells, is employed. This protocol includes the following:

Stage 1: Pluripotent stem cells, such as embryonic stem cells obtained from cell culture lines, are treated with appropriate factors to induce differentiation into cells expressing markers characteristic of definitive endoderm cells.

Stage 2: Cells resulting from Stage 1 are treated with appropriate factors to induce further differentiation into cells expressing markers characteristic of gut tube cells.

Stage 3: Cells resulting from Stage 2 are treated with appropriate factors to induce further differentiation into cells expressing markers characteristic of foregut endoderm cells.

Stage 4: Cells resulting from Stage 3 are treated with appropriate factors to induce further differentiation into cells expressing markers characteristic of pancreatic foregut precursor cells. The cells are optionally cultured at the air-liquid interface at late Stage 4.

Stage 5: Cells resulting from Stage 4 are treated with appropriate factors and cultured at the air-liquid interface to induce further differentiation into cells expressing markers characteristic of pancreatic endoderm/endocrine precursor cells.

Stage 6: Cells resulting from Stage 5 are treated with appropriate factors and cultured at the air-liquid interface to induce further differentiation into cells expressing markers characteristic of pancreatic endocrine cells.

While the invention, in certain embodiments, encompasses differentiating pluripotent stem cells (e.g. pre-Stage 1 cells) to Stage 6 cells, the invention also encompasses differentiating cells at other intermediate stages towards Stage 6. In particular, the invention encompasses differentiation of Stage 4 to Stage 6 cells. Moreover, although the process is described in discrete stages, the treatment, as well as the progress of the cells through the differentiation process, may be sequential or continuous.

Stage 1: Differentiation of pluripotent stem cells into cells expressing markers characteristic of definitive endoderm cells Pluripotent stem cells may be differentiated into cells expressing markers characteristic of definitive endoderm cells by any method known in the art or by any method proposed herein. Methods useful for differentiating pluripotent stem cells into cells expressing markers characteristic of definitive endoderm cells are disclosed in: U.S. Patent App. Pub. No. 2007/0254359; U.S. Patent App. Pub. No. 2009/0170198; U.S. Patent App. Pub. No. 2009/0170198; U.S. Patent App. Pub. No. 2011/0091971; U.S. Patent App. Pub. No. 2010/0015711; U.S. Patent App. Pub. No. 2010/0015711; U.S. Patent App. Pub. No. 2012/0190111; U.S. Patent App. Pub. No. 2012/0190112; U.S. Patent App. Pub. No. 2012/0196365; U.S. Patent App. Pub. No. 20100015711; U.S. Patent App. Pub. No. 2012/0190111; U.S. Patent App. Pub. No. 2012/0190112; U.S. Patent App. Pub. No. 2012/0196365; U.S. Patent App. Pub. No. 20100015711; U.S. Patent App. Pub. No. 2012/0190111; U.S. Patent App. Pub. No. 2012/0190112; U.S. Patent App. Pub. No. 2012/0196365; U.S. Provisional Patent Application No. 61/076,900; U.S. Provisional Patent Application No. 61/076,908; and U.S. Provisional Patent Application No. 61/076,915, which are incorporated by reference in their entireties as they relate to pluripotent stem cells and to the differentiation of pluripotent stem cells into cells expressing markers characteristic of the definitive endoderm lineage.

In one embodiment of the invention, pluripotent stem cells are treated with a medium supplemented with activin A and WNT3A to result in the generation of cells expressing markers characteristic of definitive endoderm cells. Treatment may involve contacting pluripotent stem cells with a medium containing about 50 ng/ml to about 150 ng/ml, alternatively about 75 ng/ml to about 125 ng/ml, alternatively about 100 ng/ml of activin A. The treatment may also involve contacting the cells with about 10 ng/ml to about 50 ng/ml, alternatively about 15 ng/ml to about 30 ng/ml, alternatively about 20 ng/ml of WNT3A. The pluripotent cells may be cultured for approximately two to five days, preferably about three days, to facilitate their differentiation into cells expressing markers characteristic of definitive endoderm cells. In one embodiment, the cells are cultured in the presence of activin A and WNT3A for one day, followed by culturing in the presence of activin A (without WNT3A being present) for the remainder.

In another embodiment of the invention, pluripotent stem cells are treated with a medium supplemented with growth differentiation factor 8 ("GDF8") and a glycogen synthase kinase-3 β ("GSK3β") inhibitor (such as the cyclic aniline-pyridinotriazine compounds disclosed in U.S. Patent App. Pub. No. 2010/0015711; incorporated herein by reference in its entirety) to induce differentiation into cells expressing markers characteristic of definitive endoderm cells. A preferred GSK3β inhibitor is 14-Prop-2-en-1-yl-3,5,7,14,17,23, 27-heptaazatetracyclo [19.3.1.1~2,6~0.1~8,12~]heptacosa- 1(25),2(27),3,5,8(26),9,11,21,23-nonaen-16-one, referred to herein as ("MCX Compound"). Treatment may involve contacting pluripotent stem cells with a medium supplemented with about 50 ng/ml to about 150 ng/ml, alternatively about 75 ng/ml to about 125 ng/ml, alternatively about 100 ng/ml of GDF8. The treatment may also involve contacting the cells with about 0.1 to 5 μM, alternatively about 0.5 to about 2.5 μM, preferable about 1 μM of MCX compound. The pluripotent cells may be cultured for approximately two to five days, preferably two to three days, to facilitate their differentiation into cells expressing markers characteristic of definitive endoderm cells.

In one embodiment, the cells are cultured in the presence of GDF8 and MCX compound for one day, followed by culturing in the presence of GDF8 and a lower concentration of MCX compound for one day, followed by culturing in the presence of GDF8 for one day in the absence of the MCX compound. In particular, the cells are cultured in the presence of GDF8 and about 1 μM of MCX compound for one day, followed by culturing in the presence of GDF8 and about 0.1 μM of MCX compound for one day, followed by culturing in the presence of GDF8 for one day in the absence of the MCX compound. In an alternate embodiment, the cells are cultured in the presence of GDF8 and about 1 μM of MCX compound for one day, followed by culturing in the presence of GDF8 and about 0.1 μM MCX compound for one day.

Generation of cells expressing markers characteristic of definitive endoderm cells may be determined by testing for the presence of the markers before and after following a particular protocol. Pluripotent stem cells typically do not express such markers. Thus, differentiation of pluripotent cells can be detected when the cells begin to express markers characteristic of definitive endoderm cells. Methods for assessing expression of protein and nucleic acid markers in cultured or isolated cells are standard in the art. These methods include RT-PCR, Northern blots, in situ hybridization (see, e.g., Current Protocols in Molecular Biology (Ausubel et al., eds. 2001 supplement)), and immunoassays (such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Additionally, the efficiency of differentiation may be determined by exposing a treated cell population to an agent (such as an antibody) that specifically recognizes a protein marker expressed by the differentiated cells of interest.

The differentiated cells may also be further purified. For example, after treating pluripotent stem cells with the methods of the present invention, the differentiated cells may be purified by exposing a treated cell population to an agent (such as an antibody) that specifically recognizes a protein marker characteristically expressed by the differentiated cells being purified.

Stage 2: Differentiation of cells expressing markers characteristic of definitive endoderm cells into cells expressing markers characteristic of gut tube cells The cells expressing markers characteristic of definitive endoderm cells may be further differentiated into cells expressing markers characteristic of gut tube cells. In one embodiment, the formation of cells expressing markers characteristic of gut tube cells includes culturing the cells expressing markers characteristic of definitive endoderm cells with a medium containing fibroblast growth factor ("FGF") 7 or FGF10 to differentiate these cells. For example, the culture medium may include from about 25 ng/ml to about 75 ng/ml, alternatively from about 30 ng/mL to about 60 ng/ml, alternatively about 50 ng/ml of FGF7 or FGF10, preferably FGF7. The cells may be cultured under these conditions for about two to three days, preferably about two days.

In another embodiment, differentiation into cells expressing markers characteristic of gut tube cells includes culturing cells expressing markers characteristic of definitive endoderm cells with FGF7 or FGF10 and ascorbic acid (Vitamin C). The culture medium may include from about 0.1 mM to about 0.5 mM ascorbic acid, alternatively from about 0.2 mM to about 0.4 mM, alternatively about 0.25 mM of ascorbic acid. The culture medium may also include from about 10 ng/ml to about 35 ng/ml, alternatively from about 15 ng/ml to about 30 ng/ml, alternatively about 25 ng/ml of FGF7 or FGF10, preferably FGF7. For example, the culture medium may include about 0.25 mM of ascorbic acid and about 25 ng/ml of FGF7. In one embodiment, the Stage 1 cells are treated for 2 days with FGF7 and ascorbic acid.

Stage 3: Differentiation of cells expressing markers characteristic of gut tube cells into cells expressing markers characteristic of foregut endoderm cells Cells expressing markers characteristic of gut tube cells may be further differentiated into cells expressing markers characteristic of foregut endoderm cells. In one embodiment, Stage 2 cells are further differentiated into Stage 3 cells by culturing these cells in a culture medium supplemented with a Smoothened ("SMO") receptor inhibitor (such as "MRT10" (N-[[[3-benzoylamino)phenyl]amino]thioxomethyl]-3,4,5-trimethoxybenzamide)) or Cyclopamine) or a Sonic Hedgehog ("SHH") signaling pathway antagonist (such as Smoothened Antagonist 1 ("SANT-1") ((E)-4-benzyl-N-((3,5-dimethyl-1-phenyl-1H-pyrazol-4-yl)methylene-piperazin-1-amine)), or Hedgehog Pathway Inhibitor 1 ("HPI-1") (2-methoxyethyl 1,4,5,6,7,8-hexahydro-4-(3-hydroxyphenyl)-7-(2-methoxyphenyl)-2-methyl-5-oxo-3-quinolinecarboxylate)), retinoic acid, and Noggin. Alternatively, Stage 2 cells may be differentiated into Stage 3 cells by culturing these cells in a culture medium supplemented with a SMO receptor inhibitor, SHH signaling pathway antagonist, retinoic acid, and Noggin. The cells may be cultured for approximately two to four days, preferably about two days. In one embodiment, the medium is supplemented with from about 0.1 μM to about 0.3 μM of SANT-1, from about 0.5 μM to about 3 μM of retinoic acid and from about 75 ng/ml to about 125 ng/ml of Noggin. In another embodiment, the medium is supplemented with about 0.25 μM of SANT-1, about 2 μM of retinoic acid and about 100 ng/ml of Noggin.

In an alternate embodiment, Stage 2 cells are further differentiated into Stage 3 cells by treating the Stage 2 cells with a medium supplemented with FGF7 or FGF10, retinoic acid, a SMO receptor inhibitor (such as MRT10 or Cyclopamine) or SHH signaling pathway antagonist (such as SANT-1 or HPI-1), a protein kinase C ("PKC") activator (such as ((2S,5S)-(E,E)-8-(5-(4-(Trifluoromethyl)phenyl)-2,4-pentadienoylamino)benzolactam ("TPB")) EMD Chemicals, Inc., Gibbstown, N.J.), phorbol-12,13-dibutyrute ("PDBu"), phorbol-12-myristate-13-acetate ("PMA") or indolactam V ("ILV")), a bone morphogenic protein ("BMP") inhibitor (such as LDN-193189, Noggin or Chordin), and ascorbic acid. In another embodiment, the medium may be supplemented with FGF7 or FGF10, retinoic acid, an SMO receptor inhibitor, an SHH signaling pathway antagonist (such as SANT-1), a PKC activator (such as TPB), a BMP inhibitor (such as LDN-193189), and ascorbic acid. The cells may be cultured in the presence of these growth factors, small molecule agonists, and antagonists for about two to four days, preferably about two to three days.

In a further embodiment, the medium is supplemented with from about 15 ng/ml to about 35 ng/ml of FGF7, from about 0.5 µM to about 2 µM of retinoic acid, from about 0.1 µM to about 0.4 µM of SANT-1, from about 100 to about 300 nM of TPB, from about 50 nM to about 200 nM of LDN-193189, and from about 0.15 mM to about 0.35 mM of ascorbic acid. In another embodiment, the medium is supplemented with about 25 ng/ml of FGF7, about 1 µM of retinoic acid, about 0.25 µM of SANT-1, about 200 nM of TPB, about 100 nM of LDN-193189, and from about 0.25 mM of ascorbic acid.

Generation of Stage 4 to Stage 6 Cells by Culturing at the Air-liquid Interface

Although the present invention contemplates culturing at the air-liquid interface for all stages in the path from pluripotent cell to pancreatic endocrine cell, the invention preferably provides for the formation of Stage 1 to Stage 3 cells in submerged culture, and Stage 4 to Stage 6 cells by culturing cells at the air-liquid interface. Accordingly, in certain embodiments, the present invention provides a stepwise method of differentiating pluripotent cells comprising culturing during Stages 4 to 6 at the air-liquid interface. In certain embodiments, cells may be cultured at the air-liquid interface during the entirely of Stages 4 through 6. In other embodiments, only late Stage 4 to Stage 6, or only Stages 5 and 6, or only Stages 4 and 5, or only Stages 4 and 6 include culturing at the air-liquid interface.

When cells are cultured at the air-liquid interface (air-liquid interface), the cells may be cultured on a porous substrate such that the cells are in contact with air on the top side and with cell culture media at the bottom side. For example, a sufficient volume of media may be added to the bottom of a culture vessel containing the porous substrate (e.g. a filter insert) such that the media contacts the bottom surface of cells residing on the substrate but does not encapsulate or submerge them. Suitable porous' substrates can be formed of any material that will not adversely affect the growth and differentiation of the cells. Exemplary porous substrates are made of polymers such as polyethylene terephthalate (PET), polyester, or polycarbonate. Suitable porous substrates may be coated or uncoated. In one embodiment, the porous substrate may be coated with MATRIGEL™. In one embodiment of the invention, the porous substrate is a porous filter insert, which may be coated with MATRIGEL™. Preferably, however, the porous substrate is an uncoated filter insert. The porosity of the substrate should be sufficient to maintain cell viability and promote differentiation of the cells. Suitable substrates include filter inserts having a pore size of from about 0.3 to about 3.0 µm, about 0.3 to about 2.0 µm, about 0.3 to about 1.0 µm, about 0.3 to about 0.8 µm, about 0.3 to about 0.6 µm, about 0.3 to about 0.5 µm, about 0.5 to about 3.0 µm, about 0.6 to about 3.0 µm, about 0.8 to about 3.0 µm, about 1.0 to about 3.0 µm, about 2.0 µm to about 3.0 µm, preferably about 0.4 µm, and a pore density of from about 50 to about 120 million pores/cm$^2$, about 60 to about 110 million pores/cm$^2$, about 70 to about 100 million pores/cm$^2$, preferably about 80 to about 100 million pores/cm$^2$, about 90 to about 100 million pores/cm$^2$, more preferably about 100 million pores/cm$^2$ The media may advantageously be exchanged or refreshed daily or every other day. The cells grown on top of the porous substrate are generally not single cells, rather they are in the form of a sheet or exist as an aggregate cluster of cells. Cells cultured at the air-liquid interface may experience much higher oxygen tension as compared to cells submerged in media.

The present invention thus encompasses the generation of Stage 4 to Stage 6 cells, preferably Stage 5 and Stage 6 cells, at the air-liquid interface. Stage 4 cells may be cultured entirely in planar cultures, entirely at the air-liquid interface, or the cells may be cultured in submerged planar culture during the early portion of Stage 4 and then cultured at the air-liquid interface for the latter portion of Stage 4. These cells may be produced by differentiating pluripotent stem cells or by further differentiating Stage 3, 4 or 5 cells derived from other means.

In one embodiment, the present invention provides a method for producing cells expressing markers characteristic of pancreatic endocrine cells, preferably β cells, from pluripotent stem cells, comprising culturing pluripotent stem cells, differentiating the pluripotent stem cells into cells expressing markers characteristic of foregut endoderm cells; and differentiating the cells expressing markers characteristic of foregut endoderm cells into cells expressing markers characteristic of pancreatic endocrine/β cells by culturing at the air-liquid interface.

In another embodiment, the present invention provides a method for producing cells expressing markers characteristic of pancreatic endocrine cells, preferably β cells, from pluripotent stem cells, comprising culturing pluripotent stem cells, differentiating the pluripotent stem cells into cells expressing markers characteristic of pancreatic foregut precursor cells, and differentiating the cells expressing markers characteristic of pancreatic foregut precursor cells into cells expressing markers characteristic of pancreatic endocrine cells by culturing at the air-liquid interface.

The method may include treatment with a medium supplemented with triiodothyronine (T3), thyroxine (T4), analogues of T3 or T4, or mixtures thereof (collectively referred to hereafter as "T3/T4"), or an activin receptor-like kinase ("ALK") 5 inhibitor, or both T3/T4 and an ALK5 inhibitor. Suitable thyroid hormone analogues may include: GC-1 (Sobertirome) available from R & D Systems, Inc. Catalogue #4554; DITPA (3,5-diiodothyropropionic acid); KB-141, discussed in *J. Steroid Biochem. Mol. Biol.* 2008, 111: 262-267 and *Proc. Natl. Acad. Sci. US* 2003, 100: 10067-10072; MB07344, discussed in *Proc. Natl. Acad. Sci. US* 2007, 104: 15490-15495; T0681, discussed in *PLoS One*, 2010, 5e8722 and *J. Lipid Res.* 2009, 50: 938-944; and GC-24, discussed in *PLoS One*, 2010 e8722 and *Endocr. Pract.* 2012, 18(6): 954-964, the disclosures of which are incorporated herein in their entirety. Useful ALK5 inhibitors include: ALK5 inhibitor II (Enzo, Farmingdale, N.Y.); ALK5i (Axxora, San Diego, Calif.); SD208 (R & D systems (MN)); TGF-B inhibitor SB431542 (Xcess Biosciences (San Diego, Calif.)); ITD-1 (Xcess Biosciences (San Diego, Calif.)); LY2109761 (Xcess Biosciences (San Diego, Calif.)); A83-01 (Xcess Biosciences (San Diego, Calif.)); LY2157299 (Xcess Biosciences (San Diego, Calif.)); TGF-β receptor inh V (EMD Chemicals, Gibstown, N.J.); TGF-β receptor inh I (EMD Chemicals, Gibstown, N.J.); TGF-β receptor inh IV (EMD Chemicals, Gibstown, N.J.); TGF-β receptor inh VII (EMD Chemicals, Gibstown, N.J.); TGF-β receptor inh VIII (EMD Chemicals, Gibstown, N.J.); TGF-β receptor inh II (EMD Chemicals, Gibstown, N.J.); TGF-β receptor inh VI (EMD Chemicals, Gibstown, N.J.); TGF-β receptor inh III (EMD Chemicals, Gibstown, N.J.). The method may include differentiating the cells expressing markers characteristic of foregut endoderm cells into cells expressing markers characteristic of pancreatic foregut precursor cells by treatment with a medium supplemented with T3/T4 or ALK5 inhibitor and culturing in a planar culture. The method may also include differentiating cells expressing markers characteristic of pancreatic foregut precursor cells into cells expressing markers characteristic of β cells by treatment with media supplemented with T3/T4, or an ALK5 inhibitor, or both, and culturing at the air-liquid interface.

In one embodiment, the method includes treatment with a medium supplemented with T3/T4 and an ALK5 inhibitor. In other embodiments, the method includes treating Stage 3 cells with a medium supplemented with T3/T4 or an ALK5 inhibitor. The method may also include treating cells expressing markers characteristic of pancreatic endoderm/endocrine precursor cells with a medium supplemented with T3/T4 and an ALK5 inhibitor.

One embodiment of the invention is a method of forming cells expressing markers characteristic of β cells comprising differentiating cells expressing markers characteristic of foregut endoderm cells into cells expressing markers characteristic of 0 cells by culturing at the air-liquid interface. A cell expressing markers characteristic of β cells expresses insulin and at least one of the following transcription factors: PDX1, NKX2.2, NKX6.1, NeuroD1, 1SL1, HNF3β, MAFA, PAX4, and PAX6. In one embodiment, the methods of the invention result in the formation of cells, which are positive for NKX6.1, PDX1, and HB9. Accordingly, the invention provides a method of inducing the expression of PDX1, NKX6.1 and HB9 in human cells by culturing pancreatic endoderm cells at the air-liquid interface under conditions sufficient to induce such expression. The invention also provides a method for inducing the expression of PDX1, NKX6.1 and NGN3 in human cells by culturing pancreatic endoderm cells at the air-liquid interface. The method may include treatment with a medium supplemented with T3, an ALK5 inhibitor, or both. Thus, in one embodiment, the medium may be supplemented with T3, while in another embodiment, the medium may be supplemented with an ALK5 inhibitor. In another embodiment, the medium may be supplemented with both T3 and an ALK5 inhibitor. The Stage 6 cells may be cells that are positive for NKX6.1, PDX1, and HB9. In other embodiments, the Stage 6 cells are single hormone positive cells. For example, the Stage 6 cells may be cells that (a) co-express NKX6.1 and chromogranin-A or (b) co-express NKX6.1 and insulin.

Culturing of the cells at the air-liquid interface includes seeding the cells on a porous substrate such as a porous filter insert. In certain embodiments, the substrate pore size may range from about 0.4 to about 3 microns, or any of the pore sizes mentioned herein. Seeding may be accomplished by releasing cells as single cells or clusters of cells from monolayer cultures into a suspension and subsequently aliquoting the cell suspension onto a porous substrate positioned at the air-liquid interface. The cells may be seeded onto the porous substrate from a suspension comprising about 1000 cells/μl to about 100,000 cells/μl, about 1000 cells/μl to about 90,000 cells/μl, about 1000 cells/μl to about 80,000 cells/μl, about 1000 cells/μl to about 70,000 cells/μl, about 1000 cells/μl to about 60,000 cells/μl, about 1000 cells/μl to about 50,000 cells/μl, about 1000 cells/μl to about 40,000 cells/μl, about 1000 cells/μl to about 30,000 cells/μl, about 1000 cells/μl to about 20,000 cells/μl, about 1000 cells/μl to about 10,000 cells/μl, about 1000 cells/μl to about 5000 cells/μl, about 5000 cells/μl to about 100,000 cells/μl, about 10,000 cells/μl to about 100,000 cells/μl, about 20,000 cells/μl to about 100,000 cells/μl, about 30,000 cells/μl to about 100,000 cells/μl, about 40,000 cells/μl to about 100,000 cells/μl, about 50,000 cells/μl to about 100,000 cells/μl, about 60,000 cells/μl to about 100,000 cells/μl, about 20,000 cells/μl to about 80,000 cells/μl, about 30,000 cells/μl to about 70,000 cells/μl, about 40,000 cells/μl to about 60,000 cells/μl, preferably about 50,000 cells/μl. The cells may be seeded as droplets of the cell suspension containing individual cells or clumps of cells. The resulting cell deposit may contain from about $5 \times 10^6$ to about $5 \times 10^7$ cells/cm$^2$, about $6 \times 10^6$ to about $5 \times 10^7$ cells/cm$^2$, about $7 \times 10^6$ to about $5 \times 10^7$ cells/cm$^2$, about $8 \times 10^6$ to about $5 \times 10^7$ cells/cm$^2$, about $9 \times 10^6$ to about $5 \times 10^7$ cells/cm$^2$, about $1 \times 10^7$ to about $5 \times 10^7$ cells/cm$^2$, about $2 \times 10^7$ to about $5 \times 10^7$ cells/cm$^2$, about $2 \times 10^7$ to about $5 \times 10^7$ cells/cm$^2$, about $3 \times 10^7$ to about $5 \times 10^7$ cells/cm$^2$, about $3 \times 10^7$ to about $5 \times 10^7$ cells/cm$^2$, about $4 \times 10^7$ to about $5 \times 10^7$ cells/cm$^2$, about $5 \times 10^6$ to about $4 \times 10^7$ cells/cm$^2$, about $5 \times 10^6$ to about $3 \times 10^7$ cells/cm$^2$, about $5 \times 10^6$ to about $2 \times 10^7$ cells/cm$^2$, about $5 \times 10^6$ to about $1 \times 10^7$ cells/cm$^2$, about $5 \times 10^6$ to about $9 \times 10^6$ cells/cm$^2$, about $5 \times 10^6$ to about $8 \times 10^6$ cells/cm$^2$, about $5 \times 10^6$ to about $7 \times 10^6$ cells/cm$^2$, about $5 \times 10^6$ to about $6 \times 10^6$ cells/cm$^2$, about $7 \times 10^6$ to about $4 \times 10^7$ cells/cm$^2$, about $8 \times 10^6$ to about $3 \times 10^7$ cells/cm$^2$, about $9 \times 10^6$ to about $2 \times 10^7$ cells/cm$^2$, preferably on the order of or about $1 \times 10^7$ cells/cm$^2$.

In one embodiment, the invention relates to a method of enhancing expression of HB9 protein by culturing and differentiating a population of PDX1 and NKX6.1 co-positive pancreatic endoderm precursor cells into PDX1 and NKX6.1 co-positive pancreatic endocrine cells at the air-liquid interface on a porous substrate. Alternatively, HB9 protein expression can be induced by culturing and differentiating a population of foregut endoderm cells, consisting primarily of PDX1 positive cells, at the air-liquid interface. In some embodiments, the population of pancreatic endoderm cells is obtained by a stepwise differentiation of pluripotent cells at least, in part, at the air-liquid interface.

In another embodiment, the invention provides a method of enhancing the number of single hormone positive cells (e.g. cells that co-express NKX6.1 and insulin or cells that produce NKX6.1 and chromogranin-A) by culturing and differentiating a population of PDX1 and NKX6.1 co-expressing cells at an air-liquid interface. In another embodiment, pancreatic endoderm cells cultured at the air-liquid interface are further differentiated to pancreatic endocrine cells by treatment with a compound selected from the following: ALK5 inhibitor, BMP inhibitor, gamma-secretase inhibitor, Ephrin ligands, EphB inhibitor, PKC inhibitor, EGFr inhibitor, retinoic acid, vitamin C, T3/T4, glucose, cell cycle regulators, WNT regulators, SHH inhibitor, or combinations thereof.

In some embodiments, pancreatic endoderm cells cultured at the air-liquid interface are further differentiated into pancreatic endocrine precursor cells and to pancreatic hormone expressing cells. In an alternate embodiment, the invention encompasses cells prepared by the methods of the invention that express insulin but not NKX6.1. In some embodiments, a pancreatic endoderm population generated at the air-liquid interface is transplanted into diabetic animals for further in vivo maturation to functional pancreatic endocrine cells.

Stage 4: Differentiation of cells expressing markers characteristic of foregut endoderm cells into cells expressing markers characteristic of pancreatic foregut precursor cells In one embodiment, the methods of the invention include treating Stage 3 cells with a differentiation medium comprising a growth medium supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-B inhibitor SB431542, SD208, ITD-1, LY2109761, A83-01, LY2157299, ALK5i and ALK5 inhibitor II; (b) a thyroid hormone selected from the group consisting of T3, T4, analogues of T3, analogues of T4 and mixtures thereof; (c) a smoothened receptor inhibitor selected from MRT10 or cyclopamine; (d) a SHH signaling pathway antagonist selected from SANT-1 or HPI-1; (e) a BMP Receptor Inhibitor selected from LDN-193189, Noggin or Chordin; (f) a PKC activator selected from TPB, PDBu, PMA, and ILV; (g) a fibroblast growth factor selected from FGF7 or FGF10; (h) retinoic acid; (i) ascorbic acid; (j) heparin; and (k) zinc sulfate. For example, a growth medium such as MCDB131 or BLAR may be supplemented with a SMO inhibitor (such as MRT10 or Cyclopamine) or SHH signaling pathway antagonist (such as SANT-1 or HPI-1), a BMP inhibitor (such as LDN-193189, Noggin or Chordin), ascorbic acid, and a PKC activator (such as TPB, PDBu, PMA or ILV), to provide a useful differentiation media. Culturing Stage 3 cells in such medium for about two to four days, preferably about three days, usually is sufficient to differentiate the Stage 3 cells into Stage 4 cells. In another embodiment, the medium may be supplemented with a SMO inhibitor and SHH signaling pathway antagonist. In a preferred embodiment, the Stage 3 cells may be treated with a medium supplemented with about 0.25 µM SANT-1; about 100 nM retinoic acid; about 2 ng/ml FGF7; about 100 nM LDN-193189; about 0.25 mM ascorbic acid; and about 100 nM TPB for three days. In another embodiment, the medium is further supplemented with T3, such as from about 5 nM to about 25 nM, alternatively about 10 nM of T3.

In Stage 4, the cells may be cultured on a planar culture or at the air-liquid interface. Specifically, the present invention provides an in vitro cell culture for differentiating cells derived from pluripotent stem cells at the air-liquid interface comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (e) cells derived from pluripotent stem cells disposed upon the surface of said substrate such that said medium contacts only a portion of the surface of said cells. Alternatively, cells expressing markers characteristic of foregut endoderm cells can be differentiated into cells expressing markers characteristic of pancreatic foregut precursor cells by treatment with a medium supplemented as described above in a planar culture.

In a further embodiment, the cells at the end of Stage 4 may be treated with a Rho-associated kinase ("ROCK") inhibitor such as Y27632 ((1R,4r)-4-((R)-1-aminoethyl)-N-(pyridin-4-yl)cyclohexanecarboxamide), GSK269962 (N-[3-[[2-(4-Amino-1,2,5-oxadiazol-3?-yl)-1-ethyl-1H-imidazo[4,5-c]pyridin-6-yl]oxy]phenyl]-4-[2-(4-morpholinyl)ethoxy]benzamide), H1152 ((S)-(+)-2-Methyl-1-[(4-methyl-5-isoquinolinyl)sulfonyl]homopiperazine, 2HCl,) and, SR3677 (N-[2-[2-(Dimethylamino)ethoxy]-4-(1H-pyrazol-4-yl)phenyl-2,3-dihydro-1,4-benzodioxin-2-carboxamide dihydrochloride). In certain embodiments about 10 µM of the ROCK inhibitor may be used.

In certain embodiments, only late in Stage 4 are cells cultured at the air-liquid interface. In one embodiment, only late Stage 4 cells that were treated with a ROCK inhibitor are cultured at the air-liquid interface. In certain embodiments, the cells may be treated with a cell detachment solution, such as a solution containing proteolytic and collagenolytic enzymes prior to culturing at the air-liquid interface.

In an alternate embodiment, Stage 3 cells may be treated with a differentiation medium comprising a growth medium supplemented with an ALK5 inhibitor, Noggin, and a PKC activator (such as TPB). In certain embodiments, the medium may be supplemented with about 0.1 µM ALK5 inhibitor, about 100 ng/mL of Noggin, and about 500 nM TPB. The cell culture may be in a monolayer format. The treatment may last for a total of about three days. In certain embodiments, the cells may be treated for two days and then on the last day the cells may be treated with proteolytic enzymes, collagenolytic enzymes or both, such as dispase, and broken into cell clusters having a diameter of less than about 100 microns followed by culturing in the presence of an ALK5 inhibitor and LDN-193189. In certain embodiments, the cell clusters having a diameter of less than about 100 microns may be cultured in a medium supplemented with about 200 nM ALK5 inhibitor and about 100 nM LDN-193189.

Stage 5: Differentiation of cells expressing markers characteristic of pancreatic foregut precursor cells into cells expressing markers characteristic of pancreatic endoderm/endocrine precursor cells In one embodiment, the methods of the invention include treating Stage 4 cells with a differentiation medium comprising a growth medium supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-B inhibitor SB431542, SD208, ITD-1, LY2109761, A83-01, LY2157299, ALK5i and ALK5 inhibitor II; (b) a thyroid hormone selected from the group consisting of T3, T4, analogues of T3, analogues of T4 and mixtures thereof; (c) a smoothened receptor inhibitor selected from MRT10 or cyclopamine; (d) a SHH signaling pathway antagonist selected from SANT-1 or HPI-1; (e) a BMP Receptor Inhibitor selected from LDN-193189, Noggin or Chordin; (f) a PKC activator selected from TPB, PDBu, PMA, and ILV; (g) a fibroblast growth factor selected from FGF7 or FGF10; (h) retinoic acid; (i) ascorbic acid; (j) heparin; and (k) zinc sulfate, and culturing the cells at the air-liquid interface for about two to four days, preferably about three days, to differentiate the cells into Stage 5 cells. In another embodiment, the growth medium is supplemented with a SMO inhibitor (such as MRT10 or cyclopamine) or SHH signaling pathway antagonist (such as SANT-1 or HPI-1), retinoic acid, T3, ascorbic acid, a BMP Receptor Inhibitor (such as LDN-193189, Noggin, or Chordin) and an ALK5 inhibitor. In another embodiment, the methods of the invention include treating Stage 4 cells with a medium supplemented with a SMO inhibitor, SHH signaling pathway antagonist, retinoic acid, T3, ascorbic acid, a BMP Receptor Inhibitor and an ALK5 inhibitor and culturing the cells at the air-liquid interface for about two to four days, preferably about three days, to differentiate the cells into Stage 5 cells. In one embodiment, the Stage 4 cells are differentiated into Stage 5 cells by treating the cells with a medium supplemented with about 0.25 µM SANT-1, about 50 nM retinoic acid, about 0.25 mM ascorbic acid, about 50 nM LDN-193189, about 10 nM of T3 and about 1000 nM ALK5 inhibitor. In certain embodiments, the ALK5 inhibitor is SD208 ((2-(5-Chloro-2-fluorophenyl)pteridin-4-yl]pyridin-4-yl-amine). In one embodiment, the medium is supplemented with about 1000 nM of SD208.

In yet another embodiment, the methods of the invention include treating Stage 4 cells with a medium supplemented with heparin, a SMO inhibitor or SHH signaling pathway antagonist, retinoic acid, a BMP Receptor Inhibitor and an ALK5 inhibitor and culturing the cells at the air-liquid interface for about two to four days, preferably about three days, to differentiate the cells into Stage 5 cells. In an alternate embodiment, the medium may be supplemented with both a SMO inhibitor and SHH signaling pathway antagonist, along with retinoic acid, a BMP Receptor Inhibitor and an ALK5 inhibitor.

The medium may further be supplemented with $ZnSO_4$. For example, about 10 μM $ZnSO_4$ may be added. Thus, in one embodiment, the Stage 4 cells may be differentiated into Stage 5 cells by treating the Stage 4 cells with a medium supplemented with heparin, $ZnSO_4$, a SMO inhibitor or SHH signaling pathway antagonist, retinoic acid, LDN-193189 and ALK5 inhibitor II. In an alternate embodiment, the medium may be supplemented with both a SMO inhibitor and SHH signaling pathway antagonist. In one embodiment, the Stage 4 cells are differentiated into Stage 5 cells by treating the cells with a medium supplemented with about 10 μg/ml of heparin, about 0.25 μM SANT-1, about 50 nM retinoic acid, about 50 nM LDN-193189, about 10 nM of T3 and about 1000 nM ALK5 inhibitor. Suitable ALK5 inhibitors include but are not limited to SD208, ALK5 inhibitor II, TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III and combinations thereof.

In one embodiment, the ALK5 inhibitor is ALK5 inhibitor II. In another embodiment, about 1000 nM of ALK5 inhibitor II is used. In an alternate embodiment, the Stage 4 cells are treated with a medium supplemented with about 10 μg/ml of heparin, about 0.25 μM SANT-1, about 50 nM retinoic acid, about 100 nM LDN-193189, and about 10000 nM of ALK5 inhibitor II.

In yet another alternate embodiment, the methods of the invention include treating Stage 4 cells with a medium supplemented with a SMO inhibitor or SHH signaling pathway antagonist, retinoic acid, and an ALK5 inhibitor and culturing the cells at the air-liquid interface for about 2 days to differentiate the cells into Stage 5 cells. In an alternate embodiment, the medium may be supplemented with both a SMO inhibitor and SHH signaling pathway antagonist. In one embodiment, the Stage 4 cells are differentiated into Stage 5 cells by treating the cells with a medium supplemented with about 0.25 μM SANT-1, about 50 nM retinoic acid, about 50 nM LDN-193189, and about 1000 nM of an ALK5 inhibitor (such as SD208 or ALK5 inhibitor II). In certain embodiments, the medium may be MCDB-131 (Life Technologies Corporation, Grand Island, N.Y.).

The amount of cells seeded for culturing at the air-liquid interface may vary. For example, to culture the cells at the air-liquid interface, droplets of a cell suspension containing from about $2\times10^5$ cells/μl to about $6\times10^5$ cells/μl, $3\times10^5$ cells/μl to about $6\times10^5$ cells/μl, $4\times10^5$ cells/μl to about $6\times10^5$ cells/μl, $5\times10^5$ cells/μl to about $6\times10^5$ cells/μl, $2\times10^5$ cells/μl to about $5\times10^5$ cells/μl, $2\times10^5$ cells/μl to about $4\times10^5$ cells/μl, or about $3\times10^5$ cells/μl may be seeded onto a porous substrate such as a filter located at the air-liquid interface. In some embodiments, droplets of a cell suspension containing from about $0.5\times10^5$ cells/μl to about $0.75\times10^5$ cells/μl about $0.6\times10^5$ cells/μl to about $0.75\times10^5$ cells/μl or about $0.5\times10^5$ cells/μl to about $0.6\times10^5$ cells/μl are seeded onto a porous support to be cultured at the air-liquid interface.

In another embodiment, the methods of the invention include treating Stage 4 cells with a medium supplemented with a BMP Receptor Inhibitor (e.g., LDN-193189, Noggin or Chordin) and an ALK5 inhibitor for about 1 day to differentiate Stage 4 cells into Stage 5 cells. For example, the medium may be supplemented with about 100 nM of LDN-193189 and with about 200 nM of ALK5 inhibitor. Preferably, this embodiment also includes pre-treating the cells with dispase. The cells may be in the form of clusters. In certain embodiments, the cells may be treated with a cell detachment solution, such as a solution containing proteolytic and collagenolytic enzymes prior to culturing at the air-liquid interface. In one embodiment, Stage 4 cells cultured according to embodiments of the invention are utilized and differentiated into Stage 5 cells, while in other embodiments Stage 4 cells cultured according to other protocols may be utilized.

In accordance with the foregoing method, the invention further provides a cell culture for differentiating cells expressing markers characteristic of pancreatic foregut precursor cells into cells expressing markers characteristic of pancreatic endoderm/pancreatic endocrine precursor cells comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (e) cells expressing markers characteristic of pancreatic foregut precursor cells derived from pluripotent stem cells disposed upon the surface of said substrate such that said medium contacts only a portion of the surface of said cells.

In certain embodiments, culturing cells in Stage 5 at the air-liquid interface may enhance expression of pancreatic hormones. Accordingly, the invention also provides for methods of enhancing expression of pancreatic hormones by culturing cells at the air-liquid interface. In some embodiments, the cells in Stage 5 may be treated as described herein and in the Tables VIII to XIII below. In certain embodiments, the method may also reduce expression of PTF1a, SOX9, CDX2 (intestine marker), ZIC1 (ectoderm marker), and SOX2 (anterior endoderm marker).

In one embodiment, the method includes differentiating cells expressing markers characteristic of pancreatic foregut precursor cells into cells expressing markers characteristic of pancreatic endocrine cells by treatment with a medium supplemented with T3/T4, or an ALK5 inhibitor or both T3/T4 and an ALK5 inhibitor and culturing at the air-liquid interface Stage 6: Differentiation of cells expressing markers characteristic of pancreatic endoderm/pancreatic endocrine precursor cells into cells expressing markers characteristic of pancreatic endocrine cells In one embodiment of the invention, the methods include treating Stage 5 cells with a differentiation medium comprising a growth medium supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-B inhibitor SB431542, SD208, ITD-1, LY2109761, A83-01, LY2157299, ALK5i and ALK5 inhibitor II; (b) a thyroid hormone selected from the group consisting of: T3, T4, analogues of T3, analogues of T4 and mixtures thereof; (c) a smoothened receptor inhibitor selected from MRT10 or cyclopamine; (d) a SHH signaling pathway antagonist selected from SANT-1 or HPI-1; (e) a BMP Receptor Inhibitor selected from LDN-193189, Noggin or Chordin; (f) a PKC activator selected from TPB, PDBu, PMA, and ILV; (g) a fibroblast growth factor selected from FGF7 or FGF10; (h) retinoic acid; (i) ascorbic acid; (j) heparin; and (k) zinc sulfate and culturing at the air-liquid interface for about two to four days, preferably about three days, to differentiate the Stage 5 cells into Stage 6 cells. In one embodiment, the growth medium is supplemented with a SMO inhibitor (such as MRT10 or Cyclopamine) or SHH signaling pathway antagonist (such as SANT-1 or HPI-1), retinoic acid, ascorbic acid, T3/T4, and an ALK5 inhibitor. In an alternate embodiment, the medium may be supplemented with both a SMO inhibitor and SHH signaling pathway antagonist. The Stage 5 cells may be differentiated into Stage 6 cells by treatment with a medium supplemented with about 0.25 µM SANT-1, about 50 nM RA, about 0.25 mM ascorbic acid, about 500 mM of ALK5 inhibitor, and about 0.1 nM of T3 for about three days. Alternatively, Stage 5 cells may be differentiated into Stage 6 cells by treatment with a medium supplemented with about 0.25 µM SANT-1, about 50 nM retinoic acid, about 0.25 mM ascorbic acid, about 500 nM ALK5 inhibitor and 10 nM T3 for about three days. The cells may be cultured in such media for an additional two days, or more, if desired.

Alternatively, Stage 5 cells may be differentiated into Stage 6 cells by treatment with a medium supplemented with heparin, a SMO inhibitor or SHH signaling pathway antagonist, a BMP inhibitor, T3/T4, and an ALK5 inhibitor and culturing at the air-liquid interface for about six to fourteen days, alternatively about 6 days, alternatively about 7 days, alternatively about 8 days, alternatively about 9 days, alternatively about 10 days, alternatively about 11 days, alternatively about 12 days, alternatively about 13 days, and alternatively about 14 days. In an alternate embodiment, the medium may be supplemented with both a SMO inhibitor and SHH signaling pathway antagonist. For example, the cells may be cultured in the medium supplemented with about 10 µg/ml of heparin, about 0.25 µM SANT-1, about 100 nM LDN-193189, about 1000 nM of T3 and about 500 to about 10,000 nM, about 1000 to about 10,000 nM, about 5000 to about 10,000 nM, about 600 to about 5000 nM, about 700 to about 5000 nM, about 800 to about 5000 nM, about 900 to about 5000 nM, about 1000 nM to about 5000 nM, about 600 to about 1000 nM, about 700 to about 1000 nM, about 800 to about 1000 nM, about 600 to about 1200 nM, about 700 to about 1200 nM, about 800 to about 1200 nM, about 900 to about 1200 nM, alternatively about 500 nM, alternatively about 1000 mM, and alternatively about 10,000 nM of an ALK5 inhibitor.

Suitable ALK5 inhibitors include but are not limited to SD208, ALK5 inhibitor II, TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III and combinations thereof.

In one embodiment, the ALK5 inhibitor is ALK5 inhibitor II. In another embodiment, about 1000 nM of ALK5 inhibitor II is used. Accordingly, in one embodiment, Stage 5 cells may be differentiated into Stage 6 cells by treatment with a medium supplemented with heparin, SMO inhibitor or SHH signaling pathway antagonist, a BMP inhibitor, T3/T4, and ALK5 inhibitor and culturing at the air-liquid interface for about six days. In an alternate embodiment, the medium may be supplemented with both a SMO inhibitor and SHH signaling pathway antagonist. In certain embodiments, the cells may be treated with a cell detachment solution, such as a solution containing proteolytic and collagenolytic enzymes prior to culturing at the air-liquid interface.

In another embodiment, Stage 5 cells may be differentiated into Stage 6 cells by treatment with a medium supplemented with heparin, a SMO inhibitor or SHH signaling pathway antagonist, a BMP inhibitor, T3, and ALK5 inhibitor II and culturing at the air-liquid interface for about 5 days to about 15 days, about 6 days to about 14 days, about 7 days to about 13 days, about 8 days to about 12 days, about 9 days to about 11 days, about 5 days to about 10 days, about 10 days to about 15 days, alternatively about 5 days, alternatively about 6 days, alternatively about 7 days, alternatively about 8 days, alternatively about 9 days, alternatively about 10 days, alternatively about 11 days, alternatively about 12 days, alternatively about 13 days, alternatively about 14 days, alternatively about 15 days. In one embodiment, the cells are cultured at the air-liquid interface for 5 days or more, 6 days or more, 7 days or more, 8 days or more, 9 days or more, 10 days or more, 11 days or more, 12 days or more, 13 days or more, 14 days or more, 15 days or more. In one embodiment, the cells are cultured at the air-liquid interface for 15 days or less, 14 days or less, 13 days or less, 12 days or less, 11 days or less, 10 days or less, 9 days or less, 8 days or less, 7 days or less, 6 days or less, 5 days or less. In one embodiment, the cells are cultured at the air-liquid interface for about 10 days. In another embodiment, the cells are cultured at the air-liquid interface for about 11 days. In an alternate embodiment, the cells are cultured at the air-liquid interface for about 12 days. In yet another embodiment, the cells are cultured at the air-liquid interface for about 15 days. In these embodiments, the medium may be supplemented with about 10 µg/ml of heparin, about 0.25 µM SANT-1, about 100 nM LDN-193189, about 1000 nM of T3 and about 10,000 nM of ALK5 inhibitor II. In certain embodiments, the medium may be further supplemented with Zinc sulfate (ZnSO$_4$). For example, the medium may be further supplemented with about 10 µM ZnSO$_4$. In an alternate embodiment, the medium may be supplemented with both a SMO inhibitor and SHH signaling pathway antagonist In accordance with the foregoing method, the invention further provides a cell culture for differentiating cells expressing markers characteristic of pancreatic endoderm/pancreatic endocrine precursor cells into cells expressing markers characteristic of pancreatic endocrine cells, comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (d) cells expressing markers characteristic of pancreatic endoderm/pancreatic endocrine precursor cells derived from pluripotent stem cells disposed upon the surface of said substrate such that said medium contacts only a portion of the surface of said cells.

In one embodiment, Stage 5 cells cultured according to embodiments of the invention are utilized and differentiated into Stage 6 cells, while in other embodiments Stage 5 cells cultured according to other protocols may be utilized.

In another embodiment, the methods of the invention result in the generation of Stage 6 cells, which are single-hormone positive. Thus, in one embodiment, the methods of the invention result in Stage 6 cells which co-express NKX6.1 and chromogranin-A. In another embodiment, the methods of the invention result in Stage 6 cells which co-express NKX6.1 and insulin.

In certain embodiments of the invention, the method employs BLAR a custom medium (see Table II) at Stages 4 to 6. The medium may preferably be exchanged every day or alternatively every other day. In certain embodiments of the invention, the methods include treating the Stage 4 to Stage 6 cells with the specified components in the amounts recited in Tables VIII to XIII, herein.

In another embodiment, the invention relates to a method of producing Stage 6 cells co-expressing NKX6.1 and chromogranin-A comprising culturing at the air-liquid interface in Stages 4 to 6, preferably Stages 5 and 6. In yet another embodiment, the invention relates to a method of producing single hormone insulin positive cells expressing NKX6.1 cells by culturing at the air-liquid interface in Stages 4 to 6, preferably Stages 5 and 6.

Culturing cells at the air-liquid interface during, or after, Stage 4 may significantly enhance expression of pancreatic endoderm markers along with endocrine-related markers. Accordingly, the invention provides for methods of enhancing expression of pancreatic endoderm and endocrine-related markers by culturing cells during, or after Stage 4 at the air-liquid interface.

In another embodiment, the invention also provides for methods of increasing the yield of NKX6.1 positive cells co-expressing insulin, chromogranin-A or chromagranin-A and insulin by culturing Stage 4 and subsequent cells at the air-liquid interface in the presence of an ALK5 inhibitor. In one embodiment, the ALK5 inhibitor is ALK5 inhibitor II. Other suitable ALK 5 inhibitors include but are not limited to, TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III and combinations thereof. In some embodiments, in addition to the ALK5 inhibitor, the cells may be treated as described in the Tables VIII to XIII below.

In one embodiment, the invention provides for methods of increasing the NKX6.1 positive cells co-expressing insulin, chromogranin-A or chromagranin-A and insulin by culturing cells during Stage 5 at the air-liquid interface in the presence of ALK5 inhibitor II. In one embodiment, the method further comprises culturing cells during Stage 5 in the presence of ALK5 inhibitor II and T3.

In vivo Maturation of Stage 6 Cells

In certain embodiments of the invention, Stage 6 cells prepared in accordance with the methods of the invention may be further matured in vivo. In one embodiment, these cells may be matured further by in vivo transplantation into a mammal. For example, the cells may be transplanted under the kidney capsule of a mouse. In one embodiment, the Stage 6 cells that are further matured in vivo are cells that co-express NXK6.1 and insulin. In another embodiment, the Stage 6 cells that are further matured in vivo are cells that co-express NXK6.1 and chromogranin. In an alternate embodiment, in vivo maturation of (a) cells that co-express NXK6.1 and insulin or (b) cells that co-express NXK6.1 and chromagranin results in early C-peptide production. In certain embodiments, the level of C-peptide production from transplanting approximately 3 million Stage 6 cells is similar to the amount of C-peptide produced by transplanting approximately 3,000 human islets.

Culturing at the air-liquid interface according to the methods described herein is also well-suited for use in screening compounds for their effect on the secretion of pancreatic hormones and endocrine markers. In particular, Stage 4 to Stage 6 cells cultured at the air-liquid interface can be used in various culture formats, including from 384 to 6-well formats, to evaluate the effect that the inclusion of a variety of small molecules or biologics, at various doses and time intervals, have on subsequent expression of pancreatic endoderm, pancreatic endocrine precursor, pancreatic endocrine, and pancreatic 0 cell markers. Such an evaluation may be accomplished by measuring gene expression by PCR, protein expression by FACS, immune staining, or by ELISA for secretion of factors by cells affected by the addition of the small molecules or biologics.

Cells Obtainable by the Methods of the Invention

The invention also provides a cell or population of cells obtainable by a method of the invention. The invention also provides a cell or population of cells obtained by a method of the invention.

The invention also provides a cell or population of cells, preferably expressing markers characteristic of pancreatic endocrine cells, characterized by significant co-expression of NKX6.1 and chromogranin-A. The invention also provides an insulin positive cell or a population of insulin positive cells, preferably expressing markers characteristic of pancreatic endocrine cells, characterized by NKX6.1 expression (optionally >30%). These are previously undescribed cell populations as explained in Example 10.

Methods for Treatment

The invention provides methods of treatment. In particular, the invention provides methods for treating a patient suffering from, or at risk of developing, diabetes.

The invention also provides a cell or population of cells obtainable or obtained by a method of the invention for use in a method of treatment. In particular, the invention provides a cell or population of cells obtainable or obtained by a method of the invention for use in a method of treating a patient suffering from, or at risk of developing, diabetes.

The diabetes may be Type 1 or Type 2 diabetes.

In one embodiment, the method of treatment comprises implanting cells obtained or obtainable by a method of the invention into a patient.

In one embodiment, the method of treatment comprises
differentiating pluripotent stem cells in vitro into Stage 1, Stage 2, Stage 3, Stage 4, Stage 5 or Stage 6 cells, for example as described herein,
and implanting the differentiated cells into a patient.

In one embodiment, the method further comprises the step of culturing pluripotent stem cells, for example as described herein, prior to the step of differentiating the pluripotent stem cells.

In one embodiment, the method further comprises the step of differentiating the cells in vivo, after the step of implantation.

In one embodiment, the patient is a mammal, preferably a human.

In one embodiment, the cells may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells in vivo, additional factors, such as growth factors, antioxidants or anti-inflammatory agents, can be administered before, simultaneously with, or after the administration of the cells. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one embodiment, the method of treatment further comprises incorporating the cells into a three-dimensional support prior to implantation. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

EXAMPLES

Example 1

Culturing Pancreatic Endocrine Precursor Cells at the Air-liquid Interface

This example examines and demonstrates that pancreatic endocrine precursor cells (Stage 5 cells) can be further matured upon culturing at the air-liquid interface. To culture pancreatic endocrine precursor cells at the air-liquid interface, embryonic stem cells were differentiated into pancreatic endocrine precursor cells based on the protocol discussed below.

Cells of the human embryonic stem cell line H1 were seeded as single cells at $1 \times 10^5$ cells/cm$^2$ on MATRIGEL™ (1:30 dilution; BD Biosciences, Franklin Lakes, N.J.)-coated dishes in mTESR®1 media (StemCell Technologies, Vancouver, Canada) supplemented with 10 µM of Y27632 (Rock inhibitor, Catalog No. Y0503, Sigma-Aldrich, St. Louis, Mo.). Forty-eight hours post-seeding, the cultures were washed in incomplete PBS (phosphate buffered saline without Mg or Ca). The cells were then differentiated according to the following protocol:

a) Stage 1: (3 days): 60-70% confluent adherent cultures of undifferentiated H1 cells plated on 1:30 MATRIGEL™ coated surfaces were exposed to GIBCO® RPMI 1640 medium (Life Technologies Corporation, Grand Island, N.Y.) supplemented with 0.2% fetal bovine serum (FBS) (Hyclone, Utah), 100 ng/ml activin-A (AA; Pepro-tech; Rocky Hill, N.J.), and 20 ng/ml of Wnt3A (R&D Systems, Inc., Minneapolis, Minn.) for day one only. For the next two days, the cells were cultured in GIBCO® RPMI with 0.5% FBS and 100 ng/ml AA.

b) Stage 2: (3 days): The Stage 1 cells were then exposed to Dulbecco's modified eagle's medium (DMEM-F12) (Life Technologies Corporation, NY) supplemented with 2% FBS and 50 ng/ml of FGF7 (Pepro-tech) for three days.

c) Stage 3: (4 days): The Stage 2 cells were then cultured for four days in DMEM-HG medium (Life Technologies Corporation, Grand Island, N.Y.) supplemented with 0.25 µM SANT-1 (Sigma-Aldrich; St. Louis, Mo.), 2 µM retinoic acid (Sigma-Aldrich), 100 ng/ml of Noggin (R&D Systems), and 1% (v/v) of a supplement sold under the trademark B27® by Life Technologies Corporation, Grand Island, N.Y. (Catalogue#: 17504044).

d) Stage 4: (3 days): The Stage 3 cells were then cultured for three days in DMEM-HG medium supplemented with 0.1 µM ALK5 inhibitor (ALK5i; Axxora, San Diego, Calif.), 100 ng/ml of Noggin, 500 nM TPB ((2S,5S)-(E,E)-8-(5-(4-(Trifluoromethyl)phenyl)-2,4-pentadienoylamino)benzolactam; EMD Chemicals Inc, Gibbstown N.J.) and 1% B27 in monolayer format. For the last day of culture, the cells were treated with 5 mg/ml Dispase (Becton Dickinson, Bedford, Mass., #354235) for 5 minutes, followed by gentle pipetting to mix and break into cell clusters (<100 micron). The cell clusters were transferred into a disposable polystyrene 125 ml Spinner Flask (Corning), and spun at 80 to 100 rpm overnight in suspension with DMEM-HG supplemented with 200 nM ALK5 inhibitor, 100 nM LDN-193189 (Stemgent, CA), and 1% B27.

e) Stage 5: (1 day): The Stage 4 cells were then treated with 5 mg/ml Dispase for 5 minutes, followed by gentle pipetting to mix and break into cell clusters (<100 micron). The cell clusters were transferred into a disposable polystyrene 125 ml Spinner Flask (Corning, N.Y.), and spun at 80 to 100 rpm overnight in suspension with DMEM-HG supplemented with 200 nM ALK5 inhibitor, 100 nM LDN-193189 (Stemgent, CA), and 1% B27.

Figure 1H:
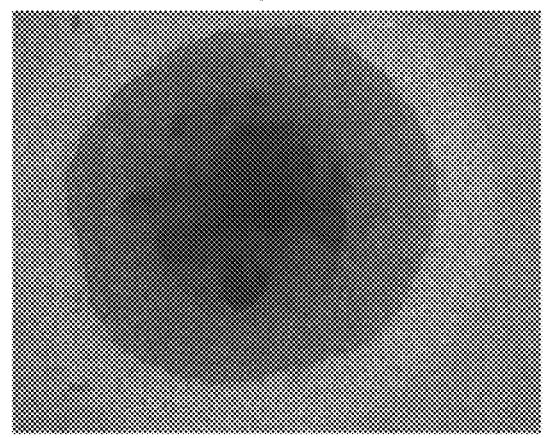
Figure 2C:
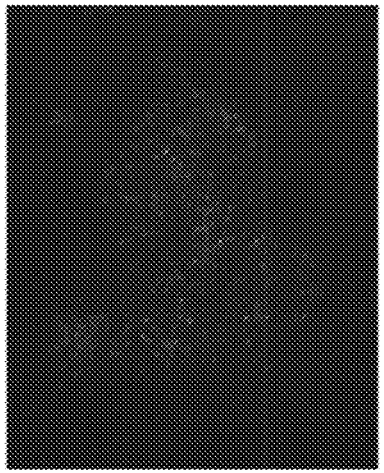
FIGS. 2A to 2K show images of cells differentiated for one week at the air-liquid interface using the methods described in Example 1 and immunostained for the following: DAPI (FIG. 2A); insulin (FIG. 2B); HB9 (FIG. 2C); DAPI (FIG. 2D); glucagon (FIG. 2E); insulin (FIG. 2F); DAPI (FIG. 2G); insulin (FIG. 2H); somatostatin (FIG. 2I); NKX6.1 (FIG. 2J); and insulin (FIG. 2K). Panels A-C, D-F, G-I and J-K were taken from the same field.
Figure 2F:
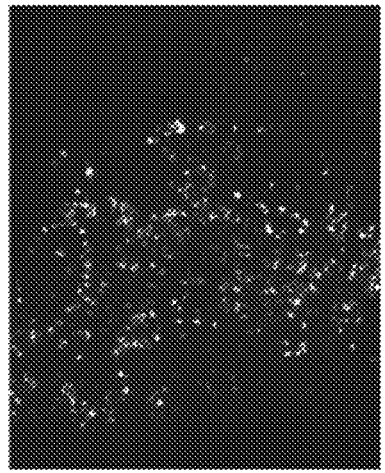
Figure 2B:
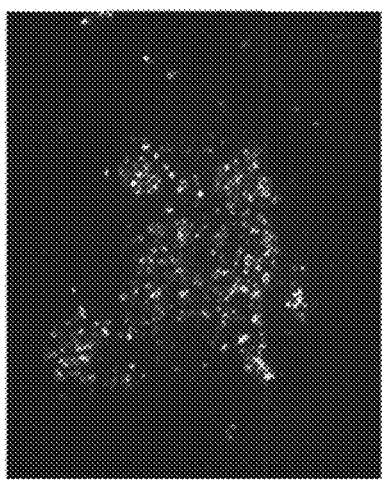
Figure 2E:
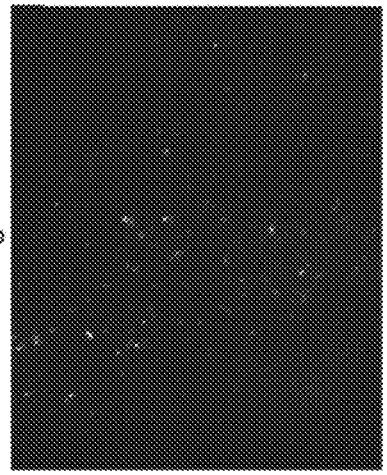
Figure 2A:
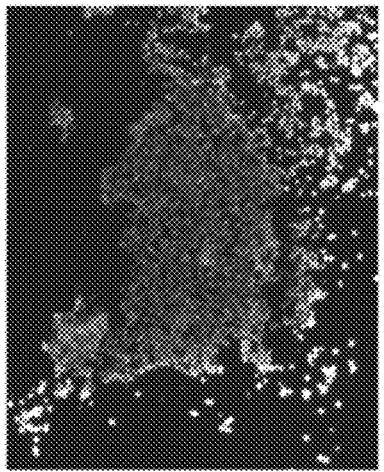
Figure 2D:
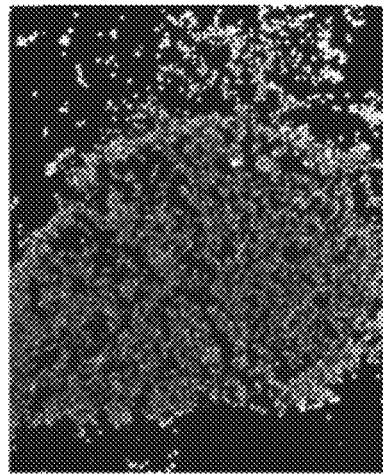
Figure 2I:
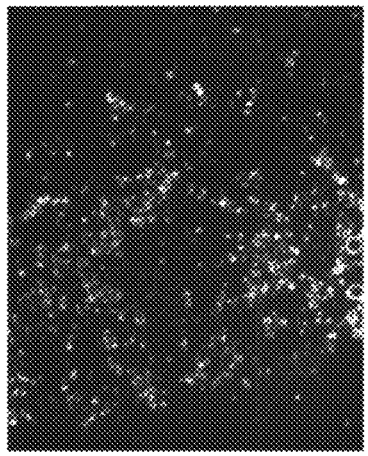
Figure 2H:
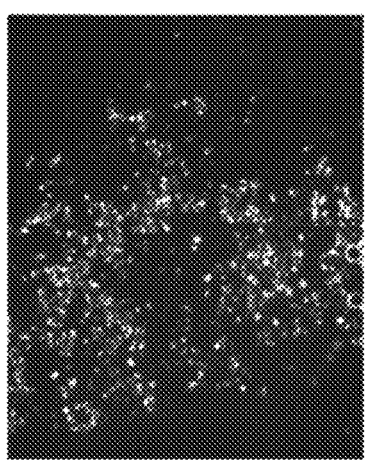
Figure 2K:
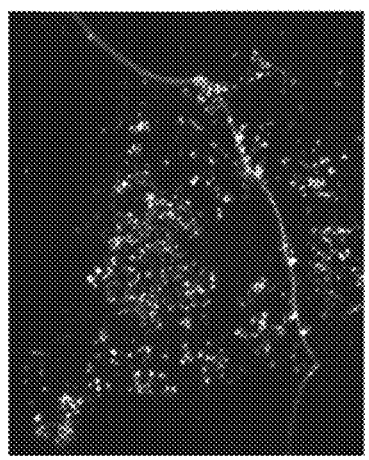
Figure 2G:
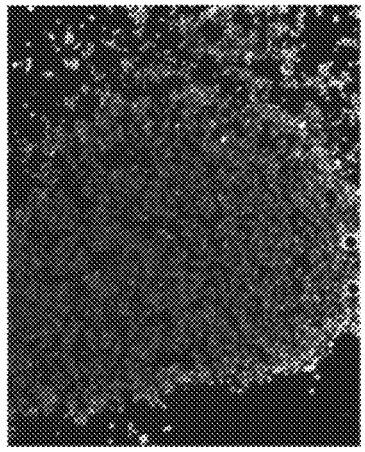
Figure 2J:
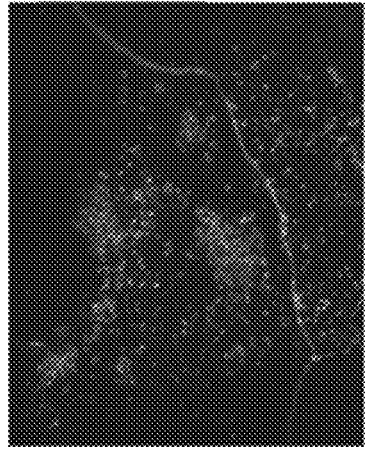
Figure 3E:
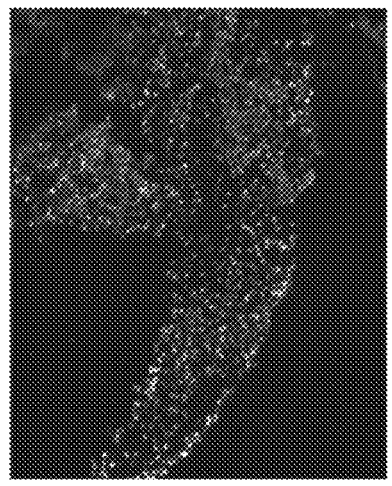
Figure 3F:
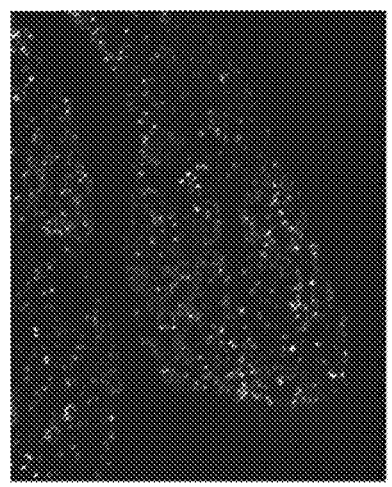
Figure 3G:
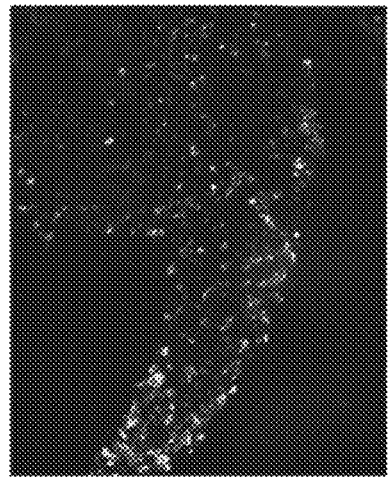
Figure 3H:
Figure 4A:
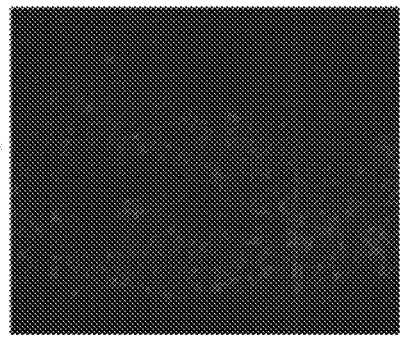
FIGS. 4A to 4D show images of cells differentiated for three weeks at the air-liquid interface using the methods described in Example 1 and immune stained for insulin (FIG. 4A), glucagon (FIG. 4B), insulin (FIG. 4C), and somatostatin (FIG. 4D). Panels A-B and C-D were taken from the same field.
Figure 4B:
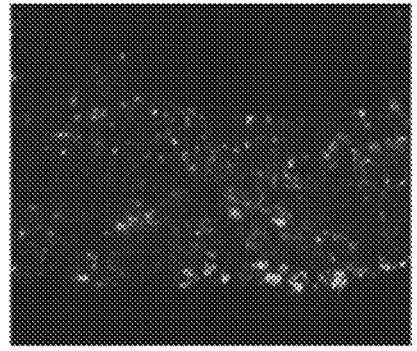
Figure 4C:
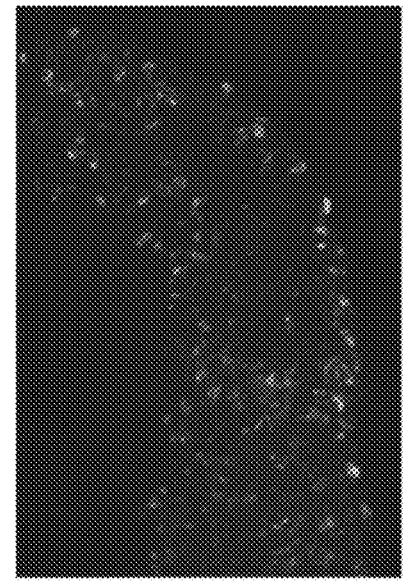
Figure 4D:
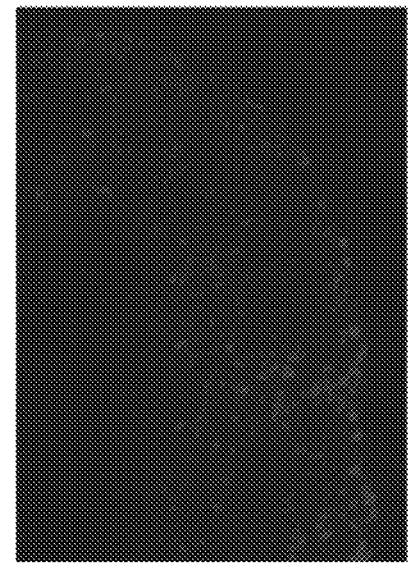

Stage 5 day 1 clusters were seeded on 0.4 micron porous cell culture filter inserts (BD Biosciences, PET membranes, #353493) in 6-well plates (in 10 microliter aliquots containing ~1 million cells) and cultured for 3 weeks at the air-liquid interface by adding 1.5 ml of DMEM-HG +1% B27 at the bottom of the insert and no media above the insert. FIGS. 1 A to H depict phase contrast images of the clusters at various time points post-seeding at the air-liquid interface. FIGS. 2 A to K show immunostaining results for the following proteins at 1 week post-seeding of the cell clusters on the filters: DAPI (FIG. 2A); insulin (FIG. 2B); HB9 (FIG. 2C); DAPI (FIG. 2D); glucagon (FIG. 2E); insulin (FIG. 2F); DAPI (FIG. 2G); insulin (FIG. 2H); somatostatin (FIG. 2I); NKX6.1 (FIG. 2J); and insulin (FIG. 2K). While FIGS. 3 A to H depict immunostaining results for the following proteins at 2 weeks post-seeding on the filters: insulin (FIG. 3A); glucagon (FIG. 3B); insulin (FIG. 3C); somatostatin (FIG. 3D); insulin (FIG. 3E); NKX6.1 (FIG. 3F); HB9 (FIG. 3G); and NKX6.1 (FIG. 3H). In FIG. 2, panels A-C, D-F, G-I and J-K were taken from the same fields. In FIG. 3, panels A-B, C-D, E-F, and G-H, respectively, were taken from the same fields. FIGS. 4 A to D depict the results of immunostaining for the following proteins at 3 weeks post-seeding on the filters: insulin (FIG. 4A); glugacon (FIG. 4B); insulin (FIG. 4C); and somatostatin (FIG. 4D). In FIG. 4, panels A-B and C-D, respectively, were taken from the same fields.

At Stage 4 and subsequent cultures, mRNA was collected for PCR analysis of relevant pancreatic endoderm/endocrine genes. Total RNA was extracted with the RNeasy® Mini Kit (Qiagen; Valencia, Calif.) and reverse-transcribed using a High Capacity cDNA Reverse Transcription Kit (Applied Biosystems, Foster City, Calif.) according to manufacturers' instructions. cDNA was amplified using Taqman Universal Master Mix and Taqman Gene Expression Assays which were pre-loaded onto custom Taqman Arrays (Applied Biosystems). The data were analyzed using Sequence Detection Software (Applied Biosystems) and normalized to undifferentiated human embryonic stem (hES) cells using the ΔΔCt method ((i.e. qPCR results corrected with internal controls ($\Delta\Delta Ct = \Delta Ct_{sample} - \Delta Ct_{reference}$)). All primers were purchased from Applied Biosystems. FACS and immunofluorescence analysis was done as previously described (*Diabetes*, 61, 20126, 2012).

Figure 5A:
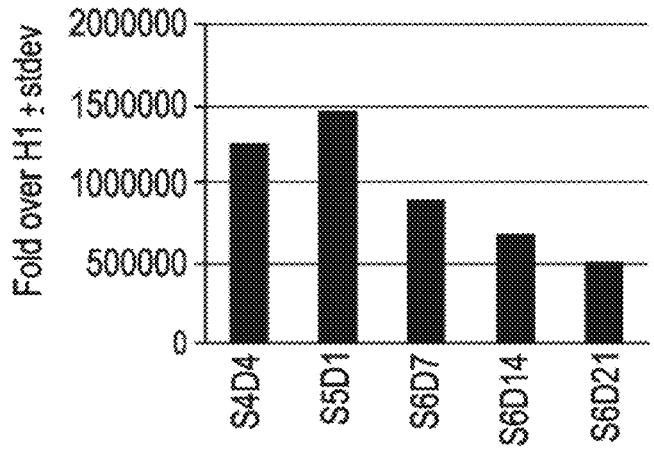
FIGS. 5A to 5R depict data from real-time PCR analyses of the expression of the following genes in cells of the human embryonic stem cell line H1 differentiated as outlined in Example 1: PDX1 (FIG. 5A); NKX6.1 (FIG. 5B); PAX4 (FIG. 5C); PAX6 (FIG. 5D); NGN3 (FIG. 5E); NKX2.2 (FIG. 5F); ABCC8 (FIG. 5G); chromogranin-A (FIG. 5H); PCSK1 (FIG. 5I); IAPP (FIG. 5J); insulin (FIG. 5K); glucagon (FIG. 5L); somatostatin (FIG. 5M); ghrelin (FIG. 5N); PTF1A (FIG. 5O); ZIC1 (FIG. 5P); CDX2 (FIG. 5Q); and SOX9 (FIG. 5R). Cells were cultured at the air-liquid interface after Stage 5.
Figure 5B:
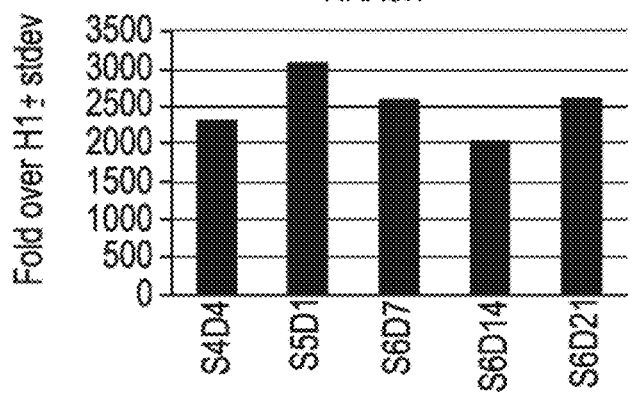
Figure 5C:
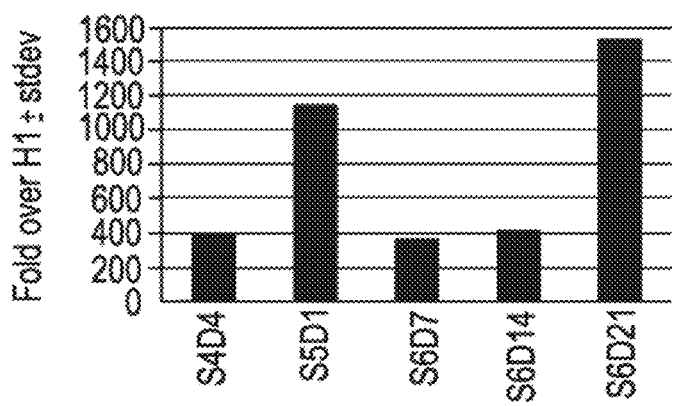
Figure 5D:
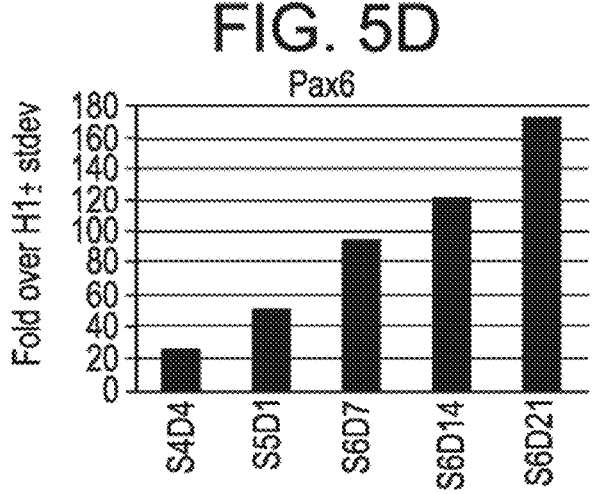
Figure 5E:
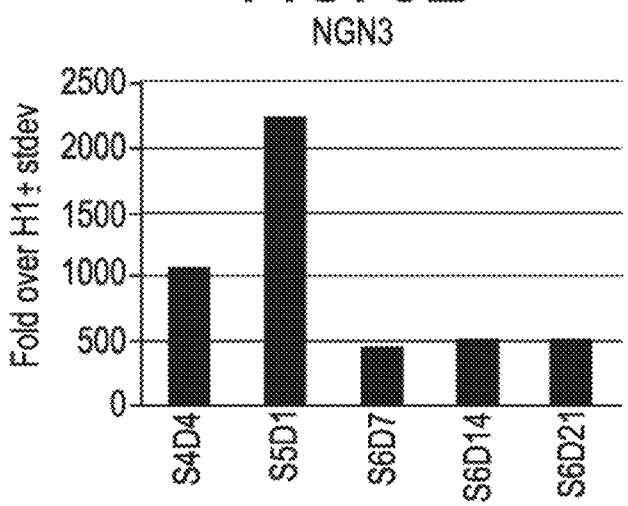
Figure 5F:
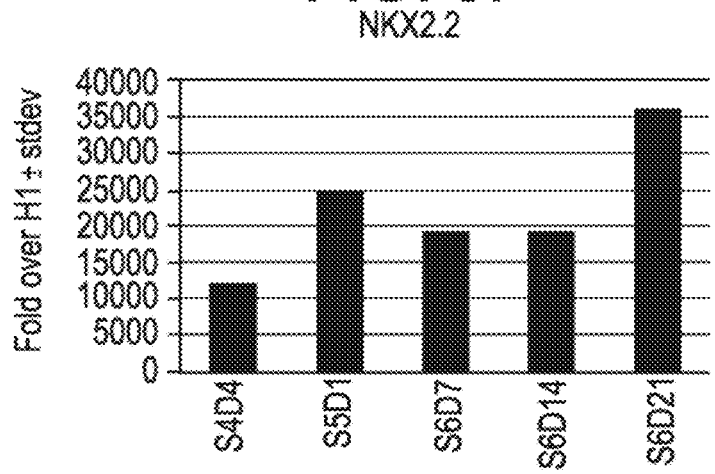
Figure 5G:
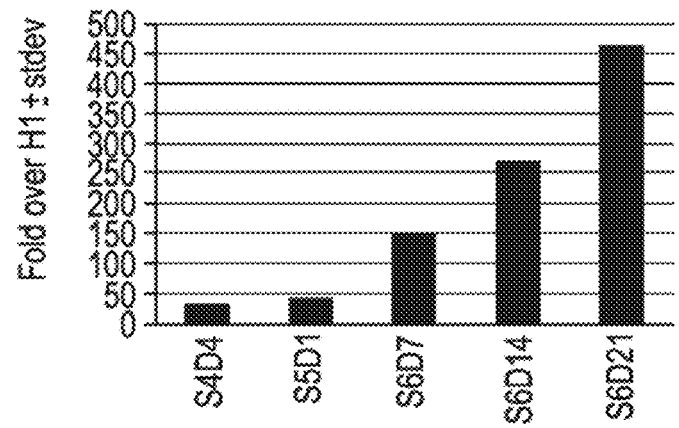
Figure 5H:
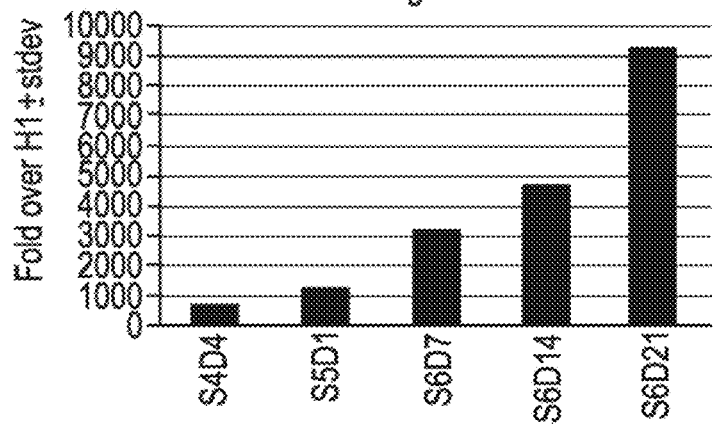
Figure 5I:
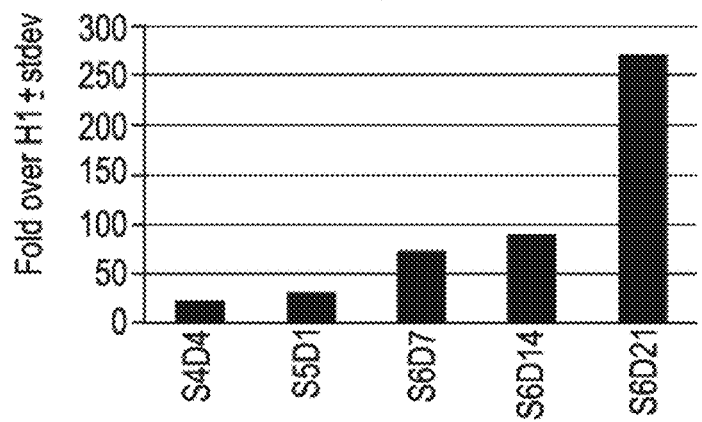
Figure 5J:
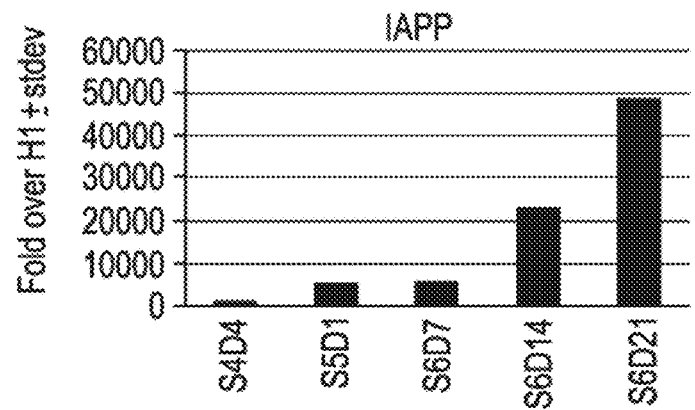
Figure 5K:
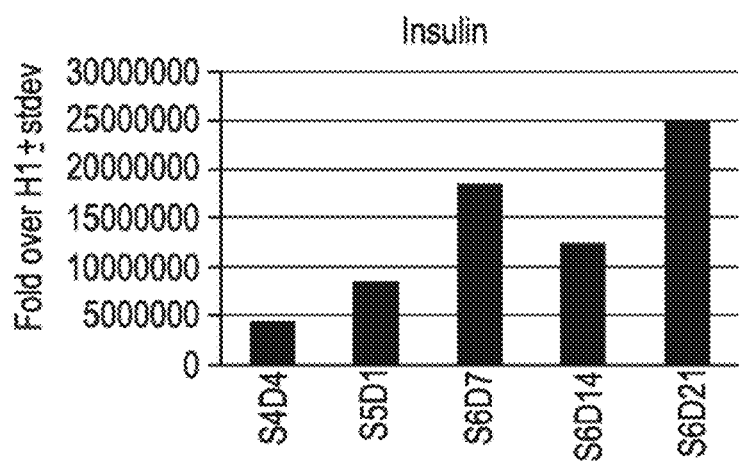
Figure 5L:
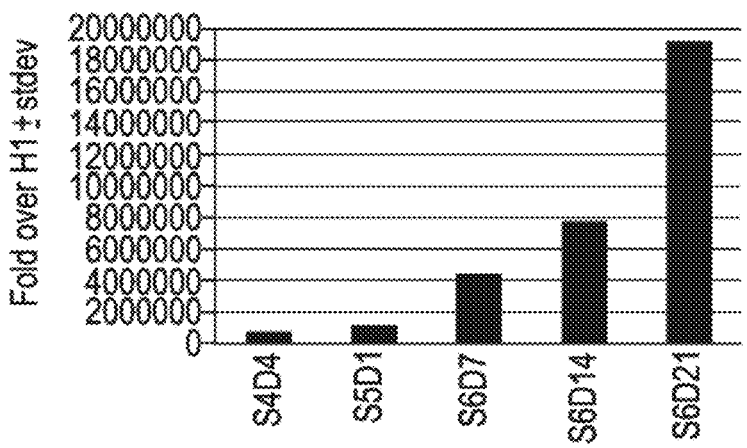
Figure 5M:
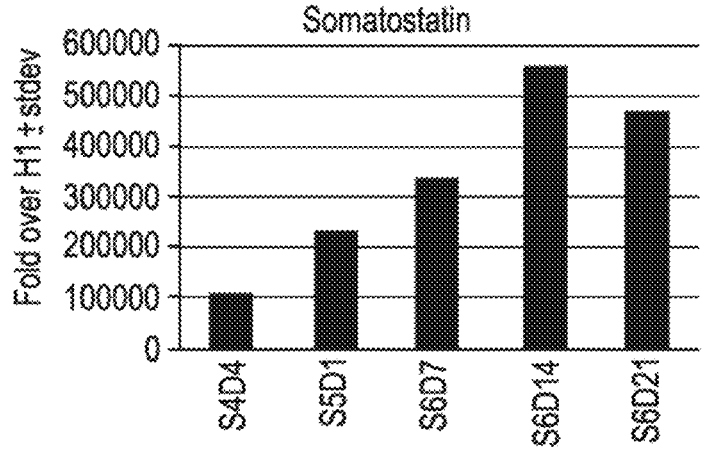
Figure 5N:
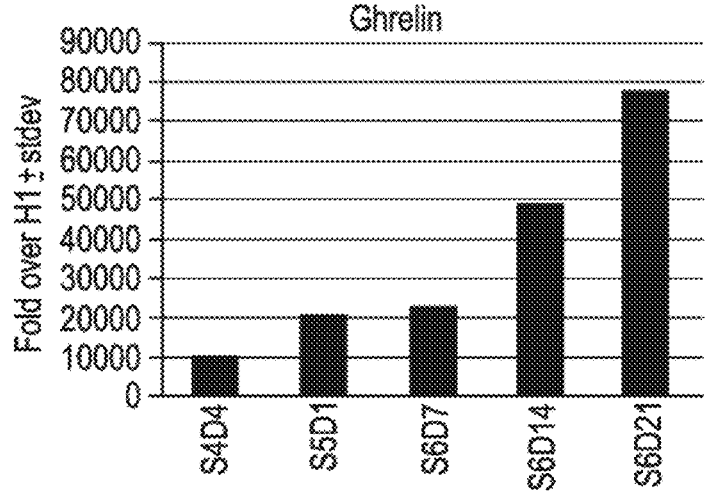
Figure 5O:
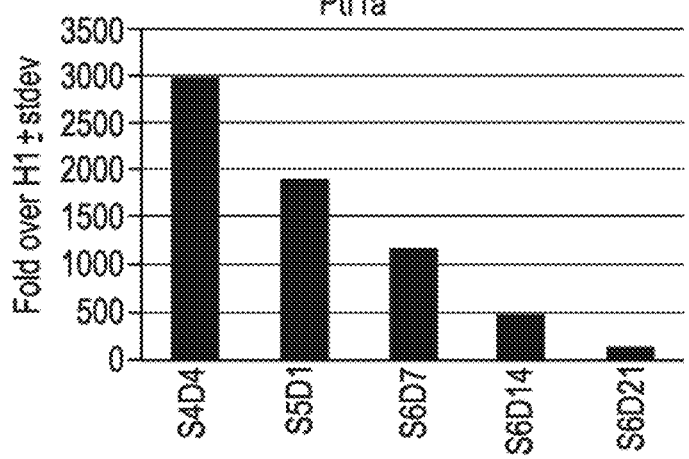
Figure 5P:
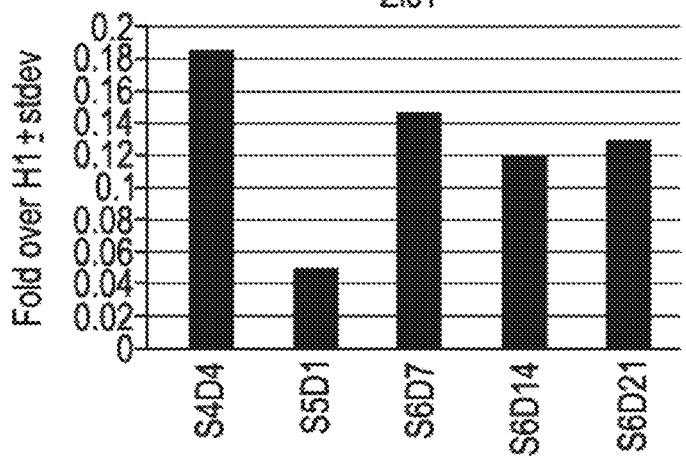
Figure 5Q:
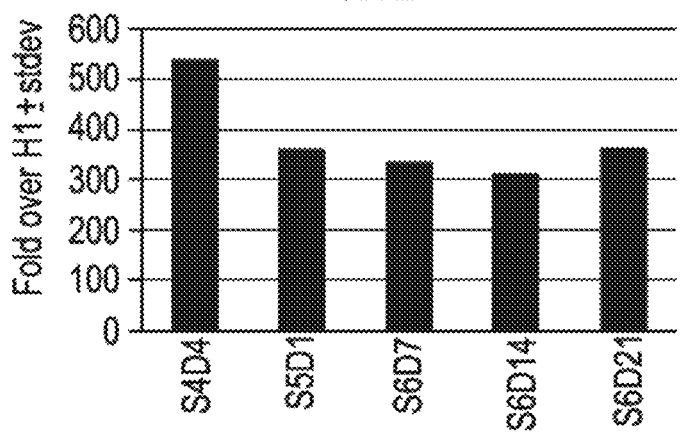
Figure 5R:
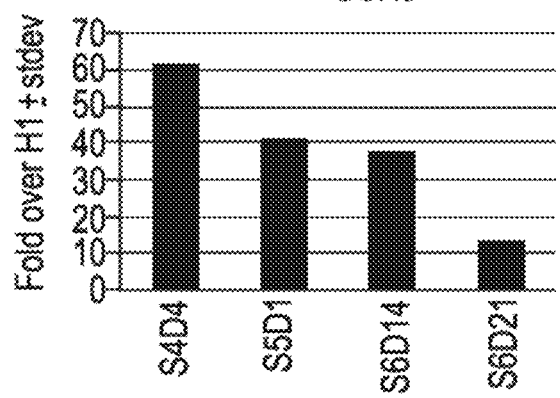
Figure 6A:
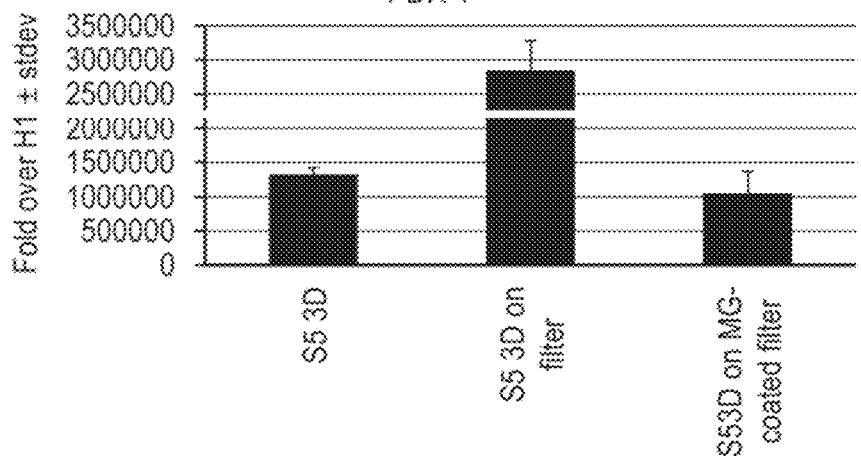
FIGS. 6A to 6L depict data from real-time PCR analyses of the expression of the following genes in cells of the human embryonic stem cell line H1 differentiated as outlined in Example 2: PDX1 (FIG. 6A); NKX6.1 (FIG. 6B); PAX4 (FIG. 6C); PAX6 (FIG. 6D); NGN3 (FIG. 6E); NKX2.2 (FIG. 6F); ABCC8 (FIG. 6G); chromogranin-A (FIG. 6H); PCSK1 (FIG. 6I); IAPP (FIG. 6J); insulin (FIG. 6K); and glucagon (FIG. 6L).
Figure 6B:
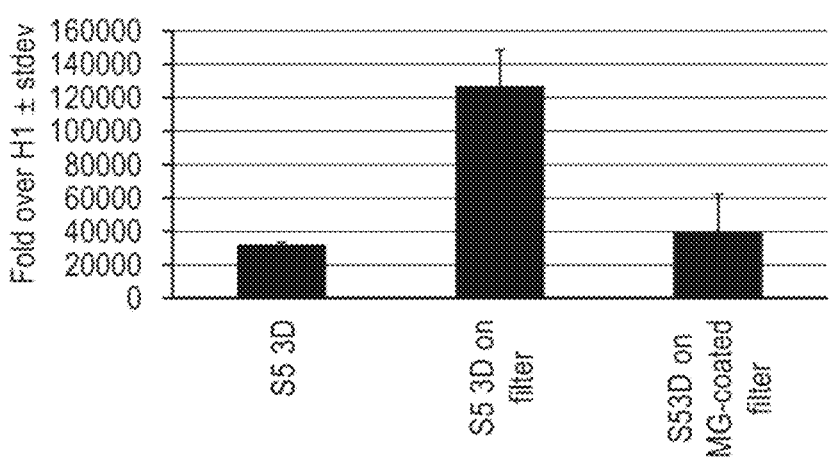
Figure 6C:
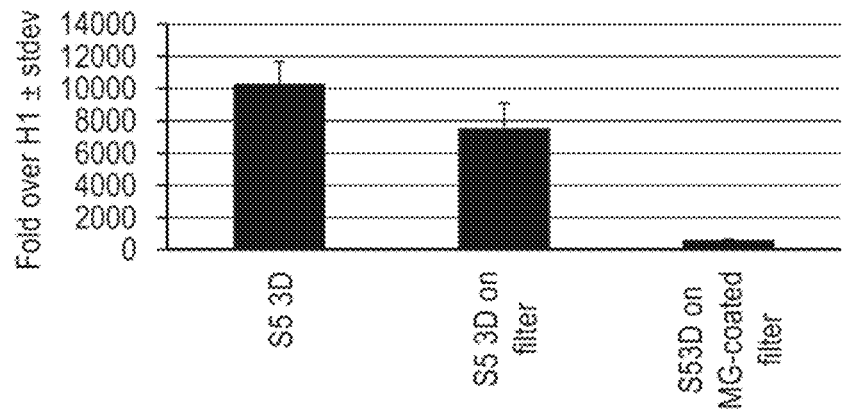
Figure 6D:
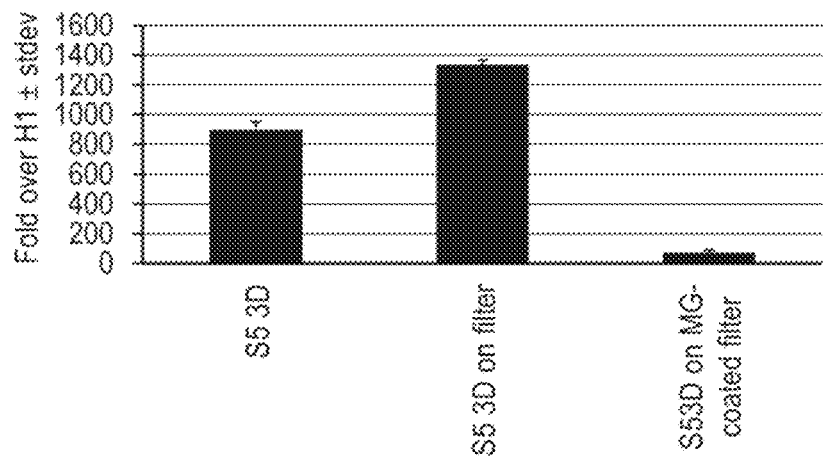
Figure 6E:
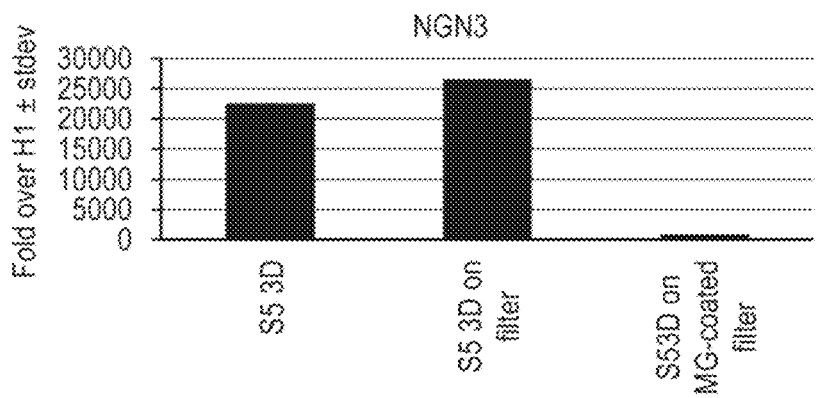
Figure 6F:
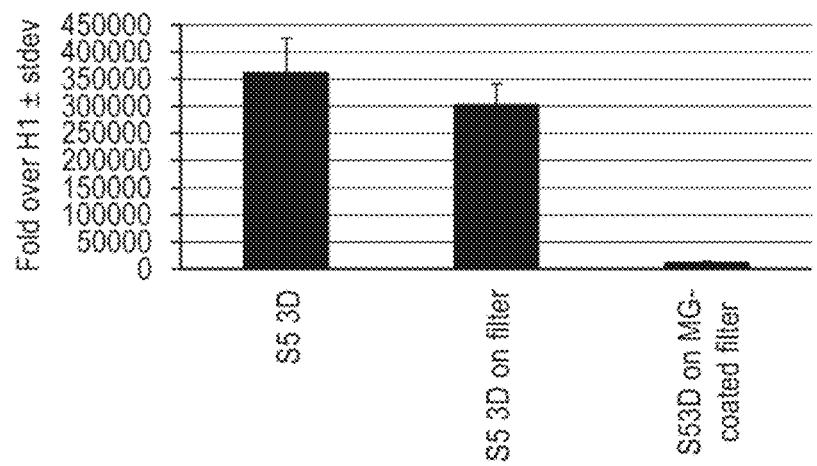
Figure 6G:
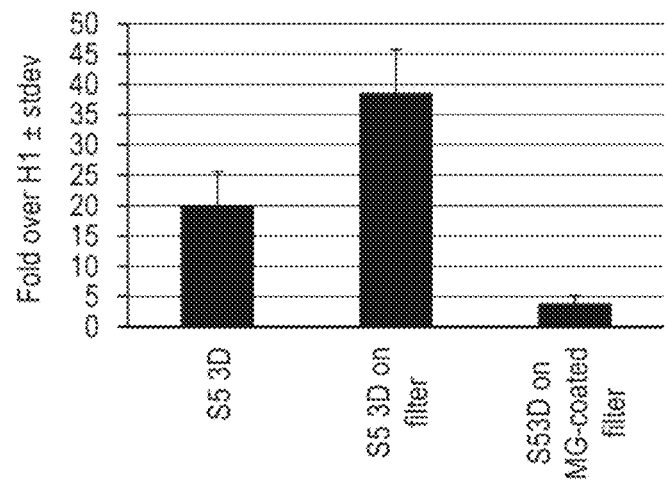
Figure 6H:
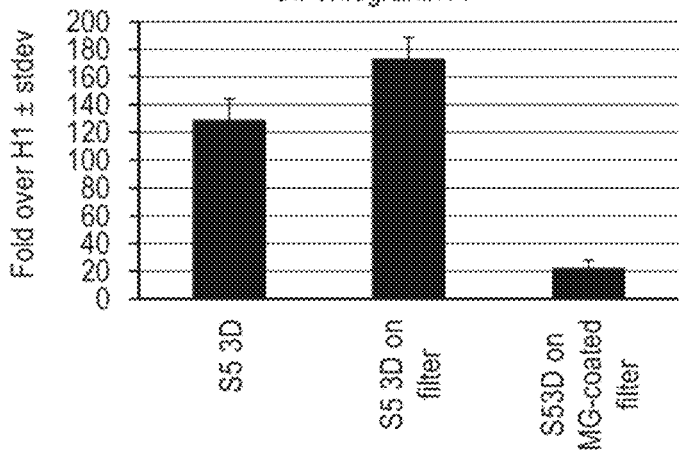
Figure 6I:
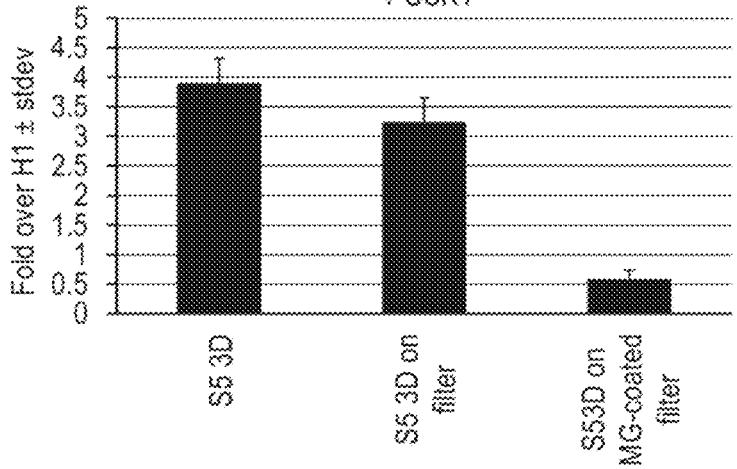
Figure 6J:
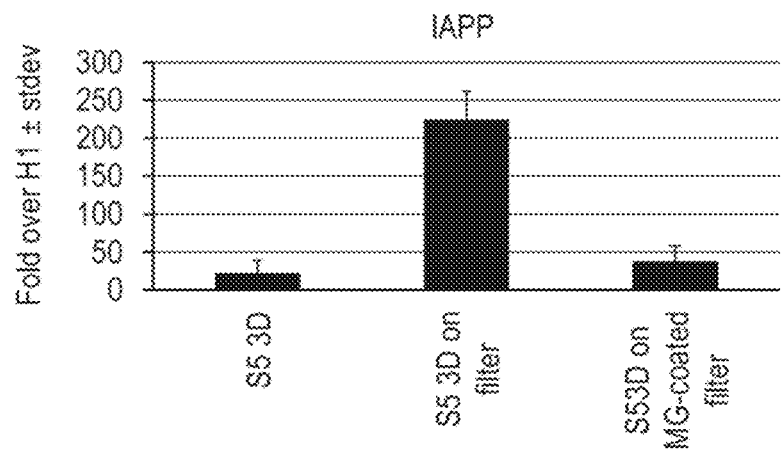
Figure 6K:
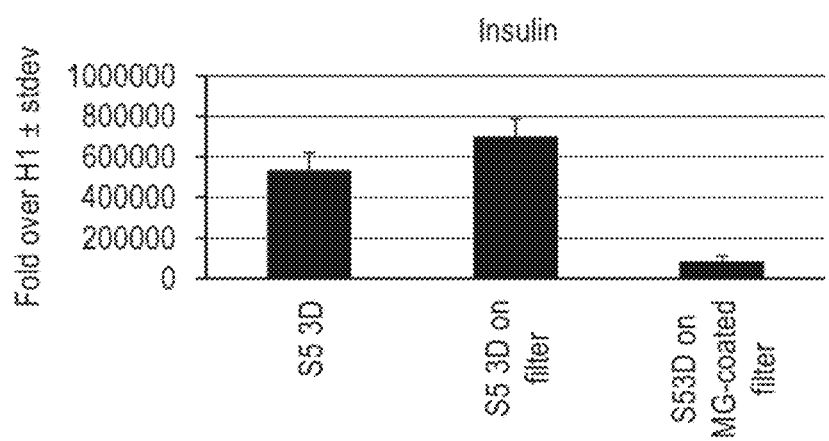
Figure 6L:
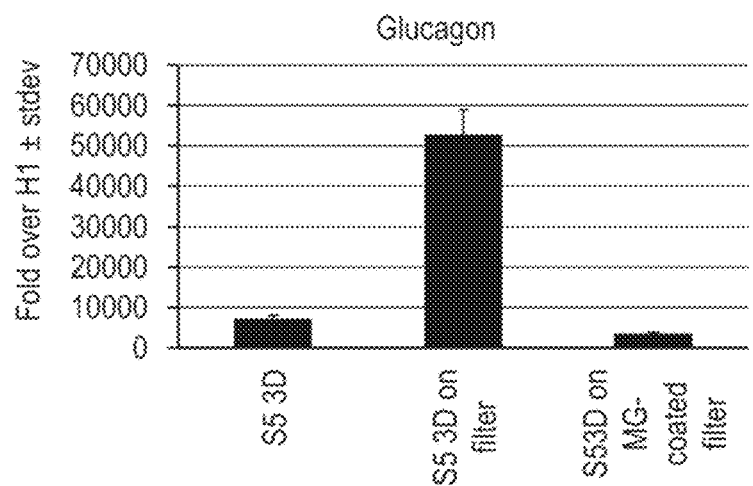
Figure 7A:
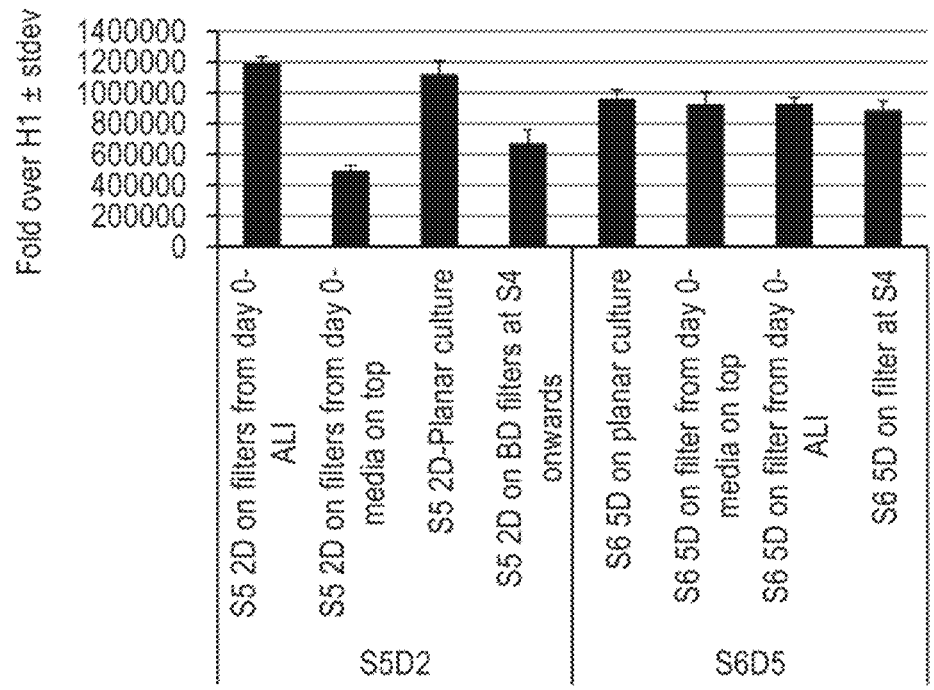
FIGS. 7A to 7L depict data from real-time PCR analyses of the expression of the following genes in cells of the human embryonic stem cell line H1 differentiated as outlined in Example 3: PDX1 (FIG. 7A); NKX6.1 (FIG. 7B); PAX4 (FIG. 7C); PAX6 (FIG. 7D); NGN3 (FIG. 7E); NKX2.2 (FIG. 7F); ABCC8 (FIG. 7G); chromogranin-A (FIG. 7H); PCSK1 (FIG. 7I); IAPP (FIG. 7J); insulin (FIG. 7K); and glucagon (FIG. 7L).
Figure 7B:
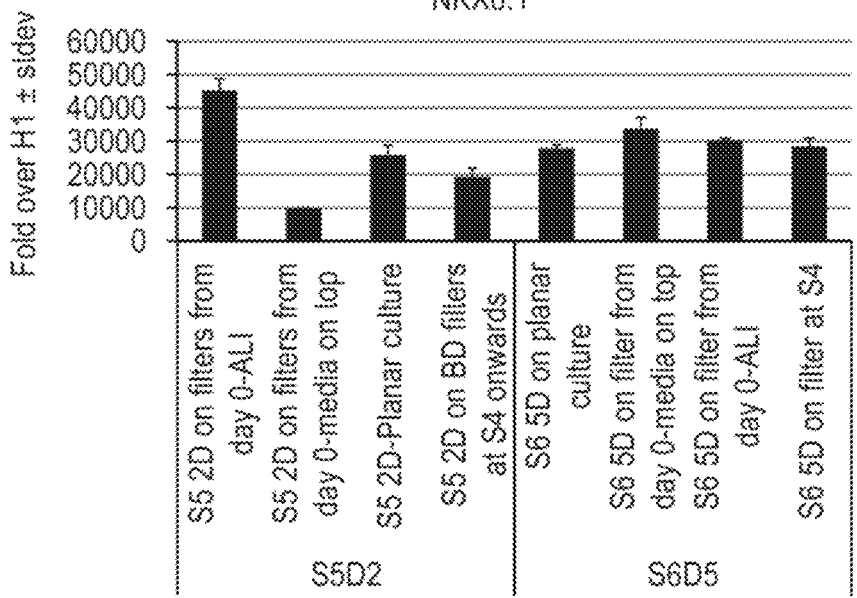
Figure 7C:
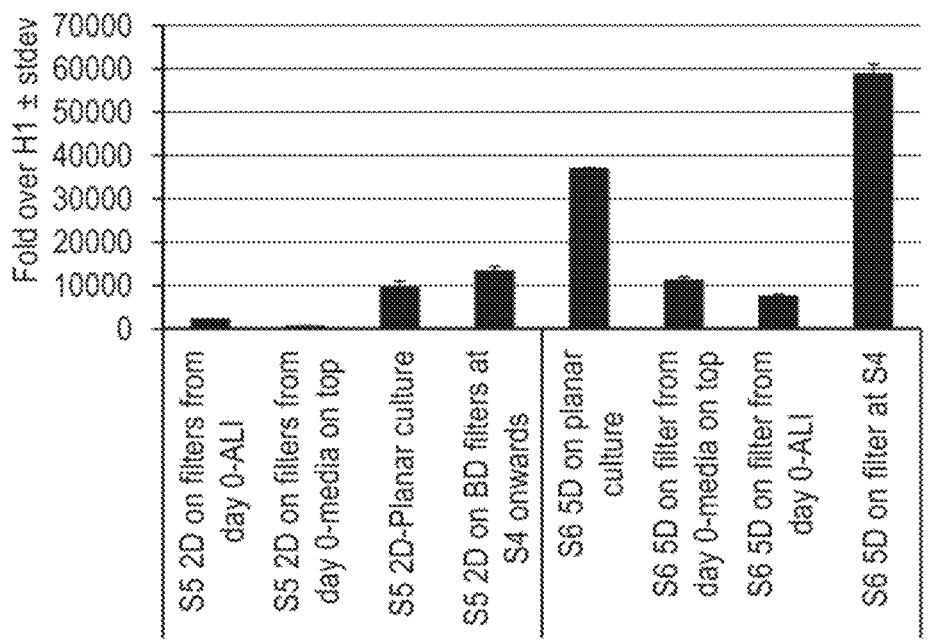
Figure 7D:
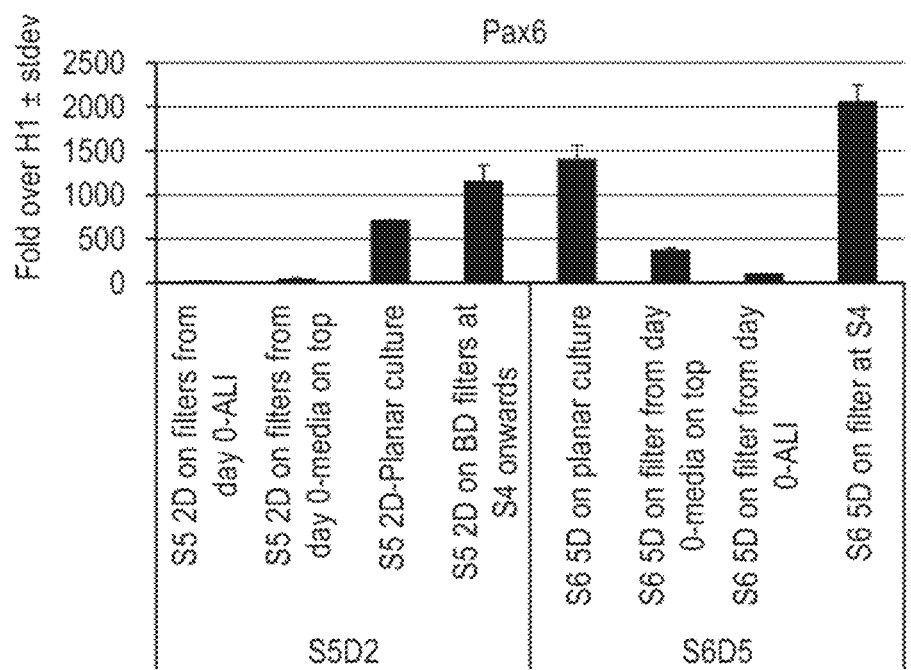
Figure 7E:
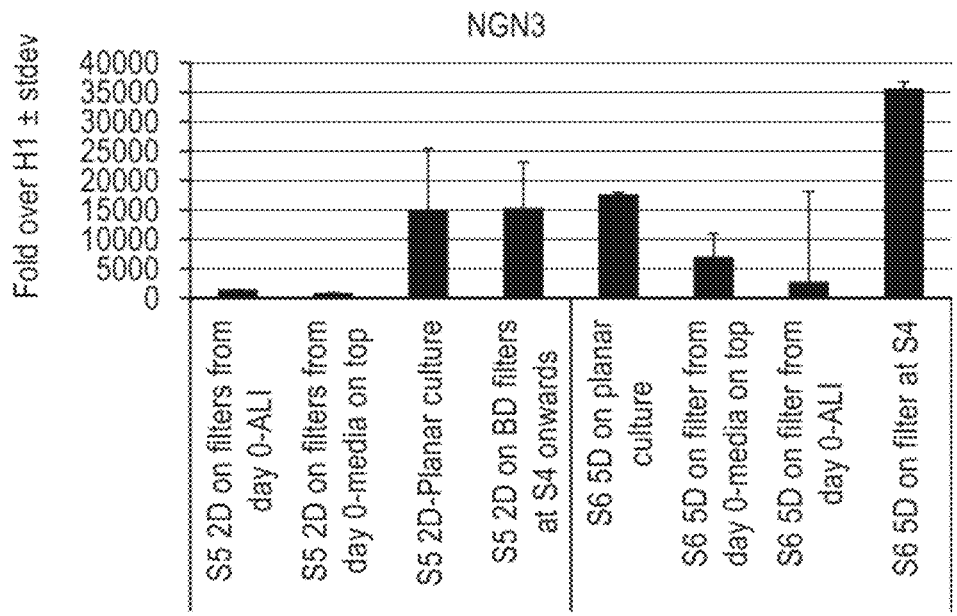
Figure 7F:
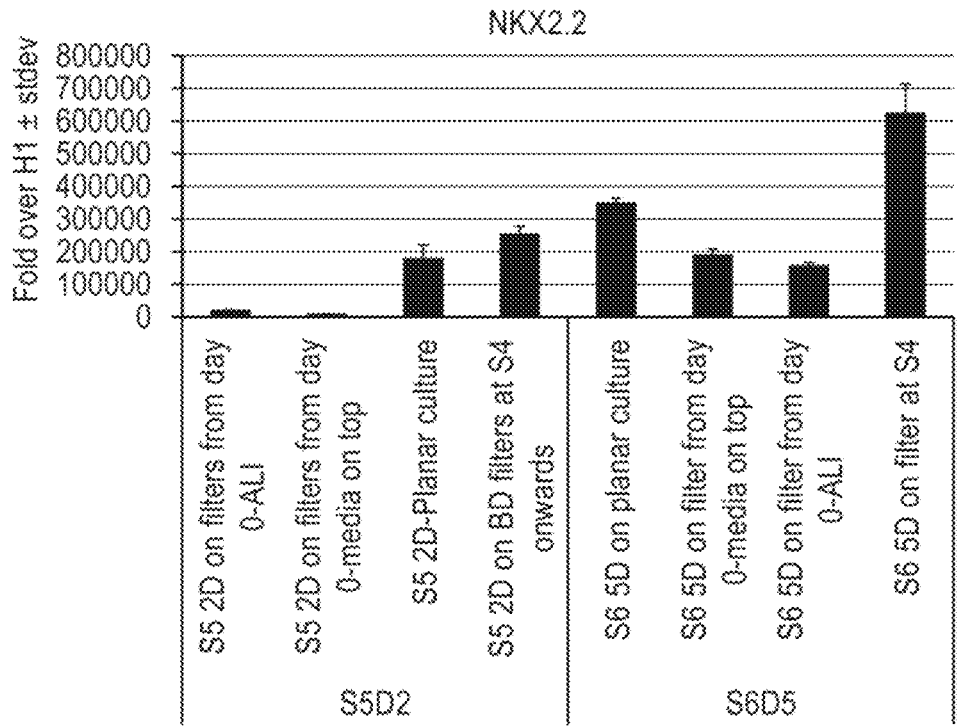
Figure 7G:
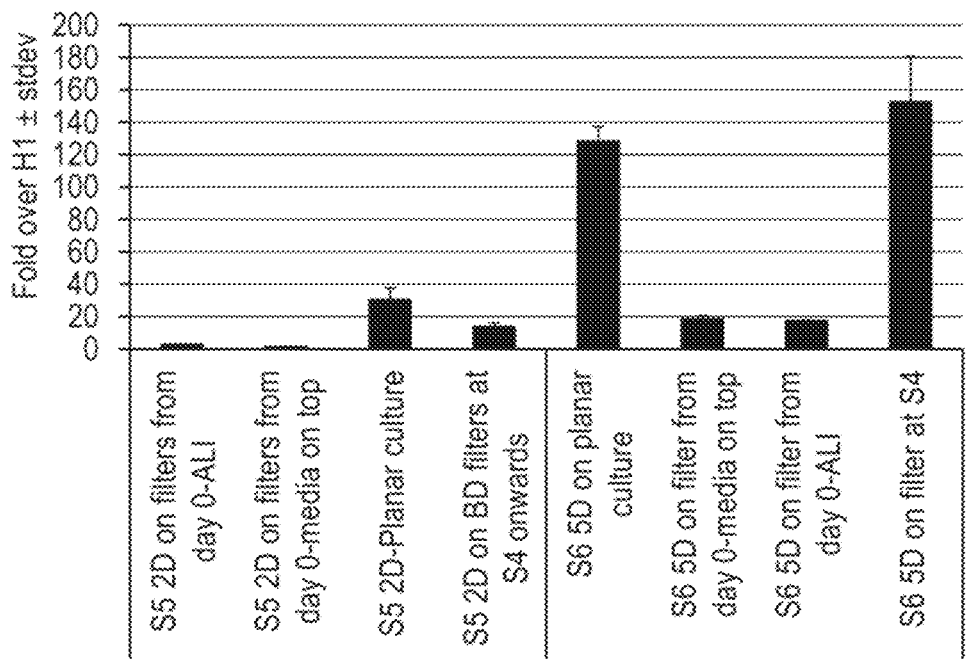
Figure 7H:
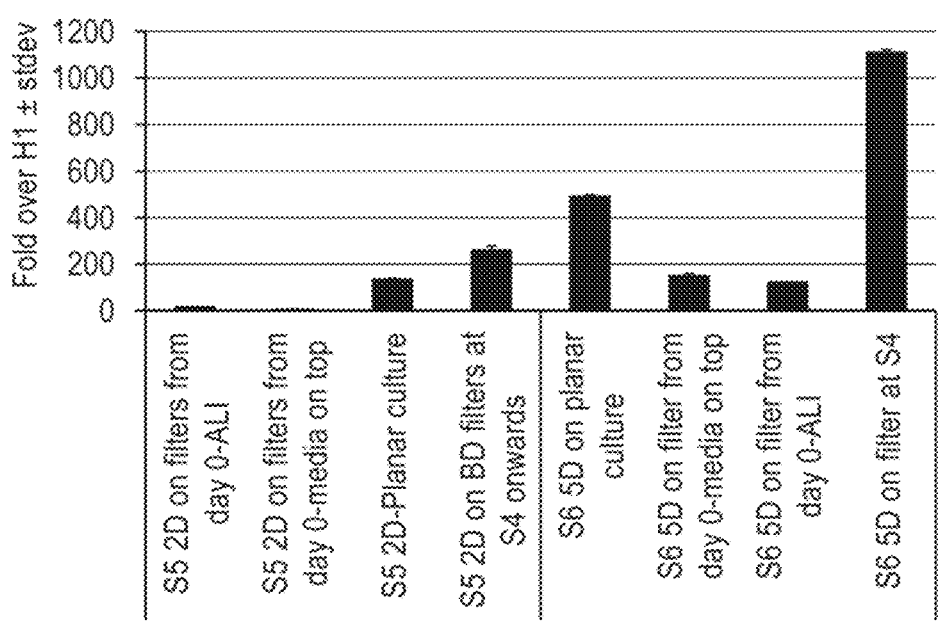
Figure 7I:
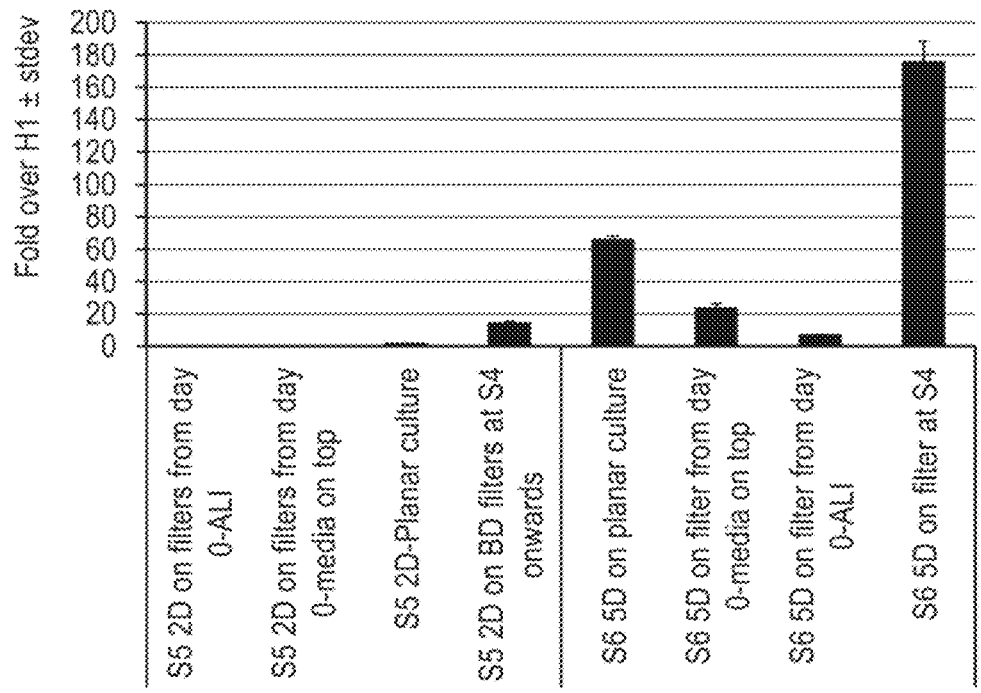
Figure 7J:
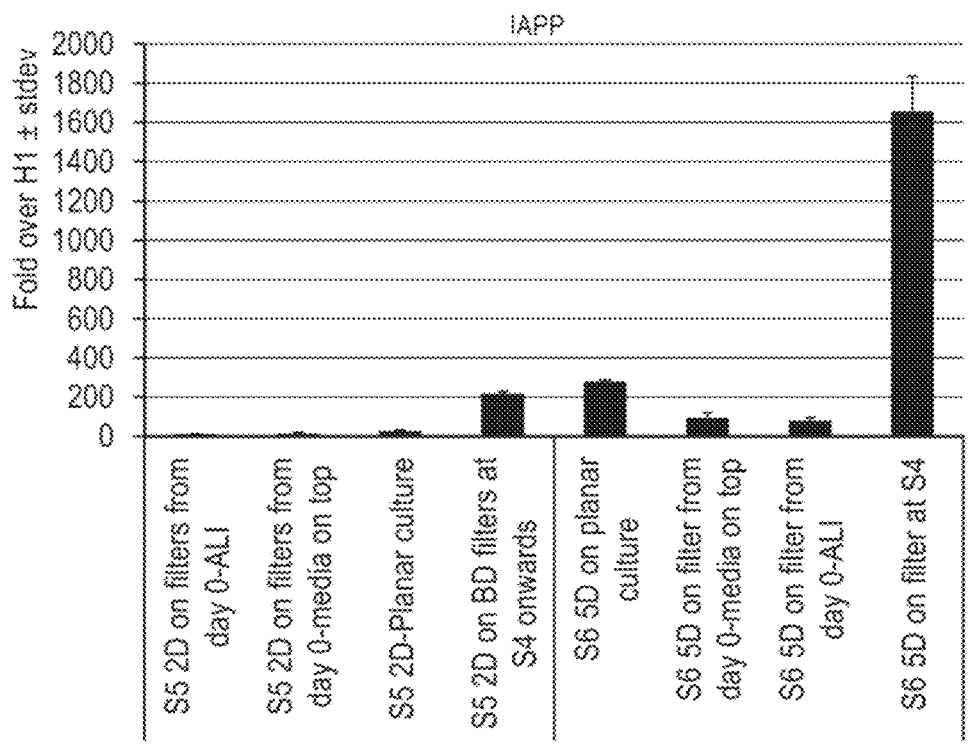
Figure 7K:
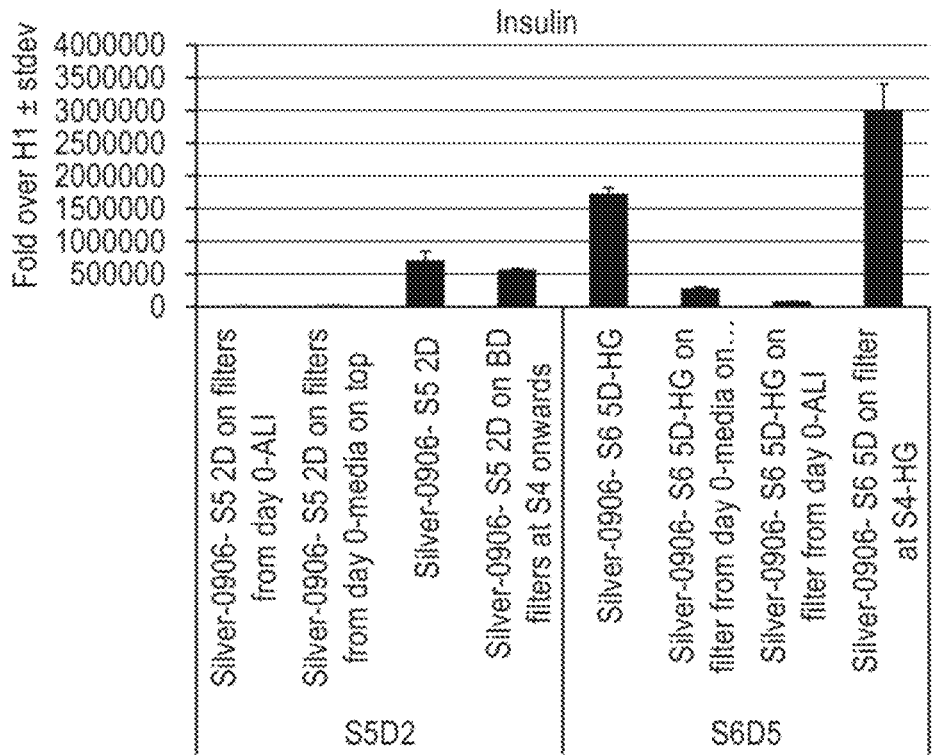
Figure 7L:
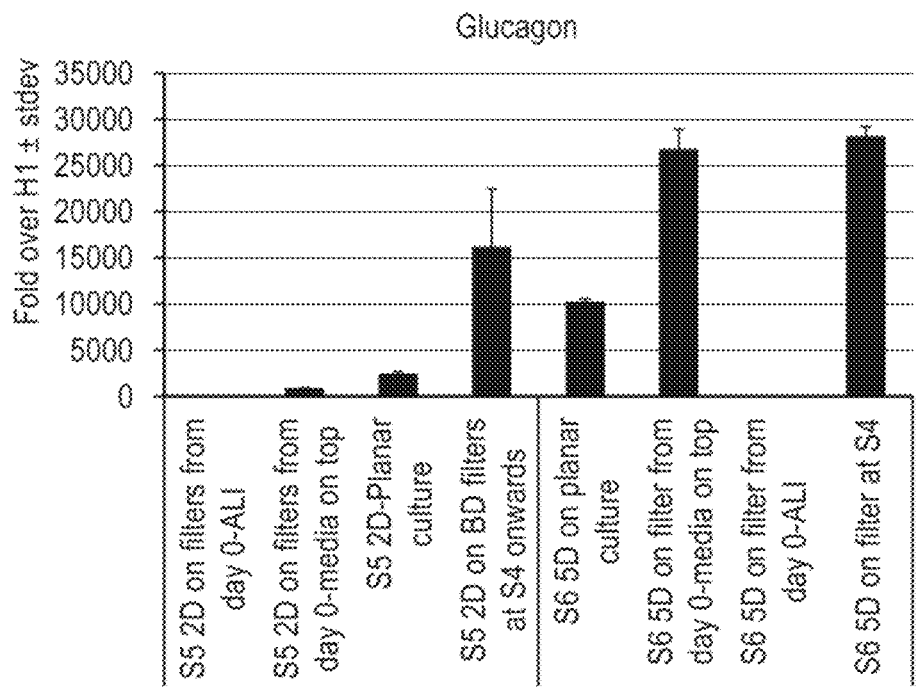

FIGS. 5A to R depict data from real-time PCR analyses of the expression of the following genes in cells of the human embryonic stem cell line H1 differentiated as outlined in Example 1: PDX1 (FIG. 5A); NKX6.1 (FIG. 5B); Pax4 (FIG. 5C); Pax6 (FIG. 5D); NGN3 (FIG. 5E); NKX2.2 (FIG. 5F); ABCC8 (FIG. 5G); chromogranin-A (FIG. 5H); PCSK1 (FIG. 5I); IAPP (FIG. 5J); insulin (FIG. 5K); glucagon (FIG. 5L); somatostatin (FIG. 5M); ghrelin (FIG. 5N); Ptf1a (FIG. 5O); Zic1 (FIG. 5P); CDX2 (FIG. 5Q); and SOX9 (FIG. 5R). Following a 3-week culture at the air-liquid interface, there was a significant time-dependent increase in the expression of markers associated with maturation of endocrine cells, such as ABCC8, IAPP (Amylin), and PCSK1. There was a significant drop in PTF1a and SOX9 expression and very low expression of CDX2 (intestine marker), ZIC1 (ectoderm marker), and SOX2 (anterior endoderm marker), while expression of NKX6.1 and PDX1 were maintained at a very high level. Expression of all of the pancreatic hormones was significantly enhanced through the 3-week culture period at the air-liquid interface.

Example 2

Culturing Pancreatic Endocrine Precursor Cells at the Air-liquid Interface Using Various Filter Inserts This example examines the type and porosity of filter inserts in differentiation of pancreatic endoderm cells at the air-liquid interface. To examine the effects of type and porosity of the filter inserts, embryonic stem cells were differentiated using the protocol discussed below.

Cells of the human embryonic stem cell line H1 (passage 40) were seeded as single cells at $1\times10^5$ cells/cm$^2$ on MATRIGEL™ (1:30 dilution; BD Biosciences, NJ)-coated dishes or MATRIGEL™-coated filter inserts (Millipore PIHT 30R 48) in a media comprising DMEM-F12 (Invitrogen, Ca), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, Sigma-Aldrich, St. Louis, Mo.). Forty-eight hours post-seeding, the cultures were washed in incomplete PBS (phosphate buffered saline without Mg or Ca). The cells were then differentiated according to the following protocol:

a. Stage 1 (3 days): Cells were cultured for one day in MCDB-131 medium (Invitrogen Catalog No. 10372-019) supplemented with 2% fatty acid-free BSA (Proliant, Catalog No. 68700), 0.0012 g/ml sodium bicarbonate (Sigma-Aldrich, Catalog No. S3187), 1× GlutaMax™ (Invitrogen, Catalog No. 35050-079), 4.5 mM D-Glucose (Sigma-Aldrich, Catalog No. G8769), 100 ng/ml GDF8 (R&D Systems) and 1 µM MCX compound. The cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Subsequently, the cells were then cultured for an additional day in MCDB-131 medium supplemented with 2% fatty acid-free BSA, 0.0012 g/ml sodium bicarbonate, 1× GlutaMax™, 4.5 mM D-Glucose, and 100 ng/ml GDF8.

b. Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c. Stage 3 (2 days): The Stage 2 cells were then treated with MCDB-131 medium supplemented with a 1:200 dilution of ITS-X (Invitrogen, CA); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d. Stage 4 (3 days): The Stage 3 cells were then treated with MCDB-131 medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; 10 nM T3 (T6397, Sigma) and 100 nM TPB for three days.

e. Stage 5 (3 days): The Stage 4 cells were then treated with MCDB-131 medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 50 nM RA; 0.25 mM ascorbic acid; 10 nM T3, 50 nM LDN-193189; 1000 nM ALK5 inhibitor SD208, for three days. SD208 (2-(5-Chloro-2-fluorophenyl)pteridin-4-yl]pyridin-4-yl-amine) is a 2,4-disubstituted pteridine, ATP-competitive inhibitor of the TGF-βR I kinase, disclosed in *Molecular Pharmacology* 2007, 72:152-161, and having the structure shown in Formula I.

Formula 1:

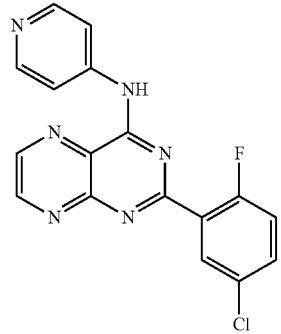

f. Stage 6 (5 days): The Stage 5 cells were then treated with MCDB-131 medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 50 nM RA; 0.025 mM ascorbic acid; 500 nM ALK5 inhibitor; 0.1 nM T3 for three days.

In some cultures, at Stage 3 to Stage 6, cells cultured on planar dishes were treated with 1× ACCUTASE™ (Stem-Cell Tech, Vancouver) for 1-3 minutes at room temperature followed by removal of the enzyme and scraping of the cells by a cell scraper. The resulting suspension of cells was seeded at a density of about $2\text{-}6\times10^6$ cells onto 0.4 micron porous cell culture filter inserts having a surface area of approximately 4.2 cm$^2$ in 6-well plates. The various filter inserts used are identified in Table I. 1.5 ml of media was added to the bottom of each insert and no further media was added to the apical side of the filter. In some cultures, the filters were coated for 1 hour at room temperature with MATRIGEL™ (1:30 dilution) and the cells were seeded on top of the coated inserts at the air-liquid interface or with the media on top of the insert. The media was replaced every other day for the duration of the study.

FIG. 6 depicts data from real-time PCR analyses of the expression of the following genes in cells of the human embryonic stem cell line H1 differentiated as outlined in Example 2: PDX1 (FIG. 6A); NKX6.1 (FIG. 6B); PAX4 (FIG. 6C); PAX6 (FIG. 6D); NGN3 (FIG. 6E); NKX2.2 (FIG. 6F); ABCC8 (FIG. 6G); chromogranin-A (FIG. 6H); PCSK1 (FIG. 6I); IAPP (FIG. 6J); insulin (FIG. 6K); and glucagon (FIG. 5L). Culturing Stage 4 cells on filter inserts (Corning, 3412, BD 353493, and Millipore PIHT 30R 48) significantly enhanced pancreatic endoderm markers along with endocrine-related markers. Coating of the filters with MATRIGEL™ significantly diminished the benefits of culturing on the filter at the air-liquid interface. Furthermore, cells cultured on low pore density filter inserts (BD 353090, Corning 3452) showed less survival and differentiation.

TABLE I

List of filter inserts evaluated in Example 2

| Filter insert | Polymer composition | Pore size (microns) | Pore density (#/cm$^2$) | Coating |
| --- | --- | --- | --- | --- |
| BD, #353493 | PET | 0.4 | 100 +/− 10 × 10$^6$ | No |
| BD, #353090 | PET | 0.4 | 2 +/− 0.2 × 10$^6$ | No |
| Corning, #3452 | Polyester | 0.4 | 4 × 10$^6$ | +/−MATRIGEL ™ coating (1:30 dilution) |
| Corning, #3412 | Polycarbonate | 0.4 | 100 × 10$^6$ | No |
| Millipore, #PIHT 30R 48 | PET | 0.4 | 100 × 10$^6$ | +/−MATRIGEL ™ coating (1:30 dilution) |

Example 3

Pancreatic Endoderm Cells Cultured at the Air-liquid Interface Showed Enhanced Expression of Endocrine Markers as Compared to Planar Cultures or Cultures Maintained on Filters at Liquid-liquid Interface This example is directed to differences in the propensity of differentiation of pancreatic endoderm cells cultured on planar substrates as compared to those cultured at the air-liquid interface. In addition, the effect of the air-liquid interface was further highlighted by differentiating cells on inserts but with media added to both the top and bottom of the inserts.

Cells of the human embryonic stem cell line H1 (passage 40) were seeded as single cells at 1×10$^5$ cells/cm$^2$ on MATRIGEL™ (1:30 dilution; BD Biosciences, NJ)-coated dishes or MATRIGEL™-coated filter inserts (Millipore PIHT 30R 48) in a media comprising of DMEM-F12 (Invitrogen, Ca), GlutaMaX™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, Sigma-Aldrich, St. Louis, Mo.). Forty-eight hours post-seeding, the cultures were washed in incomplete PBS (phosphate buffered saline without Mg or Ca). For cells cultured on filter inserts, at the beginning of Stage 1, in some cultures media was added only to the bottom of the insert and the top of the insert was kept at the air-liquid interface, while in other cultures media was also added to the top of the filter insert as well as to the bottom of the insert. The cells were then differentiated according to the following protocol:

a) Stage 1 (3 days): The cells were cultured for one day in MCDB-131 medium (Invitrogen, Catalog No. 10372-019) supplemented with 2% fatty acid-free BSA (Proliant, Catalog No. 68700), 0.0012 g/ml sodium bicarbonate (Sigma-Aldrich, Catalog No. S3187), 1× GlutaMax™ (Invitrogen, Catalog No. 35050-079), 4.5 mM D-glucose (Sigma-Aldrich, Catalog No. G8769), 100 ng/ml GDF8 (R&D Systems) and 1 µM MCX compound. The cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Subsequently the cells were cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b) Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c) Stage 3 (2 days): The Stage 2 cells were then treated with BLAR custom medium (manufactured by Invitrogen, see Table II for the components of BLAR media) supplemented with a 1:200 dilution of ITS-X (Invitrogen, CA); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d) Stage 4 (3 days): The Stage 3 cells were then treated with BLAR medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; 10 nM T3 (T6397, Sigma) and 100 nM TPB for three days.

e) Stage 5 (3 days): The Stage 4 cells were treated with BLAR medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 50 nM RA; 0.25 mM ascorbic acid; 10 nM T3; 50 nM LDN-193189; 1000 nM ALK5 inhibitor (SD208) for three days.

f) Stage 6 (5 days): The Stage 5 cells were then treated with BLAR medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 50 nM RA; 0.025 mM ascorbic acid; 500 nM ALK5 inhibitor; 0.1 nM T3 for three days.

In some cultures, at the end of Stage 3, cells cultured on planar dishes were treated with 1× ACCUTASE™ (StemCell Tech, Vancouver) for 1-3 minutes at room temperature followed by removal of the enzyme and scraping of the cells by a cell scraper. The resulting suspension of cells were seeded at a density of $2\text{-}6\times10^6$ cells (in 50-100 µl aliquots) on 0.4 micron porous cell culture filter inserts (BD 353493) in 6-well plates. 1.5 ml of media was added to the bottom of each insert and no further media was added to the apical side of the filter. The media was replaced every other day for the duration of the study.

FIG. 7 depicts data from real-time PCR analyses of the expression of the following genes in cells of the human embryonic stem cell line H1 differentiated as outlined in Example 3: PDX1 (FIG. 7A); NKX6.1 (FIG. 7B); PAX4 (FIG. 7C); PAX6 (FIG. 7D); NGN3 (FIG. 7E); NKX2.2 (FIG. 7F); ABCC8 (FIG. 7G); chromogranin-A (FIG. 7H); PCSK1 (FIG. 7I); IAPP (FIG. 7J); insulin (FIG. 7K); and glucagon (FIG. 7L).

Culturing cells on filter inserts at the air-liquid interface in Stages 4 through 6, significantly enhanced pancreatic endocrine-related markers. Furthermore, cells cultured and differentiated on MATRIGEL™-coated filter inserts from the start of Stage 1 with media on top and bottom of the filter inserts did show lower levels of pancreatic endoderm and endocrine expression as compared to cells cultured on planar cultures or at the air-liquid interface. Furthermore, pancreatic endoderm cells cultured on filter inserts at the air-liquid interface showed the highest expression of pancreatic endocrine cells as compared to all the tested configurations.

TABLE II

List of components of BLAR media

| Component | Concentration (mM) |
|---|---|
| Amino Acids | |
| Glycine | 3.0E−02 |
| Alanine | 3.0E−02 |
| Arginine | 3.0E−01 |
| Aspargine | 1.0E−01 |
| Aspartic Acid | 1.0E−01 |
| Cysteine | 2.0E−01 |
| Glutamic acid | 3.0E−02 |
| Histidine | 1.1E−01 |
| Isoleucine | 1.0E−01 |
| Leucine | 9.0E−02 |
| Lysine hydrochloride | 1.5E−01 |
| Methiane | 3.0E−02 |
| Phenylalanine | 3.0E−02 |
| Proline | 1.0E−01 |
| Serine | 1.0E−01 |
| Theronine | 3.0E−02 |
| Tryptophan | 2.0E−03 |
| Tyrosinedisodium | 1.0E−02 |
| Vair-liquid interfacene | 3.0E−02 |
| Vitamins | |
| Biotin | 3.0E−05 |
| Choline chloride | 5.0E−03 |
| D-Calcium pantothenate | 1.5E−03 |
| Folinic Acid Calcium salt | 2.3E−03 |
| Niacinamide | 4.9E−03 |

TABLE II-continued

List of components of BLAR media

| Component | Concentration (mM) |
|---|---|
| Pyridoxine hydrochloride | 9.7E−04 |
| Riboflavin | 1.0E−05 |
| Thiamine hydrochloride | 3.0E−03 |
| Vitamin B12 | 3.7E−06 |
| i-Inositol | 2.8E−03 |
| Minerals/other | |
| Calcium Chloride ($CaCl_2$—$2H_2O$) | 3.0E−01 |
| Cupric sulfate ($CuSO_4$—5H2O) | 4.8E−06 |
| Ferric sulfate ($FeSO_4$—$7H_2O$) | 1.0E−03 |
| Magnesium Sulfate (MgSO4—$7H_2O$) | 4.1E−01 |
| Potassium Chloride (KCl) | 3.8E+00 |
| Selenious Acid $H_2SeO_3$ | |
| Sodium Bicarbonate ($NaHCO_3$) | 1.4E+01 |
| Sodium Chloride (NaCl) | 1.1E+02 |
| Sodium Phosphate dibasic (Na2HPO4—$7H_2O$) | 5.0E−01 |
| Zinc Sulfate ($ZnSO_4$—$H_2O$) | 1.0E−04 |
| Adenine | 1.0E−03 |
| D-Glucose (Dextrose) | 5.0E+00 |
| Lipoic Acid | 1.2E+05 |
| Phenol Red | 1.0E−02 |
| Sodium Pyruvate | 1.0E+00 |
| Thymidine | 9.8E−05 |

Example 4

Pancreatic Endoderm Cells Cultured at the Air-liquid Interface and Treated with ALK5 Inhibitor II Showed a Significantly Larger Number of NKX6.1 Positive Cells Co-expressing Chromogranin-A and Insulin This example was carried out to show that ALK5 inhibitor II was unique in generating a significant population of cells at the air-liquid interface that expressed NKX6.1 and insulin or chromogranin-A. Furthermore, this observation was unique to cultures at the air-liquid interface. Submerged cultures in monolayer planar cultures failed to show a significant number of NKX6.1 cells expressing insulin or chromogranin-A.

Cells of the human embryonic stem cell line H1 (passage 40) were seeded as single cells at $1\times10^5$ cells/cm$^2$ on MATRIGEL™ (1:30 dilution; BD Biosciences, NJ)-coated dishes or Matrigel-coated filter inserts (Millipore PIHT 30R 48) in a media comprising of DMEM-F12 (Invitrogen, Ca), Glutamax (1:100 dilution, Invitrogen), 0.25 mM ascorbic acid (Sigma, MO), 100 ng/ml of FGF2 (R & D systems, MN), 1 ng/ml of TGF-B (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, SigmaAldrich, St. Louis, Mo.). Forty-eight hours post seeding, cultures were washed in incomplete PBS (phosphate buffered saline without Mg or Ca). The cells were then differentiated according to the following protocol:

a) Stage 1 (3 days): Cells were cultured for one day in MCDB-131 medium (Invitrogen Catalog No. 10372-019) supplemented with 2% fatty acid-free BSA (Proliant Catalog No. 68700), 0.0012 g/ml sodium bicarbonate (SigmaAldrich Catalog No. S3187), 1× GlutaMax™ (Invitrogen Catalog No. 35050-079), 4.5 mM D-Glucose (SigmaAldrich Catalog No. G8769), 100 ng/ml GDF8 (R&D Systems) and 1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-Glucose, 100 ng/ml GDF8, and 0.1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-Glucose, and 100 ng/ml GDF8.

b) Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-Glucose; 0.25 mM ascorbic acid (Sigma, MO) and 25 ng/ml FGF7 (R & D Systems, MN).

c) Stage 3 (2 days): The Stage 2 cells were then treated with BLAR custom medium (Invitrogen) supplemented with a 1:200 dilution of ITS-X (Invitrogen, Ca); 4.5 mM Glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibstown, N.J.); and 100 nM LDN-193189 (BMP receptor inhibitor; Catalog No. 04-0019; Stemgent) for two days.

d) Stage 4 (3 days): The Stage 3 cells were then treated with BLAR medium supplemented with a 1:200 dilution of ITS-X; 4.5 mM Glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; and 100 nM TPB for three days.

e) Stage 5 (−3 days): The Stage 4 cells were then treated with BLAR medium supplemented with a 1:200 dilution of ITS-X; 20 mM Glucose; 1× GlutaMax™; 0.0015 g/ml sodium bicarbonate; 2% fatty acid-free BSA; 0.25 µM SANT-1; 50 nM RA; 50 nM LDN; 500-1000 nM of various ALK5 inhibitors (see Table III for the list of inhibitors used) for three days.

f) Stage 6 (7 days): The Stage 5 cells were then treated with BLAR medium supplemented with a 1:200 dilution of ITS-X; 20 mM Glucose; 1× GlutaMax™; 0.0015 g/ml sodium bicarbonate; 2% fatty acid-free BSA; 0.25 µM SANT-1; 50 nM RA; 500-1000 nM ALK5 inhibitor (see Table III for list of inhibitors tested).

In some cultures, at the end of day one of Stage 4, cells cultured on planar dishes were treated with 1× Accutase (StemCell Tech, Vancouver) for 1-3 min at room temperature followed by removal of the enzyme and scraping of cells by a cell scraper. The resulting suspension of cells were seeded at a density of 2-4×10⁶ cells (in 25-50 µl aliquots) on 0.4 micron porous cell culture filter inserts (BD 353493) in 6-well plates. 1.5 ml of media was added to the bottom of each insert and no further media was added to the apical side of the filter. Media was replaced every other day for the duration of the study.

FIG. 8 depicts data from real-time PCR analyses of the expression of the following genes in cells of the human embryonic stem cell line H1 differentiated and cultured at the air-liquid interface as outlined in Example 4 after day 1 of Stage 4, day 3 of Stage 5 and day 6 of Stage 6 at the air-liquid interface: PDX1 (FIG. 8A), NKX6.1 (FIG. 8B), NGN3 (FIG. 8C), ABCC8 (FIG. 8D), PCSK1 (FIG. 8E), Ghrelin (FIG. 8F), glucagon (FIG. 8G), and insulin (FIG. 8H).

Figure 9C:
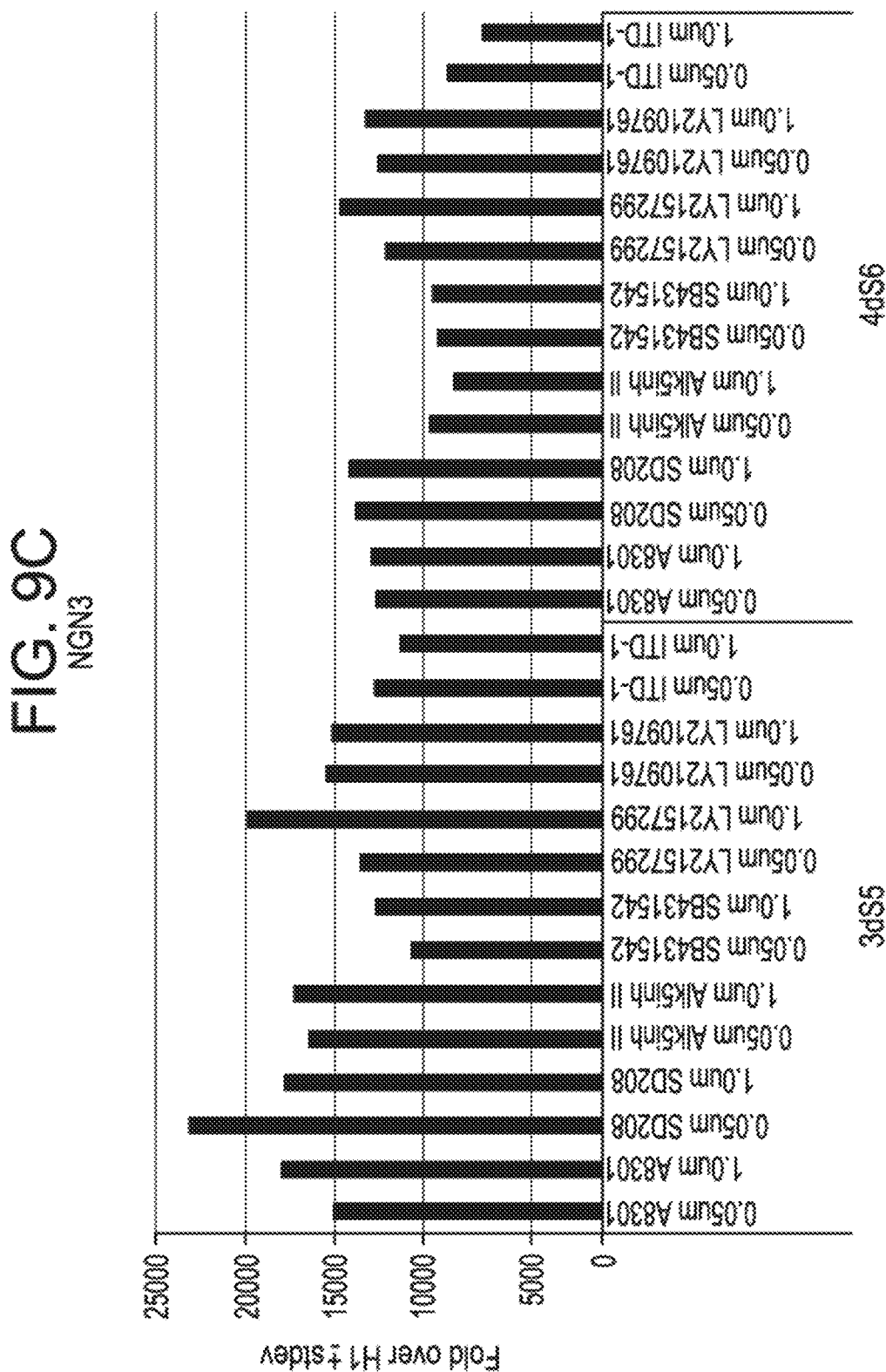
Figure 9E:
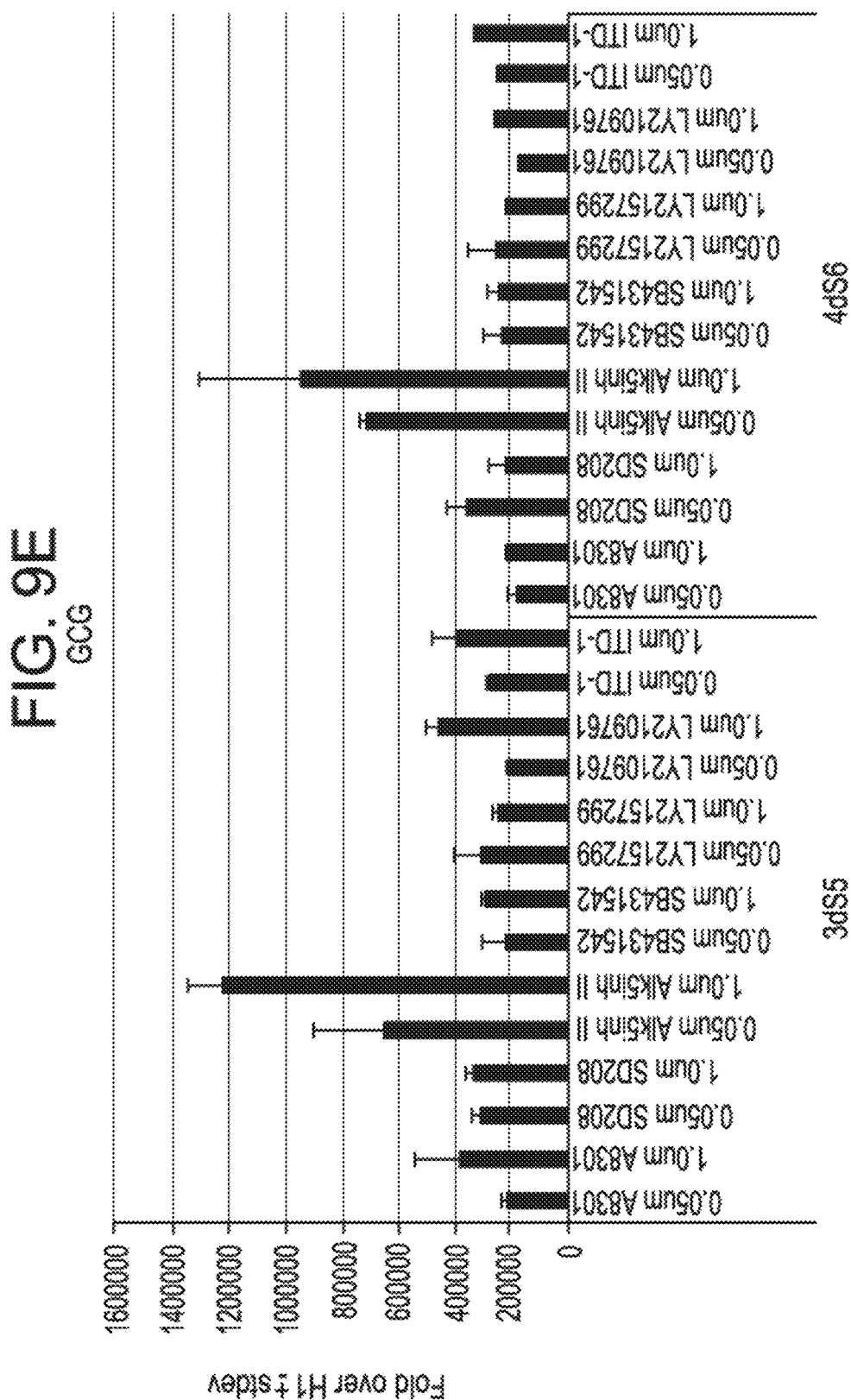

FIG. 9 depicts data from real-time PCR analyses of the expression of the following genes in cells of the human embryonic stem cell line H1 differentiated as outlined in Example 4 and cultured in planar monolayer cultures at day 3 of Stage 5 and day 4 of Stage 6 for PDX1 (FIG. 9A), NKX6.1 (FIG. 9B), NGN3 (FIG. 9C), ABCC8 (FIG. 9D), PCSK1 (FIG. 9E), Ghrelin (FIG. 9F), glucagon (FIG. 9G), and insulin (FIG. 9H). Comparison of FIGS. 8 and 9 reveal that treatment of planar cultures at Stage 5 and Stage 6 with ALK5 inhibitor II resulted in a drop in insulin expression at Stage 6 as compared to Stage 5. However, treatment of cultures at the air-liquid interface with ALK5 inhibitor resulted in enhancement of insulin expression at Stage 6 as compared to Stage 5. The same pattern also applied to NGN3 and NKX6.1 expression in the air-liquid interface cultures as compared to monolayer cultures.

FIG. 10 shows immunostaining results for Stage 6 cells cultured at the air-liquid interface in media treated either with 1 micro molar SD208 inhibitor (Panel 9A) or 1 micro molar ALK5 inhibitor II (Panel 10B) and stained for chromogranin-A (pan-endocrine marker) and NKX6.1 (Pancreatic precursor marker and β cell specific marker). Cultures treated with ALK5 inhibitor II resulted in co-expression of NKX6.1 and chromogranin-A. However, cultures treated with SD208 showed very low co-expression of NKX6.1 and chromogranin-A.

Culturing pancreatic foregut precursor cells on filter inserts at the air-liquid interface in combination with ALK5 inhibitor II significantly enhanced the number of NKX6.1 positive cells co-expressing insulin or chromogranin-A. Furthermore, the same protocol applied to cells cultured on traditional monolayer cultures failed to show significant numbers of NKX6.1 positive cells co-expressing insulin or chromogranin-A. Lastly, treatment of cells cultured at the air-liquid interface with ALK5 inhibitors other than ALK5 inhibitor II failed to show a significant number of NKX6.1 positive cells co-expressing insulin or chromogranin-A. These results indicate that a unique combination of culturing at the air-liquid interface with a medium supplemented with ALK5 inhibitor II resulted in co-expression of insulin/chromogranin-A and NKX6.1.

TABLE III

ALK5 inhibitors tested in Example 4

| Compound | Vendor | Catalogue Number |
|---|---|---|
| TGF-B inhibitor SB431542 | Xcess Biosciences (San Diego, Ca) | M60015-25s |
| SD208 | R & D systems (MN) | 3269 |
| ITD-1 | Xcess Biosciences (San Diego, Ca) | M600060-2S |
| LY2109761 | Xcess Biosciences (San Diego, Ca) | M60035-2S |
| A83-01 | Xcess Biosciences (San Diego, Ca) | M60021-2S |
| LY2157299 | Xcess Biosciences (San Diego, Ca) | M60064-2S |
| ALK5 inhibitor II | Enzo (Farmingdale, NY) | ALX-270-445 |

Example 5

Comparison of Various ALK5 Inhibitors in Stages 5 and 6 for Cells Cultured at the Air-liquid Interface This example shows that ALK5 inhibitor II was unique in generating a significant population of cells at the air-liquid interface that expressed NKX6.1 and insulin or chromogranin-A. Additional TGF-β inhibitors tested are listed in Table IV.

Cells of the human embryonic stem cell line H1 (passage 40) were seeded as single cells at 1×10⁵ cells/cm² on MATRIGEL™ (1:30 dilution; BD Biosciences, NJ)-coated dishes in a media comprising DMEM-F12 (Invitrogen, Ca), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 μM of Y27632 (Rock inhibitor, Catalog No. Y0503, Sigma-Aldrich). Forty-eight hours post-seeding, cultures were washed in incomplete PBS (phosphate buffered saline without Mg or Ca). The cells were then differentiated according to the following protocol:

a. Stage 1 (3 days): Cells were cultured for one day in MCDB-131 medium (Invitrogen Catalog No. 10372-019) supplemented with 2% fatty acid-free BSA (Proliant, Catalog No. 68700); 0.0012 g/ml sodium bicarbonate (Sigma-Aldrich, Catalog No. S3187); 1× GlutaMax™ (Invitrogen, Catalog No. 35050-079); 4.5 mM D-glucose (Sigma-Aldrich, Catalog No. G8769); 100 ng/ml GDF8 (R&D Systems); and 1 μM MCX compound. Cells were then cultured for an additional day in MCDB-131 medium supplemented with: 2% fatty acid-free BSA; 0.0012 g/ml sodium bicarbonate; 1× GlutaMax™; 4.5 mM D-Glucose; 100 ng/ml GDF8; and 0.1 μM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b. Stage 2 (2 days): The Stage 1 cells were then treated for two days with MCDB-131 medium supplemented with 2% fatty acid-free BSA; 0.0012 g/ml sodium bicarbonate; 1x GlutaMax™; 4.5 mM D-glucose; 0.25 mM ascorbic acid (Sigma, MO) and 25 ng/ml FGF7 (R & D Systems, MN).

c. Stage 3 (2 days): The Stage 2 cells were then treated with BLAR custom medium (Invitrogen) supplemented with a 1:200 dilution of ITS-X (Invitrogen, CA); 4.5 mM glucose; 1× GlutaMax™; 0.0017 g/ml sodium bicarbonate; 2% fatty acid-free BSA; 0.25 μM SANT-1 (Sigma, MO); 1 μM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d. Stage 4 (2 days): The Stage 3 cells were then treated with BLAR medium supplemented with a 1:200 dilution of ITS-X; 4.5 mM glucose; 1× GlutaMax™; 0.0017 g/ml sodium bicarbonate; 2% fatty acid-free BSA; 0.25 μM SANT-1; 100 nM RA; 2 ng/ml FGF7; 100 nM LDN-193189; 0.25 mM ascorbic acid; and 100 nM TPB for two days, then at the end of stage 4, cells cultured on planar dishes were treated for 4 hours with 10 μM of Y27632, rinsed with PBS and treated for 5 minutes at room temperature with 1× TrypLE™ (Invitrogen) followed by removal of the enzyme, rinsing with basal media and scraping of cells by a cell scraper. The resulting suspension of cells was seeded at a density of 0.5-0.75×10⁵ cells (in 10 μl aliquots) onto 0.4 micron porous cell culture filter inserts (BD 353493) in 6-well plates, or onto 10 cm filter inserts (Corning, #3419) in 10 cm dishes. 1.5 ml of media was added to the bottom of each insert in the 6-well plates and 7.5 ml of media was added to the bottom of each 10 cm insert.). No further media was added to the apical side of the filter. Media was replaced every day for the duration of the study.

e. Stage 5 (3 days): The Stage 4 cells were then cultured at the air-liquid interface in BLAR medium supplemented with a 1:200 dilution of ITS-X; 20 mM glucose; 1× GlutaMax™; 0.0015 g/ml sodium bicarbonate; 2% fatty acid-free BSA; 10 μg/ml of heparin (Sigma, #H3149), 0.25 μM SANT-1; 50 nM RA; 100 nM LDN-193189; 1000 nM of various ALK5 inhibitor (see Table IV for the list of inhibitors used) for three days.

f. Stage 6 (6 days): The Stage 5 cells were then treated with BLAR medium supplemented with a 1:200 dilution of ITS-X; 20 mM glucose; 1× GlutaMax™; 0.0015 g/ml sodium bicarbonate; 2% fatty acid-free BSA; 10 μg/ml of heparin (Sigma, #H3149), 0.25 μM SANT-1; 100 nM LDN-193189, 1000 nM T3, 1000 nM ALK5 inhibitor (see Table IV for list of inhibitors tested) for six days.

FIG. 23 depicts data from real-time PCR analyses of the expression of the following genes in cells of the human embryonic stem cell line H1 differentiated and cultured at the air-liquid interface as outlined in Example 5 after day 4 of Stage 5, and day 6 of Stage 6: PDX1 (FIG. 23A), NKX6.1 (FIG. 23B), NGN3 (FIG. 23C), ABCC8 (FIG. 23D), glucagon (FIG. 23E), and insulin (FIG. 23F). Similar to the results of Example 4, culturing pancreatic foregut precursor cells on filter inserts at the air-liquid interface and treatment with ALK5 inhibitor II significantly enhanced the expression of insulin and glucagon. Treatment of pancreatic foregut precursor cells with other ALK5 inhibitors did not result in significant expression of either insulin or glucagon.

TABLE IV

ALK5 (also referred to as TGF-β receptor) inhibitors tested in Example 5

| Compound | Vendor | Catalogue Number |
|---|---|---|
| TGF-β receptor inh V | EMD | 616456 |
| TGF-β receptor inh I | EMD | 616451 |
| TGF-β receptor inh IV | EMD | 616454 |
| TGF-β receptor inh VII | EMD | 616458 |
| TGF-β receptor inh VIII | EMD | 616459 |
| TGF-β receptor inh II | EMD | 616452 |
| TGF-β receptor inh VI | EMD | 616464 |
| TGF-β receptor inh III | EMD | 616453 |

Example 6

Effect of Seeding Cell Density at the Air-liquid Interface on Subsequent Differentiation into Endocrine Cells This example identifies a range of seeding densities at the air-liquid interface and the resulting expression of endocrine markers. To conduct the studies in this example, embryonic stem cells were differentiated using the protocol discussed below.

Cells of the human embryonic stem cell line H1 (passage 40) were seeded as single cells at 1×10⁵ cells/cm² on MATRIGEL™ (1:30 dilution; BD Biosciences, NJ)-coated dishes in a media comprising DMEM-F12 (Invitrogen, CA), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 μM of Y27632 (Rock inhibitor, Catalog No. Y0503, Sigma). Forty-eight hours post-seeding, cultures were washed in incomplete PBS (phosphate buffered saline without Mg or Ca). The cells were then differentiated according to the following protocol:

a) Stage 1 (3 days): Cells were cultured for one day in MCDB-131 medium (Invitrogen, Catalog No. 10372-019) supplemented with 2% fatty acid-free BSA (Proliant, Catalog No. 68700); 0.0012 g/ml sodium bicarbonate (Sigma-Aldrich, Catalog No. S3187); 1× GlutaMax™ (Invitrogen, Catalog No. 35050-079); 4.5 mM D-glucose (Sigma-Aldrich, Catalog No. G8769); 100 ng/ml GDF8 (R&D Systems); and 1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Subsequently, the cells were cultured for an additional day in MCDB-131 medium supplemented with 2% fatty acid-free BSA, 0.0012 g/ml sodium bicarbonate, 1× GlutaMax™, 4.5 mM D-Glucose, and 100 ng/ml GDF8.

b) Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO); and 25 ng/ml FGF7 (R & D Systems, MN).

c) Stage 3 (2 days): The Stage 2 cells were then treated with BLAR custom medium (Invitrogen) supplemented with a 1:200 dilution of ITS-X (Invitrogen, CA); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days. Then, at the end of Stage 3, cells cultured on planar dishes were treated for 4 hours with 10 µM of Y27632, rinsed with PBS and treated for 5 minutes at room temperature with 1× TrypLE™ (Invitrogen) followed by removal of the enzyme, rinsing with basal media and scraping of cells by a cell scraper. The resulting suspension of cells were seeded at a density of 0.1, 0.5, 1 and $5\times10^6$ cells (in 10 µl aliquots) onto 0.4 micron porous cell culture filter inserts (BD 353493) in 6-well plates. 1.5 ml of media was added to the bottom of each insert and no further media was added to the apical side of the filter. Media was replaced every day for the duration of the study.

d) Stage 4 (2 days): The Stage 3 cells were then cultured at the air-liquid interface in BLAR medium supplemented with a 1:200 dilution of ITS-X; 4.5 mM glucose; 1× GlutaMax™; 0.0017 g/ml sodium bicarbonate; 2% fatty acid-free BSA; 10 µg/ml of heparin (Sigma, #H3149), 0.25 µM SANT-1; 100 nM RA; 2 ng/ml FGF7; 100 nM LDN-193189; 0.25 mM ascorbic acid; and 100 nM TPB for two days.

e) Stage 5 (3 days): The Stage 4 cells were then treated with BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 0.25 µM SANT-1; 50 nM RA; 100 nM LDN-193189; 10000 nM of ALK5 inhibitor II for three days.

f) Stage 6 (14 days): The Stage 5 cells were then treated with BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 0.25 µM SANT-1; 10000 nM ALK5 inhibitor, 100 nM LDN-193189, and 1000 nM T3 for fourteen days.

Figure 11A:
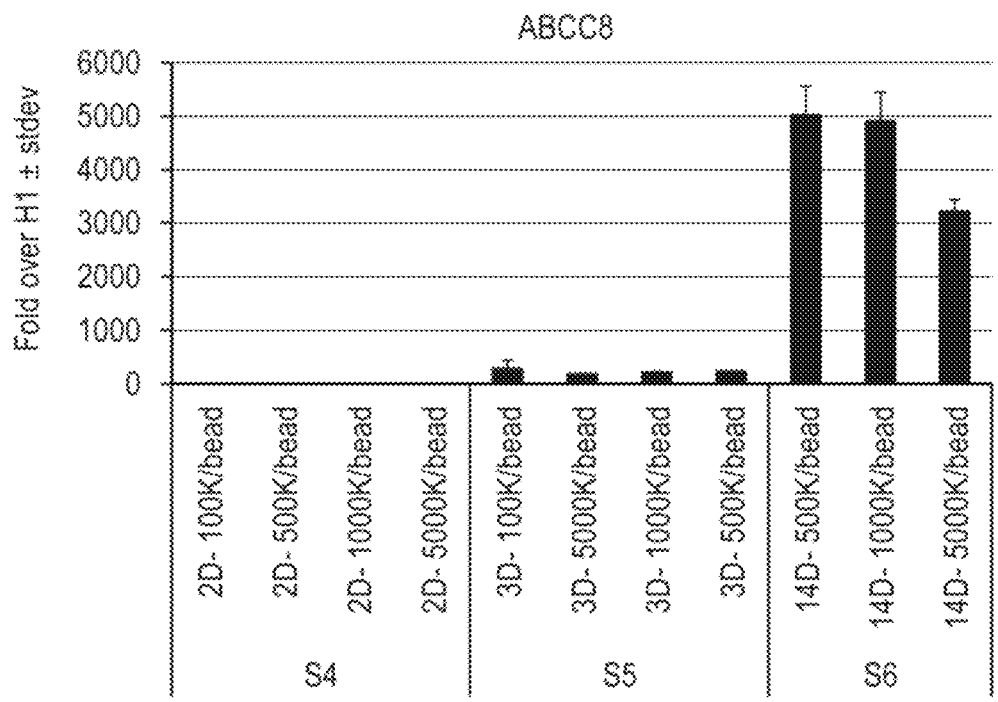
FIGS. 11A to 11H show data from real-time PCR analyses of the expression of the following genes in cells of the human embryonic stem cell line H1 differentiated as described in Example 6: ABCC8 (FIG. 11A); glucagon (FIG. 11B); amylin (FIG. 11C); insulin (FIG. 11D); NGN3 (FIG. 11E); NKX2.2 (FIG. 11F); NKX6.1 (FIG. 11G); and PDX1 (FIG. 11H). The data is shown as fold increase versus undifferentiated H1 line.
Figure 11B:
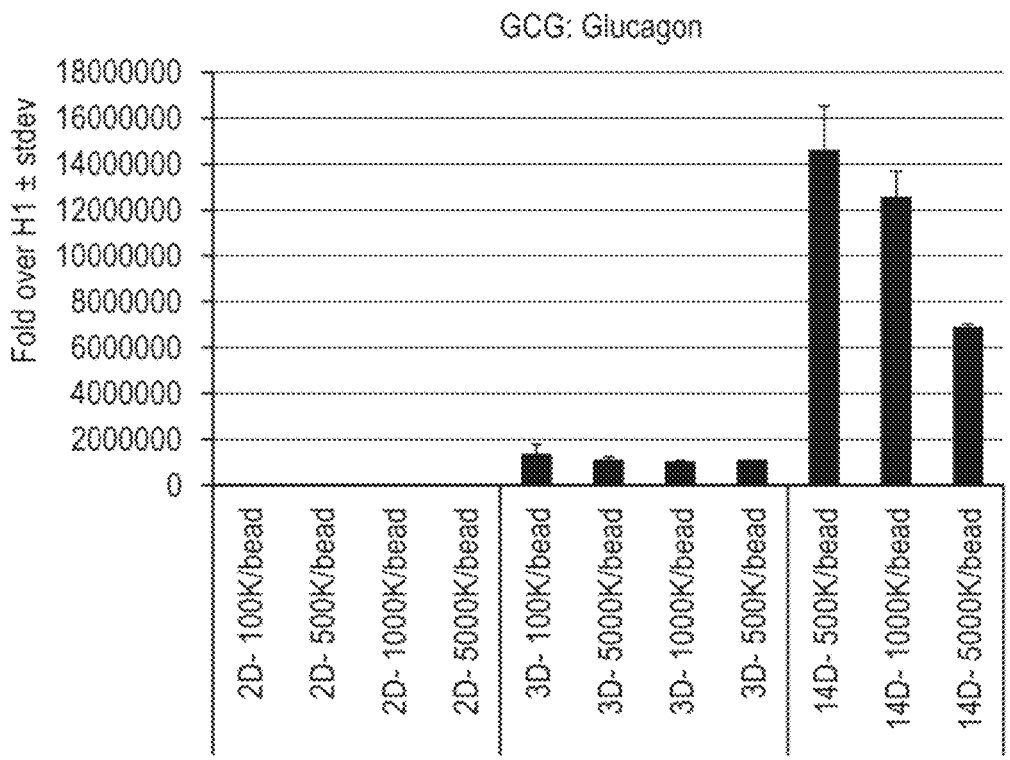
Figure 11C:
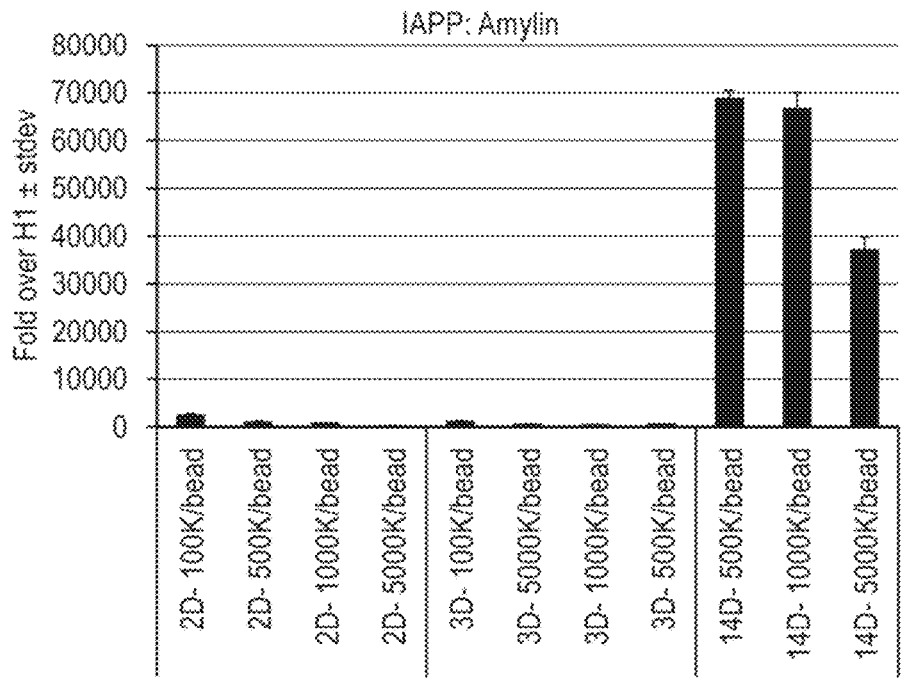
Figure 11D:
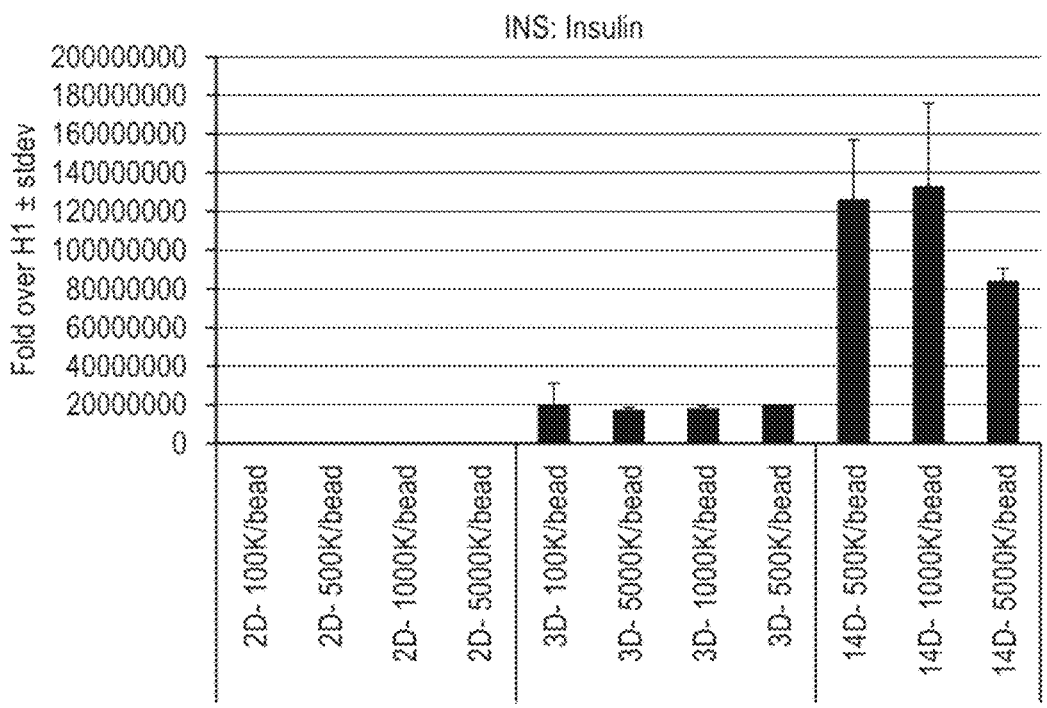
Figure 11E:
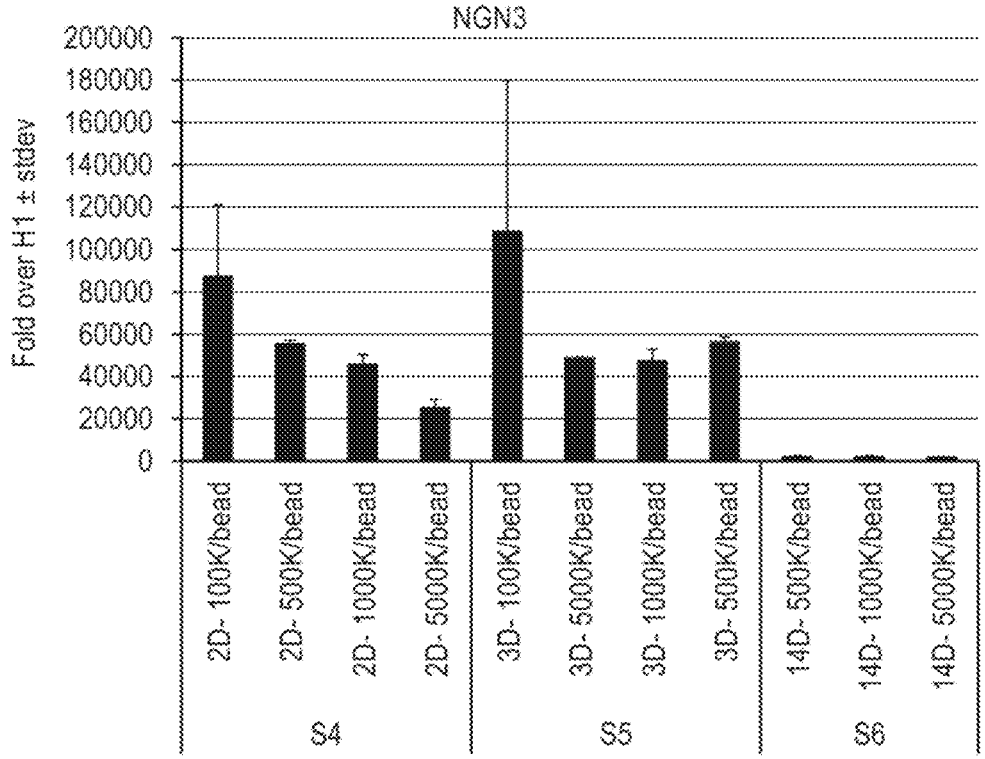
Figure 11F:
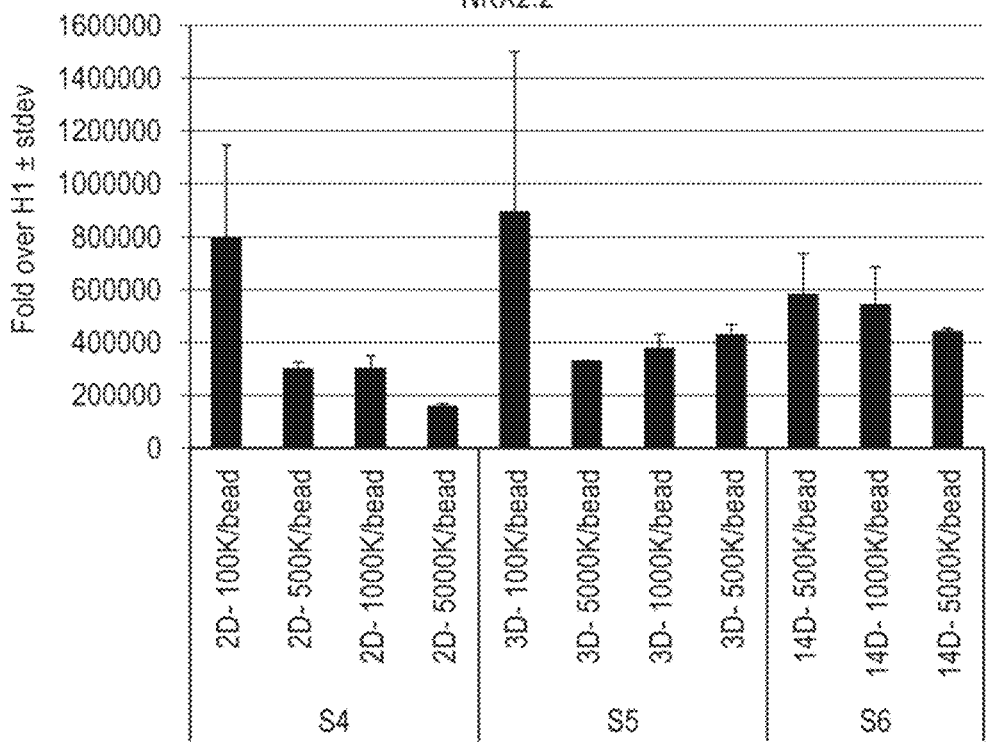
Figure 11G:
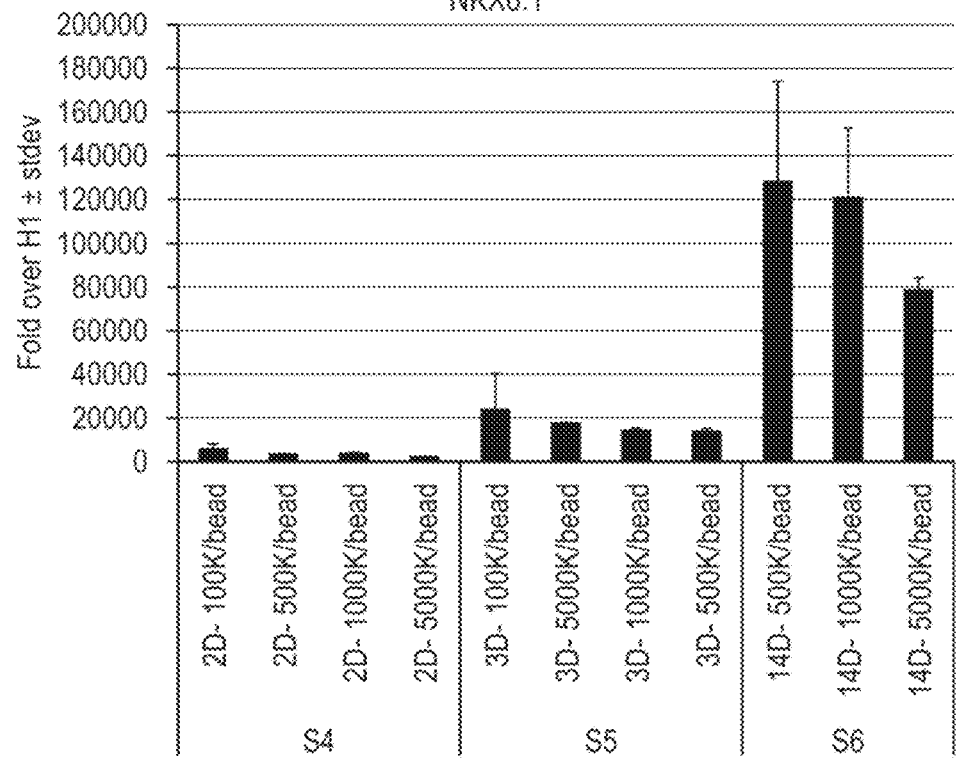
Figure 11H:
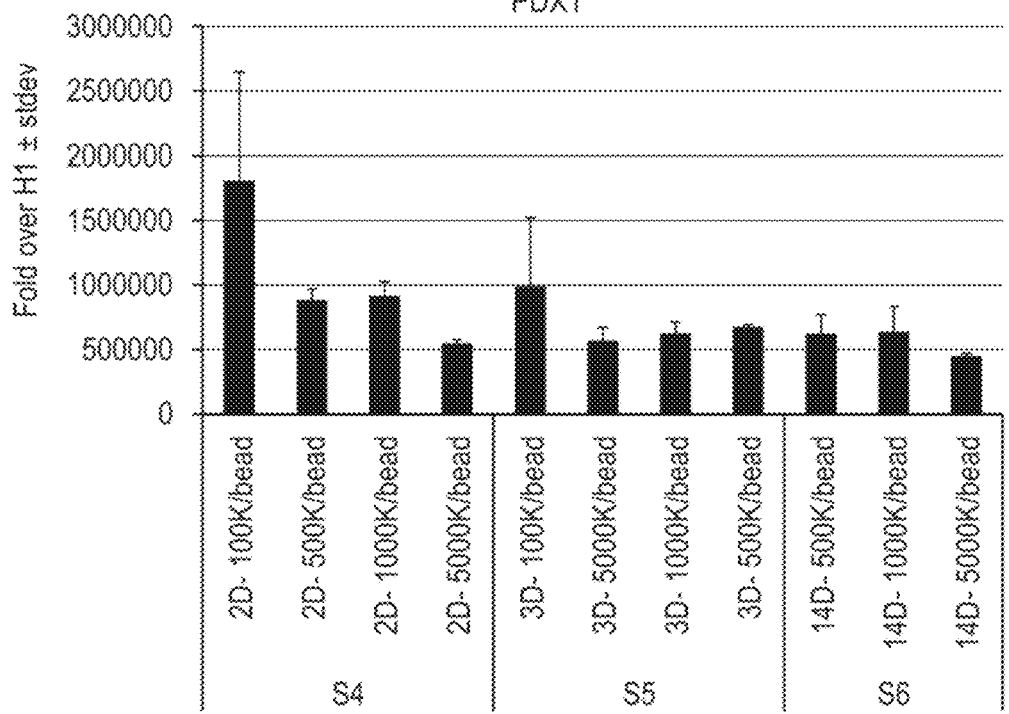

RNA samples were collected at Stages 4, 5, and 6, and analyzed by real-time PCR. FIG. 11 depicts data from real-time PCR analyses of the expression of the following genes in cells of the human embryonic stem cell line H1 differentiated as outlined in Example 6 and cultured at the air-liquid interface: ABCC8 (FIG. 11A); glucagon (FIG. 11B); amylin (FIG. 11C); insulin (FIG. 11D); NGN3 (FIG. 11E); NKX2.2 (FIG. 11F); NKX6.1 (FIG. 11G); and PDX1 (FIG. 11H). Seeding densities in the range of $0.1-1\times10^6$ cells/10 µl resulted in similar expression of pancreatic endoderm and endocrine markers at Stages 5 and 6. At the highest tested seeding density ($5\times10^6$ cells/10 µl) at the air-liquid interface, there was a drop in expression of endocrine markers.

Example 7

Comparison of 0.4, 1, and 3 Micron Pore Size Filter Inserts

This example compares the effect of filter pore size on subsequent differentiation at the air-liquid interface. To conduct the studies in this example, embryonic stem cells were differentiated using the protocol discussed below.

Cells of the human embryonic stem cell line H1 (passage 40) were seeded as single cells at $1\times10^5$ cells/cm² on MATRIGEL™ (1:30 dilution; BD Biosciences, NJ)-coated dishes in a media comprising of DMEM-F12 (Invitrogen, CA), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, Sigma). Forty-eight hours post-seeding, cultures were washed in incomplete PBS (phosphate buffered saline without Mg or Ca). The cells were then differentiated according to the following protocol:

a) Stage 1 (3 days): Cells were cultured for one day in MCDB-131 medium (Invitrogen, Catalog No. 10372-019) supplemented with 2% fatty acid-free BSA (Proliant, Catalog No. 68700); 0.0012 g/ml sodium bicarbonate (Sigma-Aldrich, Catalog No. S3187), 1× GlutaMax™ (Invitrogen Catalog No. 35050-079); 4.5 mM D-glucose (Sigma-Aldrich, Catalog No. G8769), 100 ng/ml GDF8 (R&D Systems); and 1 µM MCX. Cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-Glucose, and 100 ng/ml GDF8.

b) Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c) Stage 3 (2 days): The Stage 2 cells were then treated with BLAR custom medium (Invitrogen) supplemented with a 1:200 dilution of ITS-X (Invitrogen, CA); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d) Stage 4 (2 days): The Stage 3 cells were then treated with BLAR medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; and 100 nM TPB for two days. Then, at the end of stage 4, cells cultured on planar dishes were treated for 4 hours with 10 µM of Y27632, rinsed with PBS and treated for 5 minutes at room temperature with 1× TrypLE™ (Invitrogen) followed by removal of the enzyme, rinsing with basal media and scraping of cells by a cell scraper. The resulting suspension of cells were seeded at a density of 0.5-0.75×10$^6$ cells (in 10 µl aliquots) onto 0.4, 1, or 3 micron porous cell culture filter inserts in 6-well plates. 1.5 ml of media was added to the bottom of each insert and no further media was added to the apical side of the filter. Media was replaced every day for the duration of the study.

e) Stage 5 (3 days): The Stage 4 cells were then cultured at the air-liquid interface in BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 0.25 µM SANT-1; 50 nM RA; 100 nM LDN-193189; 10000 nM of ALK5 inhibitor II for three days.

f) Stage 6 (15 days): The Stage 5 cells were then treated with BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 0.25 µM SANT-1; 100 nM LDN-193189, 1000 nM T3, 10000 nM ALK5 inhibitor II for fifteen days.

Figure 12A:
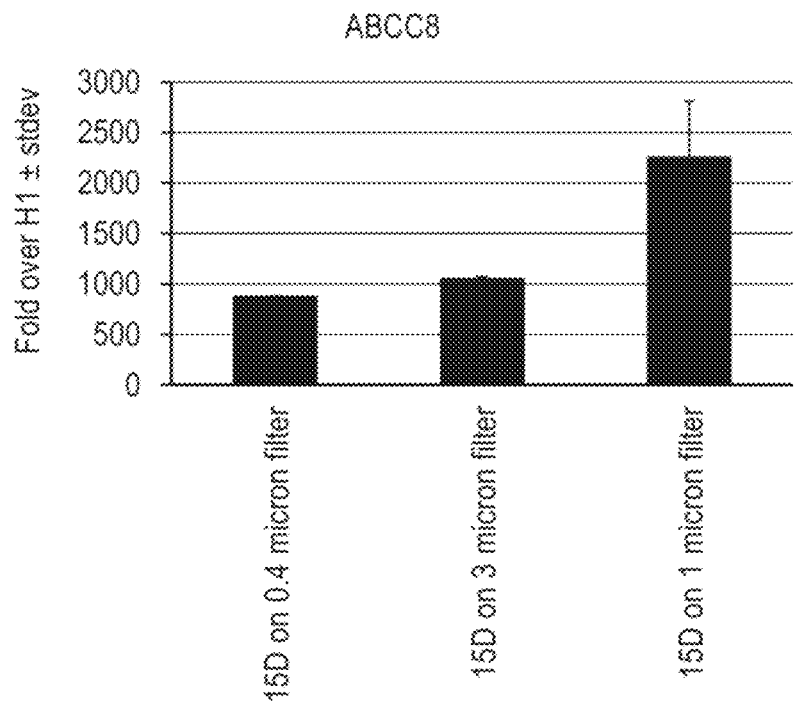
FIGS. 12A to 12H depict data from real-time PCR analyses of the expression of the following genes in cells of the human embryonic stem cell line H1 differentiated as outlined in Example 7 and cultured at the ALI: ABCC8 (FIG. 12A); glucagon (FIG. 12B); amylin (FIG. 12C); insulin (FIG. 12D); NGN3 (FIG. 12E); NKX2.2 (FIG. 12F); NKX6.1 (FIG. 12G); and PDX1 (FIG. 12H).
Figure 12B:
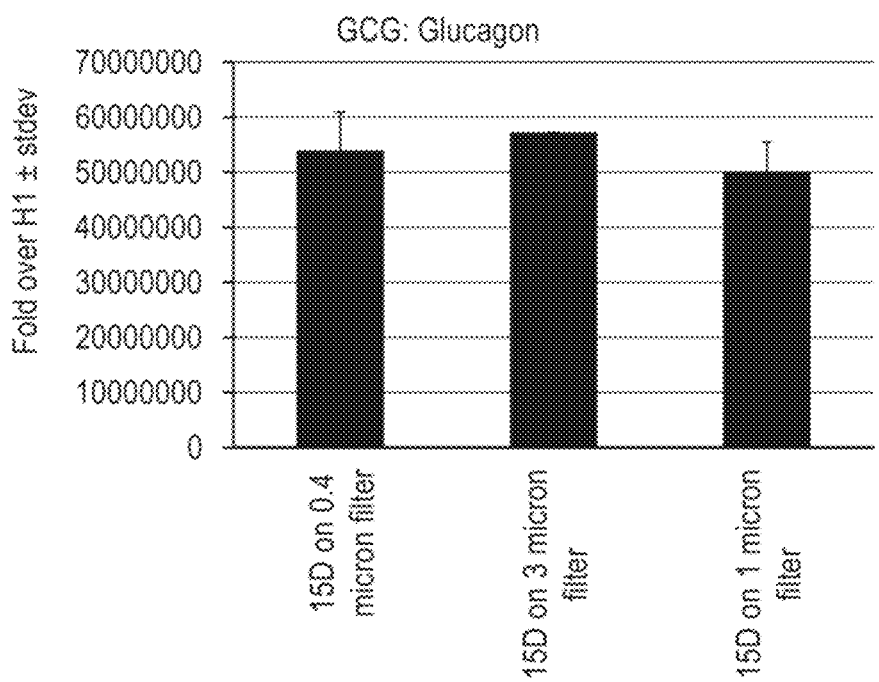
Figure 12C:
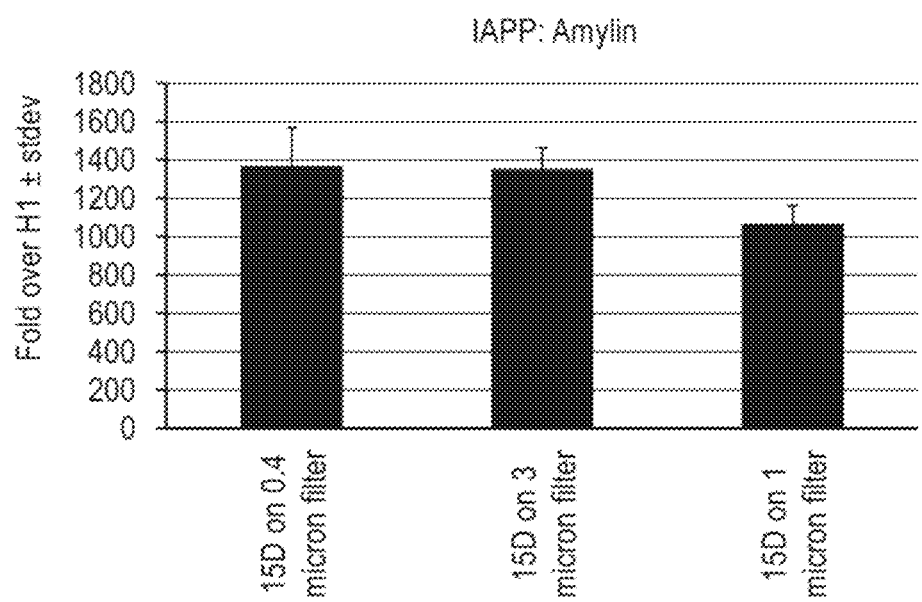
Figure 12D:
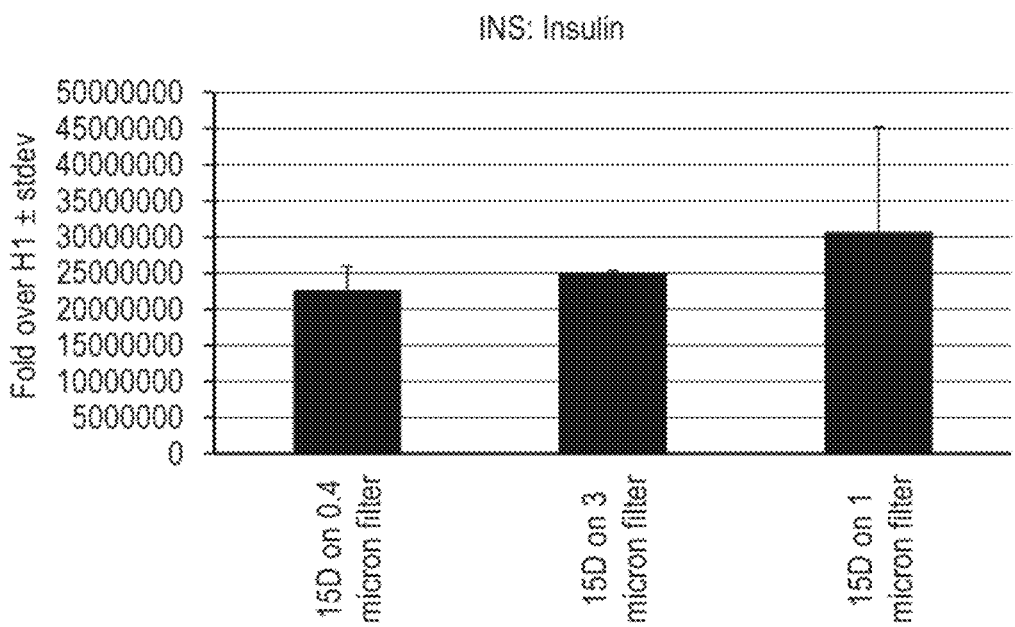
Figure 12E:
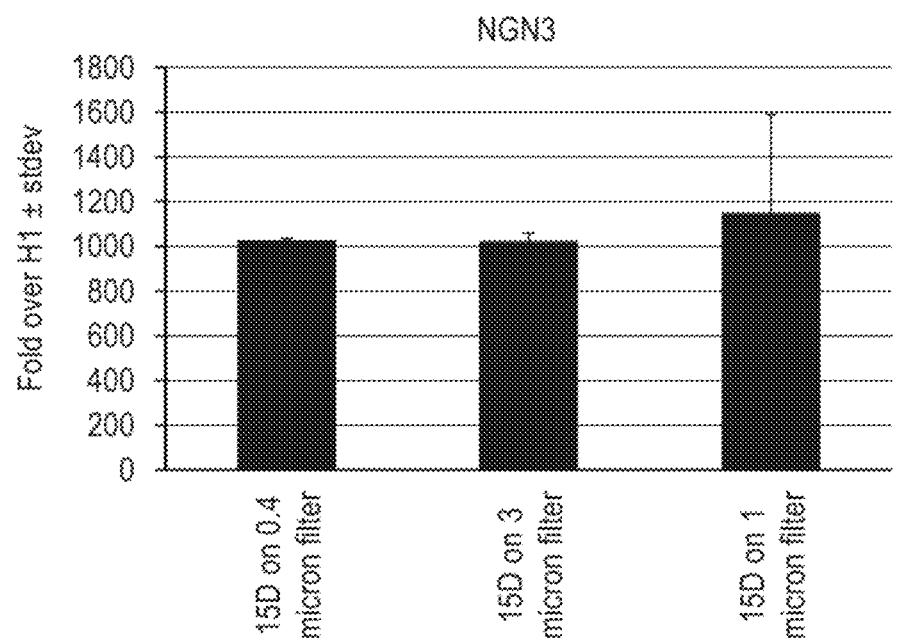
Figure 12F:
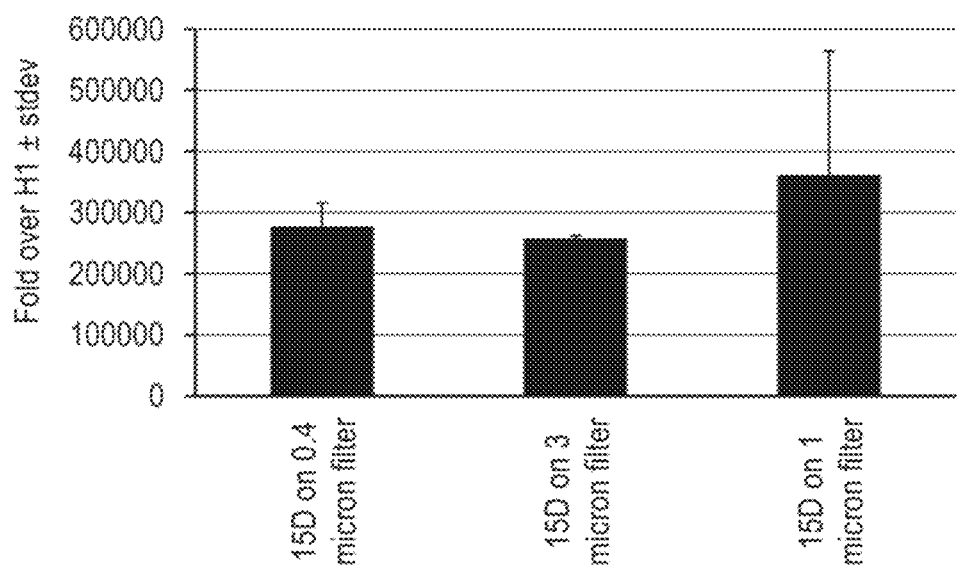
Figure 12G:
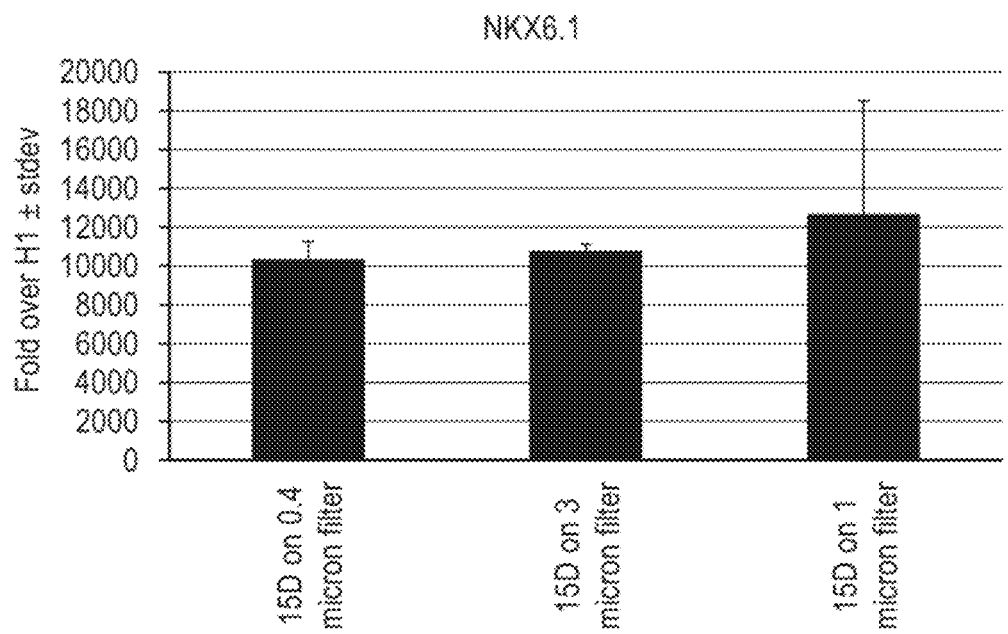
Figure 12H:
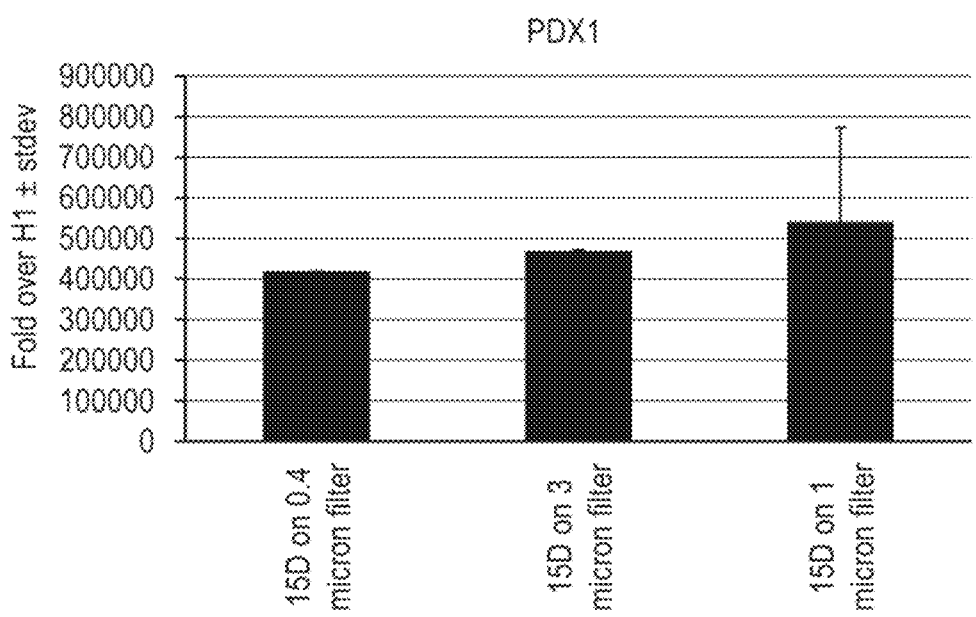

RNA samples were collected at Stage 6 and analyzed by real-time PCR. FIG. 12 depicts data from real-time PCR analyses of the expression of the following genes in cells of the human embryonic stem cell line H1 differentiated as outlined in this Example and cultured at the air-liquid interface: ABCC8 (FIG. 12A); glucagon (FIG. 12B); amylin (FIG. 12C); insulin (FIG. 12D); NGN3 (FIG. 12E); NKX2.2 (FIG. 12F); NKX6.1 (FIG. 12G); and PDX1 (FIG. 12H). Filter inserts pore sizes ranging from 0.4 to 3 micron did not significantly impact expression of pancreatic endoderm or endocrine markers at the air-liquid interface.

Example 8

Comparison of Differentiating Pancreatic Foregut Precursor Cells at the Air-liquid Interface to Liquid-liquid (L/L) Interface on Filter Inserts This example compares the impact of culturing at the air-liquid interface to culturing at the liquid-liquid interface on differentiation of pancreatic foregut precursor cells on filter inserts. To conduct the studies in this example, embryonic stem cells were differentiated using the protocol discussed below.

Cells of the human embryonic stem cell line H1 (passage 40) were seeded as single cells at 1×10$^5$ cells/cm$^2$ on MATRIGEL™ (1:30 dilution; BD Biosciences, NJ)-coated dishes in a media comprising of DMEM-F12 (Invitrogen, CA), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, Sigma-Aldrich). Forty-eight hours post-seeding, cultures were washed in incomplete PBS (phosphate buffered saline without Mg or Ca). The cells were then differentiated according to the following protocol:

a) Stage 1 (3 days): Cells were cultured for one day in MCDB-131 medium (Invitrogen Catalog No. 10372-019) supplemented with 2% fatty acid-free BSA (Proliant, Catalog No. 68700); 0.0012 g/ml sodium bicarbonate (Sigma-Aldrich Catalog No. S3187); 1× GlutaMax™ (Invitrogen, Catalog No. 35050-079), 4.5 mM D-glucose (Sigma-Aldrich, Catalog No. G8769); 100 ng/ml GDF8 (R&D Systems); and 1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b) Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c) Stage 3 (2 days): The Stage 2 cells were then treated with BLAR custom medium (Invitrogen) supplemented with a 1:200 dilution of ITS-X (Invitrogen, CA); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d) Stage 4 (2 days): The Stage 3 cells were then treated with BLAR medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; and 100 nM TPB for two days, then at the end of Stage 4, cells cultured on planar dishes were treated for 4 hours with 10 µM of Y27632, rinsed with PBS and treated for 5 minutes at room temperature with 1× TrypLE™ (Invitrogen) followed by removal of the enzyme, rinsing with basal media and scraping of cells by a cell scraper. The resulting suspension of cells were seeded at a density of 0.5-0.75×10$^6$ cells (in 10 µl aliquots) on MATRIGEL™-coated 0.4 micron porous cell culture filter inserts in 6-well plates. 1.5 ml of media was added to the bottom of each insert and no further media was added to the apical side of the filter. For L/L condition, media was also added on top of the filter inserts resulting in liquid-liquid interface. Media was replaced every day for the duration of the study.

e) Stage 5 (3 days): The Stage 4 cells were then cultured at the air-liquid interface in BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 0.25 µM SANT-1; 50 nM RA; 100 nM LDN-193189; 10000 nM of various ALK5 inhibitor II for three days.

f) Stage 6 (10 days): The Stage 5 cells were then treated with BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 0.25 µM SANT-1; 100 nM LDN-193189, 1000 nM T3, 10000 nM ALK5 inhibitor II for ten days.

Figure 13A:
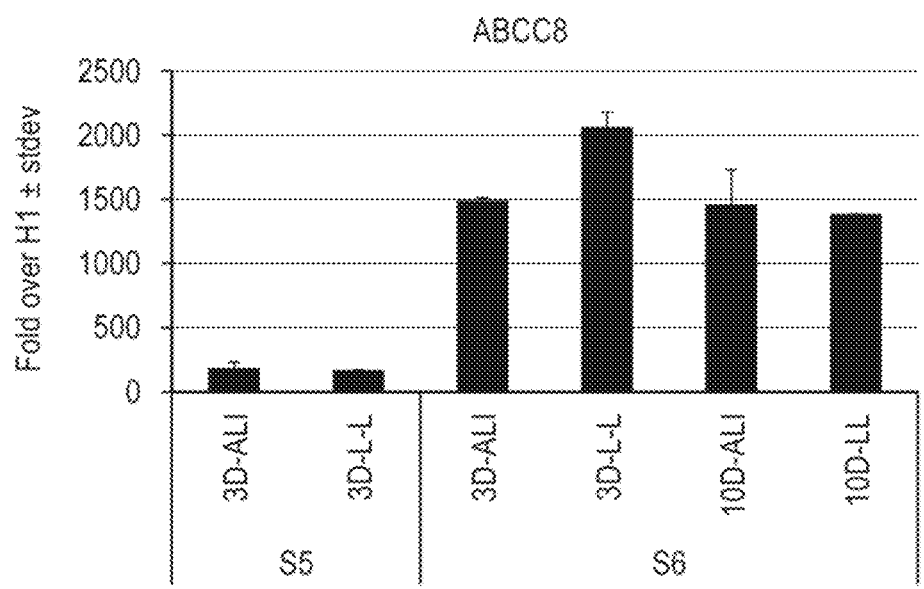
FIGS. 13A to 13H depicts data from real-time PCR analyses of the expression of the following genes in cells of the human embryonic stem cell line H1 differentiated as outlined in Example 8 and cultured at the ALI: ABCC8 (FIG. 13A); glucagon (FIG. 13B); amylin (FIG. 13C); insulin (FIG. 13D); NGN3 (FIG. 13E); NKX2.2 (FIG. 13F); NKX6.1 (FIG. 13G); and PDX1 (FIG. 13H).
Figure 13B:
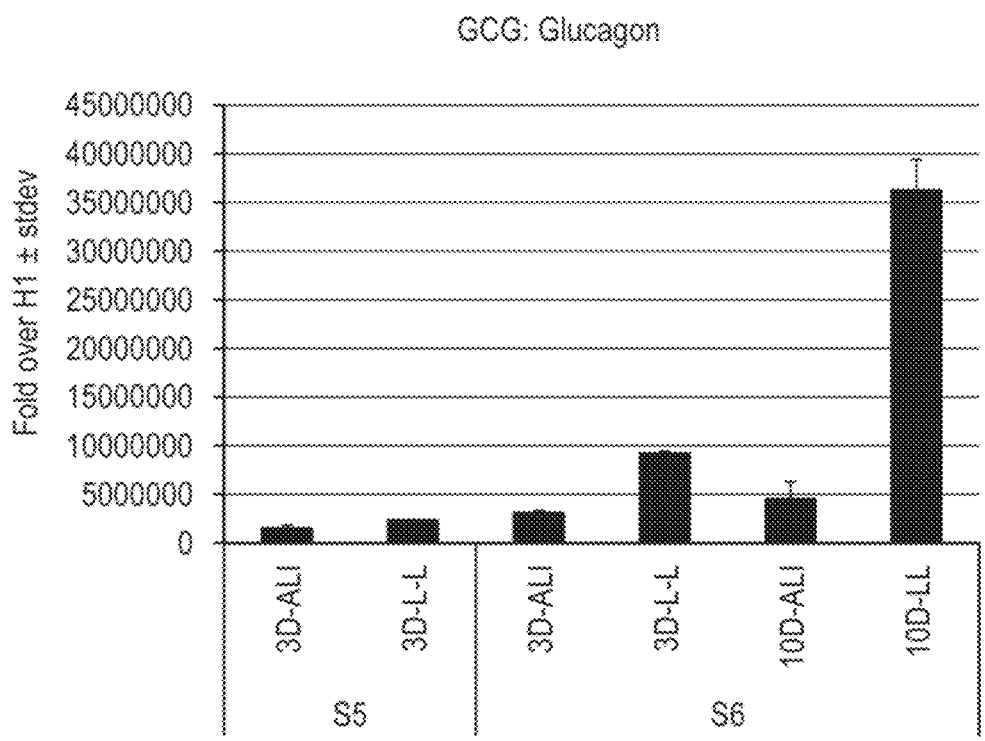
Figure 13C:
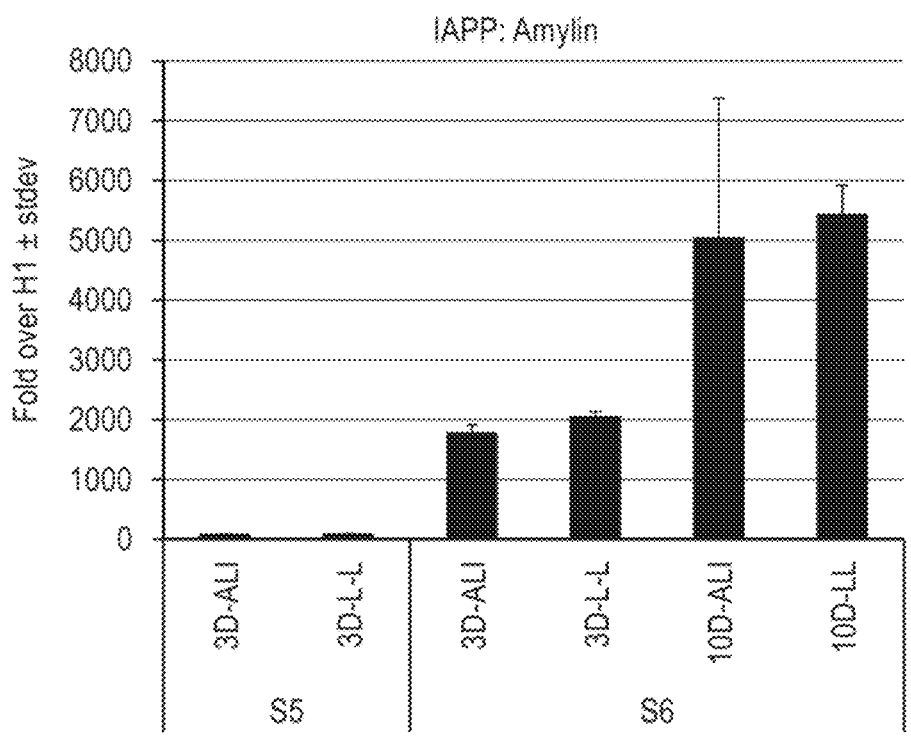
Figure 13D:
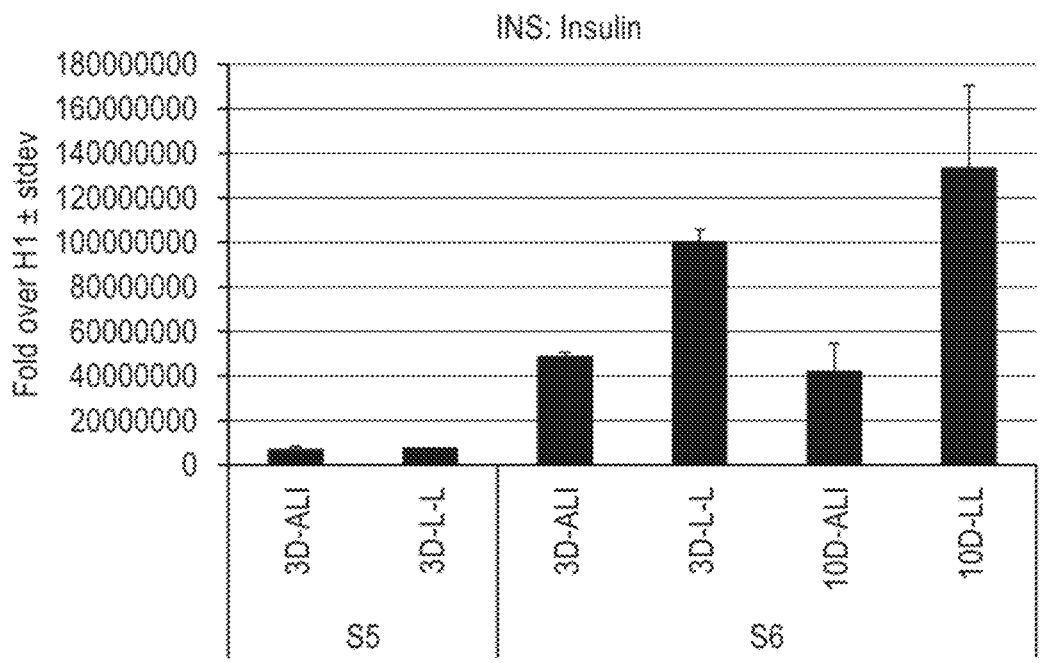
Figure 13E:
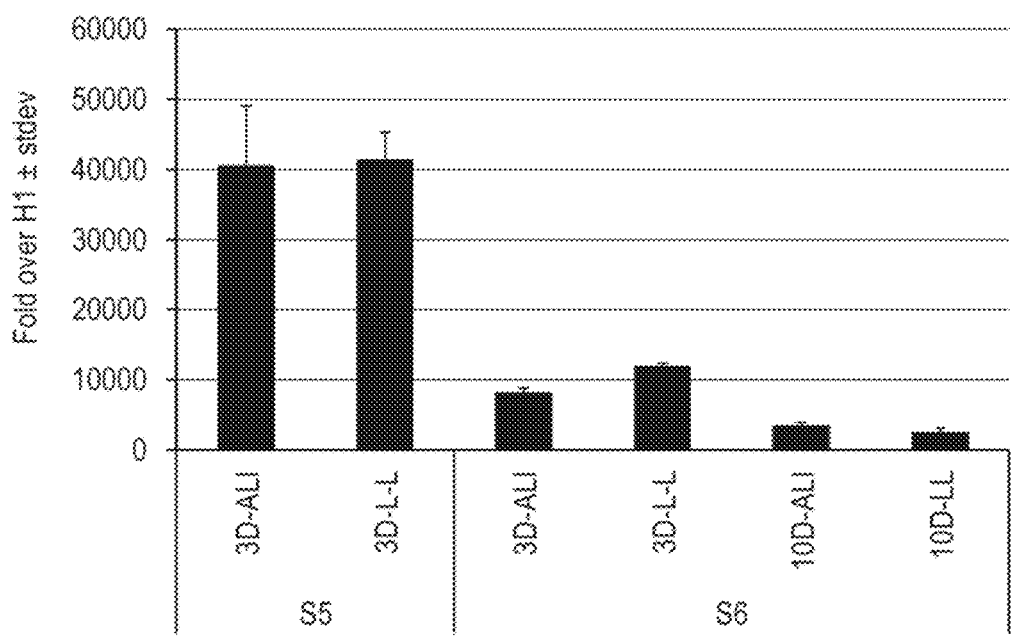
Figure 13F:
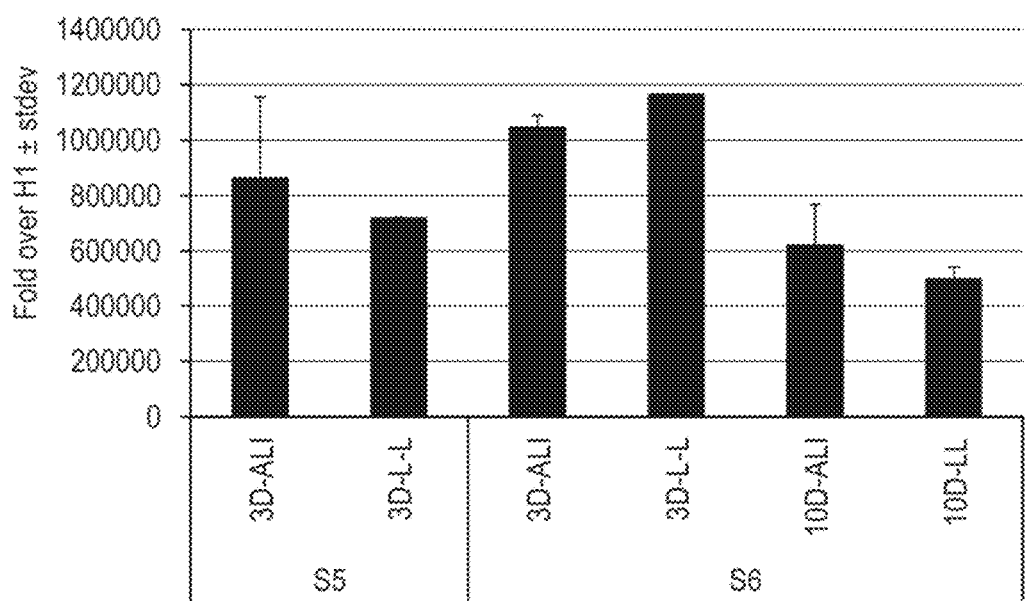
Figure 13G:
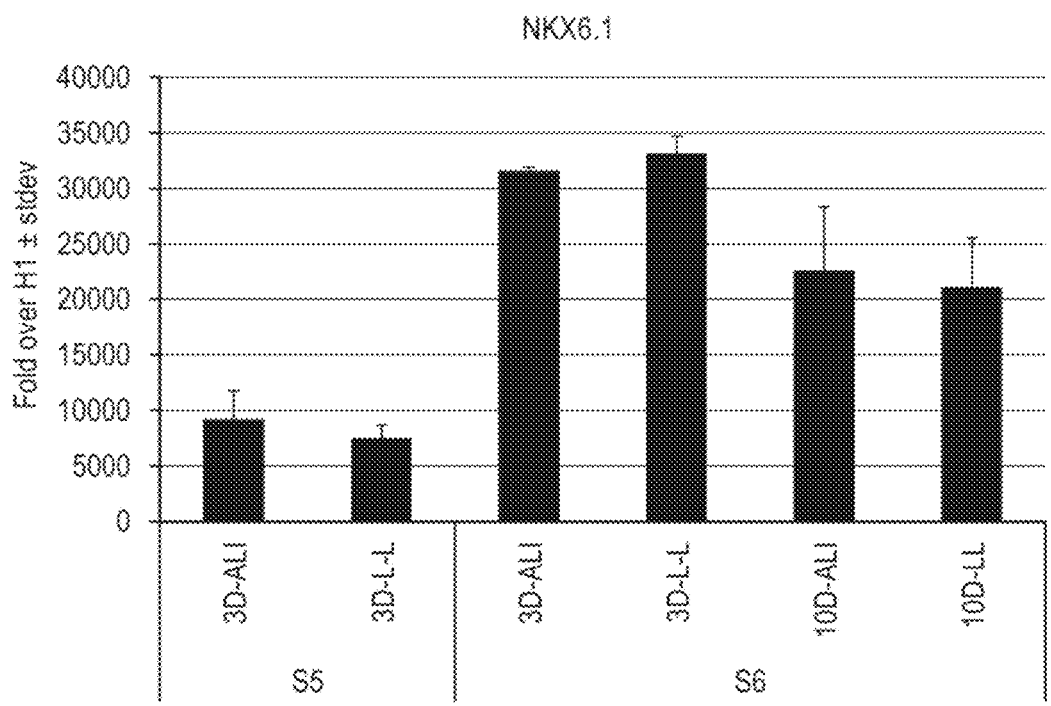
Figure 13H:
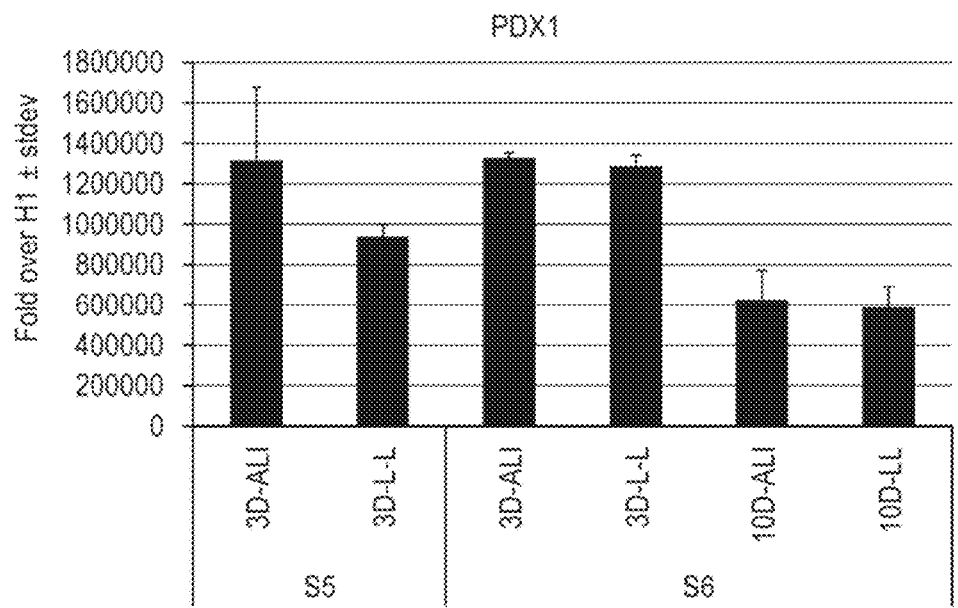

RNA samples were collected at Stages 5 and 6 and analyzed by real-time PCR. FIG. 13 depicts data from real-time PCR analyses of the expression of the following genes in cells of the human embryonic stem cell line H1 differentiated as outlined in Example 8 and cultured at the air-liquid interface: ABCC8 (FIG. 13A); glucagon (FIG. 13B); amylin (FIG. 13C); insulin (FIG. 13D); NGN3 (FIG. 13E); NKX2.2 (FIG. 13F); NKX6.1 (FIG. 13G); and PDX1 (FIG. 13H). The most dramatic difference was seen with significant up-regulation (7×) of glucagon in L/L condition as compared to the air-liquid interface.

Example 9

Pancreatic Endoderm/Endocrine Precursor Cells Cultured at the Air-liquid Interface can be used to Screen a Library of Compounds This example examines the use of air-liquid interface cultures to screen libraries of compounds. To do so embryonic stem cells were differentiated using the protocol discussed below.

Cells of the human embryonic stem cell line H1 (passage 40) were seeded as single cells at $1×10^5$ cells/cm$^2$ on MATRIGEL™ (1:30 dilution; BD Biosciences, NJ)-coated dishes in a media comprising of DMEM-F12 (Invitrogen, Ca), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, Sigma). Forty-eight hours post-seeding, cultures were washed in incomplete PBS (phosphate buffered saline without Mg or Ca). The cells were then differentiated according to the following protocol:

a) Stage 1 (3 days): Cells were cultured for one day in MCDB-131 medium (Invitrogen Catalog No. 10372-019) supplemented with 2% fatty acid-free BSA (Proliant, Catalog No. 68700), 0.0012 g/ml sodium bicarbonate (Sigma-Aldrich, Catalog No. S3187), 1× GlutaMax™ (Invitrogen, Catalog No. 35050-079), 4.5 mM D-glucose (Sigma-Aldrich, Catalog No. G8769), 100 ng/ml GDF8 (R&D Systems) and 1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b) Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c) Stage 3 (2 days): The Stage 2 cells were then treated with BLAR custom medium (Invitrogen) supplemented with a 1:200 dilution of ITS-X (Invitrogen, CA); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d) Stage 4 (2 days): The Stage 3 cells were then treated with BLAR medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; and 200 nM TPB for two days, then at the end of Stage 4, cells cultured on planar dishes were treated for 4 hours with 10 µM of Y27632, rinsed with PBS and treated for 5 minutes at room temperature with 1× TrypLE™ (Invitrogen) followed by removal of the enzyme, rinsing with basal media and scraping of cells by a cell scraper. The resulting suspension of cells were seeded at a density of $0.5$-$0.75×10^6$ cells (in 10 ml aliquots) on MATRIGEL™-coated 0.4 micron porous cell culture filter inserts in 6-well plates. 1.5 ml of media was added to the bottom of each insert and no further media was added to the apical side of the filter.

e) Stage 5 (3 days): The Stage 4 cells were then cultured at the air-liquid interface in BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 10 µM ZnSO$_4$ (Sigma, Z0251), 0.25 µM SANT-1; 50 nM RA; 100 nM LDN-193189; 10000 nM of ALK5 inhibitor II for three days.

f) Stage 6 (12 days): The Stage 5 cells were then treated with BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 10 µM ZnSO$_4$ (Sigma, Z0251), 0.25 µM SANT-1; 100 nM LDN-193189; 1000 nM T3; 10000 nM ALK5 inhibitor II for twelve days. At this stage, compounds listed in Table V were screened to identify potential compounds that affect endoderm and endocrine markers.

TABLE V

List of compounds tested at Stage 6

| Catalogue#/Vendor | Inhibitor | Target Kinase | Tested concentration |
|---|---|---|---|
| 328007-EMD | ERK Inhibitor II | ERK1, ERK2 | 2 µM |
| 420119-EMD | JNK Inhibitor II | JNK | 2 µM |

TABLE V-continued

List of compounds tested at Stage 6

| Catalogue#/ Vendor | Inhibitor | Target Kinase | Tested concentration |
|---|---|---|---|
| 420136-EMD | JNK Inhibitor IX | JNK2, JNK3 | 2 µM |
| 444939-EMD | MEK1/2 Inhibitor | MEK1/2 | 2 µM |
| 454861-EMD | MNK1 Inhibitor | MNK1 | 2 µM |
| 475863-EMD | MK2a Inhibitor | MK2a | 2 µM |
| 506156-EMD | p38 MAP Kinase Inhibitor V | p38, CK1 | 2 µM |
| 513000-EMD | PD 98059 | MEK | 2 µM |
| 553014-EMD | Raf Kinase Inhibitor IV | B-Raf | 2 µM |
| 559389-EMD | SB 203580 | p38 MAPK | 2 µM |
| 616373-EMD | Tpl2 Kinase Inhibitor | Tpl2 Kinase | 2 µM |
| 692000-EMD | ZM 336372 | c-Raf 1 | 2 µM |
| M60043-25/XcessBio | IDH1 | Isocitrate dehydrogenase | 2 µM |
| M60668-25/XcessBio | AGI5198 | Isocitrate dehydrogenase | 2 µM |

Figure 14A:
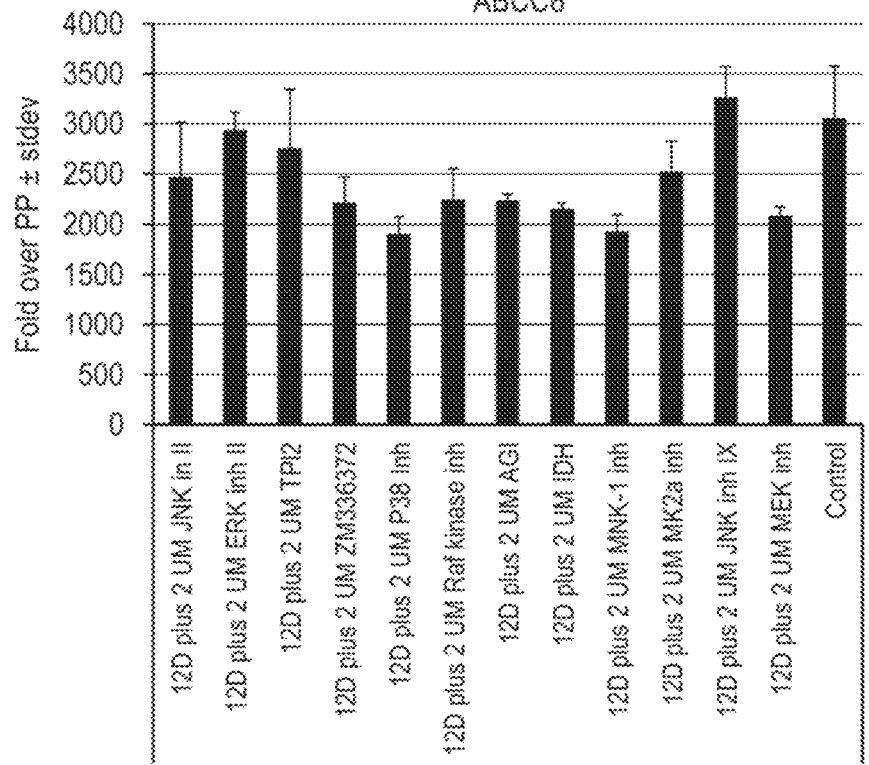
FIGS. 14A to 14H depict data from real-time PCR analyses of the expression of the following genes in cells of the human embryonic stem cell line H1 differentiated as outlined in Example 9 and cultured at the ALI: ABCC8 (FIG. 14A); glucagon (FIG. 14B); amylin (FIG. 14C); insulin (FIG. 14D); ISL-1 (FIG. 14E); MNX1 (FIG. 14F); NKX6.1 (FIG. 14G); and SLC30A8 (FIG. 14H).
Figure 14B:
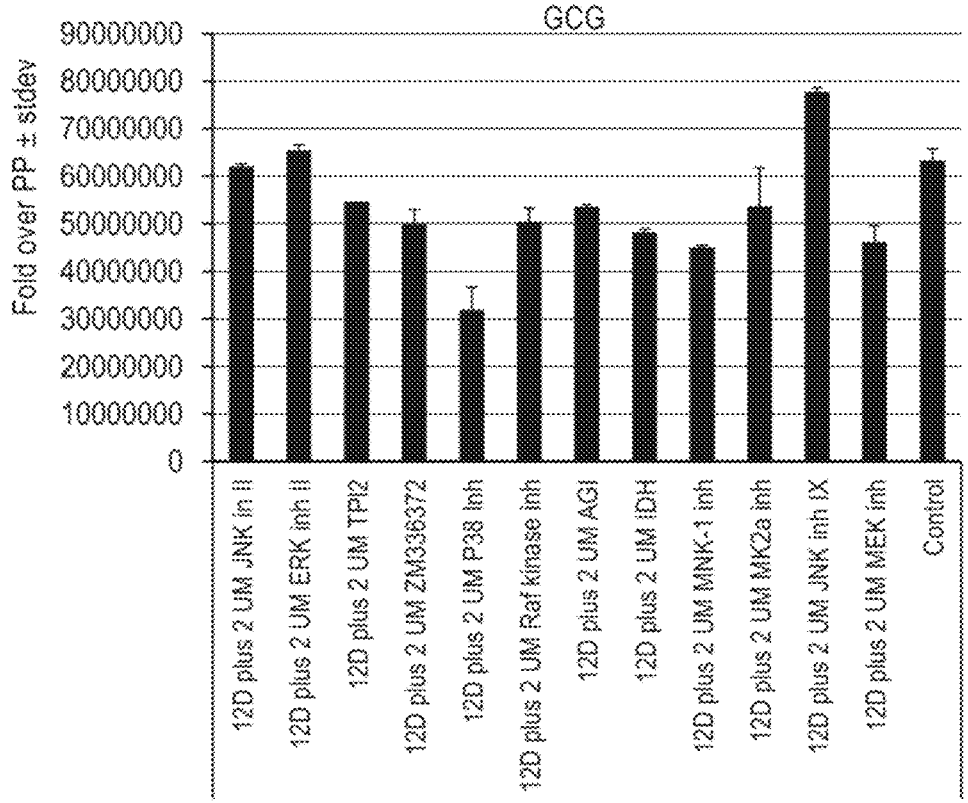
Figure 14C:
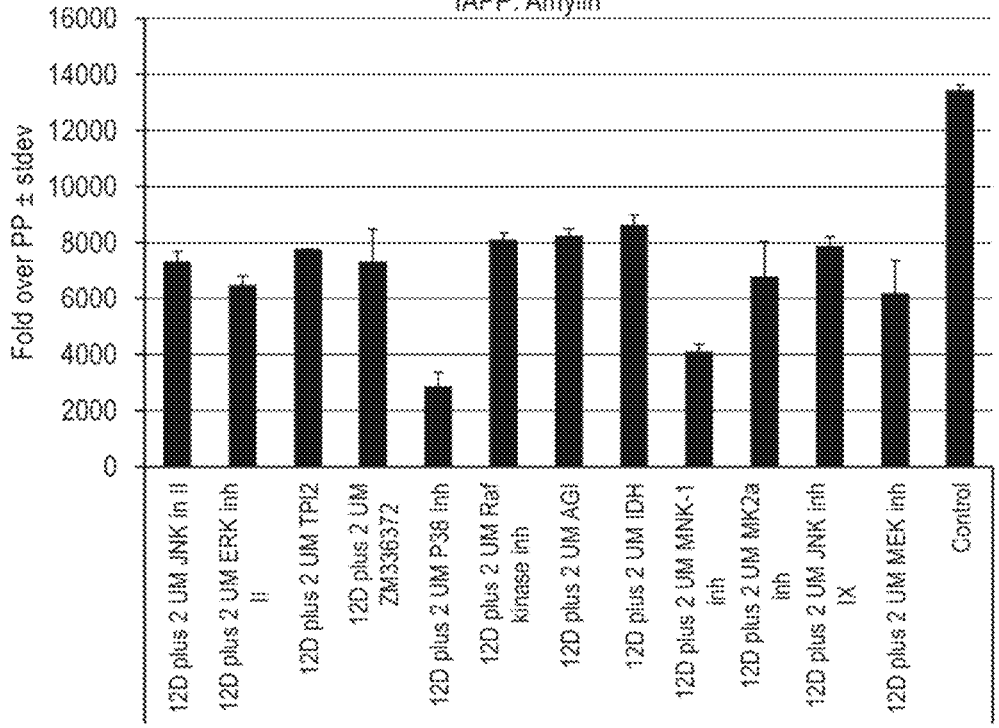
Figure 14D:
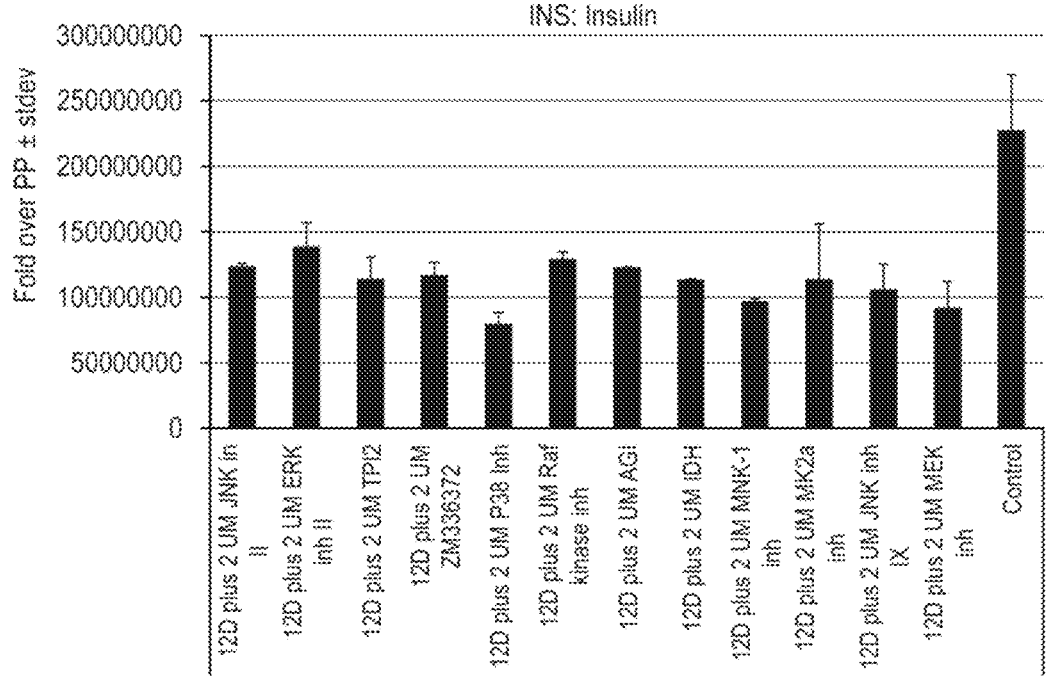
Figure 14E:
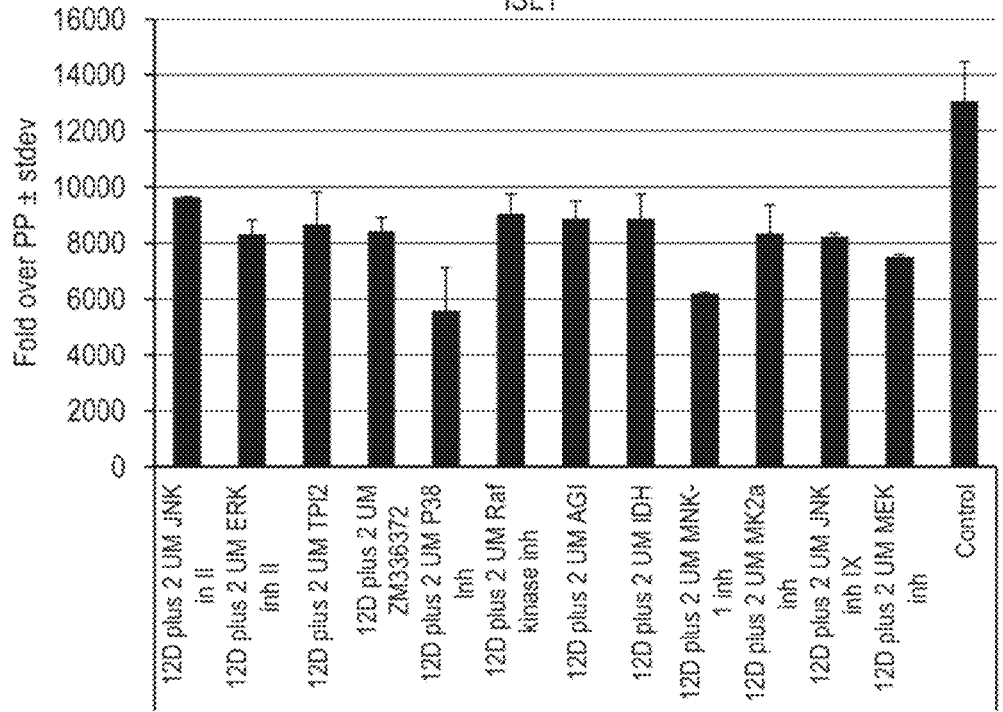
Figure 14F:
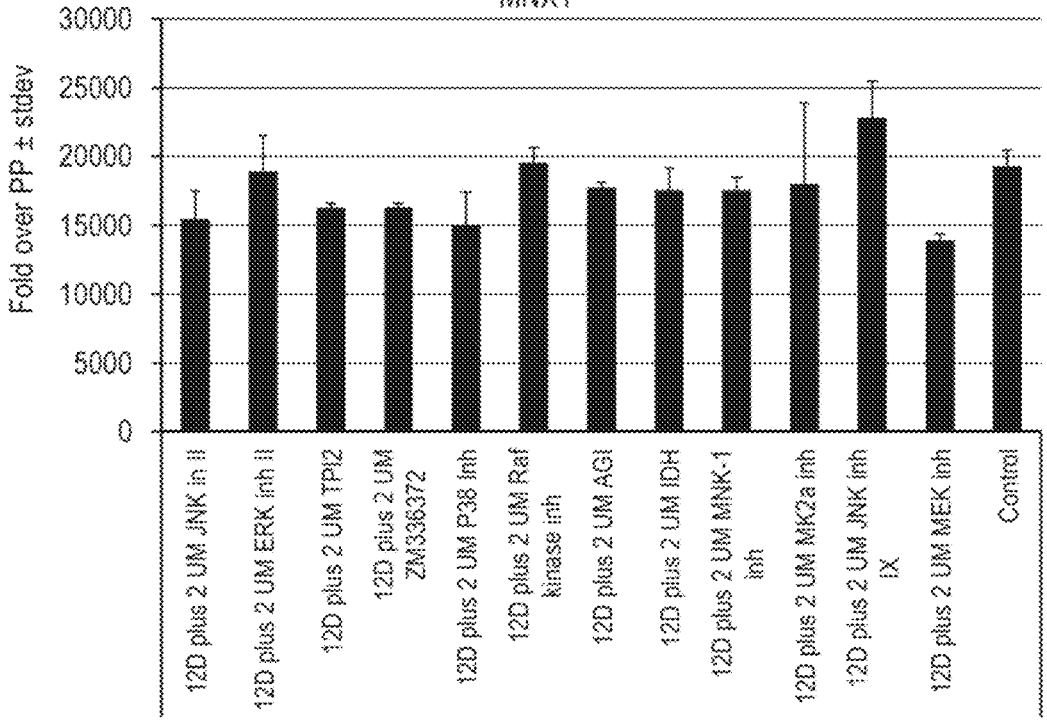
Figure 14G:
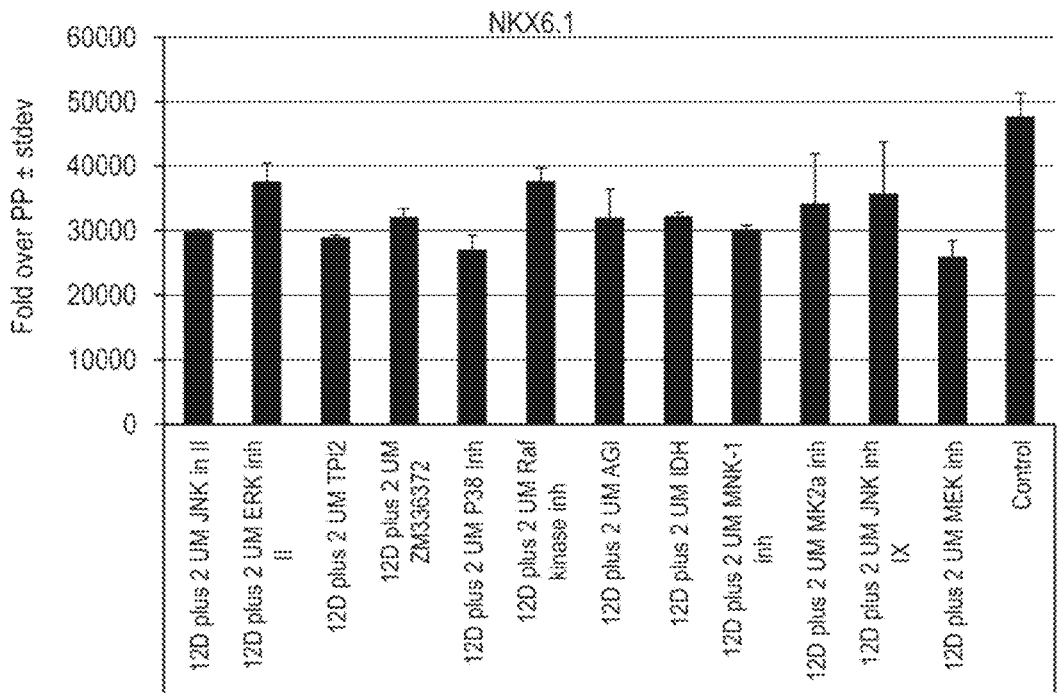
Figure 14H:
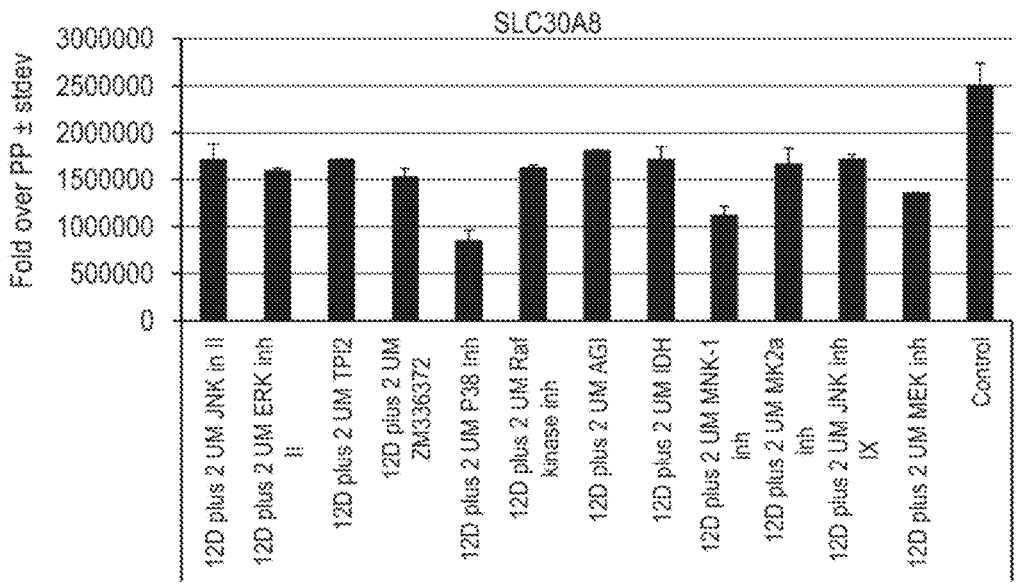

RNA samples were collected at Stage 6 and analyzed by real-time PCR. FIG. 14 depicts data from real-time PCR analyses of the expression of the following genes in cells of the human embryonic stem cell line H1 differentiated as outlined in Example 9 and cultured at the air-liquid interface: ABCC8 (FIG. 14A); glucagon (FIG. 14B); amylin (FIG. 14C); insulin (FIG. 14D); ISL-1 (FIG. 14E); MNX1 (FIG. 14F); NKX6.1 (FIG. 14G); and SLC30A8 (FIG. 14H). This example shows that the potential of cells cultured at the air-liquid interface as a screening tool.

Example 10

FACS Profile of Stage 5 and Stage 6 Cells Cultured at the Air-liquid Interface

This example studies the composition of Stage 5 and Stage 6 cultures at the air-liquid interface. To conduct the studies in this example, embryonic stem cells were differentiated into Stage 5 and Stage 6 cultures using the protocol described below.

Cells of the human embryonic stem cell line H1 (passage 40) were seeded as single cells at 1×10$^5$ cells/cm$^2$ on MATRIGEL™ (1:30 dilution; BD Biosciences, NJ)-coated dishes in a media comprising of DMEM-F12 (Invitrogen, Ca), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, Sigma). Forty-eight hours post-seeding, cultures were washed in incomplete PBS (phosphate buffered saline without Mg or Ca). The cells were then differentiated according to the following protocol:

a) Stage 1 (3 days): Cells were cultured for one day in MCDB-131 medium (Invitrogen, Catalog No. 10372-019) supplemented with 2% fatty acid-free BSA (Proliant, Catalog No. 68700), 0.0012 g/ml sodium bicarbonate (Sigma-Aldrich Catalog No. S3187); 1× GlutaMax™ (Invitrogen, Catalog No. 35050-079); 4.5 mM D-glucose (Sigma-Aldrich, Catalog No. G8769); 100 ng/ml GDF8 (R&D Systems); and 1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b) Stage 2 (2 days): the Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c) Stage 3 (2 days): The Stage 2 cells were then treated with BLAR custom medium (Invitrogen) supplemented with a 1:200 dilution of ITS-X (Invitrogen, Ca); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d) Stage 4 (3 days): The Stage 3 cells were then treated with BLAR medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; and 200 nM TPB for three days, then at the end of Stage 4, cells cultured on planar dishes were treated for 4 hours with 10 µM of Y27632, rinsed with PBS and treated for 5 minutes at room temperature with 1× TrypLE™ (Invitrogen) followed by removal of the enzyme, rinsing with basal media and scraping of cells by a cell scraper. The resulting suspension of cells were seeded at a density of 0.5-0.75×10$^6$ cells (in 10 µl aliquots) on MATRIGEL™-coated 0.4 micron porous cell culture filter inserts in 6-well plates. 1.5 ml of media was added to the bottom of each insert and no further media was added to the apical side of the filter.

e) Stage 5 (3 days): The Stage 4 cells were then cultured at the air-liquid interface in BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 10 µM ZnSO$_4$ (Sigma, Z0251), 0.25 µM SANT-1; 50 nM RA; 100 nM LDN-193189; 10000 nM of various ALK5 inhibitor II for three days.

f) Stage 6 (15 days): The Stage 5 cells were then treated with BLAR medium supplemented with a 1:200 dilution of ITS-X; 20 mM Glucose; 1× GlutaMax™; 0.0015 g/ml sodium bicarbonate; 2% fatty acid-free BSA; 10 µg/ml of heparin (Sigma, #H3149), 10 µM ZnSO$_4$ (Sigma, Z0251), 0.25 µM SANT-1; 100 nM LDN-193189, 1000 nM T3, 10000 nM ALK5 inhibitor II for 5-15 days.

Figure 16I:
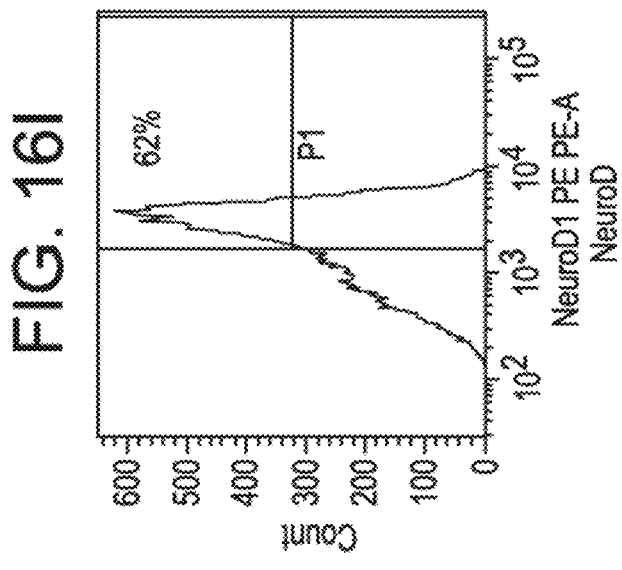
Figure 16H:
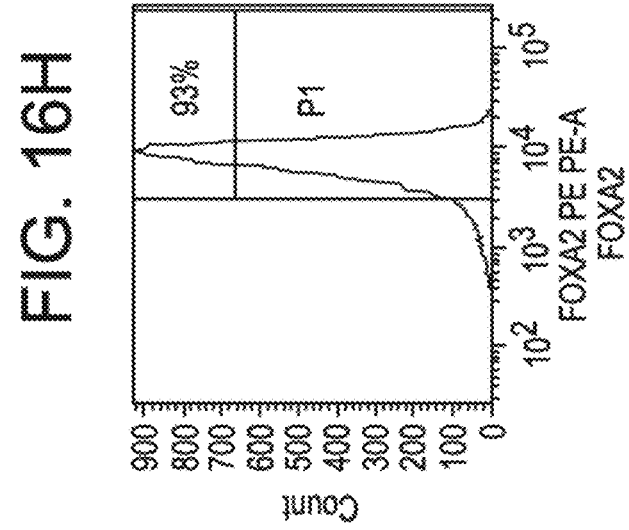
Figure 16G:
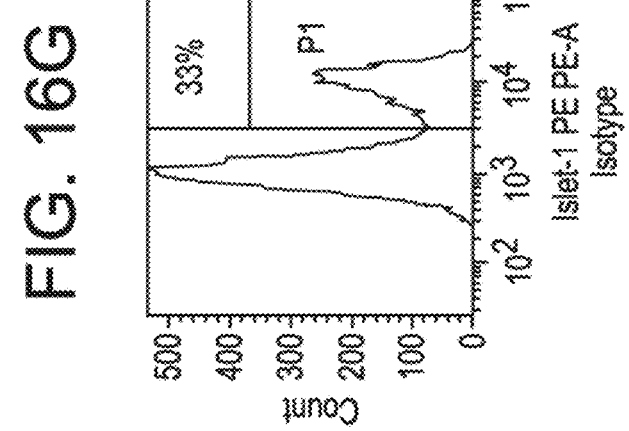
Figure 17C:
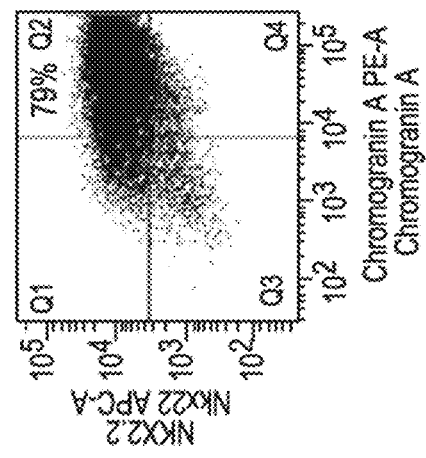
FIGS. 17A to 17I show the FACS (Fluorescence-activated cell sorting) profile of Stage 6 day 15 cells, differentiated according to Example 10, and stained for: Isotype control (FIG. 17A); NKX6.1 (Y-axis) co-stained with chromogranin-A (X-axis) (FIG. 17B); NKX2.2 (Y-axis) co-stained with chromogranin-A (X-axis) (FIG. 17C); glucagon (Y-axis) co-stained with insulin (X-axis) (FIG. 17D); NKX6.1 (Y-axis) co-stained with insulin (X-axis) (FIG. 17E); PDX1 (X-axis) co-stained with KI-67 (Y-axis) (FIG. 17F); ISL-1 (FIG. 17G); FOXA2 (FIG. 17H); and NeuroD (FIG. 17I).
Figure 17B:
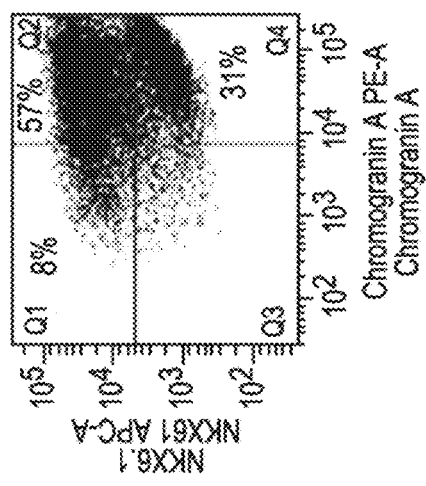
Figure 17A:
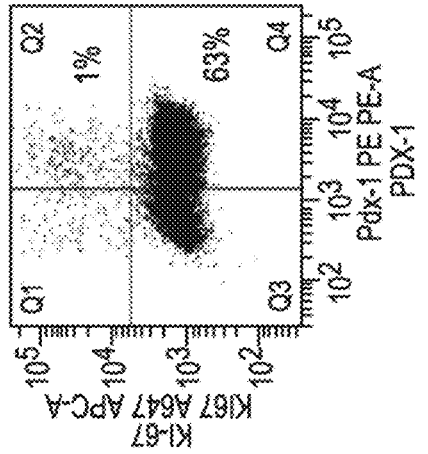
Figure 17F:
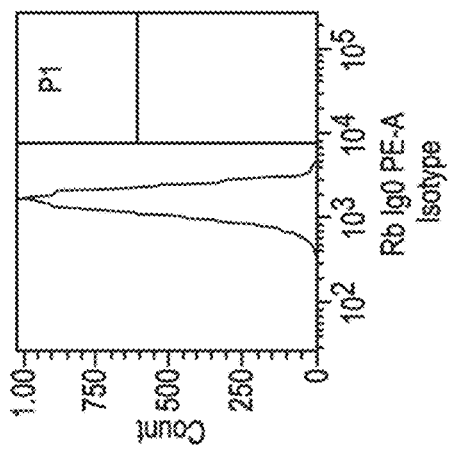
Figure 17E:
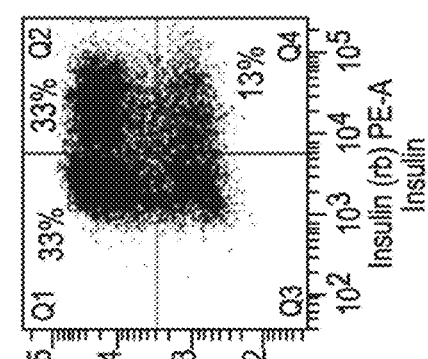
Figure 17D:
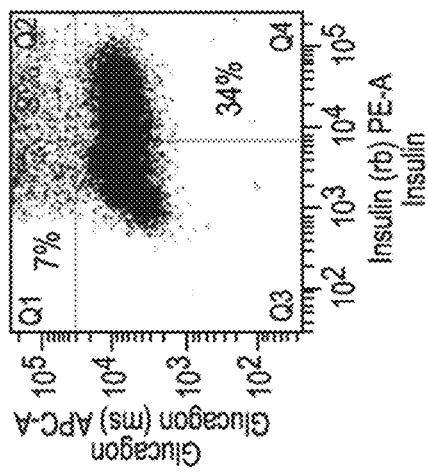
Figure 17I:
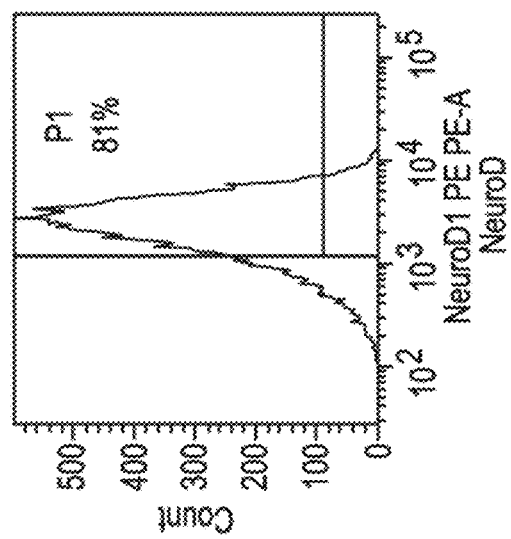
Figure 17H:
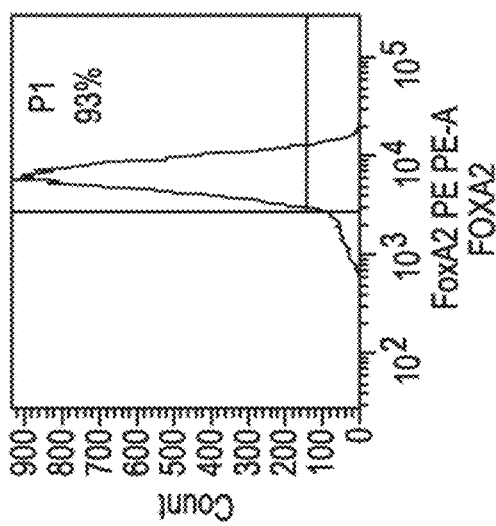
Figure 17G:
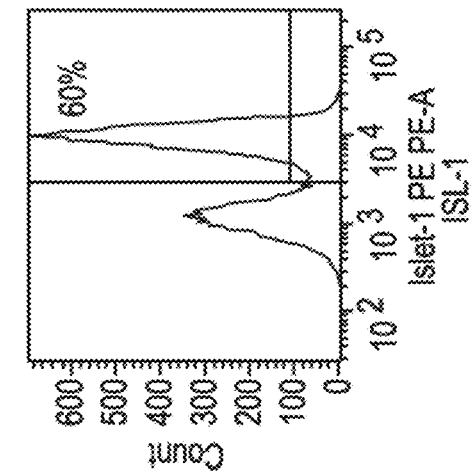

Cells were harvested at Stage 5 and various time points at Stage 6 and analyzed by FACS. FACS staining was conducted as previously described (*Diabetes*, 61, 2016, 2012) and using antibodies listed in Table VI. FIG. 15 depicts FACS profile of cells collected at Stage 5. FIG. 16 shows FACS profile of Stage 6 day 5 cells cultured at the air-liquid interface. Lastly, FIG. 17 shows profile of Stage 6 day 15 of cells cultured at the air-liquid interface. As shown in FIG. 15, at Stage 5, there were few cells co-expressing insulin and NKX6.1 (~1%) and a significant portion of PDX1 positive cells were in active cell cycle as measured by co-expression of PDX1 and KI-67 (~23%; KI-67 is indicative of cells that are in active cell cycle). However, by Stage 6 day 5 (FIG. 16), there was a significant drop in proliferating PDX1+ cells (8%) while there was a significant increase in the number of NKX6.1+ cells co-expressing chromogranin-A (51%; chromogranin-A is a pan endocrine marker) or insulin (14%). Moreover, there was a significant rise in cells expressing endocrine precursor markers ISL-1, NeuroD, and NKX2.2. This indicates that unique cultures of Stage 6 allowed for rapid maturation of cells away from a proliferating progenitor fate to early maturing endocrine cells. In addition, an increase in the percentage of cells co-expressing insulin and NXK6.1 (33%) was observed by prolonging Stage 6 to 15 days (FIG. 17). Moreover, there was further decrease in the percentage of PDX1 positive cells which were in cell cycle (1%) and a further increase in the percentage of ISL-1 and NeuroD. Lastly, the majority of hormone positive cells were single hormone insulin positive cells (34% single hormone insulin positive cells, 7% single hormone glucagon positive cells, and 8% poly hormone cells). Significant co-expression of NKX6.1 and chromogranin-A and single hormone insulin positive cells expressing NKX6.1 (>30%) highlights a previously undescribed cell population.

TABLE VI

List of Antibodies used for FACS analysis of cells generated in Example 10

| Antigen | Species | Source/Catalogue# | Dilution |
|---|---|---|---|
| Glucagon | Mouse | Sigma-Aldrich, G2654 | 1:250 |
| Insulin | Rabbit | Cell Signaling, 3014B | 1:10 |
| NKX6.1 | Mouse | Developmental Studies Hybridoma Bank; F55A12 | 1:50 |
| NKX2.2 | Mouse | Developmental Studies Hybridoma Bank; | 1:100 |
| PDX1 | Mouse | BD BioSciences, 562161 | 1:50 |
| Ki67 | Mouse | BD Biosciences, 558595 | 1:20 |
| Pax6 | Mouse | BD Biosciences, 561552 | 1:20 |
| Chromogranin-A | Rabbit | Dako, A0430 | 1:40 |
| ISL-1 | Mouse | BD Biosciences, 562547 | 1:20 |
| NeuroD | Mouse | BD Bioscience, 563001 | 1:40 |
| FOXA2 | Mouse | BD Bioscience, 561589 | 1:80 |

Example 11

In vivo Maturation of NKX6.1+Chromogranin-A+ Insulin+Cells, NKX6.1+Chromogranin-A− Insulin− and Pancreatic Progenitors Co-expressing PDX1 and NKX6.1 Versus Human Islets in SCID Mice This example highlights the in vitro composition of differentiated cells and the effect on in vivo cell performance. In particular, 5 million Stage 4 day 4 (PDX1+ NKX6.1+) pancreatic foregut precursor cells prepared according to Example 1 on planar cultures, 5 million NKX6.1+chromogranin-A negative cells cultured at the air-liquid interface, and 3 million NKX6.1+chromogranin-A positive cells prepared according to Example 10 at the air-liquid interface were transplanted into the kidney capsule of non-diabetic SCID mice as described in (Diabetes 2012, 61(8):2016-29). The mice were tracked for circulating human C-peptide as a measure of the maturation state of cells as a function of time. In addition, in separate cohorts of mice, 1500-4000 cadaveric human islet (PRODO labs, Irvine, Calif.) equivalents were transplanted as a positive control.

Figure 18A:
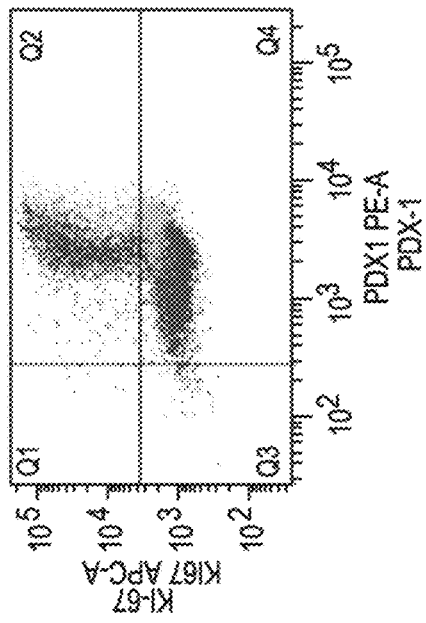
FIG. 18A to 18C show the FACS (Fluorescence-activated cell sorting) profile of Stage 4 day 4 cells, differentiated according to Example 1, and stained for: NKX6.1 (Y-axis) co-stained with chromogranin-A (X-axis) (FIG. 18A); PDX1 (X-axis) co-stained with KI-67 (Y-axis) (FIG. 18B); and NKX6.1 (Y-axis) co-stained with insulin (X-axis) (FIG. 18C).
Figure 18B:
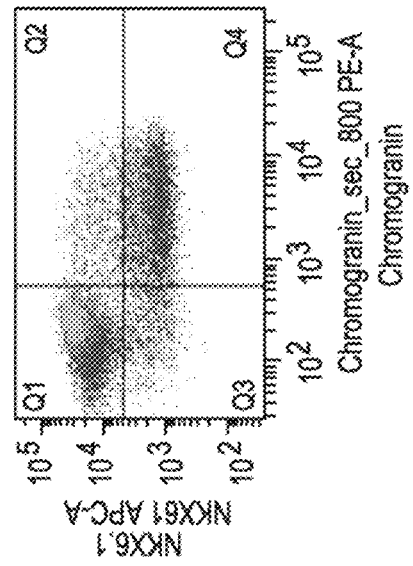
Figure 18C:
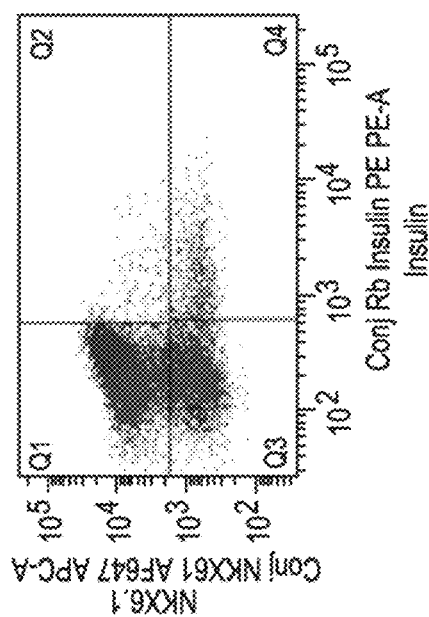

The NKX6.1+chromogranin-A negative population was prepared as follows:

Cells of the human embryonic stem cell line H1 (passage 40) were seeded as single cells at $1 \times 10^5$ cells/cm$^2$ on MATRIGEL™ (1:30 dilution; BD Biosciences, NJ)-coated dishes in a media comprising of DMEM-F12 (Invitrogen, Ca), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 μM of Y27632 (Rock inhibitor, Catalog No. Y0503, Sigma). Forty-eight hours post-seeding, cultures were washed in incomplete PBS (phosphate buffered saline without Mg or Ca). The cells were then differentiated according to the following protocol:

a. Stage 1 (3 days): Cells were cultured for one day in MCDB-131 medium (Invitrogen, Catalog No. 10372-019) supplemented with 2% fatty acid-free BSA (Proliant, Catalog No. 68700); 0.0012 g/ml sodium bicarbonate (Sigma-Aldrich, Catalog No. S3187); 1× GlutaMax™ (Invitrogen, Catalog No. 35050-079); 4.5 mM D-glucose (Sigma-Aldrich Catalog No. G8769); 100 ng/ml GDF8 (R&D Systems); and 1 μM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 μM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b. Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c. Stage 3 (2 days): The Stage 2 cells were then treated with MCDB-131 medium supplemented with a 1:200 dilution of ITS-X (Invitrogen, CA); 4.5 mM glucose; 1× GlutaMax™; 0.0017 g/ml sodium bicarbonate; 2% fatty acid-free BSA; 0.25 μM SANT-1 (Sigma, MO); 1 μM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days. Then the Stage 3 cells were treated with 1× ACCUTASE™ for 1-3 minutes at room temperature followed by removal of the enzyme and scraping of cells by a cell scraper. The resulting suspension of cells were seeded at a density of $\sim 2 \times 10^6$ cells/10 μl on 0.4 micron porous cell culture filter inserts. 1.5 ml of media was added to the bottom of each insert and no further media was added to the apical side of the filter.

d. Stage 4 (2 days): The Stage 3 cells were then cultured at the air-liquid interface in MCDB-131 medium supplemented with a 1:200 dilution of ITS-X; 4.5 mM glucose; 1× GlutaMax™; 0.0017 g/ml sodium bicarbonate; 2% fatty acid-free BSA; 0.25 μM SANT-1; 100 nM RA; 2 ng/ml FGF7; 100 nM LDN-193189; 0.25 mM ascorbic acid; 100 nM T3 (T6397, Sigma) and 100 nM TPB for two days.

e. Stage 5 (2 days): The Stage 4 cells were then treated with MCDB-131 medium supplemented with a 1:200 dilution of ITS-X; 20 mM glucose; 1× GlutaMax™; 0.0015 g/ml sodium bicarbonate; 2% fatty acid-free BSA; 0.25 µM SANT-1; 50 nM RA; 50 nM LDN-193189; 500 nM ALK5 inhibitor (SD208) for two days.

f. Stage 6 (6 days): The Stage 5 cells were then treated with MCDB-131 medium supplemented with a 1:200 dilution of ITS-X; 20 mM glucose; 1× GlutaMax™; 0.0015 g/ml sodium bicarbonate; 2% fatty acid-free BSA; 0.25 µM SANT-1; 50 nM RA; 500 nM ALK5 inhibitor; for six days Table VII below highlights the expression level of various pancreatic endoderm and endocrine markers for the three human embryonic stem cell derived populations. Specifically, Table VII compares the results of the following: (1) Stage 4 day 4 population generated according to Example 1 (Stage 4 day 4); (2) Pancreatic endoderm/endocrine precursor population generated according to Example 11 (Pancreatic endoderm/endocrine); and (3) NKX6.1+chromogranin-A+insulin+ population generated according to Example 10 (NKX6.1+chromogranin-A+insulin+). FACS profile information for each is depicted in FIGS. 17-19. Specifically, FIG. 17 depicts the FACS profile of the NKX6.1+chromogranin-A+population; FIG. 18 depicts the FACS profile of the Stage 4 day 4 cells; and FIG. 19 depicts the FACS profile of Stage 6 day 6 pancreatic endocrine cells generated according to Example 11.

TABLE VII

Comparison of expression profile of three transplanted population as measured by FACS

| | Population | | |
|---|---|---|---|
| Marker | S4 day 4[a] | Pancreatic endoderm/ endocrine[b] | NKX6.1+ chromogranin-A+ insulin+[c] |
| % PDX1+ Ki-67+ | 25 | 17 | 1 |
| % NKX6.1+ Chromogranin-A+ | 10 | 10 | 57 |
| % NKX6.1− Chromograin+ | 19 | 53 | 31 |
| % Insulin+ NKX6.1+ | 1 | 1 | 33 |

[a]S4 day 4 population was generated according to Example 1.(See FIG. 18)
[b]Pancreatic endoderm/endocrine population was generated according to Example 11. (See FIG. 19)
[c]NKX6.1+ chromogranin-A+ insulin+ population was generated according to Example 10. (See FIG. 17)

After implementation, the mice were periodically tested for the concentration of circulating human c-peptide. Circulating human C-peptide was tested by collecting blood via saphenous vein. Plasma was stored at −20° C. and later assayed using a human C-peptide by ELISA kit (Alpco Diagnostics, Salem, N.H.). The results are shown graphically in FIG. 20.

Figure 20:
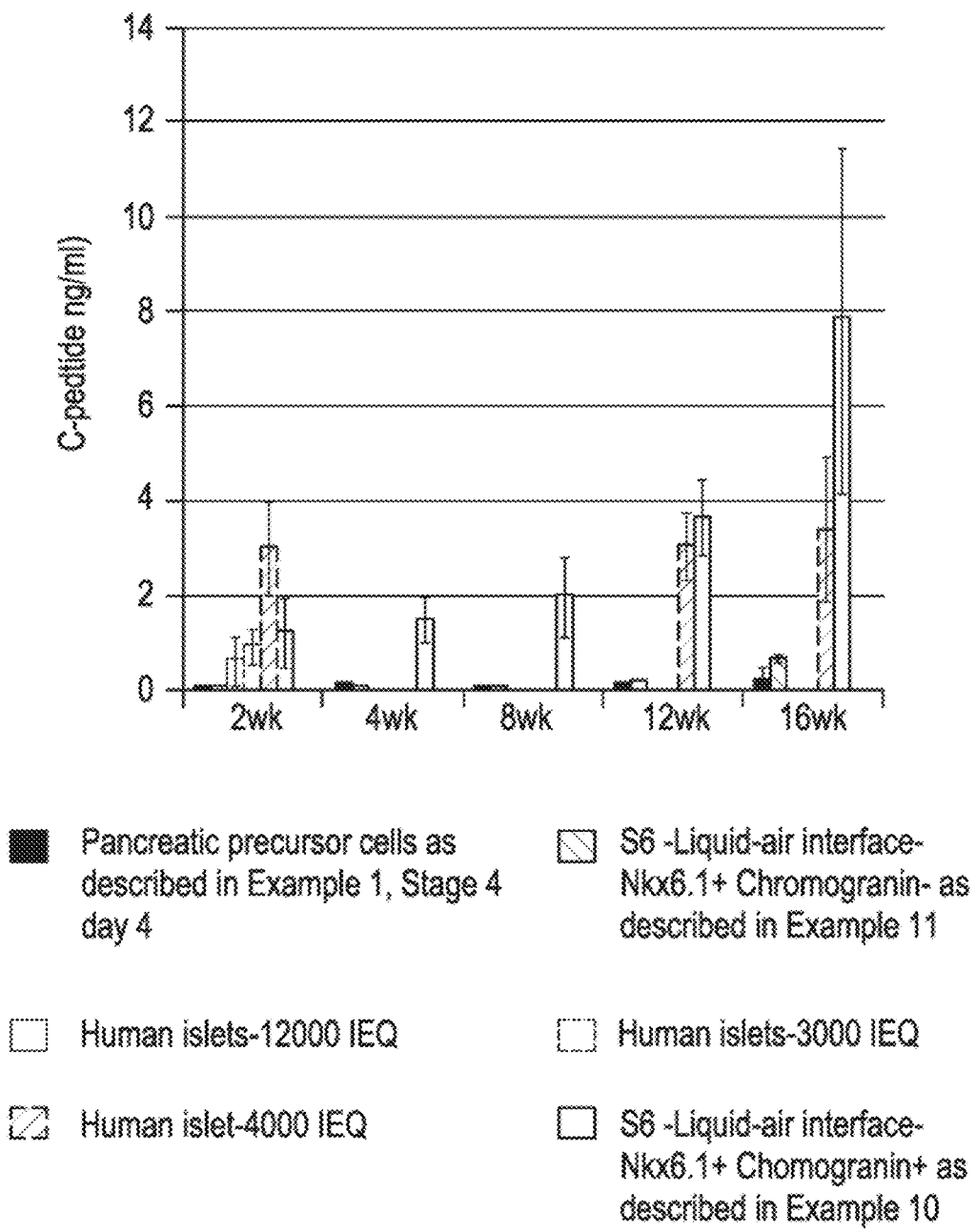
FIG. 20 shows the in vivo kinetics of human C-peptide production in NOD-SCID mice transplanted with various populations of cells as described in Example 11.
Figure 21A:
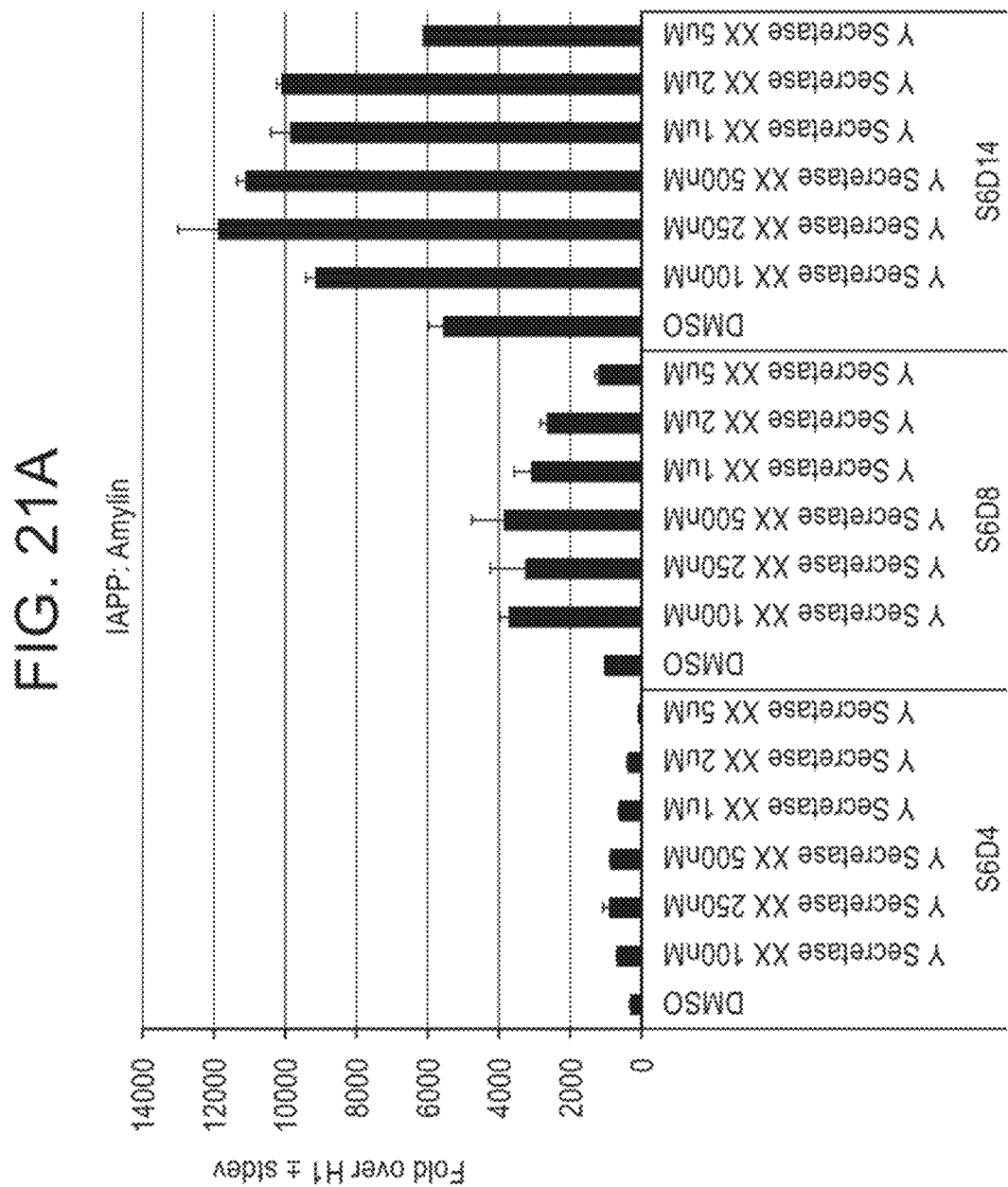
Figure 21B:
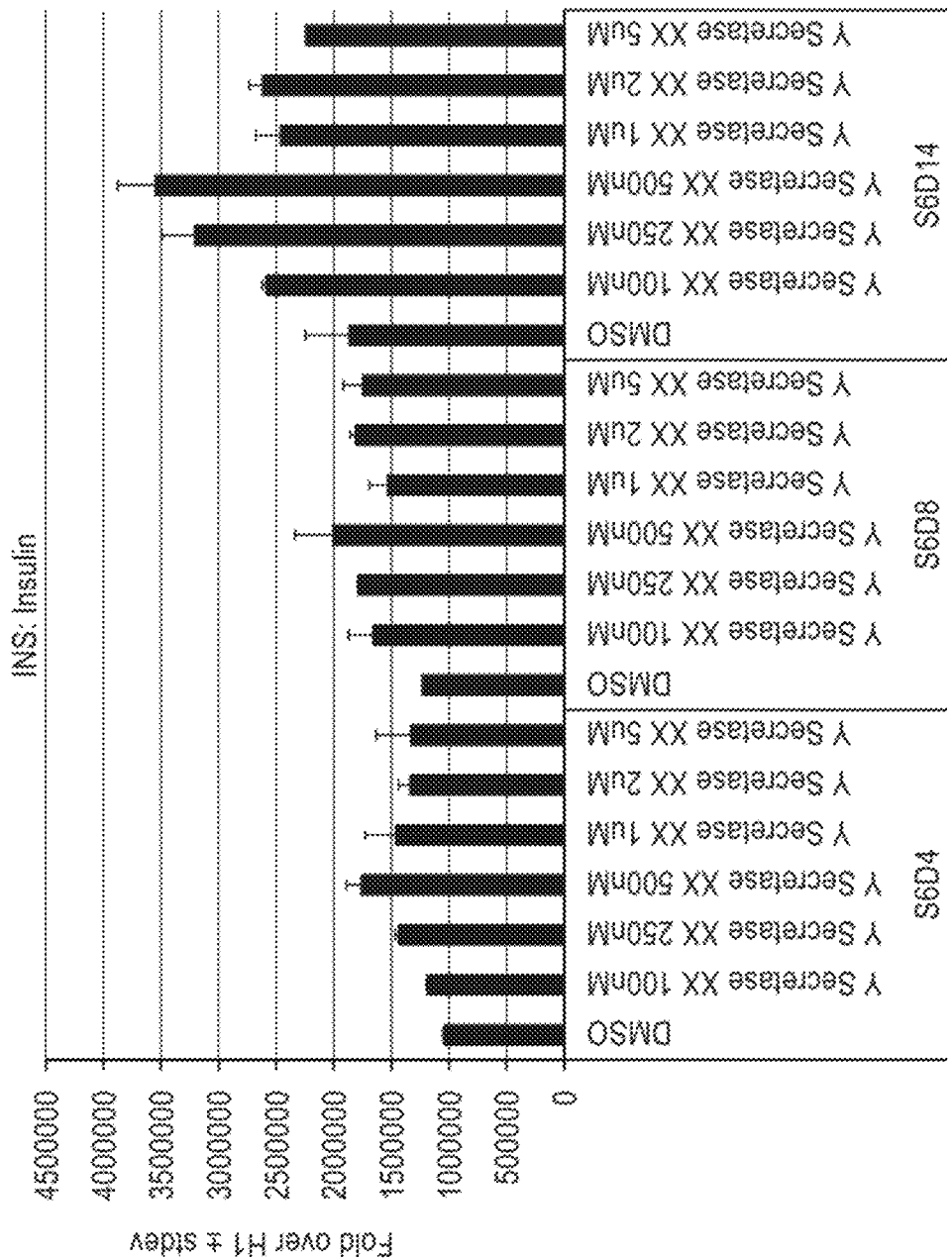
Figure 21C:
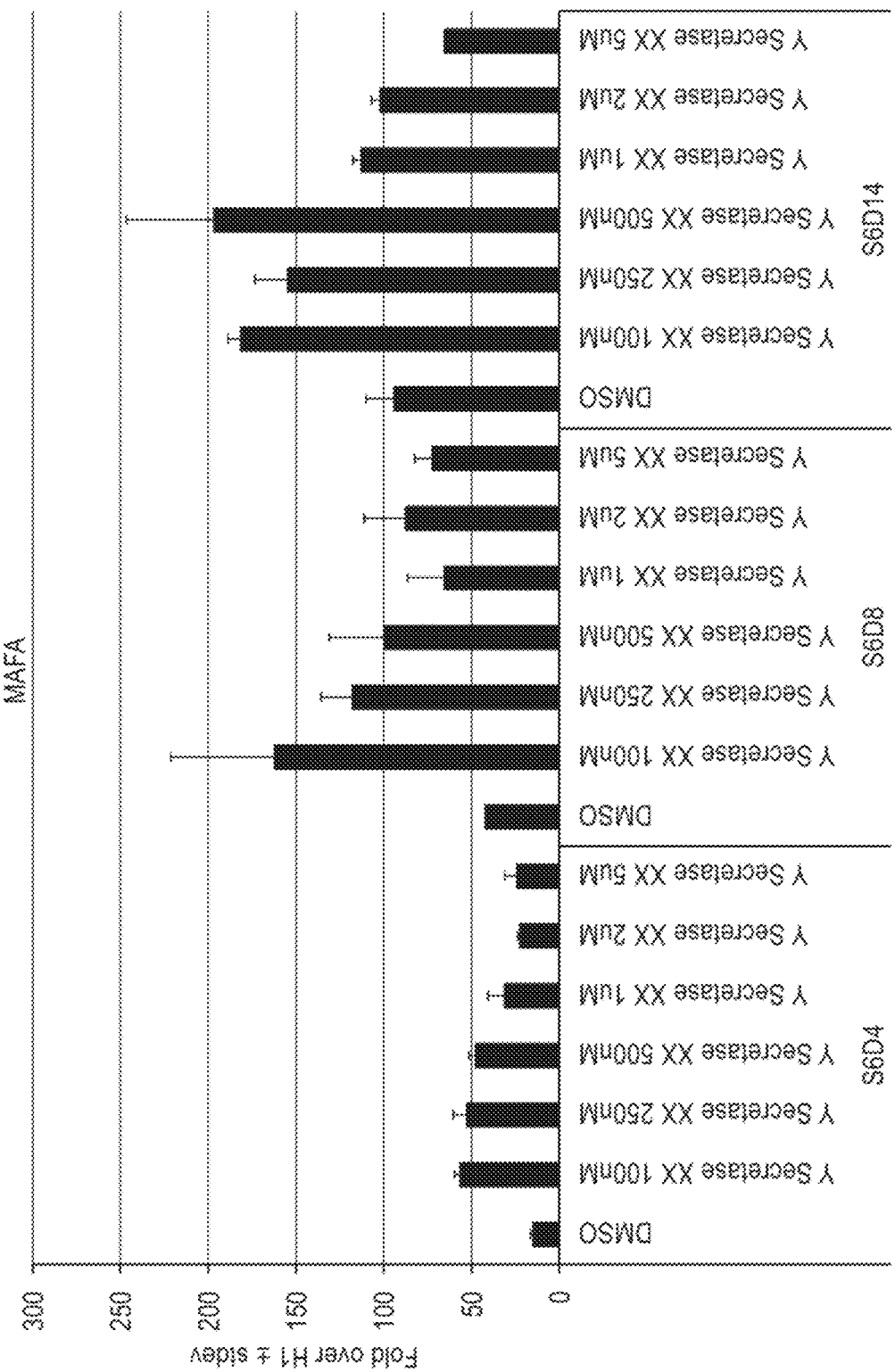
Figure 21E:
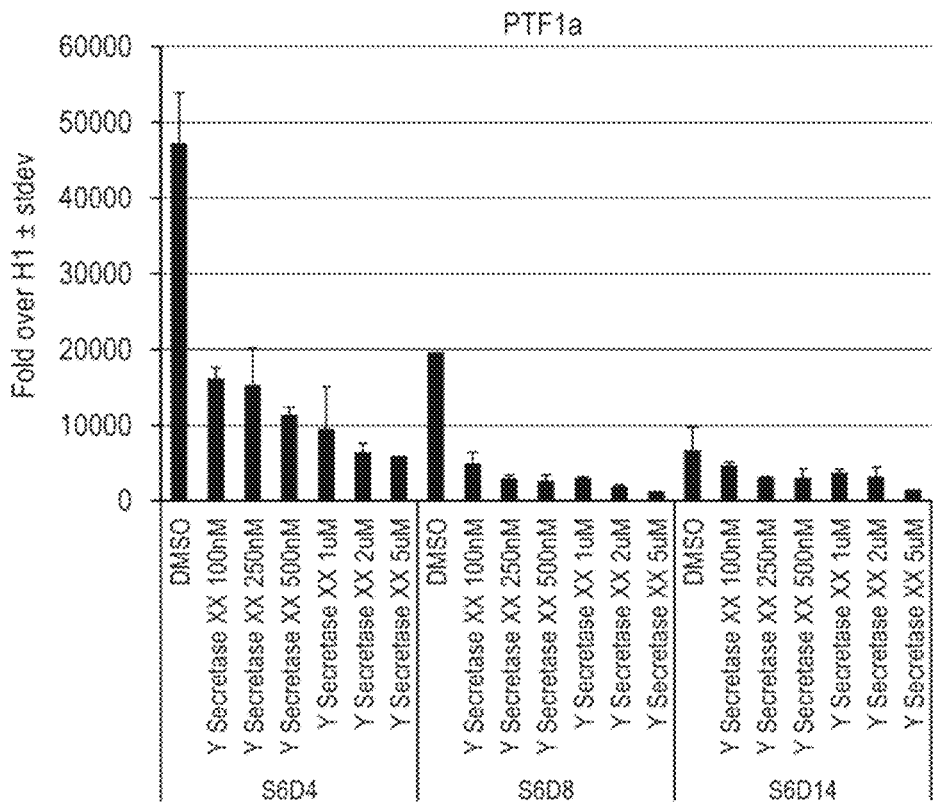
Figure 21F:
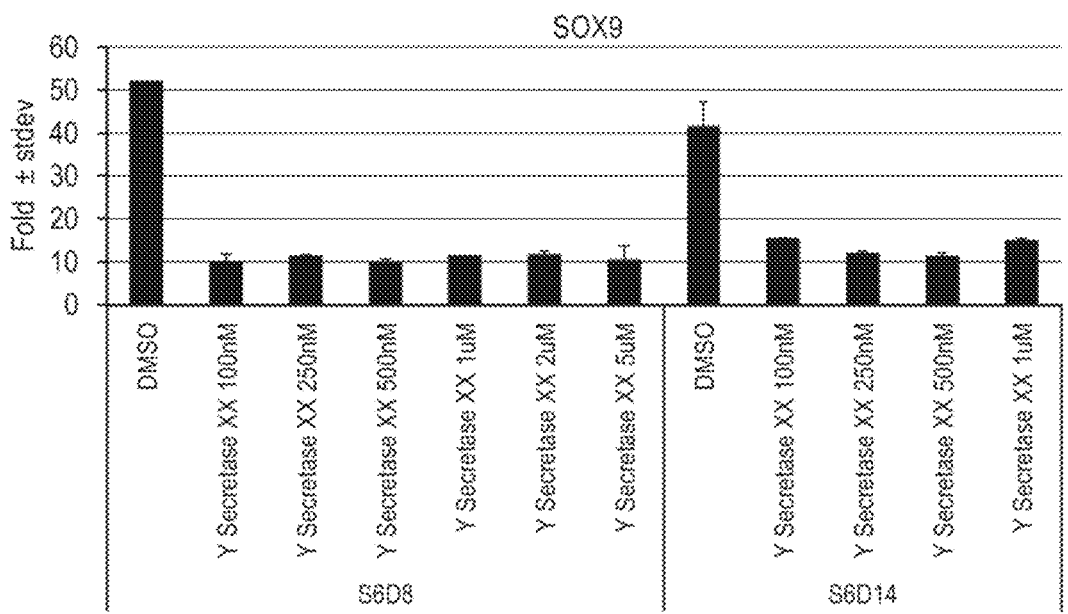

FIG. 20 shows the kinetics of C-peptide production from the three ES-derived populations as compared to various doses of human islets. The population of cells expressing substantial co-expression of NKX6.1 and chromogranin-A and NKX6.1 and insulin resulted in significant early production of C-peptide. The level of C-peptide production was similar to transplanting approximately 4000 human islets at 12 weeks. However, by 16 weeks post-transplant, the levels of human C-peptide had almost doubled the magnitude of C-peptide seen with transplanting 4000 human islets.

However, transplanting progenitor cells expressing PDX1 and NKX6.1, or a mixed population of pancreatic precursor cells and polyhormonal cells (chromogranin-A+NKX6.1−) required significantly longer periods of time to secrete equivalent levels of C-peptide as 4000 human islets.

Example 12

Addition of Gamma Secretase Inhibitor XX Further Augments Maturation Markers of Stage 6 Cells Cultured at the Air-liquid Interface This example highlights that NOTCH inhibitors, such as gamma secretase inhibitors, further enhance maturation markers of β cells while retaining expression of NKX6.1. Cells of the human embryonic stem cell line H1 (passage 42) were seeded as single cells at 1×10⁵ cells/cm² on MATRI-GEL™ (1:30 dilution; BD Biosciences, NJ)-coated dishes in a media comprising of DMEM-F12 (Invitrogen, Ca), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, Sigma). Forty-eight hours post-seeding, cultures were washed in incomplete PBS (phosphate buffered saline without Mg or Ca). The cells were then differentiated according to the following protocol:

a) Stage 1 (3 days): Cells were cultured for one day in MCDB-131 medium (Invitrogen Catalog No. 10372-019) supplemented with 2% fatty acid-free BSA (Proliant Catalog No. 68700), 0.0012 g/ml sodium bicarbonate (Sigma-Aldrich Catalog No. S3187); 1× GlutaMax™ (Invitrogen Catalog No. 35050-079); 4.5 mM D-glucose (Sigma-Aldrich Catalog No. G8769); 100 ng/ml GDF8 (R&D Systems); and 1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b) Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c) Stage 3 (2 days): The Stage 2 cells were then treated with BLAR custom medium (Invitrogen) supplemented with a 1:200 dilution of ITS-X (Invitrogen, Ca); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d) Stage 4 (3 days): The Stage 3 cells were then treated with BLAR medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; and 200 nM TPB for three days, then at end of Stage 4, cells cultured on planar dishes were treated for 4 hours with 10 µM of Y27632, rinsed with PBS and treated for 5 minutes at room temperature with 1× TrypLE™ (Invitrogen) followed by removal of the enzyme, rinsing with basal media and scraping of cells by a cell scraper. The resulting suspension of cells were seeded at a density of 0.5-0.75×10⁶ cells (in 10 µA aliquots) on MATRIGEL™-coated 0.4 micron porous cell culture filter inserts in 6-well plates. 1.5 ml of media was added to the bottom of each insert and no further media was added to the apical side of the filter.

e) Stage 5 (3 days): The Stage 4 cells were then cultured at the air-liquid interface in BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 10 µM ZnSO₄ (Sigma, Z0251), 0.25 µM SANT-1; 50 nM RA; 100 nM LDN-193189; 10000 nM of various ALK5 inhibitor II for three days.

f) Stage 6 (14 days): The Stage 5 cells were then treated with BLAR medium supplemented with a 1:200 dilution of ITS-X; 20 mM Glucose; 1× GlutaMax™; 0.0015 g/ml sodium bicarbonate; 2% fatty acid-free BSA; 10 µg/ml of heparin (Sigma, #H3149), 10 µM ZnSO₄ (Sigma, Z0251), 0.25 µM SANT-1; 100 nM LDN-193189, 1000 nM T3, 10000 nM ALK5 inhibitor II for 14 days.

At Stage 6, various doses (100 nM to 5000 nM) of gamma Secretase inhibitor XX (EMD, #565789) were tested. mRNA was collected at Stage 6 day 4 and Stage 6 day 8. FIG. 21 depicts the PCR data for key β cell maturation markers along with pancreatic progenitor markers. As shown in FIG. 21, maturation markers, such as Amylin (Panel 21A), insulin (Panel 21B), and MAFA (Panel 21C) were significantly upregulated while NKX6.1 (Panel 21D) expression was not significantly affected. However, pancreatic precursor markers, such as PTF1a (Panel 21 E) and SOX9 (Panel 21 F) were significantly down regulated.

Example 13

Presence of ALK5 Inhibitor is Essential for Upregulation of MAFA and Further Addition of T3 Further Enhances MAFA Expression This example highlights the ability of ALK5 inhibitor II addition to upregulate MAFA expression, and that addition of T3 with ALK5 inhibitor and LDN-193189 further enhances expression of MAFA.

Cells of the human embryonic stem cell line H1 (passage 42) were seeded as single cells at 1×10⁵ cells/cm² on MATRIGEL™ (1:30 dilution; BD Biosciences, NJ)-coated dishes in a media comprising of DMEM-F12 (Invitrogen, Ca), GlutaMax™ (1:100 dilution, Invitrogen), 0.25 mM ascorbic acid (Sigma, MO), 100 ng/ml of FGF2 (R & D systems, MN), 1 ng/ml of TGF-β (R & D systems), ITS-X (1:100 dilution), 2% fatty-acid free BSA (Lampire, PA), and 20 ng/ml of IGF-1 (R & D systems), supplemented with 10 µM of Y27632 (Rock inhibitor, Catalog No. Y0503, Sigma). Forty-eight hours post-seeding, cultures were washed in incomplete PBS (phosphate buffered saline without Mg or Ca). The cells were then differentiated according to the following protocol:

a) Stage 1 (3 days): Cells were cultured for one day in MCDB-131 medium (Invitrogen Catalog No. 10372-019) supplemented with 2% fatty acid-free BSA (Proliant Catalog No. 68700), 0.0012 g/ml sodium bicarbonate (Sigma-Aldrich Catalog No. S3187); 1× GlutaMax™ (Invitrogen Catalog No. 35050-079); 4.5 mM D-glucose (Sigma-Aldrich Catalog No. G8769); 100 ng/ml GDF8 (R&D Systems); and 1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. Cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b) Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c) Stage 3 (2 days): The Stage 2 cells were then treated with BLAR custom medium (Invitrogen) supplemented with a 1:200 dilution of ITS-X (Invitrogen, Ca); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN-193189 (BMP receptor inhibitor; Catalog No. 04-0019; Stemgent) for two days.

d) Stage 4 (3 days): The Stage 3 cells were then treated with BLAR medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; and 200 nM TPB for three days, then at the end of Stage 4, cells cultured on planar dishes were treated for 4 hours with 10 µM of Y27632, rinsed with PBS and treated for 5 minutes at room temperature with 1× TrypLE™ (Invitrogen) followed by removal of the enzyme, rinsing with basal media and scraping of cells by a cell scraper. The resulting suspension of cells were seeded at a density of 0.5-0.75×10⁶ cells (in 10 µl aliquots) on MATRIGEL™-coated 0.4 micron porous cell culture filter inserts in 6-well plates. 1.5 ml of media was added to the bottom of each insert and no further media was added to the apical side of the filter.

e) Stage 5 (3 days): The Stage 4 cells were then cultured at the air-liquid interface in BLAR medium supplemented with a 1:200 dilution of ITS-X; 20 mM glucose; 1× GlutaMax™; 0.0015 g/ml sodium bicarbonate; 2% fatty acid-free BSA; 10 µg/ml of heparin (Sigma, #H3149), 10 µM ZnSO₄ (Sigma, Z0251), 0.25 µM SANT-1; 50 nM RA; 100 nM LDN-193189; 10000 nM of ALK5 inhibitor II for three days.

f) Stage 6 (8 days): The Stage 5 cells were then treated with BLAR medium supplemented with a 1:200 dilution of ITS-X; 20 mM Glucose; 1× GlutaMax™; 0.0015 g/ml sodium bicarbonate; 2% fatty acid-free BSA; 10 µg/ml of heparin (Sigma, #H3149), 10 µM ZnSO₄ (Sigma, Z0251), 0.25 µM SANT-1; 100 nM LDN-193189, 1000 nM T3, 10000 nM ALK5 inhibitor II for 8 days.

Figure 22A:
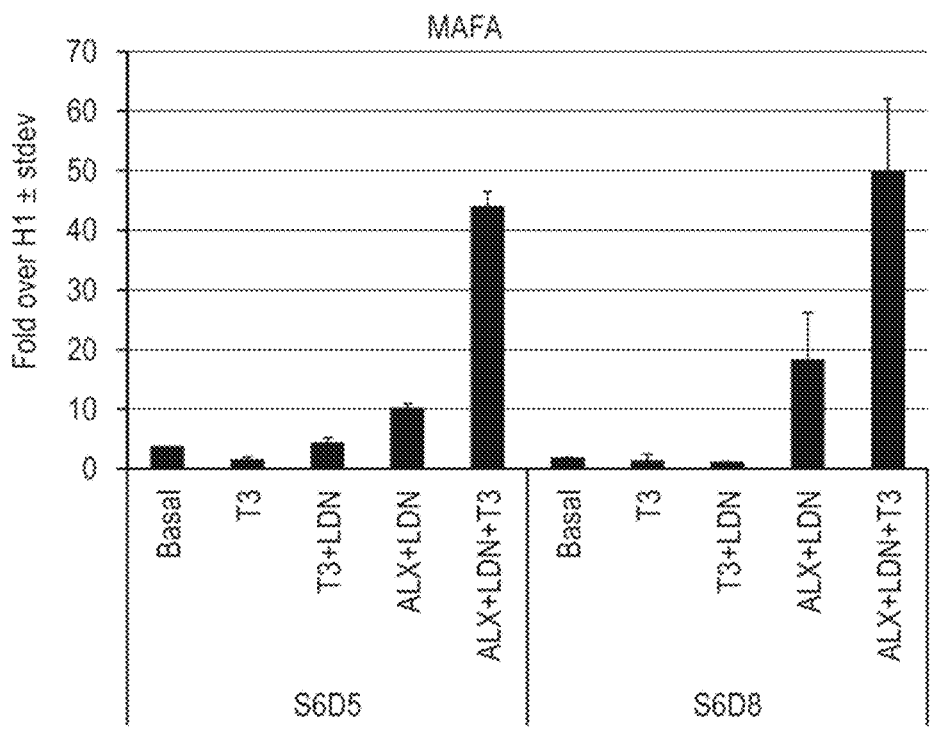
FIGS. 22A to 22D show real-time PCR data of the following genes in cells of the human embryonic stem cell line H1 differentiated as outlined in Example 13: MAFA (FIG. 22A); insulin (FIG. 22B); Amylin (FIG. 22C); and NKX6.1 (FIG. 22D).
Figure 22B:
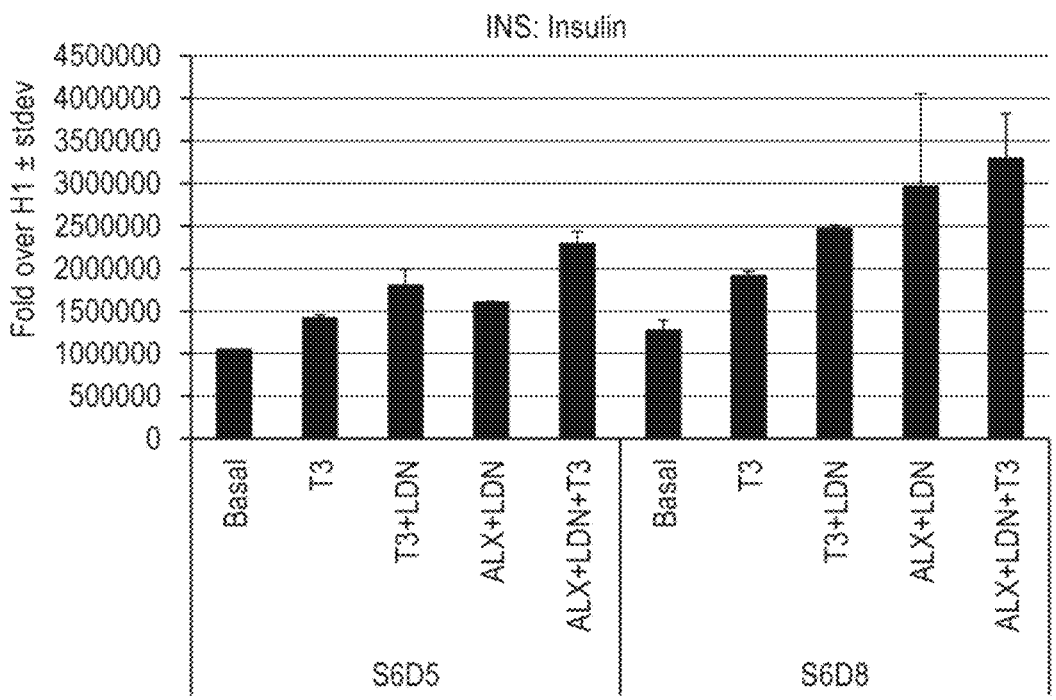
Figure 22C:
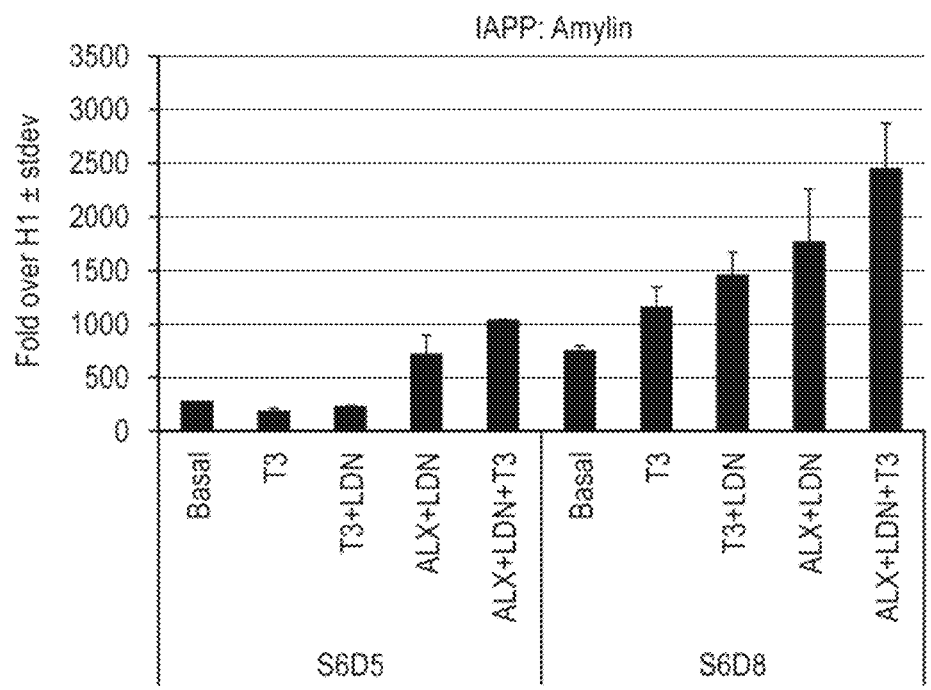
Figure 22D:
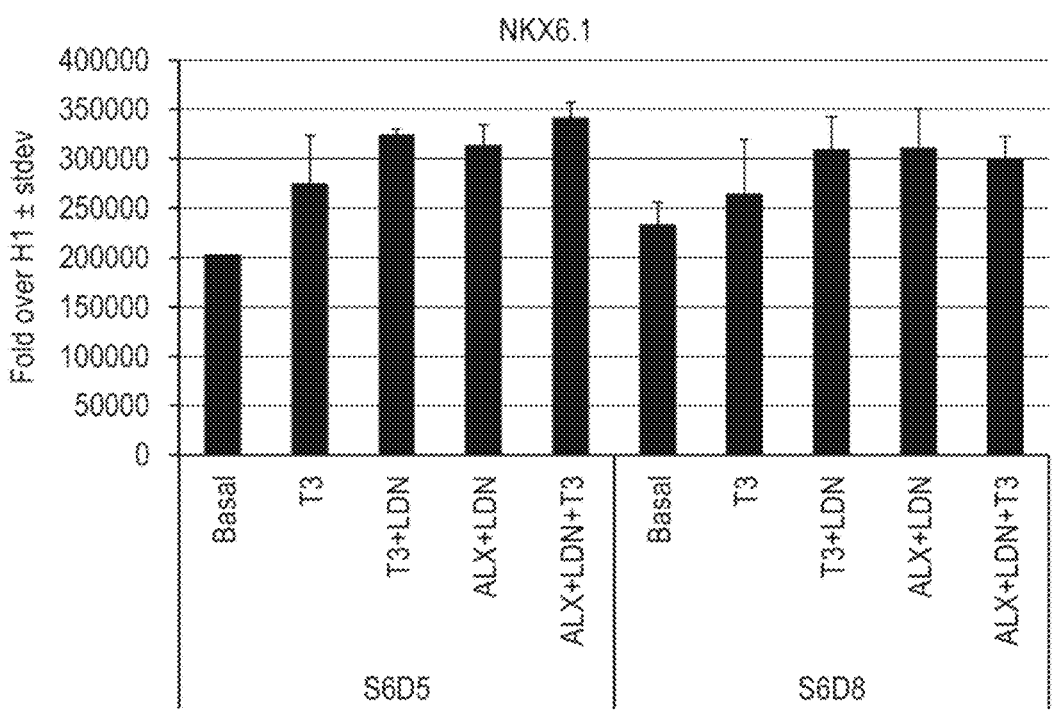
Figure 23A:
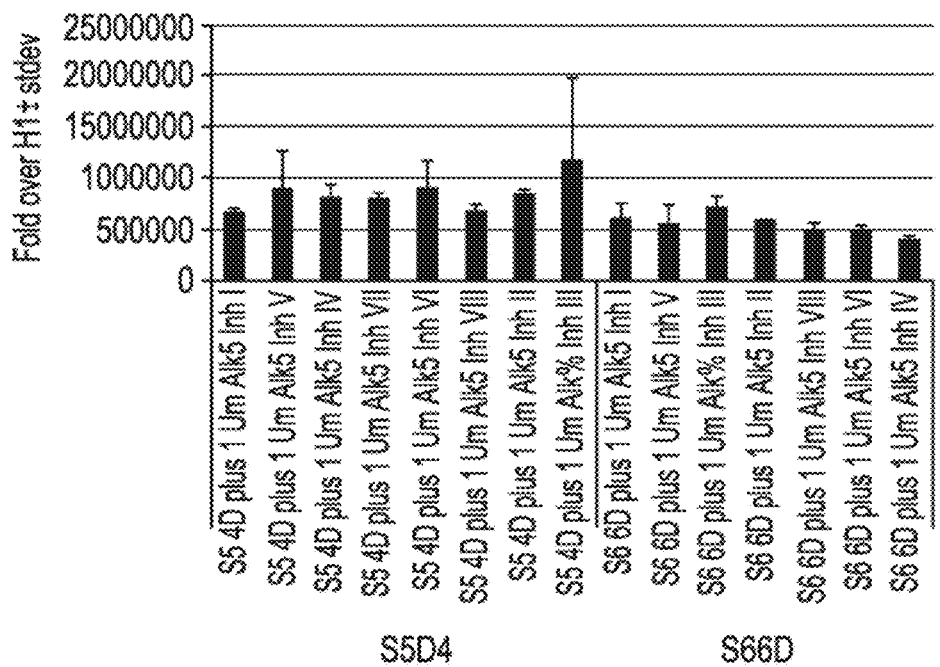
Figure 23B:
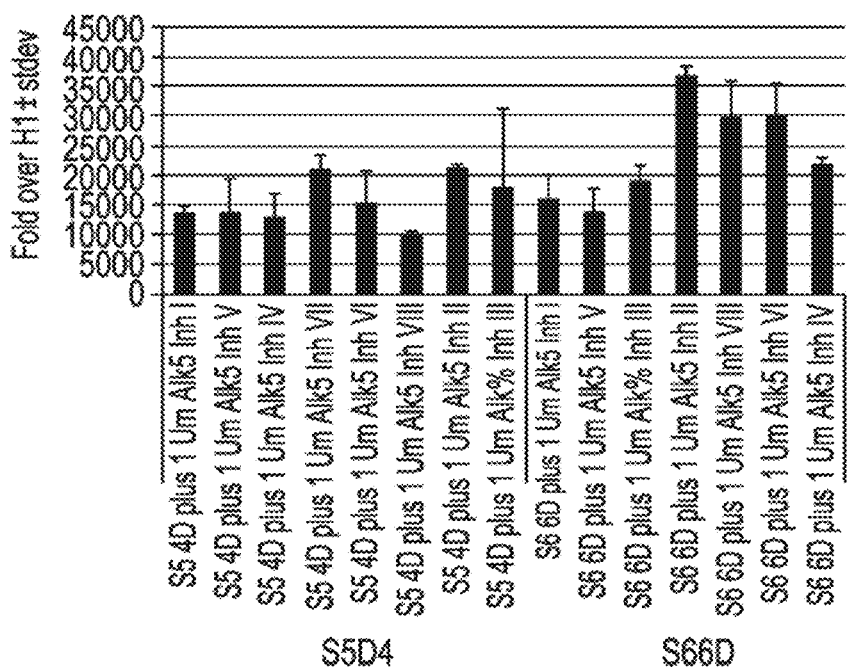
Figure 23C:
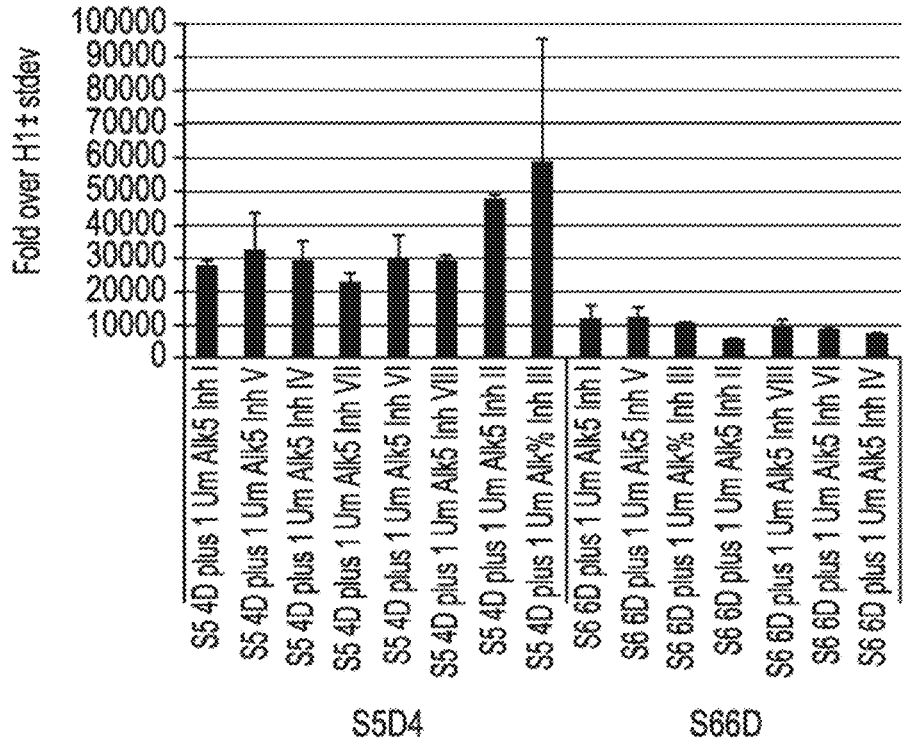
Figure 23D:
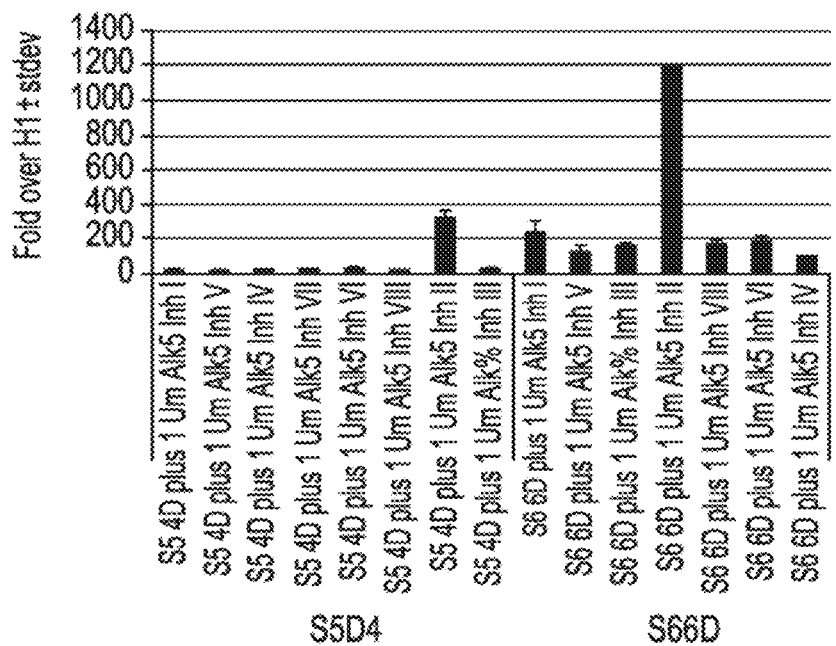

At Stage 6, ALK5 inhibitor, T3, or LDN were removed in various combinations to test for the impact of each factor on expression of NKX6.1, insulin, and MAFA. mRNA was collected at Stage 6 day 5 and Stage 6 day 8. FIG. 22 depicts the PCR data for key cell maturation markers along with pancreatic progenitor markers. As shown in FIG. 22, removal of ALK5 inhibitor at Stage 6 resulted in a dramatic drop in expression of MAFA. Whereas the combination of ALK5 inhibitor, LDN-183189 (BMP receptor inhibitor) and T3 significantly enhanced expression of MAFA (FIG. 22A), insulin (FIG. 22B), Amylin (FIG. 22C), and moderately improved expression of NKX6.1 (FIG. 22D).

Example 14

Additional Protocol for Culturing Stage 6 Cells at the Air-liquid Interface

This example discloses additional materials and methods for culturing Stage 6 cells at the air-liquid interface.

of the aggregates can be removed at once by rinsing the top of the filter with basal media. The cell aggregates are loosely attached to the inserts.

In addition to the specific culture conditions described in the foregoing Examples, other suitable culture conditions for differentiating pluripotent cells, or their progeny, into pancreatic endocring cells are set forth in Tables VIII to XIII. As used in these tables, "ALK5 inh." is ALK5 inhibitor, "RA" is retinoic acid, "Vit. C" is ascorbic acid, "inh." is inhibitor, "act." is activator, $ZnSO_4$ is Zinc Sulfate, "MCX" is MCX compound, and "AA" is activin A. In certain embodiments, any one of the treatments at one stage (e.g. Stage 4) may be combined with any one of the treatments at another stage (e.g., Stage 5).

TABLE VIII

Protocol for differentiating cells including culturing at the air-liquid interface

| | Stage 1 | Stage 2 | Stage 3 | Stage 4 | Stage 5-Filter | Stage 6-Filter |
|---|---|---|---|---|---|---|
| Basal media | MCDB131 Intermediate Bicarbonate (Total: 2.35 g/l) | MCDB131 Intermediate Bicarbonate (Total: 2.35 g/l) | BLAR High Bicarbonate (Total: 2.93 g/l) | BLAR High Bicarbonate (Total: 2.93 g/l) | BLAR Intermediate Bicarbonate (Total: 2.35 g/l) | BLAR Intermediate Bicarbonate (Total: 2.35 g/l) |
| Supplement | 0.5% FAF-BSA, 10 mM glucose | 0.5% FAF-BSA, 10 mM glucose | 2% FAF-BSA, 1:200 ITS-X, 10 mM glucose | 2% FAF-BSA, 1:200 ITS-X, 10 mM glucose | 2% FAF-BSA, 1:200 ITS-X, 20 mM glucose | 2% FAF-BSA, 1:200 ITS-X, 20 mM glucose |
| Growth factors | 100 ng/ml GDF8 | 25 ng/ml FGF7 | 25 ng/ml FGF7 | 2 ng/ml FGF7 | 10 μg/ml heparin | 10 μg/ml heparin |
| Small molecule agonist/ antagonist | 1.0 μM MCX Day 1 100 nM MCX at Day 2 | 0.25 mM Vit C | 1 μM RA 0.25 μM SANT 200 nM TPB 100 nM LDN-193189 0.25 mM Vit C | 100 nM LDN 0.25 μM SANT 100 nM TPB 100 nM RA 0.25 mM Vit C | 0.25 μM SANT 50 nM RA 10000 nM ALK5 inh 100 nM LDN-193189 10 mM $ZnSO_4$ | 10000 nM ALK5 inh 1 μM T3 100 nM LDN-193189 10 mM $ZnSO_4$ |
| Duration (days) | Approximately 2 to 5 days, preferably about 3 days | Approximately 2 to 3 days, preferably about 2 days | Approximately 2 to 4 days, preferably about 2 days | Approximately 2 to 4 days, preferably about 3 days | Approximately 2 to 4 days, preferably about 3 days | Approximately 3-15 days |
| Type of Culture | Planar | Planar | Planar | Planar | Air-liquid interface | Air-liquid interface |

Materials used include the following: 10 cm filter inserts from Corning (catalog number 3419, 0.4 micron polycarbonate membrane); MCDB-131 medium (Invitrogen, Catalog No. 10372-019) or BLAR custom medium (manufactured by Invitrogen); ITS-X (Invitrogen, Ca); thyroid hormone (T3): Sigma ALK5 inhibitor II-ENZO (Catalog number—ALX-27-445); LDN-193189-StemGent (#04-0074); heparin (Sigma, H3149); and BSA-Fatty acid-free (Proliant/Lampire, 7500804).

Preparation of stage 6 basal media: Add 1.5 grams/liter of sodium bicarbonate to MCDB131 media, plus 2% BSA, plus 1:200 X ITS-X, plus additional 15 mM glucose.

Preparation of stage 6 differentiation media: To the Stage 6 basal media, add 10 microMolar ALK5 inhibitor II, 100 nM LDN-193189, and 1 microMolar T3.

Methods

Add 7.5 ml of Stage 6 differentiation media to the bottom of a 10 cm filter insert. Add clusters of cells in small volumes (20-30 μl) to the top of the filter inserts. Typically, approximately 50 cell clusters are placed per 10 cm of insert. At seeding, each cell cluster contains approximately 0.5 M cells.

The media is preferably changed every day. Cells can be removed from the filter insert by removing cell aggregates individually, such as by using a wide mouth pipette tip, or all

TABLE IX

Reagents used in differentiation protocol described in Table VII

| Reagent | Concentration | Vendor | Catalogue # |
|---|---|---|---|
| MCDB131 BLAR (Custom media) | (Add 1:100 X Glutamax) Intermediate bicarbonate: Add 1.5 g of sodium bicarbonate/1000 ml media. High-Bicarbonate: Add 2.5 g of bicarbonate/1000 ml of media | Invitrogen | 10372019 |
| FAF-BSA | 0.5% at S1-S2 2% at S3-S6 | Proliant | 68700 |
| ITS-X | 1:200 dilution | Invitrogen | 51500056 |
| Glucose | 10 mM for S1-S4 20 mM at S5-S6 | Sigma | G8769 |
| GDF8 | 100 ng/ml | Peprotech | 120-00 |
| MCX | 1.0 μM for day 1 and 100 nM for day 2 | | |
| FGF7 | 25 ng/ml at S2, 25 ng/ml at S3, 2 ng/ml at S4 | R & D Systems | 251-KG |

TABLE IX-continued

Reagents used in differentiation protocol described in Table VII

| Reagent | Concentration | Vendor | Catalogue # |
|---|---|---|---|
| RA | 1 µM at S3<br>100 nM at S4<br>50 nM at S5 | Sigma | R2625 |
| SANT-1 (Shh inhibitor) | 0.25 µM | Sigma | S4572 |
| LDN-193189 (BMP r antagonist) | 100 nM at S3-S6 | Stemgent | 04-0019 |
| TPB (PKC activator) | 200 nM At S3,<br>100 nM at S4 | ChemPartner | Custom |
| Ascorbic acid (Vit C) | 0.25 mM at S2-S4 | Sigma | A4544 |
| ALK5 inh II | 10000 nM at S5-S6 | ENZO | ALX-270-445 |
| T3 | 1 µM at S6 | Sigma | T6397 |
| Heparin | 10 µg/ml at S5-S6 | Sigma | H3149 |
| ZnSulfate | 10 µM at S5-S6 | Sigma | Z0251 |
| Filter inserts for 6-well plates | 0.4 micron filters from BD or Millipore | BD Millipore | 353493<br>PIHT15R48 |

TABLE X

Exemplary culture conditions suitable for use in the methods of the invention

| | Stage 4 | Stage 5 | Stage 6 |
|---|---|---|---|
| Treatment of with at least | Stage 3 cells<br>ALK5 inh.; Noggin<br>RA; FGF7; Vit. C.<br>T3 | Stage 4 cells<br><br>Alk 5 inh.<br>T3 & ALK5 inh. (e.g. ALK5 inh. II)<br>T3 & ALK5 inh. (e.g. ALK5 inh. II); RA; LDN-193189<br>ALK5 inh. (e.g. ALK5 inh. II); RA; LDN-193189 | Stage 5<br><br><br><br><br><br><br><br><br><br>T3 & ALK5 inh. (e.g. ALK5 inh. II)<br>T3; ALK5 inh. (e.g. ALK5 inh. II) & LDN-193189<br>T3; ALK5 inh. (e.g. ALK5 inh. II); LDN-193189 & heparin |
| Other optional components[a] (at least one of) | PKC act. (e.g. TPB);<br>SANT-1; ROCK inh. (e.g. Y27632) | RA; Vit. C.; SANT-1;<br>ZnSO4; BMP inh. (e.g. LDN-193189); heparin | RA; Vit. C.; SANT-1;<br>ZnSO4; BMP inh. (e.g. LDN-193189); heparin |
| Culture at | Planar (the air-liquid interface optional for late Stage 4) | the air-liquid interface | the air-liquid interface |
| Duration of Treatment | Approximately 2 to 4 days;<br>preferably 2 to 3 days | Approximately 2 to 4 days;<br>preferably 2 to 3 days | Approximately 3 to 15 days |

[a] excluded from list if mentioned in "with at least" category.

Exemplary ranges of the components recited in Table X as used in the methods of the invention are shown below:

TABLE XI

Exemplary amounts of culture components suitable for use in the methods of the invention

| Component | Exemplary Suitable Amount | Alternatively |
|---|---|---|
| T3 | about 0-1500 nM | about 10 nM<br>about 1000 nM |
| ALK5 inhibitor | about to 75 nM to<br>about 15000 nM | about 100 nM<br>about 200 nM<br>about 1000 nM<br>about 2000 nM<br>about 10000 nM |
| SANT-1 | from about 0.1 µM to<br>about 0.3 µM | about 0.25 µM |
| Retinoic Acid | from about 25 nM to<br>about 150 nM | about 50 nM<br>about 100 nM |
| Ascorbic Acid | from about 0.1 to<br>about 0.4 mM | about 0.25 mM |
| FGF7 | from about 2 to<br>about 35 ng/ml | about 2 ng/ml<br>about 25 ng/ml |
| BMP Receptor Inhibitor (e.g. LDN-193189) | from about 50 to<br>about 150 mM | about 100 mM |
| PKC activator (e.g. TPB) | From about 50 to<br>about 150 mM | about 200 mM |
| Noggin | from about 50 ng/ml<br>to about 150 ng/ml | about 100 ng/ml |
| Heparin | from about 5 µg/ml<br>to about 15 µg/ml | about 10 µg/ml |
| ROCK inhibitor (e.g. Y27632) | from about 5 µM<br>to about 15 µM | about 10 µM |
| Zn Sulfate | from about 5 µM<br>to about 15 µM | about 10 µM |

Table XI shown below, illustrates alternate exemplary culture conditions suitable for use in embodiment of methods of the invention.

TABLE XII

Exemplary culture conditions suitable for use in embodiments of the methods of the invention

| | Stage 1 | Stage 2 | Stage 3 | Stage 4 | Stage 5 | Stage 6 |
|---|---|---|---|---|---|---|
| Treatment of | Pluripotent stem cells | Stage 1 Cells | Stage 2 Cells | Stage 3 cells | Stage 4 cells | Stage 5 |
| With at least | GDF8 & MCX AA & Wnt3A | FGF7 & Vit C | FGF7; RA; SANT; TPB; LDN & Vit C | ALK5 inh., Noggin RA, FGF7, Vit. C. T3 FGF7; LDN-193189; SANT; TPB; RA & Vit C | Alk 5 inh. T3 & ALK5 inh. T3 & ALK5 inh., RA ALK5 inh., RA, LDN heparin; SANT; RA; ALK5 inh; LDN; ZnSO$_4$ | T3 & ALK5 inh. T3, ALK5 inh. & LDN T3, ALK5 inh., LDN & heparin heparin; ALK5 inh.; T3; LDN; ZnSO$_4$ |
| Other optional components$^a$ (at least one of) | | | | PKC act. (e.g. TPB); SANT-1; ROCK inh. (e.g. Y27632) | RA; Vit. C.; SANT-1; ZnSO$_4$; BMP inh. (e.g. LDN); heparin | RA; Vit. C.; SANT-1; ZnSO$_4$; BMP inh. (e.g. LDN); heparin |
| Duration (days) | Approximately 2 to 5 days, preferably about 3 days | Approximately 2 to 3 days, preferably about 2 days | Approximately 2 to 4 days, preferably about 2 days | Approximately 2 to 4 days, preferably about 3 days | Approximately 2 to 4 days, preferably about 3 days | Approximately 3 to 15 days, preferably about 7 to 15 days |
| Type of Culture | Planar | Planar | Planar | Planar (optional air-liquid interface late Stage 4) | Air Liquid Interface (Filter) | Air Liquid Interface (Filter) |

$^a$excluded from list if mentioned in "with at least category"

Table XII shown below, illustrates alternate exemplary culture conditions suitable for use in embodiment of methods of the invention.

TABLE XIII

Exemplary culture conditions suitable for use in embodiments of the methods of the invention

| | Stage 1 | Stage 2 | Stage 3 | Stage 4 | Stage 5 | Stage 6 |
|---|---|---|---|---|---|---|
| Treatment of | Pluripotent stem cells | Stage 1 Cells | Stage 2 Cells | Stage 3 cells | Stage 4 cells | Stage 5 |
| With at least | GDF8 and MCX | FGF7 and Vit C | FGF7; RA; SANT; TPB; LDN and Vit C | FGF7; LDN; SANT; TPB; RA and Vit C | heparin; SANT; RA; ALK5 inh; LDN; ZnSO$_4$ | heparin; ALK5 inh.; T3; LDN; ZnSO$_4$ |

TABLE XIII-continued

Exemplary culture conditions suitable for use in embodiments of the methods of the invention

| | Stage 1 | Stage 2 | Stage 3 | Stage 4 | Stage 5 | Stage 6 |
|---|---|---|---|---|---|---|
| Exemplary amounts | ~100 ng/ml GDF8 and ~1.0 μM MCX Day 1 ~100 nM MCX at Day 2 | ~25 ng/ml FGF7; ~0.25 mM Vit C | ~25 ng/ml FGF7; ~1 μM RA ~0.25 μM SANT ~200 nM TPB ~100 nM LDN ~0.25 mM Vit C | ~2 ng/ml FGF7; ~100 nM LDN ~0.25 μM SANT ~100 nM TPB ~100 nM RA ~0.25 mM Vit C | ~0.25 μM SANT ~50 nM RA ~10000 nM ALK5 inh ~100 nM LDN ~10 mM ZnSO$_4$ | ~10 μg/ml heparin; ~100000 nM ALK5 inh ~1 μM T3 ~100 nM LDN ~10 mM ZnSO$_4$ |
| Duration (days) | Approximately 2 to 5 days, preferably about 3 days | Approximately 2 to 3 days, preferably about 2 days | Approximately 2 to 4 days, preferably about 2 days | Approximately 2 to 4 days, preferably about 3 days | Approximately 2 to 4 days, preferably about 3 days | Approximatey 3 to 15 days, preferably about 7 to 15 days |
| Type of Culture | Planar | Planar | Planar | Planar | Air Liquid Interface (Filter) | Air Liquid Interface (Filter) |

As detailed above, the present invention provides, inter alia, a method of forming cells expressing markers characteristic of β cells comprising differentiating cells expressing markers characteristic of foregut endoderm cells into cells expressing markers characteristic of β cells by treatment with a medium supplemented with T3/T4, or an ALK5 inhibitor, or both T3/T4 and an ALK5 inhibitor and culturing at the air-liquid interface. In one embodiment, only Stage 4 to Stage 6 cells are cultured at the air-liquid interface. The Stage 6 cells may be positive for NKX6.1, PDX1, and HB9. Accordingly, the invention also provides a method of inducing PDX1, NKX6.1, and HB9 expression in cells derived from pluripotent stem cells comprising: (a) culturing pluripotent stem cells; (b) differentiating the pluripotent stem cells into cells expressing markers characteristic of the foregut endoderm cells; and (c) differentiating the cells expressing markers characteristic of the foregut endoderm cells into cells expressing PDX1, NKX6.1, and HB9 by treatment with a medium supplemented with T3/T4, or an ALK5 inhibitor, or both T3/T4 and an ALK5 inhibitor, and culturing at the air-liquid interface. Further, the resulting Stage 6 cells may be single hormone positive cells. In one embodiment, the Stage 6 cells co-express NKX6.1 and chromogranin-A. In another embodiment, the stage 6 cells co-express NKX6.1 and insulin.

In certain embodiments, the methods include treating Stage 5 cells with a medium supplemented with T3/T4 and an ALK5 inhibitor, such as ALK5 inhibitor II. In these embodiments, the medium may advantageously be supplemented further with one or more of retinoic acid, ascorbic acid, SANT-1 or LDN-139189.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

What is claimed is:

1. An in vitro method for producing pancreatic endocrine cells from human pluripotent stem cells, comprising the steps of:
    a) differentiating human pluripotent stem cells into pancreatic foregut precursor cells; and
    b) differentiating the pancreatic foregut precursor cells into pancreatic endocrine cells by culturing the pancreatic foregut precursor cells at an air-liquid interface in i) a medium comprising an ALK5 inhibitor and a thyroid hormone or ii) a medium comprising a thyroid hormone, wherein the thyroid hormone is triiodothyronine, thyroxine, an analogue of triiodothyronine, an analogue of thyroxine or a mixture thereof.

2. The method of claim 1, wherein the pancreatic endocrine cells are positive for NKX6.1, PDX1, and HB9.

3. The method of claim 1, wherein the pancreatic endocrine cells co-express NKX6.1 and chromogranin-A.

4. The method of claim 3, wherein at least thirty percent of the pancreatic endocrine cells co-express NKX6.1 and chromogranin-A.

5. The method of claim 1, wherein the pancreatic endocrine cells co-express NKX6.1 and insulin.

6. The method of claim 5, wherein at least thirty percent of the pancreatic endocrine cells co-express NKX6.1 and insulin.

7. The method of claim 1, wherein the method comprises culturing the pancreatic foregut precursor cells at the air-liquid interface in a medium comprising triiodothyronine and an ALK5 inhibitor.

8. The method of claim 1, wherein culturing pancreatic foregut precursor cells at the air-liquid interface comprises culturing the pancreatic foregut precursor cells on a porous substrate.

9. The method of claim 8, wherein the porous substrate is uncoated.

10. The method of claim 1, wherein said ALK5 inhibitor is selected from the group consisting of: SD208, TGF-B inhibitor SB431542, ITD-1, LY2109761, A83-01, LY2157299, TGF-β receptor inh V, TGF-β receptor inh I, TGF-β receptor inh I TGF-β receptor inh IV, TGF-β receptor inh VII, TGF-β receptor inh VIII, TGF-β receptor inh II, TGF-β receptor inh VI, and TGF-β receptor inh III.

11. The method of claim 1, wherein said ALK5 inhibitor is ALK5 inhibitor II.

12. The method of claim 3, wherein the method increases the number of NXK6.1 positive cells that co-express insulin, chromogranin-A or both chromogranin-A and insulin.

13. The method of claim 1, wherein the human pluripotent stem cells are of non-embryonic origin.

14. The method of claim 1, wherein the pancreatic endocrine cells are β cells.

15. An in vitro method of inducing PDX1, NKX6.1, and HB9 expression in cells derived from human pluripotent stem cells, comprising:
   a) differentiating human pluripotent stem cells into pancreatic foregut precursor cells; and
   b) differentiating the pancreatic foregut precursor cells into cells expressing PDX1, NKX6.1, and HB9 by culturing the pancreatic foregut precursor cells at an air-liquid interface in a medium comprising i) an ALK5 inhibitor and a thyroid hormone, or ii) in a medium comprising a thyroid hormone, wherein the thyroid hormone is triiodothyronine, thyroxine, an analogue of triiodothyronine, an analogue of thyroxine or a mixture thereof.

16. The method of claim 15, wherein the human pluripotent stem cells are of non-embryonic origins.

17. The method of claim 15, wherein the ALK5 inhibitor is ALK5 inhibitor II.

18. The method of claim 15, wherein the medium further comprises one or more of retinoic acid, ascorbic acid, SANT-1 or LDN-193189.

19. The method of claim 1, wherein the method comprises culturing pancreatic foregut cells at the air-liquid interface in the medium comprising the thyroid hormone triiodothyronine, thyroxine, an analogue of triiodothyronine, an analogue of thyroxine, or a and mixture thereof.

20. The method of claim 1, wherein the method comprises culturing pancreatic foregut precursor cells at the air-liquid interface in the medium comprising the ALK5 inhibitor and the thyroid hormone.

21. The method of claim 20, wherein the thyroid hormone is selected from triiodothyronine, thyroxine, analogues of triiodothyronine, analogues of thyroxine and mixtures thereof.

22. The method of claim 15, wherein the method comprises differentiating pancreatic foregut precursor cells into cells expressing PDX1, NKX6.1, and HB9 by culturing the pancreatic foregut precursor cells at the air-liquid interface in a medium comprising a thyroid hormone, wherein the thyroid hormone is triiodothyronine, thyroxine, an analogue of triiodothyronine, an analogue of thyroxine or a mixture thereof.

23. The method of claim 15, wherein the method comprises differentiating pancreatic precursor foregut cells into cells expressing PDX1, NKX6.1, and HB9 by culturing the pancreatic foregut precursor cells at the air-liquid interface in medium comprising both an ALK5 inhibitor and a thyroid hormone.

24. The method of claim 23, wherein the thyroid hormone is selected from triiodothyronine, thyroxine, analogues of triiodothyronine, analogues of thyroxine and mixtures thereof.

25. An in vitro method for differentiating human pancreatic foregut precursor cells into pancreatic endocrine cells comprising culturing the human pancreatic foregut precursor cells at an air-liquid interface in i) a medium comprising with an ALK5 inhibitor and a thyroid hormone, or ii) a medium comprising a thyroid hormone, wherein the thyroid hormone is triiodothyronine, thyroxine, an analogue of triiodothyronine, an analogue of thyroxine or a mixture thereof.

26. The method of claim 25, wherein the method comprises culturing the human pancreatic foregut precursor cells at the air-liquid interface in the medium comprising the thyroid hormone selected from triiodothyronine, thyroxine, the analogue of triiodothyronine, the analogue of thyroxine or the mixture thereof.

27. The method of claim 25, wherein the method comprises culturing the human pancreatic foregut precursor cells at the air-liquid interface in the medium comprising both the ALK5 inhibitor and thyroid hormone.

28. The method of claim 25, wherein the medium further comprises one or more of a BMP receptor inhibitor, retinoic acid, ascorbic acid, heparin; and zinc sulfate.

29. The method of claim of 25, wherein the medium further comprising (i) a BMP receptor inhibitor, (ii) retinoic acid, or (iii) a BMP receptor inhibitor and retinoic acid.

30. The method of claim 27, wherein the medium further comprises (i) a BMP receptor inhibitor, (ii) retinoic acid, or (iii) a BMP receptor inhibitor and retinoic acid.

31. The method of claim 15, wherein the ALK5 inhibitor, the thyroid hormone, or both the ALK5 inhibitor and the thyroid hormone are present in an amount sufficient to induce expression of PDX1 , NKX6.1 and HB9.

32. An in vitro method for producing pancreatic endocrine cells comprising differentiating pancreatic endoderm cells into pancreatic endocrine cells by culturing the pancreatic endoderm cells at an air-liquid interface in i) a medium comprising an ALK5 inhibitor and a thyroid hormone; or ii) a medium comprising, the thyroid hormone, wherein the thyroid hormone is triiodothyronine, thyroxine, an analogue of triiodothyronine, an analogue of thyroxine or a mixtures thereof.

33. The method of claim 32, wherein the method comprises culturing in i) the medium comprising the ALK5 inhibitor and the thyroid hormone.

34. The method of claim 32, wherein the method comprises culturing in ii) the medium comprising the thyroid hormone.

35. The method of claim 1, wherein the medium further comprises one or more of retinoic acid, SANT-1 , and LDN-139189.

* * * * *